United States Patent
Voytas et al.

(10) Patent No.: US 9,758,775 B2
(45) Date of Patent: **\*Sep. 12, 2017**

(54) TAL EFFECTOR-MEDIATED DNA MODIFICATION

(71) Applicants: Regents of the University of Minnesota, Minneapolis, MN (US); Iowa State University Research Foundation, Inc., Ames, IA (US)

(72) Inventors: Daniel F. Voytas, Falcon Heights, MN (US); Adam J. Bogdanove, Ithaca, NY (US); Feng Zhang, Plymouth, MN (US)

(73) Assignees: Regents of the University of Minnesota, Minneapolis, MN (US); Iowa State University Research Foundation, Inc., Ames, IA (US)

( * ) Notice: Subject to any disclaimer, the term of this patent is extended or adjusted under 35 U.S.C. 154(b) by 159 days.

This patent is subject to a terminal disclaimer.

(21) Appl. No.: 14/252,019

(22) Filed: Apr. 14, 2014

(65) Prior Publication Data

US 2014/0335618 A1 Nov. 13, 2014

Related U.S. Application Data

(63) Continuation of application No. 13/738,381, filed on Jan. 10, 2013, now Pat. No. 8,697,853, which is a continuation of application No. 12/965,590, filed on Dec. 10, 2010, now Pat. No. 8,586,363.

(60) Provisional application No. 61/285,324, filed on Dec. 10, 2009, provisional application No. 61/352,108, filed on Jun. 7, 2010, provisional application No. 61/366,685, filed on Jul. 22, 2010.

(51) Int. Cl.
| | |
|---|---|
| C12N 5/00 | (2006.01) |
| C12N 9/22 | (2006.01) |
| C12N 15/10 | (2006.01) |
| C12N 15/62 | (2006.01) |
| C12N 15/63 | (2006.01) |
| C12N 15/01 | (2006.01) |

(52) U.S. Cl.
CPC ............... *C12N 9/22* (2013.01); *C12N 15/01* (2013.01); *C12N 15/102* (2013.01); *C12N 15/1082* (2013.01); *C12N 15/62* (2013.01); *C12N 15/63* (2013.01); *C12Y 301/21004* (2013.01)

(58) Field of Classification Search
CPC ........... C12N 9/22; C12N 15/10; C12N 15/63
See application file for complete search history.

(56) References Cited

U.S. PATENT DOCUMENTS

| | | | |
|---|---|---|---|
| 4,179,337 A | 12/1979 | Davis et al. | |
| 4,683,195 A | 7/1987 | Mullis et al. | |
| 4,761,373 A | 8/1988 | Anderson et al. | |
| 4,769,061 A | 9/1988 | Comai | |
| 4,810,648 A | 3/1989 | Stalker | |
| 4,940,835 A | 7/1990 | Shah et al. | |
| 4,959,317 A | 9/1990 | Sauer | |
| 4,975,374 A | 12/1990 | Goodman et al. | |
| 5,006,333 A | 4/1991 | Saifer et al. | |
| 5,013,659 A | 5/1991 | Bedbrook et al. | |
| 5,162,602 A | 11/1992 | Somers et al. | |
| 5,204,253 A | 4/1993 | Sanford et al. | |
| 5,276,268 A | 1/1994 | Strauch et al. | |
| 5,356,802 A | 10/1994 | Chandrasegaran | |
| 5,436,150 A | 7/1995 | Chandrasegaran | |
| 5,487,994 A | 1/1996 | Chandrasegaran | |
| 5,501,967 A | 3/1996 | Offringa et al. | |
| 5,538,880 A | 7/1996 | Lundquist et al. | |
| 5,554,798 A | 9/1996 | Lundquist et al. | |
| 5,561,236 A | 10/1996 | Leemans et al. | |
| 5,591,616 A | 1/1997 | Hiei et al. | |
| 5,767,366 A | 6/1998 | Sathasivan et al. | |
| 5,792,640 A | 8/1998 | Chandrasegaran | |
| 5,879,903 A | 3/1999 | Strauch et al. | |
| 5,928,937 A | 7/1999 | Kakefuda et al. | |
| 6,084,155 A | 7/2000 | Volrath et al. | |
| 6,326,166 B1 | 12/2001 | Pomerantz et al. | |
| 6,329,571 B1 | 12/2001 | Hiei | |
| 6,368,227 B1 | 4/2002 | Olson | |
| 6,451,732 B1 | 9/2002 | Beckett et al. | |
| 6,451,735 B1 | 9/2002 | Ottaway et al. | |
| 6,824,978 B1 | 11/2004 | Cox, III et al. | |
| 6,933,113 B2 | 8/2005 | Case et al. | |
| 6,979,539 B2 | 12/2005 | Cox, III et al. | |
| 7,001,768 B2 | 2/2006 | Wolffe | |
| 7,013,219 B2 | 3/2006 | Case et al. | |
| 7,070,934 B2 | 7/2006 | Cox, III et al. | |
| 7,163,824 B2 | 1/2007 | Cox, III et al. | |
| 7,189,691 B2 | 3/2007 | Hemenway | |

(Continued)

FOREIGN PATENT DOCUMENTS

| | | |
|---|---|---|
| EP | 0242246 | 10/1987 |
| EP | 2206723 | 7/2010 |

(Continued)

OTHER PUBLICATIONS

Bogdanov et al. Science 333:1843-1846, 2011.*

(Continued)

*Primary Examiner* — Marcia S Noble

(74) *Attorney, Agent, or Firm* — Fish & Richardson P.C.

(57) ABSTRACT

Materials and Methods related to gene targeting (e.g., gene targeting with transcription activator-like effector nucleases; "TALENS") are provided.

15 Claims, 66 Drawing Sheets

(56) References Cited

U.S. PATENT DOCUMENTS

| | | | |
|---|---|---|---|
| 7,220,719 B2 | 5/2007 | Case et al. | |
| 7,262,054 B2 | 8/2007 | Jamieson et al. | |
| 7,273,923 B2 | 9/2007 | Jamieson et al. | |
| 7,285,416 B2 | 10/2007 | Choo et al. | |
| 7,361,635 B2 | 4/2008 | Miller et al. | |
| 7,521,241 B2 | 4/2009 | Choo et al. | |
| 7,842,489 B2 | 11/2010 | Arnould et al. | |
| 8,420,782 B2 | 4/2013 | Bonas et al. | |
| 8,440,431 B2 | 5/2013 | Voytas et al. | |
| 8,440,432 B2 | 5/2013 | Voytas et al. | |
| 8,450,471 B2 | 5/2013 | Voytas et al. | |
| 8,586,363 B2 | 11/2013 | Voytas et al. | |
| 8,697,853 B2 | 4/2014 | Voytas et al. | |
| 2001/0016956 A1 | 8/2001 | Ward et al. | |
| 2005/0064474 A1 | 3/2005 | Urnov et al. | |
| 2007/0141038 A1 | 6/2007 | Choulika et al. | |
| 2008/0160513 A1 | 7/2008 | Anton et al. | |
| 2009/0133158 A1 | 5/2009 | Lahaye et al. | |
| 2009/0271881 A1 | 10/2009 | Arnould et al. | |
| 2009/0305402 A1 | 12/2009 | Liljedahl et al. | |
| 2010/0132069 A1 | 5/2010 | Lahaye et al. | |
| 2011/0041195 A1* | 2/2011 | Doyon | A01K 67/0276 800/13 |
| 2011/0129898 A1 | 6/2011 | Doyon et al. | |
| 2011/0136895 A1 | 6/2011 | Gregory et al. | |
| 2011/0158957 A1 | 6/2011 | Bonini et al. | |
| 2011/0167521 A1 | 7/2011 | DeKelver et al. | |
| 2011/0201055 A1 | 8/2011 | Doyon et al. | |
| 2011/0201118 A1 | 8/2011 | Yang et al. | |
| 2011/0203012 A1 | 8/2011 | Dotson et al. | |
| 2011/0207221 A1 | 8/2011 | Cost et al. | |
| 2011/0239315 A1 | 9/2011 | Bonas et al. | |
| 2011/0247089 A1 | 10/2011 | Doyon | |
| 2011/0265198 A1 | 10/2011 | Gregory et al. | |
| 2011/0269234 A1 | 11/2011 | Doyon et al. | |
| 2011/0287545 A1 | 11/2011 | Cost et al. | |
| 2011/0301073 A1 | 12/2011 | Gregory et al. | |
| 2012/0064620 A1 | 3/2012 | Bonas et al. | |
| 2012/0110685 A1 | 5/2012 | Bonas et al. | |
| 2012/0122205 A1 | 5/2012 | Bonas et al. | |
| 2012/0246764 A1 | 9/2012 | Hlubek et al. | |
| 2012/0284877 A1 | 11/2012 | Hlubek et al. | |
| 2012/0324603 A1 | 12/2012 | Hlubek et al. | |
| 2014/0335592 A1 | 11/2014 | Voytas | |

FOREIGN PATENT DOCUMENTS

| | | | |
|---|---|---|---|
| EP | 2392208 | 12/2011 | |
| WO | WO 94/18313 | 8/1994 | |
| WO | WO 95/09233 | 4/1995 | |
| WO | WO 2007/060495 | 5/2007 | |
| WO | WO 2009/095793 | 8/2009 | |
| WO | WO 2010/079430 | 7/2010 | |
| WO | WO 2010/079430 A1 * | 7/2010 | C07K 14/415 |
| WO | WO 2011/017293 | 2/2011 | |
| WO | WO 2011/019385 | 2/2011 | |
| WO | WO 2011/072246 | 6/2011 | |
| WO | WO 2011/100058 | 8/2011 | |
| WO | WO2011097036 A1 | 8/2011 | |
| WO | WO 2011/146121 | 11/2011 | |
| WO | WO 2011/154393 | 12/2011 | |
| WO | WO2011159369 A1 | 12/2011 | |

OTHER PUBLICATIONS

Voytas and Gao. PLOS Biology 12(6):1-6, 2014.*
U.S. Appl. No. 61/225,043, filed Jul. 13, 2009, Bonas et al.
"TAL effector nucleases," Nature Reprint Collection [online]. Oct. 2011, [retrieved on Mar. 14, 2012]. Retrieved from the Internet: URL <http://www.nature.com/nbt/collections/talen/index.html>, 32 pages, Marshall (ed.).
Alam and Sittman, "Characterization of the cytotoxic effect of a chimeric restriction enzyme, H1°-FokI," Gene Ther Mol Biol, 10:147-160, 2006.
Alam, "Characterization of the cytotoxic effect of a novel chimeric restriction nuclease, H1°-FokI, in mouse fibroblast cells: Implications for chromatin mapping and gene therapy studies," Ph.D. Thesis, The University of Mississippi Medical Center, 223 pages, 2006.
Al-Saadi et al., "All five host-range variants of Xanthomonas citri carry one pthA homolog with 17.5 repeats that determines pathogenicity on citrus, but none determine host-range variation," Mol Plant Microbe Interact, 20(8): 934-943, 2007.
Antony et al., "Rice xa13 recessive resistance to bacterial blight is defeated by induction of the disease susceptibility gene Os—11N3," Plant Cell, 22(11):3864-3876, 2010.
Antony, "Molecular basis of avrXa7 mediated virulence in bacterial blight of rice," [abstract of dissertation] Kansas State University, 99 pages, 2010.
Arimondo et al., "Exploring the cellular activity of camptothecin-triple-helix-forming oligonucleotide conjugates," Mol Cell Biol, 26:324-333, 2006.
Athinuwat et al., "Xanthomonas axonopodis pv. glycines soybean cultivar virulence specificity is determined by avrBs3 homolog avrXg1," Phytopathology, 99(8):996-1004, 2009.
Bai et al., "Xanthomonas oryzae pv. oryzae avirulence genes contribute differently and specifically to pathogen aggressiveness," Mol Plant Microbe Interact, 13(12):1322-1329, 2000.
Ballvora et al., "Genetic mapping and functional analysis of the tomato Bs4 locus governing recognition of the Xanthomonas campestris pv. vesicatoria AvrBs4 protein," Mol Plant Microbe Interact, 14(5):629-638, 2001.
Beretta et al., "Tethering a type IB topoisomerase to a DNA site by enzyme fusion to a heterologous site-selective DNA-binding protein domain," Cancer Res, 59:3689-3697, 1999.
Bibikova et al., "Enhancing gene targeting with designed zinc finger nucleases," Science, 300(5620):764, 2003.
Bibikova et al., "Stimulation of homologous recombination through targeted cleavage by chimeric nucleases," Mol Cell Biol, 21(1): 289-297, 2001.
Bitinaite et al., "FokI dimerization is required for DNA cleavage," Proc Natl Acad Sci USA, 95:10570-10575, 1998.
Boch and Bonas. "Xanthomonas AvrBs3 family-type III effectors: discovery and function." Annu Rev Phytopathol, 48, 419-436, 2010.
Boch et al., "Breaking the code of DNA binding specificity of TAL-type III effectors," Science, 326:1509-1512, 2009.
Boch et al., "Molecular characterization of three AvrBs3-like effectors from the Arabidopsis pathogen Xanthomonas campestris pv. armoraciae," (abstract), XIV International Congress on Molecular Plant-Microbe Interactions, Quebec City, Canada, Jul. 19-23, 2009, 2 pages.
Bogdanove et al., "TAL effectors: Customizable Proteins for DNA Targeting," Science, 333: 1843-1846, 2011.
Bogdanove et al., "TAL effectors: finding plant genes for disease and defense," Curr Opin Plant Biol, 13:394-401, 2010.
Boller and He, "Innate immunity in plants: an arms race between pattern recognition receptors in plants and effectors in microbial pathogens," Science, 324:742-744, 2009.
Bonas et al., "Resistance in tomato to Xanthomonas campestris pv. vesicatoria is determined by alleles of the pepper-specific avirulence gene avrBs3," Mol Gen Genet, 328: 261-269, 1993.
Bonas et al., "Genetic and structural characterization of the avirulence gene avrBs3 from Xanthomonas campestris pv. Vesicatoria," Mol Gen Genet, 218:127-136, 1989.
Bonas et al., "How the bacterial plant pathogen Xanthomonas campestris pv. vesicatoria conquers the host," Mol Plant Pathol, 1(1):73-76, 2000.
Bonas et al., "Resistance in tomato to Xanthomonas campestris pv vesicatoria is determined by alleles of the pepper-specific avirulence gene avrBs3," Mol Gen Genet, 238(1-2):261-269, 1993.
Bonas, "How Xanthomonas manipulates the plant cell," (abstract), XIV International Congress on Molecular Plant-Microbe Interactions, Quebec City, Canada, Jul. 19-23, 2009, 2 pages.
Borevitz et al., "Activation tagging identifies a conserved MYB regulator of phenylpropanoid biosynthesis," Plant Cell, 12:2383-2394, 2000.

(56) References Cited

OTHER PUBLICATIONS

Busk, "Regulatory elements in vivo in the promoter of the abscisic acid responsive gene rab17 from maize," *Plant J*, 11:1285-1295, 1997.

Büttner and Bonas, "Getting across—bacterial type III effector proteins on their way to the plant cell," *EMBO J*, 2002, 21(20):5313-5322, 2002.

Büttner et al., "Functional analysis of HrpF, a putative type III translocon protein from Xanthomonas campestris pv. vesicatoria," *J Bacteriol*, 184(9):2389-2398, 2002.

Büttner et al., "HpaB from Xanthomonas campestris pv. vesicatoria acts as an exit control protein in type III-dependent protein secretion," *Mol Microbiol*, 54(3):755-768, 2004.

Büttner et al., "Targeting of two effector protein classes to the type III secretion system by a HpaC- and HpaB-dependent protein complex from Xanthomonas campestris pv. vesicatoria," *Mol Microbiol*, 59(2):513-527, 2006.

Canteros et al., "A gene from Xanthomonas campestris pv. vesicatoria that determines avirulence in tomato is related to avrBs3," *Mol Plant Microbe Interact*, 4(6):628-632, 1991.

Carlson et al., "Targeting DNA With Fingers and TALENs," *Mol Ther Nucl Acids*, 1:e3, doi:10.1038/mtna.2011.5, 4 pages, 2012.

Cathomen et al., "Zinc-finger nucleases: the next generation emerges," *Mol Ther*, 16(7):1200-1207, 2008.

Cermak et al., Poster and Abstract—"Engineered TAL effector nucleases: new tools for genome editing," Northwest Genome Engineering Consortium Workshop on Genome Engineering, 3 pages, 2010.

Chevalier et al., "Design, activity, and structure of a highly specific artificial endonuclease," *Mol Cell*, 10(4):895-905, 2002.

Choo et al., "In vivo repression by a site-specific DNA-binding protein designed against an oncogenic sequences," *Nature*, 372(6507):642-645, 1994.

Choulika et al., "Induction of homologous recombination in mammalian chromosomes by using the I-ScI system of *Saccharomyces cerevisiae*," *Mol Cell Biol*, 15(4):1968-1973, 1995.

Christian et al., "Targeting DNA Double-Strand Breaks with TAL Effector Nucleases," *Genetics*, 186(2):757-761, 2010.

Christian et al., Poster and Abstract—"Fusions of TAL effectors to the FokI endonuclease confer site specificity in DNA cleavage," IAPB 12th World Congress and In Vitro Biology Meeting, 4 pages, Jun. 2010.

Cole et al., "The Jpred 3 secondary structure prediction server," *Nucl Acids Res*, 36:W197-W201, 2008.

Cornelis, "The type III secretion injectisome," *Nat Rev Microbiol*, 4:811-825, 2006.

De Feyter et al., "Gene-for genes interactions between cotton R genes and Xanthomonas campestris pv. malvacearum avr genes," *Mol Plant Microbe Interact*, 6(2):225-237, 1993.

DeFrancesco, "Move over ZFNs," *Nat Biotechnol*, 29: 681-684, 2011.

Desjarlais and Berg, "Toward rules relating zinc finger protein sequences and DNA binding site preferences," *Proc Natl Acad Sci USA*, 89:7345-7349, 1992.

Domingues et al., "The Xanthomonas citri effector protein PthA interacts with citrus proteins involved in nuclear transport, protein folding and ubiquitination associated with DNA repair," *Mol Plant Pathol*, 11(5):663-675, DOI : 10.1111/J .1364-3703.2010.00636.X, 13 pages, 2010.

Durai et al., "Zinc finger nucleases: custom-designed molecular scissors for genome engineering of plant and mammalian cells," *Nucl Acids Res*, 33(1): 5978-5990, 2005.

Eisenschmidt et al., "Developing a programmed restriction endonuclease for highly specific DNA cleavage," *Nucl Acids Res*, 33:7039-7047, 2005.

Engler et al. "A One Pot, One Step, Precision Cloning Method with High Throughput Capability," *PLoS One*, 3: e3647, 7 pages, 2008.

Engler et al., "Golden Gate Shuffling: A One-Pot DNA Shuffling Method Based on Type IIs Restriction Enzymes," *PLoS One*, 4:e5553, 9 pages, 2009.

Fajardo-Sanchez et al., "Computer design of obligate heterodimer meganucleases allows efficient cutting of custom DNA sequences," *Nucl Acids Res*, 36(7):2163-2173, 2008.

Foley et al., "Rapid Mutation of Endogenous Zebrafish Genes Using Zinc Finger Nucleases Made by Oligomerized Pool ENgineering (OPEN)," *PLoS One*, 13 pages, 4:e4348, 2009.

Fonfara et al., "Creating highly specific nucleases by fusion of active restriction endonucleases and catalytically inactive homing endonucleases," Nucl Acids Res, 40(2):847-860, 2011.

Fujikawa et al., "Suppression of defense response in plants by the avrBs3/pthA gene family of *Xanthomonas* spp," *Mol Plant Microbe Interact*, 19(3):342-349, 2006.

Gabriel et al.,"An unbiased genome-wide analysis of zinc-finger nuclease specificity," *Nat Biotechnol*, 29:816-823, 2011.

Geilβler et al., "Transcriptional activators of human genes with programmable DNA-specificity," *PLoS One*, 6(5):e19509, May 2011.

GenBank Accession No. AAT46122, Nov. 12, 2004, 2 pages.
GenBank Accession No. ACD58243, May 19, 2008, 2 pages.
GenBank Accession No. AY986492, Jun. 24, 2005, 2 pages.
GenBank Accession No. CP000967, GI: 188518722, May 19, 2008, 606 pages.
GenBank Accession No. J04623, Apr. 26, 1993, 2 pages.
GenBank Accession No. M28828, Apr. 26, 1993, 3 pages.
GenBank Accession No. P14727, Jun. 28, 2011, 3 pages.
GenBank Accession No. X16130, Oct. 15, 2007, 3 pages.

Göhre and Robatzek, "Breaking the barriers: microbial effector molecules subvert plant immunity," *Ann Rev Phytopathol*, 46:189-215, 2008.

Gonchar et al., PspXI, a novel restriction endonuclease that recognizes the unusual DNA sequence 5'-VC↓TCGAGB-3', *Bulletin of biotechnology and physico-chemical biology*, 1(1):18-24, 2005, Translation by Ovchinnikov, "Science sibenzyme.com" [online], [retrieved on Aug. 11, 2011]. Retrieved from the Internet: URL: <http://science.sibenzyme.com/article8_article_3_1.phtml>, 4 pages.

Gonzalez et al., "Molecular and pathotypic characterization of new Xanthomonas oryzae strains from West Africa," *Mol Plant Microbe Interact*, 20(5):534-546, 2007.

Greisman and Pabo, "A general strategy for selecting high-affinity zinc finger proteins for diverse DNA target sites," *Science*, 275(5300):657-661, 1997.

Gu et al., "Transcription activator-like type III effector AvrXa27 depends on OsTFIIAgamma5 for the activation of Xa27 transcription in rice that triggers disease resistance to Xanthomonas oryzae pv. oryzae," *Mol Plant Pathol*, 10(6):829-835, 2009.

Gu et al.,"R gene expression induced by a type-III effector triggers disease resistance in rice," *Nature*, 2005, 435:1122-1125.

Guan et al., "Heritable endogenous gene regulation in plants with designed polydactyl zinc finger transcription factors," *Proc Natl Acad Sci USA*, 99(20):13296-13301, 2002.

Gürlebeck et al., "Dimerization of the bacterial effector protein AvrBs3 in the plant cell cytoplasm prior to nuclear import," *Plant J*, 42:175-187, 2005.

Gürlebeck et al., "Type III effector proteins from the plant pathogen *Xanthomonas* and their role in the interaction with the host plant," *J Plant Physiol*, 163(3):233-255, 2006 (Epub 2005).

Gürlebeck et al., "Visualization of novel virulence activities of the Xanthomonas type III effectors AvrBsl, AvrBs3, and AvrBs4," *Mol Plant Pathol*, 10(2):175-188, 2009.

Haber, "In vivo biochemistry: Physical monitoring of recombination induced by site-specific endonucleases," *Bioessay*, 17:609-620, 1995.

Hahn et al., "New mechanistic insights into the virulence activity of the Xanthomonas type III effector AvrBs3," (abstract), XIV International Congress on Molecular Plant-Microbe Interactions, Quebec City, Canada, Jul. 19-23, 2009, 2 pages.

Halford et al., "The reaction mechanism of FokI excludes the possibility of targeting zinc finger nucleases to unique DNA sites," *Biochem Soc Trans*, 39:584-588, 2011.

Handel et al., "Expanding or restricting the target site repertoire of zinc-finger nucleases: the inter-domain linker as a major determinant of target site selectivity," *Mol Ther*, 17:104-111, 2009.

(56) References Cited

OTHER PUBLICATIONS

Herbers et al., "Race-specificity of plant resistance to bacterial spot disease determined by repetitive motifs in a bacterial avirulence protein," *Nature*, 356:172-174, 1992.

Heuer et al., "Repeat domain diversity of avrBs3-like genes in Ralstonia solanacearum strains and association with host preferences in the field," *Appl Environ Microbiol*, 73(13):4379-4384, 2007.

Hockemeyer et al., "Genetic engineering of human pluripotent cells using TALE nucleases," *Nat Biotechnol*, 29(8):731-734, 2011.

Hopkins et al., "Identification of a family of avirulence genes from Xanthomonas oryzae pv. oryzae," *Mol Plant Microbe Interact*, 5(6):451-459, 1992.

Hu et al., "Avirulence gene and insertion element-based RFLP as well as RAPD markers reveal high levels of genomic polymorphism in the rice pathogen *Xanthomonas oryzae* pv. *oryzae*," *Syst Appl Microbiol*, 30:587-600, 2007.

Huang et al., "Heritable gene targeting in zebrafish using customized TALENs," *Nat Biotechnol*, 29(8):699-700, 2011.

Hummel et al., "Rice gene activation by transcription activator-like effectors of Xanthomonas oryzae pvs. oryzae and oryzicola," poster presentation, and "A cipher-like mechanism governs TAL effector-DNA recognition," poster #13-517, XIV International Congress on Molecular Plant-Microbe Interactions, Jul. 19-23, 2009, Quebec City, Canada, 3 pages.

Hurt et al., "Highly specific zinc finger proteins obtained by directed domain shuffling and cell-based selection," *Proc Natl Acad Sci USA*, 100(21):12271-12276, 2003.

Isalan et al., "A rapid, generally applicable method to engineer zinc fingers illustrated by targeting the HIV-1 promoter," *Nat Biotechnol*, 19(7):656-660, 2001.

Jackel et al., "Protein design by directed devolution," Annu Rev Biophys, 37:155-173, 2008.

Jones and Dangl, "The plant immune system," *Nature*, 444:323-329, 2006.

Jordan et al., "Physical delimitation of the pepper Bs3 resistance gene specifying recognition of the AvrBs3 protein from Xanthomonas campestris pv. vesicatoria," *Theor Appl Genet*, 113(5):895-905, 2006.

Kay and Bonas, "How Xanthomonas type III effectors manipulate the host plant," *Curr Opin Microbiol*, 12:37-43, 2009.

Kay et al., "A Bacterial Effector Acts as a Plant Transcription Factor and Induces a Cell Size Regulator," *Science*, 318:648-651, 2007.

Kay et al., "Characterization of AvrBs3-like effectors from a *Brassicaceae* pathogen reveals virulence and avirulence activities and a protein with a novel repeat architecture," *Mol Plant Microbe Interact*, 18(8):838-848, 2005.

Kay et al., "Detailed analysis of the DNA recognition motifs of the Xanthomonas type III effectors AvrBs3 and AvrBs3deltarep16," *Plant J*, 59(6):859-871, 2009.

Kay et al., "Supporting Online Material for Bacterial Effector Acts as a Plant Transcription Factor and Induces a Cell Size Regulator," *Science*, 318(5850):648-651, 2007.

Keshavarzi et al., "Basal defenses induced in pepper by lipopolysaccharides are suppressed by Xanthomonas campestris pv. vesicatoria," *Mol Plant Microbe Interact*, 17(7):805-815, 2004.

Kim and Chandrasegaran, "Chimeric restriction endonuclease," Proc Natl Acad Sci USA, 1994, 91, No. 3 (Feb.), pp. 883-887.

Kim et al., "Comparative analysis of three indigenous plasmids from Xanthomonas axonopodis pv. glycines," *Plasmid*, 56(2):79-87, 2006.

Kim et al., "Construction of a Z-DNA-specific restriction endonuclease," *Proc Natl Acad Sci USA*, 94(24):12875-12879, 1997.

Kim et al., "Hybrid restriction enzymes: zinc finger fusions to FokI cleavage," *Proc Natl Acad Sci USA*, 93:1156-1160, 1996.

Kim et al., "Site-specific cleavage of DNA-RNA hybrids by zinc finger/FokI cleavage domain fusions," *Gene*, 203(1):43-49, 1997.

Knoop et al., "Expression of avirulence gene avrBs3 from Xanthomonas campestris pv. vesicatoria is not under the control of hrp genes and is independent of plant factors," *J Bacteriol*, 173(22):7142-7150, 1991.

Lahaye and Bonas, "Molecular secrets of bacterial type III effector proteins," *Trends Plant Sci*, 6(10):479-485, 2001.

Ledford, "Plant genes get fine tailoring," Nature News [online], Apr. 29, 2009 [retrieved on May 21, 2009]. Retrieved from the Internet: <URL: http://www.nature.com/news/2009/090429/full/news.2009.415.html>, 3 pages.

Li et al., "Functional domains in FokI restriction endonuclease," *Proc Natl Acad Sci USA*, 89(10):4275-4279, 1992.

Li et al., "Modularly assembled designed TAL effector nucleases for targeted gene knockout and gene replacement in eukaryotes," *Nucl Acids Res*, 39:6315-6325, 2011.

Li et al., "TAL nucleases (TALNs): hybrid proteins composed of TAL effectors and FokI DNA-cleavage domain," *Nucleic Acids Research*, 39(1):359-372, 2010.

Liang et al., "Cloning and characterization of a novel avirulence gene (arp3) from Xanthomonas oryzae pv. oryzae," *DNA Seq*, 15(2):110-117, 2004.

Liu et al., "Design of polydactyl zinc-finger proteins for unique addressing within complex genomes," *Proc Natl Acad Sci USA*, 94(11):5525-5530, 1997.

Mahfouz et al., "De novo-engineered transcription activator-like effector (TALE) hybrid nuclease with novel DNA binding specificity creates double-strand breaks," *Proc Natl Acad Sci USA*, 108:2623-2628, 2011.

Mak, "Sequence-specific DNA-binding TALEs," *Nat Biotechnol*, 29:43, 2011.

Marois et al., "The xanthomonas type III effector protein AvrBs3 modulates plant gene expression and induces cell hypertrophy in the susceptible host," *Mol Plant Microbe Interact*, 15(7):637-646, 2002.

Miller et al., "A TALE nuclease architecture for efficient genome editing," *Nat Biotechnol*, 29:143-148, 2011.

Miller et al., "An improved zinc-finger nuclease architecture for highly specific genome editing," *Nature Biotechnol*, 25:778-785, 2007.

Minczuk et al., "Development of a single-chain, quasi-dimeric zinc-finger nuclease for the selective degradation of mutated human mitochondrial DNA," *Nucleic Acids Res*, 36(12):3926-3938, 2008.

Mino et al., "Efficient double-stranded DNA cleavage by artificial zinc-finger nucleases composed of one zinc-finger protein and a single-chain FokI dimer," *J Biotechnol*, 140(3-4):156-161, 2009.

Moore et al., "Transactivated and chemically inducible gene expression in plants," *Plant J*, 45:651-683, 2006.

Morbitzer et al., "Assembly of custom TALE-type DNA binding domains by modular cloning," *Nucleic Acids Research*, 39(13):5790-5799, 2011.

Morbitzer et al., "Regulation of selected genome loci using de novo-engineered transcription activator-like effector (TALE)-type transcription factors," *Proc Natl Acad Sci U S A.*, 107(50):21617-21622, 2010.

Moscou and Bogdanove, "A Simple Cipher Governs DNA Recognition by TAL Effectors," *Science* 326(5959): 1501, 2009.

Murakami et al., "The repeat domain of the type III effector protein PthA shows a TPR-like structure and undergoes conformational changes upon DNA interaction," *Proteins*, 78:3386-3395, 2010.

Mussolino et al. "A novel TALE nuclease scaffold enables high genome editing activity in combination with low toxicity." *Nucleic Acids Res*, 39(21): 9283-9293, 2011.

Nakagawa et al., "Development of series of gateway binary vectors, pGWBs, for realizing efficient construction of fusion genes for plant transformation," *J Biosci Bioeng*, 104:34-41, 2007.

Niño-Liu et al., "*Xanthomonas oryzae* pathovars: model pathogens of a model crop," *Mol Plant Pathol*, 7(5):303-324, 2006.

Nissan et al. "The type III effectors HsvG and HsvB of gall-forming Pantoea agglomerans determine host specificity and function as transcriptional activators." *Molecular Microbiology*, 61(5): 1118-1131, 2006.

(56) References Cited

OTHER PUBLICATIONS

Noel et al., "XopC and XopJ, two novel type III effector proteins from Xanthomonas campestris pv. vesicatoria," *J Bacteriol*, 185(24):7092-7102, 2003.
Ovchinnikov et al., "PspXI, a novel restriction endonuclease that recognizes the unusual DNA sequence 5-VCTCGAGB-3," Bull Biotech Physio-Chemical Biol, 2005, 1(1):18-24, retrieved from the Internet: http://science.sibenzyme.com/article8_article_3_1.phtml.
Padidam, "Chemically regulated gene expression in plants," *Curr Opin Plant Biol*, 6:169-177, 2003.
Paques and Duchateau, "Meganucleases and DNA Double-Strand Break-Induced recombination: Perspectives for Gene Therapy," *Curr Gene Ther*, 7:49-66, 2007.
Park et al., "Avirulence gene diversity of Xanthomonas axonopodis pv. Glycines isolated in Korea," *J Microbiol Biotechnol*, 18(9):1500-1509, 2008.
Pattanayak et al., "Revealing off-target cleavage specificities of zinc-finger nucleases by in vitro selection," *Nat Methods*, 8:765-770, 2011.
Pavletich and Pabo, "Zinc finger-DNA recognition: crystal structure of a Zif268-DNA complex at 2.1 A," *Science*, 252:809-817, 1991.
Pearson, "The fate of fingers," *Nature*, 455:160-164, 2008.
Pennisi, "The Tale of the TALES," *Science*, 338(6113):1408-1411, 2012.
Pingoud and Silva, "Precision genome surgery," *Nature Biotechnol*, 25(7):743-744, 2007.
Podhajska and Szybalski, "Conversion of the FokI endonuclease to a universal restriction enzyme: cleavage of phage M13mp7 DNA at predetermined sites," *Gene*, 40(2-3):175-182, 1985.
Pomerantz et al., "Structure-based design of transcription factors," *Science*, 267(5194):93-96, 1995.
Porteus and Baltimore, "Chimeric nucleases stimulate gene targeting in human cells," *Science*, 300:763, 2003.
Porteus and Carroll, "Gene targeting using zinc finger nucleases," *Nature Biotechnol*, 23:967-973, 2005.
Porteus, "Zinc fingers on target," *Nature*, 459: 337-338, 2009.
Potenza et al., "Targeting transgene expression in research, agricultural, and environmental applications: Promoters used in plant transformation," *In vitro Cell Dev Biol*, 40(1):1-22, 2004.
Puchta et al., "Homologous recombination in plant cells is enhanced by in vivo induction of double strand breaks into DNA by a site-specific endonuclease," *Nucl Acids Res*, 21(22):5034-5040, 1993.
Radecke et al., "Zinc-finger nuclease-induced gene repair with oligodeoxynucleotides: wanted and unwanted target locus modifications," *Mol Ther*, 18(4):743-753, 2010.
Römer et al., "Plant pathogen recognition mediated by promoter activation of the pepper Bs3 resistance gene," *Science*, 318(5850):645-648, 2007.
Römer et al., "A single plant resistance gene promoter engineered to recognize multiple TAL effectors from disparate pathogens," *Proc Natl Acad Sci USA*, 106(48):20526-31, 2009.
Römer et al., "Promoter elements of rice susceptibility genes are bound and activated by specific TAL effectors from the bacterial blight pathogen, Xanthomonas oryzae pv. oryzae," *New Phytol*, 187:1048-1057, 2010.
Römer et al., "Recognition of AvrBs3-Like Proteins is Mediated by Specific Binding to Promoters of Matching Pepper Bs3 Alleles," *Plant Physiol*, 150:1697-1712, 2009.
Romero et al., "Temperature Sensitivity of the Hypersensitive Response of Bell Pepper to Xanthomonas axonopodis pv. vesicatoria," *Phytopathology*, 92(2):197-203, 2002.
Rossier et al., "HrpB2 and HrpF from Xanthomonas are type III-secreted proteins and essential for pathogenicity and recognition by the host plant," *Mol Microbiol*, 38(4):828-838, 2000.
Rossier et al., "The Xanthomonas Hrp type III system secretes proteins from plant and mammalian bacterial pathogens," *Proc Natl Acad Sci USA*, 96(16):9368-9373, 1999.
Rouet et al., "Expression of a site-specific endonuclease stimulates homologous recombination in mammalian cells," *Proc Natl Acad Sci USA*, 91(13):6064-6068, 1994.
Rouet et al., "Introduction of double-strand breaks into the genome of mouse cells by expression of a rare-cutting endonuclease," *Mol Cell Biol*, 14(12):8096-8106, 1994.
Rybak et al., "Identification of Xanthomonas citri ssp. citri host specificity genes in a heterologous expression host," *Mol Plant Pathol*, 10(2):249-262, 2009.
Santiago et al., "Targeted gene knockout in mammalian cells by using engineered zinc-finger nucleases," *Proc Natl Acad Sci USA*, 105(15):5809-5814, 2008.
Scholze and Boch, "TAL effectors are remote controls for gene activation," *Curr Opin Microbiol*, 14:47-53, 2011.
Scholze and Boch. "TAL effector-DNA specificity," *Virulence*, 1(5):428-432, 2010.
Schornack et al., "Characterization of AvrHah1, a novel AvrBs3-like effector from Xanthomonas gardneri with virulence and avirulence activity," *New Phytol*, 179:546-556, 2008.
Schornack et al., "Expression levels of avrBs3-like genes affect recognition specificity in tomato Bs4- but not in pepper BS3-mediated perception," *Mol Plant-Microbe Interact*, 18(11):1215-1225, 2005.
Schornack et al., "Gene-for-gene mediated recognition of nuclear-targeted AvrBs3-like bacterial effector proteins," *J Plant Physiol*, 163:256-272, 2006.
Schornack et al., "The tomato resistance protein Bs4 is a predicted non-nuclear TIR-NB-LRR protein that mediates defense responses to severely truncated derivatives of AvrBs4 and overexpressed AvrBs3," *Plant J*, 37(1):46-60, 2004.
Segal et al., "Endonuclease-induced, targeted homologous extrachromosomal recombination in Xenopus oocytes," *Proc Natl Acad Sci USA*, 92(3):806-810, 1995.
Sera, "Inhibition of virus DNA replication by artificial zinc finger proteins," *J Virol*, 79(4):2614-2619, 2005.
Shukla et al., "Precise genome modification in the crop species Zea mays using zinc-finger nucleases," *Nature*, 459(7245):437-441, 2009.
Simon et al., "Targeting DNA with triplex-forming oligonucleotides to modify gene sequence," *Biochimie*, 90:1109-1116, 2008.
Skipper, "Technology: The holy grail for plant biologists," *Nature Reviews Genetics*, 10(6):350, 2009.
Studholme et al., "Genome-wide sequencing data reveals virulence factors implicated in banana Xanthomonas wilt," *FEMS Microbiol Lett.*, 310(2):182-192, 2010.
Sugio et al., "Two type III effector genes of Xanthomonas oryzae pv. oryzae control the induction of the host genes OsTFIIAγ1 and OsTFX1 during bacterial blight of rice," *Proc Natl Acad Sci USA*, 104:10720-10725, 2007.
Swamp et al., "An Xanthomonas citri pathogenicity gene, pthA, pleiotropically encodes gratuitous avirulence on nonhosts," *Mol Plant Microbe Interact*, 5(3):204-213, 1992.
Szurek et al. "Type III-dependent translocation of the Xanthomonas AvrBs3 protein into the plant cell," *Mol Microbiol*, 46(1): 13-23, 2002.
Szurek et al., "Eukaryotic features of the Xanthomonas type III effector AvrBs3: protein domains involved in transcriptional activation and the interaction with nuclear import receptors from pepper," *Plant J*, 26(5):523-534, 2001.
Takenaka et al., "Inhibition of tomato yellow leaf curl virus replication by artificial zinc-finger proteins," *Nucl Acids Symposium Series*, 51(1):429-430, 2007.
Thieme et al., "New type III effectors from Xanthomonas campestris pv. vesicatoria trigger plant reactions dependent on a conserved N-myristoylation motif" *Mol Plant Microbe Interact*, 20(10):1250-1261, 2007
Thierry et al., "Cleavage of yeast and bacteriophage T7 genomes at a single site using the rare cutter endonuclease I-Sce I," *Nucl Acids Res*, 19(1):189-190, 1991.
Third Party Observations Pursuant to ART. 115 EPC—EP 2 379 583 (Appl.: Bonas, Boch, Schornack, Lahaye)—Title: Modular DNA-binding domains and methods of use, EPO—Munich, 6 pages, 2012.

(56) References Cited

OTHER PUBLICATIONS

Tovkach et al., "A toolbox and procedural notes for characterizing novel zinc finger nucleases for genome editing in plant cells," *Plant J*, 57:747-757, 2009.
Townsend et al., "High-frequency modification of plant genes using engineered zinc-finger nucleases," *Nature*, 459:442-445, 2009.
Urnov et al., "Highly efficient endogenous human gene correction using designed zinc-finger nuclease," *Nature*, 435(7042):646-651, 2005.
Van den Ackerveken et al., "Recognition of the bacterial avirulence protein AvrBs3 occurs inside the host plant cell," *Cell*, 87(7):1307-1316, 1996.
Vergunst et al., "VirB/D4-Dependent Protein Translocation from Agrobacterium into Plant Cells," *Science*, 290:979-982, 2000.
Voytas et al., "Plant science. DNA binding made easy," *Science*, 326(5959):1491-1492, 2009.
Wah et al., "Structure of FokI has implications for DNA cleavage," *Proc Natl Acad Sci USA*, 95(18):10564-10569, 1998.
Wah et al., "Structure of the multimodular endonuclease FokI bound to DNA," *Nature*, 388(3):97-100, 1997.
Wang et al., "Chemically regulated expression systems and their applications in transgenic plants," *Transgenic Res*, 12:529-540, 2003.
Weber et al., "The type III-dependent Hrp pilus is required for productive interaction of Xanthomonas campestris pv. vesicatoria with pepper host plants," *J Bacteriol*, 187(7):2458-2468, 2005.
White and Yang, "Host and pathogen factors controlling the rice/Xanthomonas oryzae interaction," *Plant Physiol*, 150:1677-1686, 2009.
White et al., "The type III effectors of Xanthomonas," *Mol Plant Pathol*, 10:749-766, 2009.
Wright et al., "High-frequency homologous recombination in plants mediated by zinc-finger nucleases," *Plant J*, 44(4):693-705, 2005.
Yang and White, "Diverse members of the AvrBs3/PthA family of type III effectors are major virulence determinants in bacterial blight disease of rice," *Mol Plant Microbe Interact*, 17(11):1192-1200, 2004.
Yang et al. "The virulence factor AvrXa7 of Xanthomonas oryzae of Oryzae is a type III secretion pathway-dependent nuclear-localized double stranded DNA binding protein," *Proc Natl Acad Sci USA*, 97(17): 9807-9812, 2000.
Yang et al., "Avoidance of host recognition by alterations in the repetitive and C-terminal regions of AvrXa7, a type III effector of Xanthomonas oryzae pv. oryzae," *Mol Plant Microbe Interact*, 18(2):142-149, 2005.
Yang et al., "Os8N3 is a host disease-susceptibility gene for bacterial blight of rice," *Proc Natl Acad Sci USA*, 103:10503-10508, 2006.
Yuan et al., "Characterization of Xanthomonas oryzae-responsive cis-acting element in the promoter of rice race-specific susceptibility gene Xa13," *Mol Plant*, 4(2):300-309, 2011.
Zhang et al., "Efficient construction of sequence-specific TAL effectors for modulating mammalian transcription," *Nat Biotechnol*, 29(2):149-153, 2011.
Zhang et al., "High frequency targeted mutagenesis in Arabidopsis thaliana using zinc finger nucleases," *Proc Natl Acad Sci USA*, 107:12028-12033, 2010.
Zhu et al., "The C terminus of AvrXa10 can be replaced by the transcriptional activation domain of VP16 from the herpes simplex virus," *Plant Cell*, 11(9):1665-1674, 1999.
Zhu et al., "AvrXa10 Contains an Acidic Transcriptional Activation Domain in the Functionally Conserved C Terminus," *Molecular Plant-Microbe Interactions*, 11(8): 824-832, 1998.
Zhu et al., "The rsma-like gene rsmA(XOO) of Xanthomonas oryzae pv. oryzae regulates bacterial virulence and production of diffusible of signal factor," *Mol Plant Pathol*, 12(3):227-237, 2011, Epub 2010.
Zou et al., "Identification of an avirulence gene, avrxa5, from the rice pathogen *Xanthomonas oryzae* pv. *oryzae*," *Sci China Life Sci*, 53(12):1440-1449, 2010.

Zuo and Chua, "Chemical-inducible systems for regulated expression of plant genes," *Curr Opin Biotechnol*, 11:146-151, 2000.
European Search Report for EP 09165328.7-2403, Jan. 12, 2009, 5 pages.
Examination Report for Singapore Application No. 201105017-6, mailed Nov. 8, 2012, 5 pages.
Examiner's Interview Summary in U.S. Appl. No. 13/362,660, mailed Oct. 22, 2012.
First Examination Report for Australia Patent Application No. 2010204105, 2012, 2 pages.
International Search Report and Written Opinion in International Application No. PCT/US2011/024515, mailed Oct. 20, 2011, 13 pages.
International Search Report, PCT/US2010/059932, mailed Nov. 22, 2011, 9 pages.
Invitation to Pay Additional Fees, in International Application No. PCT/US2010/059932, dated May 24, 2011, 6 pages.
Notice of Allowance and Examiner's Amendment in U.S. Appl. No. 13/362,660, mailed Dec. 26, 2012.
Response to Office Action in U.S. Appl. No. 13/362,660, dated Oct. 19, 2012.
Substantive correspondence with the USPTO in U.S. Appl. No. 13/016,297, retrieved Jan. 29, 2013, 47 pages.
Substantive correspondence with the USPTO in U.S. Appl. No. 13/016,297, retrieved May 30, 2013, 57 pages.
Substantive correspondence with the USPTO in U.S. Appl. No. 13/019,526, retrieved Jan. 29, 2013, 43 pages.
Substantive correspondence with the USPTO in U.S. Appl. No. 13/019,526, retrieved May 30, 2013, 45 pages.
Substantive correspondence with the USPTO in U.S. Appl. No. 13/218,050, retrieved Jan. 29, 2013, 147 pages.
Substantive correspondence with the USPTO in U.S. Appl. No. 13/218,050, retrieved May 30, 2013, 174 pages.
Substantive correspondence with the USPTO in U.S. Appl. No. 13/362,660, retrieved Jan. 29, 2013, 53 pages.
Substantive correspondence with the USPTO in U.S. Appl. No. 13/362,660, retrieved May 30, 2013, 75 pages.
Third Party Observations Pursuant to Art. 115 EPC for European Application No. EP 10799163.0, filed Jun. 13, 2013, 62 pages.
Third Party Post Issuance Submission under 37 CFR § 1.501 for U.S. Pat. No. 8,440,431, mailed Jun. 21, 2013, 64 pages.
Third Party Post Issuance Submission under 37 CFR § 1.501 for U.S. Pat. No. 8,440,432, mailed Jun. 21, 2013, 64 pages.
Third Party Post Issuance Submission under 37 CFR § 1.501 for U.S. Pat. No. 8,450,471, mailed Jun. 21, 2013, 64 pages.
Third Party Pre Issuance Submission under 37 CFR § 1.290 for U.S. Appl. No. 13/738,381, mailed Jun. 21, 2013, 63 pages.
Search Report for Chinese Application No. 201080063489.7, dated Mar. 12, 2014, 4 pages.
Third Party Observation for Application No. EP201007991963, dated May 9, 2014, 16 pages.
Mühlhardt, Der Experimentator: "Das Werkzeug," [The experimenter: The Tool] Molekularbiologie/Genomics, Chpt. 3, pp. 41-43, 2002 [machine translation].
European Search Report for App. No. 14183521.5 mailed Nov. 21, 2014, 10 pages.
Kilburn & Strode, "Opposition against European patent EP2510096," Jul. 21, 2015, 37 pages.
"World first use of gene-edited immune cells to treat 'incurable' leukaemia," Retrieved from the Internet: <URL: http://www.gosh.nhs.uk/news/press-releases/2015-press-release-archive/world-first-use-gene-edited-immune-cells-treat-incurable-leukaemia>, Nov. 5, 2015.
Blakely, "DNA restriction and modification," Encyclopedia of MicroBiology, pp. 538-549, 2009.
Mulhardt, "Restriction enzymes," *Molekularbiologie/Genomics*, 5 pages, 2002.
Rockoff, "Why gene-editing technology has scientists excited," The Wall Street Journal, Jun. 29, 2015, 1 page.

\* cited by examiner

Figure 3

MDPIRSRTPSPARELLPGPQPDGVQPTADRGVSPPAGGPLDGLPARRTMSRTRLPSPPAPSPAFSAGSFSDLLRQFDPSLFNTSL
FDSLPPFGAHHTEAATGEWDEVQSGLRAADAPPPTMRVAVTAARPPRAKPAPRRRAAQPSDASPAAQVDLRTLGYSQQQEKI
KPKVRSTVAQHHEALVGHGFTHAHIVALSQHPAALGTVAVKYQDMIAALPEATHEAIVGVGKQWSGARALEALLTVAGELRGPPL
QLDTGQLLKIAKRGGVTAVEAVHAWRNALTGAPLNLTPEQVVAIASHDGGKQALETVQRLLPVLCQAHGLTPQQVVAIASNGGGK
QALETVQRLLPVLCQAHGLTPQQVVAIASNSGGKQALETVQRLLPVLCQAHGLTPEQVVAIASNGGGKQALETVQRLLPVLCQAH
GLTPEQVVAIASNIGGKQALETVQALLPVLCQAHGLTPEQVVAIASNGGGKQALETVQRLLPVLCQAHGLTPEQVVAIASNIGGKQA
LETVQALLPVLCQAHGLTPEQVVAIASNGGGKQALETVQRLLPVLCQAHGLTPEQVVAIASNSGGKQALETVQRLLPVLCQAHGLT
PQQVVAIASNGGGKQALETVQRLLPVLCQAHGLTPEQVVAIASNGGGKQALETVQALLPVLCQAHGLTPEQVVAIASNSGGKQAL
ETVQRLLPVLCQAHGLTPEQVVAIASHDGGKQALETVQRLLPVLCQAHGLTPEQVVAIASHDGGKQALETVQRLLPVLCQAHGLT
PEQVVAIASHDGGKQALETVQRLLPVLCQAHGGRPALETVQRLLPVLCQAHGLTPEQVVAIASHDGGKQAL
ETVQRLLPVLCQAHGLTPQQVVAIASNGGGKQALESIVAQLSRPDPALAALTNDHLVALACLGGRPALDAVKKGLPHAPALIKRTN
RRIPERTSHRVADHAQVRVLGFFQCHSHPAQAFDDAMTQFGMSRHGLLQLFRRVGVTELEARSGTLPPASQRWDRILQASGM
KRAKPSPTSTQTPDQASLHAFADSLERDLDAPSPMHEGDQTRASSRKRSRSDRAVTGPSAQQSFEVRVPEQRDALHLPLSWRV
KRPRTSIGGGLPDPGTPTAADLAASSTVMREQDEDPFAGAADDFPAFNEEELAWLMELLPQ (SEQ ID NO:12)

Figure 4 gaattcaaggtgtcaaaaagcgataggcggaattatagatgtacttgatgaacttatcaacgccagttagtgaacggttcgacaaagcgaaccaacaccaggcgcgaaagccttgccg
caatgctttccggcaatgtgaccaggcattgaccgaagcgctaggaattcggaacacgacggtagggaaatgctctaccgccggtcacgcaaaagcactctgcctgccagacgcgc
actgcgtggaattggccgttatgtccgctgcgcctggccgcgtagtgcttgcagcgacgcagccagcaaatcaaacatcactgttgataggtcgatcatgacatgccatttcgaggt
cggcagggattcgttaaaaaacagccaaaagtgagctaactgcgtcagcacagaaatttcacaacctcgcgatcctccatgcggtccgtgatcgcctcatgctcgcgcttcaccctgt
cgtcgagggttgccaggatcaccgaagttgtactgccggaagtatgtaggaaccacagaccgctagttcgaggcgcaatgtaaagaggtatgcctgatgaatccattcg
ttcgcacaccaagtcctgcccgagctctgcccgaccctcagccgactgcagatcgtgggttcagccagcttcagttacgttcagttcagccgcccctggaggcttgcccgctcggcg
gacgatgtccggaccccgcctgccatctccccctgcccttcacctggttccggggcagcttcagtgacctttaatacatcgctttttgatcattgcctcctt
cggcctcaccatacagaggtgccacagaggtgccaaggcggtcgggcagccgacgccccccaccatcggctgttcacgccgccgcgcgcgcg
ccaagccggcgccgacggtcgccaaccctccgacgcttgccggatgatctacgcacgctggctacgccacaaccccggcagtgatctacgcagccacaacaggagaatcaaaccgaaggtcg
ttcgacagtggccgcacaccagaggcactgttggccatggttaccacacgccacatcgttgcctcagccaaacaccgagccttgtcacggtggcagagttgaaggtccaccgttacagttga
cagcggtccagaggcgacacagaaagccatcgttggccctgccaaacagttgccggcgacccgccaatcagaatcaggagtgtggccatgtggccatgtggccagagcgcagttgtggccat
cacaggccaacttctcaagattgccaaaacgtggaccggtgacctgaagccagtgaggcagtgcaatgccactgaggtgccccctgaaccgacccggacgcagttgtggccat
cgccagccacgatggcgcagcaggccgctggagacggtgcagcgttgccgctgtgccaggccaatgccagccacagcggtggccatggcagctaccagttgtgcgctgtgcagcagcagg
agcaggcgttgccggtgctgtgccagcccatgccagcaggtggtggccatgccagcacaggccgtgcaggccaagcaggtgcaggccgctggagacggtgcagcgttgccgtcgtgct
cagcggcgttgccggtgctgtgccagcccatgccagcaggtggtggccatgccagcaggtggtggccatgccaagcaggtgcaggccgctggagacggtgcagcgttgccggtgtgt
gccaggccatgccagcccggagcaggtggccatgccagcaggtggccatggccgcgctggagacggtgcagcgttgccgtctgtgccagcccatgccagcaggtggtggccatgcc
cggagcaggtggtggccatgccaagcaggtgcaggccgctggagacggtgcagcgttgccgtctgtgccagcccatgccagcaggtggtggccatgccaagcaggtggtggccatgc
ccagcaatattggtgcaagcaggccaggccgcagctgtgccagcaggtggccatgccagcaggtgccaagcaggtgccaagcaggccgctggagacggccgcaagc
aggcctgagacggtgcagcaggccgctgttgccggtgctgtgccagcccatgccagcaggtggtggccatgccagcaggtggccatggccgcgctggagacggccgcaagcaggccgcaag
cggctgttgccggtgctgtgccagcccatgccagcaggtggtggccatgccagcaggtggccatggccgcgctggagacggtgcagcgttccggtgctgtgcc
agcccatgccatgccagcccggagcaggtggccatgccagcaggtggccatggccgcgctggagacggtgcagcgttgccggtgctgtgccagcccatgccagcctgacccccg
cagcaggtggtgccatgccagcaatatgggtgccaggccgctggagacggtcagcgcgttgccccctgatccgccgatctatctcgccgtccgatcgtgaccaagcaccctgccttggcc
tgcctcgcggacggtcctgcgctggatcagtcagtgaaaaaggattgccactccacccagcgagcgttgatgaccgccgtatccaggccatcaggatcaggagatcagacgcgcgtaaacggcgcaaaccggtggcgcaaccgg
aagtggttcgcgtgctgggttttcagtgcagtgcgctgcgcagtgcaaaaaggatctgcgcagcgaccaaccgtgggacaacgacacggttacagcttccgaacggtcacggtccacgg
aacttgcgaagccgaagccgcgcagtgaacgtccactcccagcgctgaccttgacctgagcgtgaccgtatccagccaatgcaggcatcaggagagcaggatcagacgcagtcaggatgaaaagggcaaacgtccctactcaactcaaaccgcgatcaggcgt
ctttgcatgcattcgccgattcgctgaggtgccgttccggagcgtccccgaaccagcgctcccattgcccctcaggtcccctcagttgaggggagaacgccgctaccagtatcggggcggcctcccgaccgtcacccggtacgccc
ccgcacagcaatcgttcgaggtgcgcttccggaacaagcgcgatcgctgcctgcgcgagtcagccgcgatcgggaaacgcgatcgggccgctacgagtcaggaaagccgattcccgcagctggaacgtccagtatcggggcgatgtccacctgcgcctgccctcaggggcgccctcagttgatcaactcaagccgcagttcccgaacattcagggggcttccggatgcggcaggggcaaacggcccg
acggctgccagctggcctgcagcaccgtgatgcggaacaagatgaggaacccttcgcaggtcagcggatgattccggcattcaaccgaagaggagctgcatggttgatggagctat
tgcctcagtgaggctcagtcggtgactacctgagcgtgcagggattggtaagtaaccttactgacgcagcgagttagcccactttggctgttttacacaataacctctgcctccctctggttgcacca
cacccgtacaccaagccgcgcggcccgaagccgcccgaagccacccaggtcggtgcgtgccccgagtggtggttttcgctgcggtggttgcttccctaaccaggcggtgctatacgctcaagctgcgtgcaccggcggtggcgatcgacgacg
aaatg (SEQ ID NO:13)

Figure 8

```
LTPEQVVAIASHDGGKQALETVQRLLPVLCQAHG
LTPQQVVAIASNGGGKQALETVQRLLPVLCQAHG
LTPQQVVAIASNSGGKQALETVQRLLPVLCQAHG
LTPEQVVAIASNGGGKQALETVQRLLPVLCQAHG
LTPEQVVAIASNIGGKQALETVQALLPVLCQAHG
LTPEQVVAIASNIGGKQALETVQRLLPVLCQAHG
LTPEQVVAIASNIGGKQALETVQALLPVLCQAHG
LTPEQVVAIASHDGGKQALETVQRLLPVLCQAHG
LTPEQVVAIASNGGGKQALETVQRLLPVLCQAHG
LTPQQVVAIASNSGGKQALETVQALLPVLCQAHG
LTPEQVVAIASNGGGKQALETVQRLLPVLCQAHG
LTPEQVVAIASHDGGKQALETVQRLLPVLCQAHG
LTPEQVVAIASHDGGKQALETVQRLLPVLCQAHG
LTPEQVVAIASNGGGRPALETVQRLLPVLCQAHG
LTPEQVVAIASHDGGKQALETVQRLLPVLCQAHG
LTPQQVVAIASNGGGRPALE (SEQ ID NO: 16)
```

```
                   MscI
CTGACCCCGGGCACAGGTGGTGGCCATCGCCAGCNNNNNNGGCGGCAAGCAGGCTGGAGACGGTGCAGGGCTGTTGCCGGTCTGTGCCAGGACCATGGC  (SEQ ID NO:17)
 L  T  P  A  Q  V  V  A  I  A  S  X  X  X  G  G  K  Q  A  L  E  T  V  Q  R  L  L  P  V  L  C  Q  D  H  G      (SEQ ID NO:18)
 1  2  3  4  5  6  7  8  9 10 11 12 13 14 15 16 17 18 19 20 21 22 23 24 25 26 27 28 29 30 31 32 33 34
```

B

```
                   MscI
CTGACCCCGGGCACAGGTGGTGGCCATCGCCAGCNNNNNNGGCGGCAAGCAGGCCTCGAGAGC  (SEQ ID NO:19)
 L  T  P  A  Q  V  V  A  I  A  S  X  X  X  G  G  K  Q  A  L  E  S      (SEQ ID NO:20)
 1  2  3  4  5  6  7  8  9 10 11 12 13 14 15 16 17 18 19 20
```

```
     XhoI                         MscI
5'-TCGAGACGGTGCAGGCGCTGTTGCCGGTGCTGTGCCAGGACCATGGGCCTGACCCCGGACCAAGTGGTGGCCAGCAACATTGGGCGCAAGCAAGCGC-3' (SEQ ID NO:24)
3'-CTGCCACGTCGCGACAACGGCCACGACGGTCCTGGTACCCGGACTGGGGCCTGGTTCACCACCGGTCGTTGTAACCCGCGTTCGTTCGCGAGCT-5' (SEQ ID NO:25)
                                                                                                PspXI/XhoI
  E  T  V  Q  A  L  L  P  V  L  C  Q  D  H  G  L  T  P  D  Q  V  V  A  S  N  I  G  G  K  Q  A  L  E  (SEQ ID NO:26)
  21 22 23 24 25 26 27 28 29 30 31 32 33 34  1  2  3  4  5  6  7  8  9 10 11 12 13 14 15 16 17 18 19 20
```

B pCS502  RVD=NI
pCS503  RVD=HD
pCS504  RVD=NI
pCS505  RVD=NG pCS502
3060bp

Figure 19

| Plasmid | Description |
|---|---|
| pCS802 | NI |
| pCS803 | HD |
| pCS804 | NN |
| pCS805 | NG |

| Plasmid | Description |
|---|---|
| pCS806 | NI-NI |
| pCS807 | NI-HD |
| pCS808 | NI-NN |
| pCS809 | NI-NG |
| pCS810 | HD-NI |
| pCS811 | HD-HD |
| pCS812 | HD-NN |
| pCS813 | HD-NG |
| pCS814 | NN-NI |
| pCS815 | NN-HD |
| pCS816 | NN-NN |
| pCS817 | NN-NG |
| pCS818 | NG-NI |
| pCS819 | NG-HD |
| pCS820 | NG-NN |
| pCS821 | NG-NG |

| Plasmid | Description |
|---|---|
| pCS822 | NI-NI-NI |
| pCS823 | NI-NI-HD |
| pCS824 | NI-NI-NN |
| pCS825 | NI-NI-NG |
| pCS826 | NI-HD-NI |
| pCS827 | NI-HD-HD |
| pCS828 | NI-HD-NN |
| pCS829 | NI-HD-NG |
| pCS830 | NI-NN-NI |
| pCS831 | NI-NN-HD |
| pCS832 | NI-NN-NN |
| pCS833 | NI-NN-NG |
| pCS834 | NI-NG-NI |
| pCS835 | NI-NG-HD |
| pCS836 | NI-NG-NN |
| pCS837 | NI-NG-NG |

| Plasmid | Description |
|---|---|
| pCS838 | HD-NI-NI |
| pCS839 | HD-NI-HD |
| pCS840 | HD-NI-NN |
| pCS841 | HD-NI-NG |
| pCS842 | HD-HD-NI |
| pCS843 | HD-HD-HD |
| pCS844 | HD-HD-NN |
| pCS845 | HD-HD-NG |
| pCS846 | HD-NN-NI |
| pCS847 | HD-NN-HD |
| pCS848 | HD-NN-NN |
| pCS849 | HD-NN-NG |
| pCS850 | HD-NG-NI |
| pCS851 | HD-NG-HD |
| pCS852 | HD-NG-NN |
| pCS853 | HD-NG-NG |

| Plasmid | Description |
|---|---|
| pCS854 | NN-NI-NI |
| pCS855 | NN-NI-HD |
| pCS856 | NN-NI-NN |
| pCS857 | NN-NI-NG |
| pCS858 | NN-HD-NI |
| pCS859 | NN-HD-HD |
| pCS860 | NN-HD-NN |
| pCS861 | NN-HD-NG |
| pCS862 | NN-NN-NI |
| pCS863 | NN-NN-HD |
| pCS864 | NN-NN-NN |
| pCS865 | NN-NN-NG |
| pCS866 | NN-NG-NI |
| pCS867 | NN-NG-HD |
| pCS868 | NN-NG-NN |
| pCS869 | NN-NG-NG |

| Plasmid | Description |
|---|---|
| pCS870 | NG-NI-NI |
| pCS871 | NG-NI-HD |
| pCS872 | NG-NI-NN |
| pCS873 | NG-NI-NG |
| pCS874 | NG-HD-NI |
| pCS875 | NG-HD-HD |
| pCS876 | NG-HD-NN |
| pCS877 | NG-HD-NG |
| pCS878 | NG-NN-NI |
| pCS879 | NG-NN-HD |
| pCS880 | NG-NN-NN |
| pCS881 | NG-NN-NG |
| pCS882 | NG-NG-NI |
| pCS883 | NG-NG-HD |
| pCS884 | NG-NG-NN |
| pCS885 | NG-NG-NG |

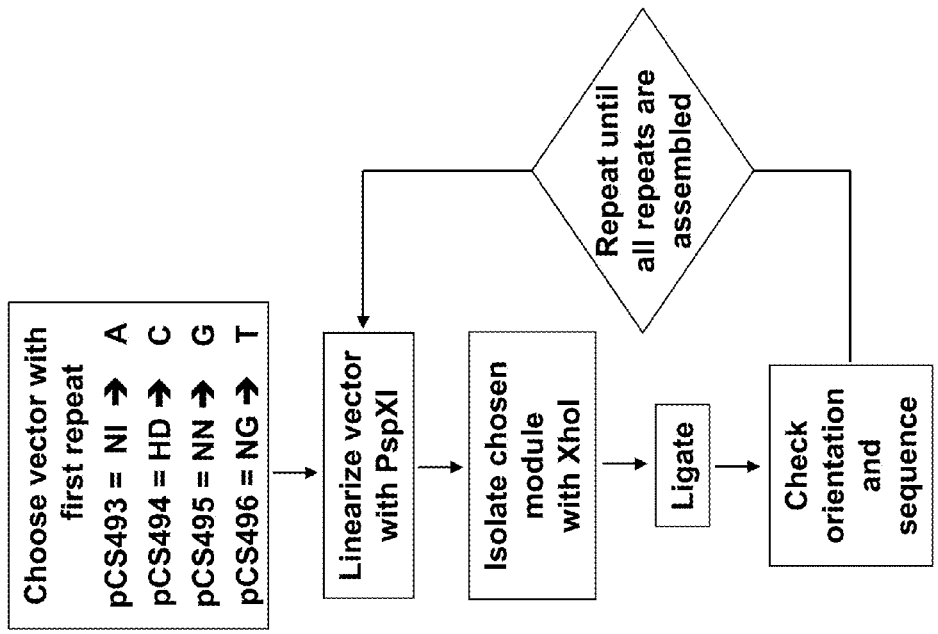

Figure 21A

Adh Target DNA  A  T  C  A  A  G  A  T  C  T  C  T  T  C  A  C  T (SEQ ID NO:29)
Adh RVDs  NI NG HD NI NI NN NI NN NG NG HD NG NG HD NI HD NG

| | | | | | | | | | | | | | | | | | |
|---|---|---|---|---|---|---|---|---|---|---|---|---|---|---|---|---|---|
| pMAT 55 | NI 493 | NI NG 493 | NI NG HD 519 | | | | | | | | | | | | | | |
| pMAT 56 | | NI NG HD pMAT55 | NI NG HD NI 519 | NI NG HD NI NI NN 524 | | | | | | | | | | | | | |
| pMAT 57 | | | NI NG HD NI pMAT56 | NI NG HD NI NI NN pMAT56 | NI NG HD NI NI NN NI NN 537 | | | | | | | | | | | | |
| pMAT 58 | | | | NI NG HD NI NI NN pMAT57 | NI NG HD NI NI NN NI NN pMAT57 | NI NG HD NI NI NN NI NN NG NG HD 551 | | | | | | | | | | | |
| pMAT 59 | | | | | NI NG HD NI NI NN NI NN pMAT58 | NI NG HD NI NI NN NI NN NG NG HD pMAT58 | NI NG HD NI NI NN NI NN NG NG HD NG NG HD 583 | | | | | | | | | | |
| pMAT 60 | | | | | | NI NG HD NI NI NN NI NN NG NG HD pMAT59 | NI NG HD NI NI NN NI NN NG NG HD NG NG HD pMAT59 | NI NG HD NI NI NN NI NN NG NG HD NG NG HD NI HD NG 529 | | | | | | | | |

Figure 21B

```
Adh Target DNA    C  C  C  A  G  A  A  G  T  A  A  A  C  A  T    (SEQ ID NO:30)
Adh RVDs         HD HD HD HD HI NN NI NI NI NN NG NI NI NI HD NI NG
```

|  | | | | | | | | | | | | | | | | |
|---|---|---|---|---|---|---|---|---|---|---|---|---|---|---|---|---|
| pMAT 61 | HD HD HD pMAT1 | | | | | | | | | | | | | | | |
| pMAT 62 | HD HD HD pMAT1 | NI NN NI 530 | | | | | | | | | | | | | |
| pMAT 63 | HD HD HD HI NN NI NI NN NG pMAT61 533 | | | | | | | | | | | | | | | |
| pMAT 64 | HD HD HD HI NN NI NI NN NG NI NI NI pMAT62 522 | | | | | | | | | | | | | | | |
| | HD HD HD HI NN NI NI NN NG NI NI NI HD NI NG pMAT63 541 | | | | | | | | | | | | | | | |

Figure 23

MDPIRSRTPSPARELLPGPGPQPDRVQPTADRGGAPPAGGPLDGLPARRTMSRTRLPSPPAPSPAFSAGSFSDLLRQFDPS
LLDTSLLDSMPAVGTPHTAAPAECDEVQSGLRAADDPPPTVRVAVTAARPPRAKPAPRRRAAQPSDASPAAQVDLRTL
GYSQQQQEKIKPKVGSTVAQHHEALVGHGFTHAHIVALSRHPAALGTVAVKYQDMIAALPEATHEDIVGVGKQWSGARA
LEALLTVAGELRGPPLQLDTGQLVKIAKRGGVTAVEAVHASRNALTGAPLNLTPAQVVAIASNNGGKQALETVQRLLPVLC
QAHGLTPAQVVAIASHDGGKQALETVQRLLPVLCQAHGLPPDQVVAIASNGGKQALETVQRLLPVLCQAHGLTPDQVVA
IASHGGGKQALETVQRLLPVLCQAHGLTPDQVVAIASHDGGKQALETVQRLLPVLCQAHGLTPDQVVAIASNGGGKQALE
TVQRLLPVLCQAHGLTPDQVVAIASNGGKQALETVQQLLPVLCQAHGLTPDQVVAIASHDGGKQALETVQRLLPVLCQTH
GLTPAQVVAIASHDGGKQALETVQQLLPVLCQAHGLTPDQVVAIASNGGKQALATVQRLLPVLCQAHGLTQVQVVAIASN
GGGKQALETVQRLLPVLCQAHGLTPAQVVAIASHDGGKQALETVQRLLPVLCQAHGLTPDQVVAIASNGGKQALETVQR
LLPVLCQAHGLTPAQVVAIASNGGKQALETVQRLLPVLCQDHGLTPDQVVAIASNGGKQALETVQRLLPVLCQAHGLT
QEQVVAIASNGGKQALETVQRLLPVLCQDHGLTLAQVVAIASNIGGKQALETVQRLLPVLCQAHGLTQDQVVAIASNGG
GKQALETVQRLLPVLCQDHGLTPDQVVAIASNIGGKQALETVQRLLPVLCQDHGLTLDQVVAIASNGGKQALETVQRLLP
VLCQDHGLTPDQVVAIASNGGKQALETVQRLLPVLCQDHGLTPNQVVAIASNGGKQALESIVAQLSRPDPALAALTNDHLVALACLGGRPAM
DAVKKGLPHAPELIRRVNRRIGERTSHRVADYAQVVRLEFFQCHSHPAYAFDEAMTQFGMSRNGLVQLFRRVGVTELE
ARGGTLPPASQRWDRILQASGMKRAKPSPTSAQTPDQASLHAFADSLERDLDAPSPMHEGDQTGASSRKRSRSDRAVT
GPSAQHSFEVRVPEQRDALHLPLSWRVKRPRTRIGGGLPDPGTPIAADLAASSTVMWEQDAAPFAGAADDFPAFNEEEL
AWLMELLPQSGSVGGTI (SEQ ID NO:31)

Figure 24 atgggatcccattcgttcgcacgccaagtctgcccgcgagctctgcccgaccccaaccggataggttcagccgactgcagatggggggggctccgcctgctggccgccccctgga
tggcttgcccgctggcggacgatgtccggacccggtccgcatctccccctgcccctgcgcctgcgagatcgctcctcagcgatcgctccgtcagttgatccgtcgtcttgatacat
cgcttcttgattcgatcgctgcgtcggcacgcgcatacagcggctgcccagcacgagtgcgalgagtgcaatcggttcctgcgtcgtcagccgatgaccgccaccaccgtcgtcgctgt
cactgccgccgggccggccgcggccaagctgcgcgcgacggcggcccaagtggggttcgacagtggcgcagccaacgaggcactggcgcagccacccgagggtlcacacgcgtcacacgctggctcagtcagcagcagc
aagagaaagatcaaacgaagggtgggttcgacagtggcggcttaccagaggcgacacacgaaagacatcgttggtgtcgcaaacagtgtccggcacgcccctgaagccttgctcacgtggcg
ccgtcgtcaagttatcgagacatgatcggcgttaccagaggcgacaccagaggcagacacgaaagacatcgttggtgtcgcaaacagtgtccggcacgcccctgaagccttgctcacgtggcg
ggagagtttgagaggtcacgcacgttacagttggacacaggccaactgtcaacaggtggacaacgcggcgcggcgtgagacggtgcagcggctgttgcccggtcgtcctgtcaaggccatgcctgaccccgc
gcaggttggccatgccagccagccagccgcgcagcagcagcggccagcacgatgcggtgccaagcagcagcagaggcagcacgatgcggcagcggagacggtgccatgcgg
gcaggcgcgtgagacggtcgcaggcgcgtttgccgtgctgttgcccgtgcccagccgacgcatgtcctgcaggccatcgccaaccgtggcatgcaccggtgggccatcgtcagcacgatgcgggcaagcagggctgagacggtgccagcggggacggtttcgagcggcagggctgggagcggtagtgcttcgcagccttgcccggtg
gccagccatgtctgacccggacccaggttgcatcgccagcaggcgcgctgaaggcagacgctgtgcatctgaccccggaccaggtggcgcagcaggcggcgcgctgtgcaggtcagcgctgcgcctgacccagaccc
atcggccacaccatggccaagagtggccgagctgagacgcatgccagccagcagcagcggcatggccagcaaacaggtgccatcctgtgcaggccatgaccaggtggtggccatccc
cggaccaggtcgcagcacaggcggccaccaggtgcaccaggtgcatgttcggtgccagcaggtcgcagcaccgtgcccatgcgcagcaggtcgcggtcgcagcagccaggctgttgcccggtctgt
ggccgaacaacggcaggcgaggtggcagccgatggctgcaggacaggtgcgcatgagcagagtgtgagacggtgccagcaggcacgtcgccatgctgaggcagcagcagcacgtgggcaaggtgcaaccagccagcagcagcagcagcagccaggcgacgcatgggcaaccaaccagccagcggagccagcggaggtgccatgccagccagccagccagcagcagctgcaggctgcgggccagccaggctgcatgcag
cggccactgcaggcaggcaggcaaaattggccgagaccagcaaccagcgcgctgtcaggtacctcaggctgcagcacagggtccactctcaacaagcagaagggagagatgcagaccagccagcagcagcaggctgttgggcctgcagccatgccatgcaggccatgccagcagcagcagggccatcgtgccagcaatgaccgtgcagcaaaggttgccatgcaggtgaccgaacgcagcacagcagggaaagaggagagccagccagcagcagtctgggagccagcggccaggccagcatgcagcaggctcgtgcgagttatcgccctattcgggttgccgccgttgaccaacgaccacctgctgttgcctgttcgccgagcactcgccttggcctcagccagccgaattgatcagaagtcaatcgccgtattgcgaacgcacgtccatgcgttgccgactacgcaagtgttcgcgttcggaagttttccagtgccactccaccagctacgcattgat
gaggccatgaccgcagttcggatgagcagcagcagcaaaggccaaaccgtccactcctttcgggatagcgaagacggttctgcctttgcccctccacaagacggtcacgcaagtggaagcctcccccccagccagctgaagtacgtttcggcccctccccccccagcggttggaaccagccagcctcgcagcagggtggaacc
gatatcctccagccatcaggggatcagcagcagcagaaggccaaaaacgtccccctacttcagctccaaacaccggaacgcgttctcgtgcaggccatgacaacacctttcgccgatttcgccgatttcgctgagcgttgctggcctggtggcctcaggtgaccactttcgaggtgccgttccggccctagccc
aatgcaccagggatcagacaggggcaaggcagggcaaggccaagcaaccgtcacacagccgatcgggtgctgcaccagaaaacgccccggtaaaacccgtaccagatagccgagccacacagctctcggggtaaaacccgtaccagatgggggcgcctcccggatcctggtacgcccatgcgcccgacactcgtcctgctgggtgccgacctgccgaccgtgcaccgtgatgtgggaaca
agatgcggccccttgcagggcagccagccgcgatgattccgcattcaacgaaggccgatgttgatggagctagtgccttgcctcagctcagctcagttcaggctcaggctcagtcggaggacgatcga (SEQ ID NO:32)

Figure 26 avrBs3_TALEN
MASSPPKKKRKVSWKDASGWSRMHADPIRSRTPS
PARELLPGPQPDGVQPTADRGVSPPAGGPLDGLP
ARRTMSRTRLPSPPAPSPAFSAGSFSDLLRQFDP
SLFNTSLFDSLPPFGAHHTEAATGEWDEVQSGLR
AADAPPPTMRVAVTAARPPRAKPAPRRRAAQPSD
ASPAAQVDLRTLGYSQQQQEKIKPKVRSTVAQHH
EALVGHGFTHAHIVALSQHPAALGTVAVKYQDMI
AALPEATHEAIVGVGKQWSGARALEALLTVAGEL
RGPPLQLDTGQLLKIAKRGGVTAVEAVHAWRNAL
TGAPLNLTPEQVVAIASHDGGKQALETVQRLLPV
LCQAHGLTPQQVVAIASNGGGKQALETVQRLLPV
LCQAHGLTPQQVVAIASNSGGKQALETVQRLLPV
LCQAHGLTPEQVVAIASNGGGKQALETVQRLLPV
LCQAHGLTPEQVVAIASNIGGKQALETVQALLPV
LCQAHGLTPEQVVAIASNIGGKQALETVQALLPV
LCQAHGLTPEQVVAIASNIGGKQALETVQALLPV
LCQAHGLTPEQVVAIASHDGGKQALETVQRLLPV
LCQAHGLTPEQVVAIASHDGGKQALETVQRLLPV
LCQAHGLTPQQVVAIASNGGGKQALETVQRLLPV
LCQAHGLTPEQVVAIASNSGGKQALETVQALLPV
LCQAHGLTPEQVVAIASNSGGKQALETVQRLLPV
LCQAHGLTPEQVVAIASHDGGKQALETVQRLLPV
LCQAHGLTPEQVVAIASHDGGKQALETVQRLLPV
LCQAHGLTPEQVVAIASHDGGKQALETVQRLLPV
LCQAHGLTPQQVVAIASNGGGRPALETVQRLLPV
LCQAHGLTPEQVVAIASHDGGKQALETVQRLLPV
LCQAHGLTPQQVVAIASNGGGRPALESIVAQLSR
PDPALAALTNDHLVALACLGGRPALDAVKKGLPH
APALIKRTNRRIPERTSHRVADHAQVVRVLGFFQ
CHSHPAQAFDDAMTQFGMSRHGLLQLFRRVGVTE
LEARSGTLPPASQRWDRILQASGMKRAKPSPTST
QTPDQASLHAFADSLERDLDAPSPMHEGDQTRAS
SRKRSRSDRAVTGPSAQQSFEVRVPEQRDALHLP
LSWRVKRPRTSIGGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:33)

Figure 27

```
pthXo1_TALEN
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNNGGKQALETVQRLLPV
LCQAHGLTPAQVVAIASHDGGKQALETMQRLLPV
LCQAHGLPPDQVVAIASNIGGKQALETVQRLLPV
LCQAHGLTPDQVVAIASHGGGKQALETVQRLLPV
LCQAHGLTPDQVVAIASHDGGKQALETVQRLLPV
LCQAHGLTPDQVVAIASNGGGKQALETVQRLLPV
LCQAHGLTPDQVVAIASNGGKQALETVQRLLPVL
CQAHGLTPDQVVAIASHDGGKQALETVQRLLPVL
CQTHGLTPAQVVAIASHDGGKQALETVQQLLPVL
CQAHGLTPDQVVAIASNIGGKQALATVQRLLPVL
CQAHGLTPDQVVAIASNGGGKQALETVQRLLPVL
CQAHGLTPDQVVAIASNGGGKQALETVQRLLPVL
CQAHGLTQVQVVAIASNIGGKQALETVQRLLPVL
CQAHGLTPAQVVAIASHDGGKQALETVQRLLPVL
CQAHGLTPDQVVAIASNGGGKQALETVQRLLPVL
CQAHGLTQEQVVAIASNNGGKQALETVQRLLPVL
CQAHGLTPDQVVAIASNGGGKQALETVQRLLPVL
CQAHGLTPAQVVAIASNIGGKQALETVQRLLPVL
CQDHGLTLAQVVAIASNIGGKQALETVQRLLPVL
CQAHGLTQDQVVAIASNIGGKQALETVQRLLPVL
CQDHGLTPDQVVAIASNIGGKQALETVQRLLPVL
CQDHGLTLDQVVAIASNGGKQALETVQRLLPVLC
QDHGLTPDQVVAIASNSGGKQALETVQRLLPVLC
QDHGLTPNQVVAIASNGGKQALESIVAQLSRPDP
ALAALTNDHLVALACLGGRPAMDAVKKGLPHAPE
LIRRVNRRIGERTSHRVADYAQVVRVLEFFQCHS
HPAYAFDEAMTQFGMSRNGLVQLFRRVGVTELEA
RGGTLPPASQRWDRILQASGMKRAKPSPTSAQTP
DQASLHAFADSLERDLDAPSPMHEGDQTRASSRK
RSRSDRAVTGPSAQQAVEVRVPEQRDALHLPLSW
RVKRPRTRIWGGLPDPISRSQLVKSELEEKKSEL
RHKLKYVPHEYIELIEIARNSTQDRILEMKVMEF
FMKVYGYRGKHLGGSRKPDGAIYTVGSPIDYGVI
VDTKAYSGGYNLPIGQADEMQRYVEENQTRNKHI
NPNEWWKVYPSSVTEFKFLFVSGHFKGNYKAQLT
RLNHITNCNGAVLSVEELLIGGEMIKAGTLTLEE
VRRKFNNGEINF (SEQ ID NO:34)
```

Figure 29A

| Custom TALEN | 1 | 2 | 3 | 4 | 5 | 6 | 7 | 8 | 9 | 10 | 11 | 12 | 13 |
|---|---|---|---|---|---|---|---|---|---|---|---|---|---|
| ADH1-360-12 | NI<br>A | NG<br>T | HD<br>C | NI<br>A | NI<br>A | NN<br>G | NI<br>A | NG<br>T | NG<br>T | HD<br>C | NG<br>T | HD<br>C | |
| ADH1-408-12r | HD<br>C | HD<br>C | HD<br>C | NI<br>A | NN<br>G | NI<br>A | NI<br>A | NN<br>G | NG<br>T | NI<br>A | NI<br>A | NI<br>A | |
| ADH1-928-12 | HD<br>C | HD<br>C | NN<br>G | NN<br>G | NI<br>A | NG<br>T | NN<br>G | HD<br>C | NG<br>T | HD<br>C | HD<br>C | NG<br>T | |
| ADH1-975-12r | NI<br>A | NN<br>G | NI<br>A | HD<br>C | NI<br>A | NI<br>A | NI<br>A | HD<br>C | HD<br>C | NI<br>A | HD<br>C | NI<br>A | |
| gridlock-2356-13r | NI<br>A | HD<br>C | HD<br>C | HD<br>C | HD<br>C | NG<br>T | HD<br>C | NG<br>T | HD<br>C | HD<br>C | NN<br>G | HD<br>C | NG<br>T |

```
telomerase-TALEN124_9RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASHDGGKQALETVQRLLPV
LCQDHGLTPDQVVAIANNNGGKQALETVQRLLPV
LCQDHGLTPDQVVAIANNNGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:35)
```

Figure 34B

```
gridlock-TALEN105_10RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASHDGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:36)
```

Figure 34C

```
adh1-TALEN58_12RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:37)
```

Figure 34D

```
adh1-TALEN63_12RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIANNNGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASNIGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:38)
```

Figure 34E

```
adh1-TALEN68_12RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASHDGGKQALETVQRLLPV
LCQDHGLTPDQVVAIASHDGGKQALETVQRLLPV
LCQDHGLTPDQVVAIANNNGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:39)
```

Figure 34F adh1-TALEN73_12RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF(SEQ ID NO:40)

Figure 34G adh1-TALEN89_12RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIANNNGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASHDGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:41)

Figure 34H

```
gridlock-TALEN106_13RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:42)
```

Figure 34I

```
adh1-TALEN64_15RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIANNNGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:43)
```

Figure 34J adh1-TALEN69_15RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASHDGGKQALETVQRLLPV
LCQDHGLTPDQVVAIASHDGGKQALETVQRLLPV
LCQDHGLTPDQVVAIANNNGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:44)

Figure 34K

```
adh1-TALEN74_15RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:45)
```

Figure 34L

```
tt4-TALEN90_15RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIANNNGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:46)
```

Figure 34M

```
telomerase-TALEN121_15RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASHDGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIANNNGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:47)
```

Figure 34N

```
telomerase-TALEN126_15RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASHDGGKQALETVQRLLPV
LCQDHGLTPDQVVAIANNNGGKQALETVQRLLPV
LCQDHGLTPDQVVAIANNNGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIANNNGGKQALETVQRLLPV
LCQDHGLTPDQVVAIASNGGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:48)
```

Figure 34O

```
gridlock-TALEN107_16RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:49)
```

Figure 34P

```
gridlock-TALEN117_16RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVKQWSGARALEALLTDAGEL
RGPPLQLDTGQLVKIAKRGGVTAMEAVHASRNAL
TGAPLNLTPAQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNNGGKQALETVQRLLPV
LCQDHGLTPDQVVAIASNNGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASNNGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNNGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASNNGGKQALETVQRLLPV
LCQDHGLTPDQVVAIASHDGGKQALETVQRLLPV
LCQDHGLTPDQVVAIASNGGGKQALESIVAQLSR
PDPALAALTNDHLVALACLGGRPAMDAVKKGLPH
APELIRRVNRRIGERTSHRVADYAQVVRVLEFFQ
CHSHPAYAFDEAMTQFGMSRNGLVQLFRRVGVTE
LEARGGTLPPASQRWDRILQASGMKRAKPSPTSA
QTPDQASLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:50)
```

Figure 34Q telomerase-TALEN131_16RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIANNGGKQALETVQRLLPV
LCQDHGLTPDQVVAIASNIGGKQALETVQRLLPV
LCQDHGLTPDQVVAIANNGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF(SEQ ID NO:51)

Figure 34R telomerase-TALEN136_17RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIANNNGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIANNNGGKQALETVQRLLPV
LCQDHGLTPDQVVAIASNGGGKQALETVQRLLPV
LCQDHGLTPDQVVAIANNNGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIANNNGGKQALETVQRLLPV
LCQDHGLTPDQVVAIASHDGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NDO:52)

Figure 34S adh1-TALEN60_18RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIANNNGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNGGGKQALESIVAQLSR
RDPALAALTNDHLVALACLGGRPALDAVKKGLPH
APEFIRRVNRRIAERTSHRVADYAHVVRVLEFFQ
CHSHPAHAFDEAMTQFGMSRHGLVQLFRRVGVTE
FEARYGTLPPASQRWDRILQASGMKRAKPSPTSA
QTPDQTSLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:53)

Figure 34T tt4-TALEN85_18RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNIGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNNGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASNNGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASNNGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNGGGKQALESIVAQLSR
PDPALAALTNDHLVALACLGGRPAMDAVKKGLPH
APELIRRVNRRIGERTSHRVADYAQVVRVLEFFQ
CHSHPAYAFDEAMTQFGMSRNGLVQLFRRVGVTE
LEARGGTLPPASQRWDRILQASGMKRAKPSPTSA
QTPDQASLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:54)

Figure 34U gridlock-TALEN102_18RVDs
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASNNGGKQALETVQRLLPV
LCQDHGLTPDQVVAIASNNGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNNGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALESIVAQLSR
PDPALAALTNDHLVALACLGGRPAMDAVKKGLPH
APELIRRVNRRIGERTSHRVADYAQVVRVLEFFQ
CHSHPAYAFDEAMTQFGMSRNGLVQLFRRVGVTE
LEARGGTLPPASQRWDRILQASGMKRAKPSPTSA
QTPDQASLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:55)

```
AvrHah1   LDTGQLFKIAKRGGVTAVEAVHAWRNALTGAPLN  (SEQ ID NO:65)
AvrBs3    LDTGQLLKIAKRGGVTAVEAVHAWRNALTGAPLN  (SEQ ID NO:66)
PthXo1    LDTGQLVKIAKRGGVTAVEAVHASRNALTGAPLN  (SEQ ID NO:67)
PthA      LDTGQLLKIAKRGGVTAVEAVHAWRNALTGAPLN  (SEQ ID NO:68)
Tal1C     LDTGQLVKIAKRGGVTAMEAVHASRNALTGAPLN  (SEQ ID NO:69)
```

B

```
                  HHHHHHHHHH                  HHHHHHHHHHHHHHH
"0th" repeat   LDTGQLVKIA*KRGGVTAMEAVHASRNALTGAPLN  (SEQ ID NO:70)
               -- ---  --  --------
1st repeat     LTPAQVVAIASNNGGKQALETVQRLLPVLCQAHG   (SEQ ID NO:71)
                 HEEEEE       HHHHHHHHHHHHHHHHH
```

Figure 40A

HPRT-3254-17
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVKQWSGARALEALLTDAGEL
RGPPLQLDTGQLVKIAKRGGVTAMEAVHASRNAL
TGAPLNLTPAQVVAIASNNGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASNGGGKQALESIVAQLSR
PDPALAALTNDHLVALACLGGRPAMDAVKKGLPH
APELIRRVNRRIGERTSHRVADYAQVVRVLEFFQ
CHSHPAYAFDEAMTQFGMSRNGLVQLFRRVGVTE
LEARGGTLPPASQRWDRILQASGMKRAKPSPTSA
QTPDQASLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:72)

Figure 40B

HPRT-3286-20r
MASSPPKKKRKVSWKDASGWSRMHADPIRPRRPS
PARELLPGPQPDRVQPTADRGVSAPAGSPLDGLP
ARRTVSRTRLPSPPAPSPAFSAGSFSDLLRPFDP
SLLDTSLLDSMPAVGTPHTAAAPAEWDEAQSALR
AADDPPPTVRVAVTAARPPRAKPAPRRRAAQPSD
ASPAAQVDLRTLGYSQQQQEKIKPKVRSTVAQHH
EALVGHGFTHAHIVALSQHPAALGTVAVTYQHII
TALPEATHEDIVGVGKQWSGARALEALLTDAGEL
RGPPLQLDTGQLVKIAKRGGVTAMEAVHASRNAL
TGAPLNLTPAQVVAIASHDGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASNNGGKQALETVQRLLPV
LCQDHGLTPDQVVAIASNIGGKQALETVQRLLPV
LCQDHGLTPDQVVAIASNNGGKQALETVQRLLPV
LCQDHGLTPDQVVAIASNNGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASNGGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASNIGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASHDGGKQALETVQRLLPV
LCQDHGLTPDQVVAIASNGGGKQALESIVAQLSR
PDPALAALTNDHLVALACLGGRPAMDAVKKGLPH
APELIRRVNRRIGERTSHRVADYAQVVRVLEFFQ
CHSHPAYAFDEAMTQFGMSRNGLVQLFRRVGVTE
LEARGGTLPPASQRWDRILQASGMKRAKPSPTSA
QTPDQASLHAFADSLERDLDAPSPMHEGDQTRAS
SRKRSRSDRAVTGPSAQQAVEVRVPEQRDALHLP
LSWRVKRPRTRIWGGLPDPISRSQLVKSELEEKK
SELRHKLKYVPHEYIELIEIARNSTQDRILEMKV
MEFFMKVYGYRGKHLGGSRKPDGAIYTVGSPIDY
GVIVDTKAYSGGYNLPIGQADEMQRYVEENQTRN
KHINPNEWWKVYPSSVTEFKFLFVSGHFKGNYKA
QLTRLNHITNCNGAVLSVEELLIGGEMIKAGTLT
LEEVRRKFNNGEINF (SEQ ID NO:73)

TAL EFFECTOR-MEDIATED DNA MODIFICATION

CROSS-REFERENCE TO RELATED APPLICATIONS

This application is a continuation of U.S. Ser. No. 13/738,381, filed Jan. 10, 2013, which is a continuation of U.S. Ser. No. 12/965,590, filed on Dec. 10, 2010, which claims benefit of priority from U.S. Provisional Application Ser. No. 61/285,324, filed on Dec. 10, 2009, U.S. Provisional Application Ser. No. 61/352,108, filed on Jun. 7, 2010, and U.S. Provisional Application Ser. No. 61/366,685, filed on Jul. 22, 2010, all of which are incorporated herein by reference in their entirety.

STATEMENT AS TO FEDERALLY SPONSORED RESEARCH

This invention was made with government support under grant nos. 0820831 and 0504304, awarded by the National Science Foundation. The government has certain rights in the invention.

TECHNICAL FIELD

The present document relates to methods for gene targeting, and particularly to methods that include the use of transcription activator-like (TAL) effector sequences.

BACKGROUND

The ability to modify chromosomes through homologous recombination (gene targeting) has been a long sought goal of biologists. In plants, for example, gene targeting may help to discern the function of plant genes, opening up new possibilities for crop improvement. For example, with gene targeting it is possible to carry out the genetic surgery required to reorchestrate metabolic pathways to create high value crops, including seed with altered oil or carbohydrate profiles, food with enhanced nutritional qualities, or plants with increased resistance to disease and stress. In animals (e.g., mammals), gene targeting may be used for treatment of disease. For example, gene targeting may be used to engineer corrections in genes that are defective due to various types of mutations. Efficient methods for such gene targeting have been difficult to achieve.

SUMMARY

TAL effectors of plant pathogenic bacteria in the genus *Xanthomonas* play important roles in disease, or trigger defense, by binding host DNA and activating effector-specific host genes (see, e.g., Gu et al. (2005) *Nature* 435:1122; Yang et al. (2006) *Proc. Natl. Acad. Sci. USA* 103:10503; Kay et al. (2007) *Science* 318:648; Sugio et al. (2007) *Proc. Natl. Acad. Sci. USA* 104:10720; and Römer et al. (2007) *Science* 318:645). Specificity depends on an effector-variable number of imperfect, typically 34 amino acid repeats (Schornack et al. (2006) *J. Plant Physiol.* 163:256). Polymorphisms are present primarily at repeat positions 12 and 13, which are referred to herein as the repeat variable-diresidue (RVD).

The present document is based in part on the fact that the RVDs of TAL effectors correspond to the nucleotides in their target sites in a direct, linear fashion, one RVD to one nucleotide, with some degeneracy and no apparent context dependence. This surprising finding represents a novel mechanism for protein-DNA recognition that enables target site prediction for new target specific TAL effector. As described herein, these proteins may be useful in research and biotechnology as targeted chimeric nucleases that can facilitate homologous recombination in genome engineering (e.g., to add or enhance traits useful for biofuels or biorenewables in plants). These proteins also may be useful as, for example, transcription factors, and especially for therapeutic applications requiring a very high level of specificity such as therapeutics against pathogens (e.g., viruses) as non limiting examples.

In one aspect, this document features a method for modifying the genetic material of a cell, comprising (a) providing a cell containing a target DNA sequence; and (b) introducing a transcription activator-like (TAL) effector-DNA modifying enzyme into the cell, the TAL effector-DNA modifying enzyme comprising (i) a DNA modifying enzyme domain that can modify double stranded DNA, and (ii) a TAL effector domain comprising a plurality of TAL effector repeat sequences that, in combination, bind to a specific nucleotide sequence in the target DNA sequence, such that the TAL effector-DNA modifying enzyme modifies the target DNA within or adjacent to the specific nucleotide sequence in the cell or progeny thereof. The method can further comprise providing to the cell a nucleic acid comprising a sequence homologous to at least a portion of the target DNA sequence, such that homologous recombination occurs between the target DNA sequence and the nucleic acid. The cell can be a eukaryotic cell, a mammalian cell, a plant cell, or a prokaryotic cell. The target DNA can be chromosomal DNA. The introducing can comprise transfecting the cell with a vector encoding the TAL effector-DNA modifying enzyme, mechanically injecting the TAL effector-DNA modifying enzyme into the cell as a protein, delivering the TAL effector-DNA modifying enzyme into the cell as a protein by means of the bacterial type III secretion system, or introducing the TAL effector-DNA modifying enzyme into the cell as a protein by electroporation. The DNA modifying enzyme can be an endonuclease (e.g., a type II restriction endonuclease, such as FokI).

The TAL effector domain that binds to a specific nucleotide sequence within the target DNA can comprise 10 or more DNA binding repeats, and preferably 15 or more DNA binding repeats. Each DNA binding repeat can include a repeat variable-diresidue (RVD) that determines recognition of a base pair in the target DNA sequence, wherein each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T. Each DNA binding repeat can comprise a RVD that determines recognition of a base pair in the target DNA sequence, wherein each DNA binding repeat is responsible for recognizing one base pair in the target DNA sequence, and wherein the RVD comprises one or more of: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

In another aspect, this document features a method for generating a nucleic acid encoding a TAL effector specific for a selected nucleotide sequence, comprising: (1) linearizing a starter plasmid with PspXI, the starter plasmid comprising a nucleotide sequence that encodes a first TAL effector DNA binding repeat domain having a repeat variable-diresidue (RVD) specific for the first nucleotide of the selected nucleotide sequence, wherein the first TAL effector DNA binding repeat domain has a unique PspXI site at its 3' end; (2) ligating into the starter plasmid PspXI site a DNA module encoding one or more TAL effector DNA binding repeat domains that have RVDs specific for the next nucleotide(s) of the selected nucleotide sequence, wherein the DNA module has XhoI sticky ends; and (3) repeating steps (1) and (2) until the nucleic acid encodes a TAL effector capable of binding to the selected nucleotide sequence. The method can further comprise, after the ligating, determining the orientation of the DNA module in the PspXI site. The method can comprise repeating steps (1) and (2) from one to 30 times.

In another aspect, this document features a method for generating a nucleic acid encoding a transcription activator-like effector endonuclease (TALEN), comprising (a) identifying a first nucleotide sequence in the genome of a cell; and (b) synthesizing a nucleic acid encoding a TALEN that comprises (i) a plurality of DNA binding repeats that, in combination, bind to the first unique nucleotide sequence, and (ii) an endonuclease that generates a double-stranded cut at a position within or adjacent to the first nucleotide sequence, wherein each DNA binding repeat comprises a RVD that determines recognition of a base pair in the target DNA, wherein each DNA binding repeat is responsible for recognizing one base pair in the target DNA, and wherein the TALEN comprises one or more of the following RVDs: HD for recognizing C; NG for recognizing T; NI for recognizing A; NN for recognizing G or A; NS for recognizing A or C or G or T; N* for recognizing C or T; HG for recognizing T; H* for recognizing T; IG for recognizing T; NK for recognizing G; HA for recognizing C; ND for recognizing C; HI for recognizing C; HN for recognizing G; NA for recognizing G; SN for recognizing G or A; and YG for recognizing T.

The TALEN can comprises one or more of the following RVDs: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T; HG for recognizing T; H* for recognizing T; and IG for recognizing T.

The first nucleotide sequence can meet at least one of the following criteria: i) is a minimum of 15 bases long and is oriented from 5' to 3' with a T immediately preceding the site at the 5' end; ii) does not have a T in the first (5') position or an A in the second position; iii) ends in T at the last (3') position and does not have a G at the next to last position; and iv) has a base composition of 0-63% A, 11-63% C, 0-25% G, and 2-42% T.

The method can comprise identifying a first nucleotide sequence and a second nucleotide sequence in the genome of the cell, wherein the first and second nucleotide sequences meet at least one of the criteria set forth above and are separated by 15-18 bp. The endonuclease can generate a double-stranded cut between the first and second nucleotide sequences.

In another embodiment, this document features a TALEN comprising an endonuclease domain and a TAL effector DNA binding domain specific for a target DNA, wherein the DNA binding domain comprises a plurality of DNA binding repeats, each repeat comprising a RVD that determines recognition of a base pair in the target DNA, wherein each DNA binding repeat is responsible for recognizing one base pair in the target DNA, and wherein the TALEN comprises one or more of the following RVDs: HD for recognizing C; NG for recognizing T; NI for recognizing A; NN for recognizing G or A; NS for recognizing A or C or G or T; N* for recognizing C or T; HG for recognizing T; H* for recognizing T; IG for recognizing T; NK for recognizing G; HA for recognizing C; ND for recognizing C; HI for recognizing C; HN for recognizing G; NA for recognizing G; SN for recognizing G or A; and YG for recognizing T. The TALEN can comprise one or more of the following RVDs: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T; HG for recognizing T; H* for recognizing T; and IG for recognizing T. The endonuclease domain can be from a type II restriction endonuclease (e.g., FokI).

In still another aspect, this document features a TALEN comprising an endonuclease domain and a TAL effector domain, wherein the amino acid sequence of said TALEN is selected from the group consisting of SEQ ID NO:33 to SEQ ID NO:55, SEQ ID NO:72, and SEQ ID NO:73.

This document also features a method for generating an animal, comprising: providing a eukaryotic cell comprising a target DNA sequence into which it is desired to introduce a genetic modification; generating a double-stranded cut within the target DNA sequence with a TALEN comprising an endonuclease domain and a TAL effector domain that binds to the target DNA sequence; and generating an animal from the cell or progeny thereof in which a double-stranded cut has occurred. The method can further comprise introducing into the cell an exogenous nucleic acid comprising a sequence homologous to at least a portion of the target DNA, wherein the introducing is under conditions that permit homologous recombination to occur between the exogenous nucleic acid and the target DNA sequence in the cell or progeny thereof; and generating an animal from the cell or progeny thereof in which homologous recombination has occurred. The animal can be a mammal. The genetic modification can comprise a substitution, an insertion, or a deletion.

In yet another aspect, this document features a method for generating a plant, comprising providing a plant cell comprising a target DNA sequence into which it is desired to introduce a preselected genetic modification; generating a double-stranded cut within the target DNA sequence with a TALEN comprising an endonuclease domain and a TAL effector domain that binds to the target DNA sequence; and generating a plant from the cell or progeny thereof in which a double-stranded cut has occurred. The method can further comprise introducing into the plant cell an exogenous nucleic acid comprising a sequence homologous to at least a portion of the target DNA sequence, wherein the introducing is under conditions that permit homologous recombination to occur between the exogenous nucleic acid and the target DNA sequence in the cell or progeny thereof; and generating a plant from the cell or progeny thereof in which homologous recombination has occurred.

In another aspect, this document features a method for targeted genetic recombination in a cell, comprising introducing into the cell a nucleic acid encoding a TAL effector endonuclease targeted to a selected DNA target sequence; inducing expression of the TAL effector endonuclease within the cell; and identifying a cell in which the selected DNA target sequence exhibits a mutation. The mutation can be selected from the group consisting of deletion of genetic material, insertion of genetic material, and both deletion and insertion of genetic material. The method can further comprise introducing donor DNA into the cell. The cell can be an insect cell, a plant cell, a fish cell, or a mammalian cell.

In another aspect, this document features a method for generating a TAL effector having enhanced targeting capacity for a target DNA, comprising generating a nucleic acid encoding a TAL effector that comprises DNA binding domain having a plurality of DNA binding repeats, wherein each repeat comprises a RVD that determines recognition of a base pair in the target DNA, wherein each DNA binding repeat is responsible for recognizing one base pair in the target DNA, wherein the generating comprises incorporating a nucleic acid encoding a variant 0th DNA binding repeat sequence with specificity for A, C, or G, thus eliminating the requirement for T at position −1 of the binding site.

In another aspect, this document features a method for generating a TAL effector having enhanced targeting capacity for a target DNA, comprising generating a nucleic acid encoding a TAL effector that comprises DNA binding domain having a plurality of DNA binding repeats, wherein each repeat comprises a RVD that determines recognition of a base pair in the target DNA, wherein each DNA binding repeat is responsible for recognizing one base pair in the target DNA, wherein the generating comprises incorporating one or more nucleic acids encoding TAL effector DNA binding domains that contain RVDs having enhanced specificity for G, and wherein said RVDs are selected from the group consisting of RN, R*, NG, NH, KN, K*, NA, NT, DN, D*, NL, NM, EN, E*, NV, NC, QN, Q*, NR, NP, HN, H*, NK, NY, SN, S*, ND, NW, TN, T*, NE, NF, YN, Y*, and NQ, wherein * indicates a gap at the second position of the RVD.

This document also features a method for producing a polypeptide that selectively recognizes at least one base pair in a target DNA sequence, comprising synthesizing a polypeptide comprising a repeat domain, wherein the repeat domain comprises at least one repeat unit derived from a transcription activator-like (TAL) effector, wherein the repeat unit comprises a hypervariable region which determines recognition of a base pair in the target DNA sequence, wherein the repeat unit is responsible for the recognition of one base pair in the DNA sequence, and wherein the hypervariable region comprises a member selected from the group consisting of: (a) HD for recognition of C/G; (b) NI for recognition of A/T; (c) NG for recognition of T/A; (d) NS for recognition of C/G or A/T or T/A or G/C; (e) NN for recognition of G/C or A/T; (f) IG for recognition of T/A; (g) N for recognition of C/G; (h) HG for recognition of C/G or T/A; (i) H for recognition of T/A; and (j) NK for recognition of G/C. In addition, this document features a polypeptide produced by the above method, and a DNA comprising a coding sequence for the polypeptide produced by the method. Also featured is an expression cassette comprising a promoter operably linked to the above-mentioned DNA, and a non-human host cell comprising the expression cassette. In another aspect, this document features a transformed, non-human organism comprising the expression cassette.

In still another aspect, this document features a method for selectively recognizing a base pair in a DNA sequence by a polypeptide, comprising constructing a polypeptide comprising a repeat domain, wherein the repeat domain comprises at least one repeat unit derived from a TAL effector, wherein the repeat unit comprises a hypervariable region which determines recognition of a base pair in the DNA sequence, wherein the repeat unit is responsible for the recognition of one base pair in the DNA sequence, and wherein the hypervariable region comprises a member selected from the group consisting of (a) HD for recognition of C/G; (b) NI for recognition of A/T; (c) NG for recognition of T/A; (d) NS for recognition of C/G or A/T or T/A or G/C; (e) NN for recognition of G/C or A/T; (f) IG for recognition of T/A; (g) N for recognition of C/G; (h) HG for recognition of C/G or T/A; (i) H for recognition of T/A; and (j) NK for recognition of G/C.

This document also features a method of modulating expression of a target gene in a cell, wherein cells are provided which contain a polypeptide wherein the polypeptide comprises a repeat domain, wherein the repeat domain comprises at least one repeat unit derived from a TAL effector, wherein the repeat unit comprises a hypervariable region which determines recognition of a base pair in a DNA sequence, wherein the repeat unit is responsible for the recognition of one base pair in the DNA sequence, and wherein the hypervariable region comprises a member selected from the group consisting of (a) HD for recognition of C/G; (b) NI for recognition of A/T; (c) NG for recognition of T/A; (d) NS for recognition of C/G or A/T or T/A or G/C; (e) NN for recognition of G/C or A/T; (f) IG for recognition of T/A; (g) N for recognition of C/G; (h) HG for recognition of C/G or T/A; (i) H for recognition of T/A; and (j) NK for recognition of G/C.

In another aspect, this document features a polypeptide comprising a repeat domain, wherein the repeat domain comprises at least one repeat unit derived from a TAL effector, wherein the repeat unit comprises a hypervariable region which determines recognition of a base pair in a DNA sequence, wherein the repeat unit is responsible for the recognition of one base pair in the DNA sequence, and wherein the hypervariable region comprises a member selected from the group consisting of (a) HD for recognition of C/G; (b) NI for recognition of A/T; (c) NG for recognition of T/A; (d) NS for recognition of C/G or A/T or T/A or G/C; (e) NN for recognition of G/C or A/T; (f) IG for recognition of T/A; (g) N for recognition of C/G; (h) HG for recognition of C/G or T/A; (i) H for recognition of T/A; and (j) NK for recognition of G/C. This document also features a DNA comprising a coding sequence for the above-mentioned polypeptide.

In another aspect, this document features a DNA which is modified to include a base pair located in a target DNA sequence so that the base pair can be specifically recognized by a polypeptide comprising a repeat domain, wherein the repeat domain comprises at least one repeat unit derived from a TAL effector, wherein the repeat unit comprises a hypervariable region which determines recognition of a base pair in the DNA sequence, wherein the repeat unit is responsible for the recognition of one base pair in the DNA sequence, and wherein, to receive a selective and determined recognition by the hypervariable region, the base pair is selected from the group consisting of (a) C/G for recognition by HD; (b) A/T for recognition by NI; (c) T/A for recognition by NG; (d) CT or A/T or T/A or G/C for recognition by NS; (e) G/C or A/T for recognition by NN; (f) T/A for recognition by IG; (g) C/G or T/A for recognition by N; (h) T/A for recognition by HG; (i) T/A for recognition by H; and (j) G/C for recognition by NK. Also featured are a vector comprising the above-mentioned DNA, a non-human host cell comprising the DNA, and a transformed, non-human organism comprising the DNA.

In yet another aspect, this document features a method for producing a DNA comprising a target DNA sequence that is selectively recognized by a polypeptide comprising a repeat domain, wherein the repeat domain comprises at least one repeat unit derived from a TAL effector, wherein the repeat unit comprises a hypervariable region which determines recognition of a base pair in the target DNA sequence, and wherein the repeat unit is responsible for the recognition of one base pair in the target DNA sequence, the method comprising synthesizing a DNA comprising a base pair that is capable of being recognized by the repeat unit, wherein the base pair is selected from the group consisting of (a) C/G for recognition by HD; (b) A/T for recognition by NI; (c) T/A for recognition by NG; (d) CT or A/T or T/A or G/C for recognition by NS; (e) G/C or A/T for recognition by NN; (f) T/A for recognition by IG; (g) C/G or T/A for recognition by N; (h) T/A for recognition by HG; (i) T/A for recognition by H; and (j) G/C for recognition by NK.

In one aspect, the present document features a method for modifying the genetic material of a plant cell. The method can include (a) introducing into the plant cell (i) a first recombinant nucleic acid comprising a modified target nucleotide sequence, wherein the modified target nucleotide sequence comprises one or more modifications in nucleotide sequence with respect to a corresponding target nucleotide sequence present in the plant cell, and wherein the target nucleotide sequence further comprises a recognition site for a sequence-specific TAL effector endonuclease (TALEN); and (ii) a second recombinant nucleic acid comprising a nucleotide sequence encoding the sequence-specific transcription activator-like (TAL) effector endonuclease; (b) generating a plant containing the plant cell; (c) analyzing cells, seed, or tissue obtained from the plant, or progeny thereof, for recombination at the target nucleotide sequence. The method can further include introducing into the plant cell (iii) a third recombinant nucleic acid comprising a nucleotide sequence encoding a selectable marker; and determining if the plant or progeny thereof expresses the selectable marker. The method can further include the step of screening the plant or progeny thereof for the absence of the selectable marker. The nucleotide sequence encoding the selectable marker may or may not be flanked on one or both sides by a sequence that is similar or identical to a sequence that is endogenous to the plant cell (e.g., a sequence at the site of cleavage for a second sequence-specific nuclease). The nucleotide sequence encoding the selectable marker may be flanked on both sides by recognition sites for a sequence-specific recombinase. The method can further include the step of out-crossing the plant, with or without the step of screening progeny of the out-cross for the absence of the selectable marker. The first and second recombinant nucleic acids can be simultaneously introduced into the plant cell. One or both of the recombinant nucleic acids can be linearized prior to the introducing step. The first and second recombinant nucleic acids may be present in the same construct.

In another aspect, the present document features another method for modifying the genetic material of a cell. The method can include providing a primary cell containing chromosomal target DNA sequence in which it is desired to have homologous recombination occur; providing a TALEN comprising an endonuclease domain that can cleave double stranded DNA, and a TAL effector domain comprising a plurality of TAL effector repeat sequences that, in combination, bind to a specific nucleotide sequence within the target DNA in the cell; and contacting the target DNA sequence with the TALEN in the cell such that the TALEN cleaves both strands of a nucleotide sequence within or adjacent to the target DNA sequence in the cell. The method can further include providing a nucleic acid comprising a sequence homologous to at least a portion of the target DNA, such that homologous recombination occurs between the target DNA sequence and the nucleic acid. The target DNA sequence can be endogenous to the cell. The cell can be a plant cell, a mammalian cell, a fish cell, an insect cell or cell lines derived from these organisms for in vitro cultures or primary cells taken directly from living tissue and established for in vitro culture. The contacting can include transfecting the cell with a vector comprising a TALEN coding sequence, and expressing the TALEN protein in the cell, mechanically injecting a TALEN protein into the cell, delivering a TAL effector endonuclease protein into the cell by means of the bacterial type III secretion system, or introducing a TALEN protein into the cell by electroporation. The endonuclease domain can be from a type II restriction endonuclease (e.g., FokI). The TAL effector domain that binds to a specific nucleotide sequence within the target DNA can include 10 or more DNA binding repeats, more preferably 15 or more DNA binding repeats. The cell can be from any prokaryotic or eukaryotic organism.

In another aspect, the present document features a method for designing a sequence specific TALEN capable of cleaving DNA at a specific location. The method can include identifying a first unique endogenous chromosomal nucleotide sequence adjacent to a second nucleotide sequence at which it is desired to introduce a double-stranded cut; and designing a sequence specific TALEN comprising (a) a plurality of DNA binding repeat domains that, in combination, bind to the first unique endogenous chromosomal nucleotide sequence, and (b) an endonuclease that generates a double-stranded cut at the second nucleotide sequence.

The present document also features a TALEN comprising an endonuclease domain and a TAL effector DNA binding domain specific for a particular DNA sequence. The TALEN can further include a purification tag. The endonuclease domain can be from a type II restriction endonuclease (e.g., FokI).

In another aspect, the present document features a method for generating a genetically modified animal into which a desired nucleic acid has been introduced. The method can include providing a primary cell comprising an endogenous chromosomal target DNA sequence into which it is desired to introduce the nucleic acid; generating a double-stranded cut within the endogenous chromosomal target DNA sequence with a TALEN comprising an endonuclease domain and a TAL effector domain that binds to the endogenous chromosomal target DNA sequence; introducing an exogenous nucleic acid comprising a sequence homologous to at least a portion of the endogenous chromosomal target DNA into the primary cell under conditions that permit homologous recombination to occur between the exogenous nucleic acid and the endogenous chromosomal target DNA; and generating an animal from the primary cell in which homologous recombination has occurred. The animal can be a mammal. The homologous sequence can be a nucleotide sequence selected from the group consisting of a nucleotide sequence that disrupts a gene after homologous recombination, a nucleotide sequence that replaces a gene after homologous recombination, a nucleotide sequence that introduces a point mutation into a gene after homologous recombination, and a nucleotide sequence that introduces a regulatory site after homologous recombination.

In still another aspect, the present document features a method for generating a genetically modified plant in which a desired nucleic acid has been introduced. The method can include providing a plant cell comprising an endogenous target DNA sequence into which it is desired to introduce the nucleic acid; generating a double-stranded cut within the endogenous target DNA sequence with a TALEN comprising an endonuclease domain and a TAL effector domain that binds to the endogenous target nucleotide sequence; introducing an exogenous nucleic acid comprising a sequence homologous to at least a portion of the endogenous target DNA into the plant cell under conditions that permit homologous recombination to occur between the exogenous nucleic acid and the endogenous target DNA; and generating a plant from the plant cell in which homologous recombination has occurred.

In another aspect, the present document features a method for targeted genetic recombination in a cell. The method can include introducing into the cell a nucleic acid molecule encoding a TALEN targeted to a selected DNA target sequence; inducing expression of the TALEN within the cell; and identifying a cell in which the selected DNA target sequence exhibits a mutation. The mutation can be selected from the group consisting of a deletion of genetic material, an insertion of genetic material, and both a deletion and an insertion of genetic material. The method can further include introducing donor DNA into the cell. The cell can be an insect cell, a plant cell, a fish cell, or a mammalian cell.

In yet another aspect, the present document features a method for generating a nucleic acid encoding a sequence specific TALEN, comprising (1) selecting a starter plasmid comprising a nucleotide sequence that encodes a first TAL effector DNA binding repeat domain having a RVD specific for the first nucleotide of a selected nucleotide sequence, wherein the first TAL effector DNA binding repeat domain has a unique PspXI site at its 3' end; (2) linearizing the starter plasmid with PspXI; (3) ligating into the PspXI site a DNA module encoding one or more TAL effector DNA binding repeat domains that have RVDs specific for the next nucleotide(s) of the selected nucleotide sequence, wherein the DNA module has XhoI sticky ends; and (4) repeating steps (2) and (3) until the nucleic acid encodes a TALEN capable of binding to the selected nucleotide sequence. In some cases, the method can further include, after the ligating in step (3), checking the orientation of the DNA module in the PspXI site.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a diagram of a generic TAL effector, showing the repeat region (open boxes) and a representative repeat sequence (SEQ ID NO:1) with the RVD underlined. FIG. 1B is a diagram showing best pattern matches (low entropy alignments) for various TAL effector RVDs and target gene promoter sequences (SEQ ID NOS:2-11). An asterisk indicates a deletion at residue 13. FIG. 1C is a diagram showing RVD-nucleotide associations in the alignments in B, plus ten more alignments obtained by scanning all rice promoters with 40 additional X. oryzae TAL effectors, retaining for each effector the best alignment for which the downstream gene was activated during infection. FIG. 1D is a diagram showing flanking nucleotide frequencies for the 20 TAL effector target sites. Positions are relative to the 5' end of the target site; N, length of target site. Logos were generated using WebLogo.

FIG. 2A is a picture of semi quantitative RT-PCR results, showing relative transcript abundance of OsHen1, with an actin gene for reference, in rice leaves 24 hours after inoculation with BLS256 marker exchange mutant M51, M51 carrying the empty cosmid vector (ev), M51 carrying cosmid pIJF92, which contains tal1a, tal1b, and tal1c, and the wild type (WT) strain. FIG. 2B is a schematic based on mapping of the single marker exchange mutation in M51 by rescue and end sequencing of a marker-containing XmaI fragment. The genome region, the coordinates of the rescued fragment, and the coordinates of the BLS256 genomic fragment contained in cosmid pIJF92 are shown.

FIG. 3 is a reference AvrBs3 amino acid sequence (SEQ ID NO:12).

FIG. 4 is a reference AvrBs3 nucleic acid sequence (SEQ ID NO:13).

FIG. 8 is the amino acid sequence (SEQ ID NO:16) of the 17 and a half tandem repeats of the AvrBs3 recognition domain. Hypervariable amino acids at positions 12 and 13 are boxed.

FIGS. 12A and 12B depict a single representative TAL effector repeat (FIG. 12A), as well as a representative truncated repeat (FIG. 12B) that is present at the end of the repeat region in most TAL effectors. Nucleotide and encoded amino acid sequences as shown. Ns represent nucleotides encoding the RVDs, which are indicated as "XX." Numbers are given for the amino acid positions. Sequences are taken from tal1c.

FIG. 17A depicts nucleotide and encoded amino acid sequences for a single repeat module with the RVD NI. The 5' XhoI compatible cohesive end, the MscI site, and the 3' PspXI/XhoI compatible cohesive end are underlined. The RVD and the nucleotides encoding it are in bold type. Three other repeat modules were constructed that are identical to that shown except for the RVD encoding sequences, which encode HD, NI, and NG, respectively. FIG. 17B is a map of the single repeat module plasmid designated pCS502, which contains the repeat encoding sequence shown in FIG. 17A. Plasmids designated pCS503, pCS504, and pCS505 also were generated, and are identical to pCS502 except for the RVDs they encode (given at right).

FIG. 19 is a list of the complete set of one-, two-, and three-repeat module plasmids.

FIG. 20 is a flow chart depicting the steps in a method that can be used to assemble any sequence of repeats into the tal1c "backbone" to generate a custom TAL effector gene.

FIGS. 21A and 21B are schematics depicting assembly of repeat modules in construction of TAL endonucleases that will target the nucleotide sequences shown. In FIG. 21A, repeat modules from plasmids designated pCS519, pCS524, pCS537, pCS551, pCS583, and pCS529 are sequentially added to the sequence in the starter plasmid designated pCS493, resulting in plasmids designated pMAT55, pMAT56, pMAT57, pMAT58, pMAT59, and pMAT60. In FIG. 21B, repeat modules from plasmids designated pCS530, pCS533, pCS522, and pCS541 are sequentially added to the sequence in the plasmid designated pMAT1, resulting in plasmids designated pMAT61, pMAT62, pMAT63, and pMAT64.

FIG. 23 is a reference PthXo1 amino acid sequence (SEQ ID NO:31).

FIG. 24 is a reference PthXo1 nucleic acid sequence (SEQ ID NO:32).

FIG. 26 shows the amino acid sequence of avrBs3_TALEN (SEQ ID NO:33).

FIG. 27 shows the amino acid sequence of pthXo1_TALEN (SEQ ID NO:34).

FIG. 29A is a table showing the RVD sequences of individual custom TALENs and their respective DNA recognition sequences.

FIGS. 34A-34U show the amino acid sequences of TALENs generated as described in Example 9 herein. FIG. 34A, telomerase-TALEN124; FIG. 34B, gridlock-TALEN105;

FIG. 34C, adh1-TALEN58; FIG. 34D, adh1-TALEN63; FIG. 34E, adh1-TALEN68; FIG. 34F, adh1-TALEN73; FIG. 34G, adh1-TALEN89; FIG. 34H, gridlock-TALEN106; FIG. 34I, adh1-TALEN64; FIG. 34J, adh1-TALEN69; FIG. 34K, adh1-TALEN74; FIG. 34L, tt4-TALEN90; FIG. 34M, telomerase-TALEN121; FIG. 34N, telomerase-TALEN126; FIG. 34O, gridlock-TALEN107; FIG. 34P, gridlock-TALEN117; FIG. 34Q, telomerase-TALEN131; FIG. 34R, telomerase-TALEN136; FIG. 34S, adh1-TALEN60; FIG. 34T, tt4-TALEN85; FIG. 34U, gridlock-TALEN102.

FIG. 38A shows 0th repeat sequences of several phylogenetically distinct TAL effectors, AvrHah1 from *Xanthomonas gardneri*, AvrBs3 from *X. campestris* pv. *vesicatoria*, PthXo1 from *X. oryzae* pv. *oryzae*, PthA from *X. citri*, and Tal1c from *X. oryzae* pv. *oryzicola*. Polymorphic positions are boxed. FIG. 38B is a schematic showing the 0th and 1st repeats of PthXo1. The "0th" repeat immediately precedes the 1st repeat, shows 35% identity, and has a similar predicted secondary structure. The RVD of the 1st repeat and the candidate analogous residues of the 0th repeat are underlined. *, gap; H, helix; E, extended. The structure was predicted using JPred (Cole et al. (2008) *Nucl. Acids Res.* 36:W197-W201).

FIG. 40A shows the amino acid sequence of TALEN HPRT-3254-17, and FIG. 40B shows the amino acid sequence of TALEN HPRT-3286-20r.

DETAILED DESCRIPTION

Figure 1:
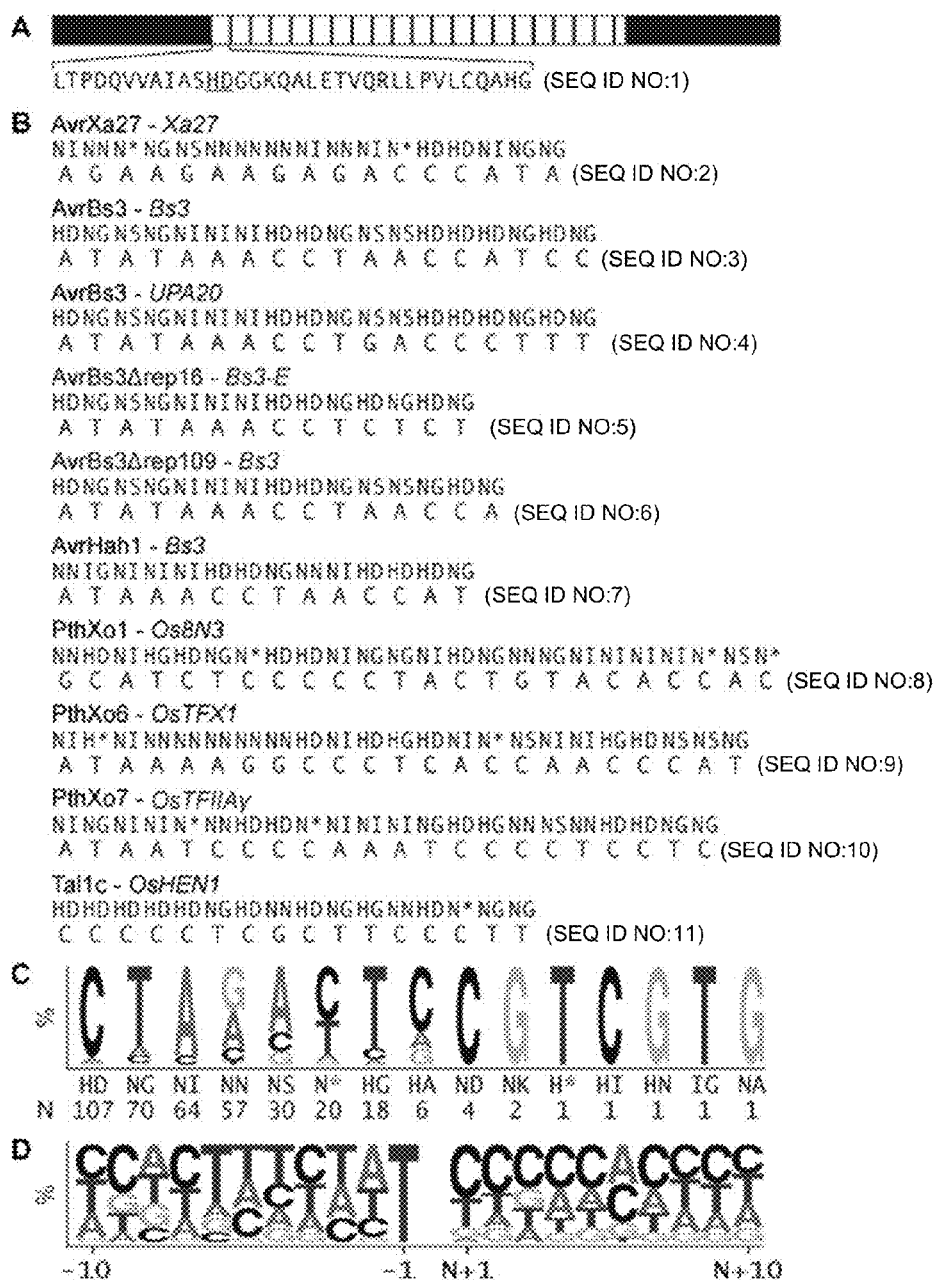
FIGS. 1A-1D depict the TAL effector-DNA recognition cipher.
Figure 2:
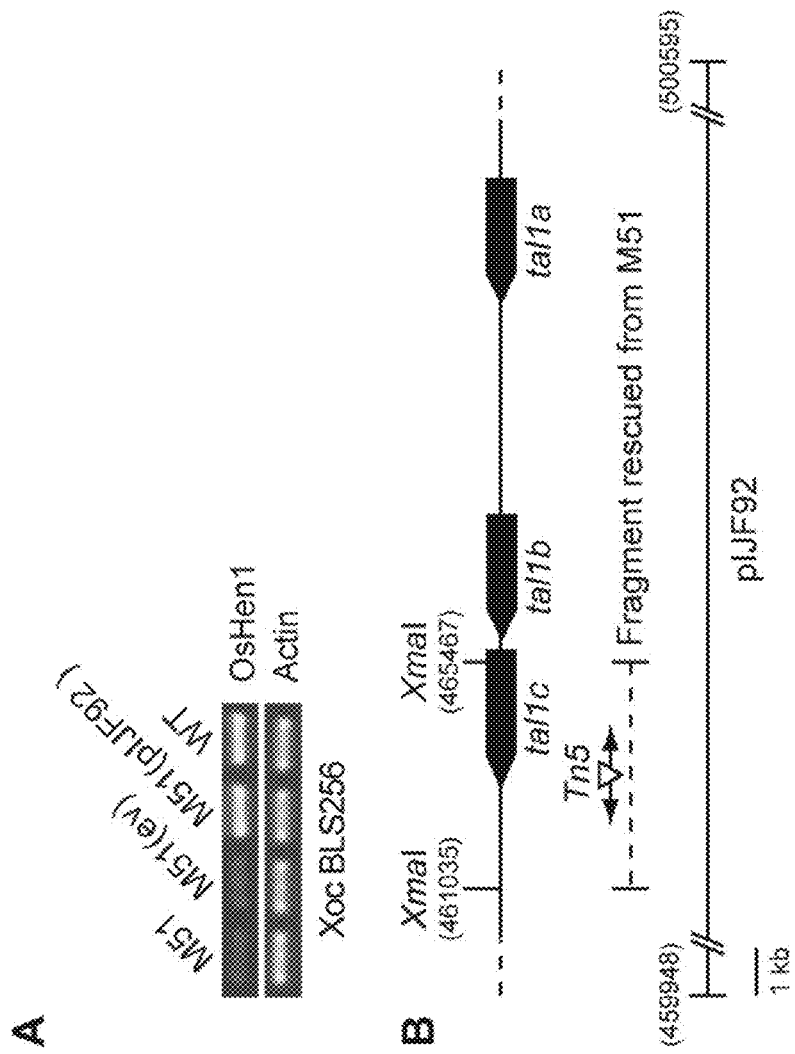
FIGS. 2A and 2B provide evidence that OsHen1 is activated by Tal1c of Xanthomonas oryzae pv. oryzicola strain BLS256.

The present patent application provides materials and methods related to sequence specific DNA recognition mediated by TAL effectors. As described herein, the primary amino acid sequences of TAL effectors dictate the nucleotide sequences to which they bind. The inventors have found that relationships between TAL effector amino acid sequences and their DNA target sequences are direct, enabling target site prediction for TAL effectors, and also allowing for TAL effector customization to bind to particular nucleotide sequences. Such prediction and customization can be harnessed for a variety of purposes. In one example, particular TAL effector sequences can be fused to endonuclease sequences, allowing for endonuclease targeting to specific DNA sequences, and subsequent cutting of the DNA at or near the targeted sequences. Cuts (i.e., double-stranded breaks) in DNA can dramatically increase the frequency of homologous recombination. Thus, in combination with DNA constructs that carry sequences having a high degree of sequence similarity to a particular target DNA sequence, TALENs can be used to facilitate site directed mutagenesis in complex genomes, that is, to knock out or alter gene function, or to add genes or other sequences with great precision and high efficiency.

Thus, included in the subject matter provided herein are, inter alia, materials and methods for making genetically modified organisms (including, without limitation, plants, fungi, *Drosophila*, nematodes, zebrafish, mice, other mammals and humans). Such methods can include, for example, transfecting a cell with several recombinant nucleic acids. For example, a cell (e.g., a eukaryotic cell) can be transformed with a first recombinant nucleic acid construct containing a donor nucleotide sequence that includes alterations relative to a corresponding target nucleotide sequence found within the cell, and a second recombinant nucleic acid construct encoding a TAL-nuclease. In some embodiments, the cell also can be transformed with a third recombinant nucleic acid construct encoding a selectable marker. A nucleic acid sequence from the donor nucleic acid construct can become incorporated into the genome of the transformed cell as described herein. For example, plant cells produced using methods as described herein can be grown to produce plants having the altered donor nucleotide sequence incorporated into their genomes. Seeds from such plants can be used to produce plants having a phenotype such as, for example, an altered growth characteristic (e.g., increased resistance or tolerance to various biotic and abiotic stresses), altered appearance (e.g., altered color or height), or altered composition (e.g., increased or decreased levels of carbon, nitrogen, oil, protein, carbohydrate (e.g., sugar or starch), amino acid, fatty acid, or secondary metabolites) with respect to unmodified plants.

Polynucleotides and Polypeptides

Isolated nucleic acids and polypeptides are provided herein. The terms "nucleic acid" and "polynucleotide" are used interchangeably, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

The polypeptides of the present document (such as TAL effector-DNA modifying enzyme as non-limiting example) can be introduced in a cell by using a vector encoding said polypeptides for example or as polypeptides per se by using delivery vectors associated or combined with any cellular permeabilization techniques such as sonoporation or electroporation or derivatives of these techniques.

As used herein, "isolated," when in reference to a nucleic acid, refers to a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., a pararetrovirus, a retrovirus, lentivirus, adenovirus, or herpes virus), or the genomic DNA of a prokaryote or eukaryote. In addition, an isolated nucleic acid can include a recombinant nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be made by, for example, chemical synthesis or polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be obtained by mutagenesis. For example, a donor nucleic acid sequence can be mutated using standard techniques, including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992.

The term "polypeptide" as used herein refers to a compound of two or more subunit amino acids regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers.

By "isolated" or "purified" with respect to a polypeptide it is meant that the polypeptide is separated to some extent from the cellular components with which it is normally found in nature (e.g., other polypeptides, lipids, carbohydrates, and nucleic acids). An purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

Recombinant Constructs

Recombinant nucleic acid constructs (e.g., vectors) also are provided herein. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more expression control sequences, and an "expression control sequence" is a DNA sequence that controls and regulates the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The terms "regulatory region," "control element," and "expression control sequence" refer to nucleotide sequences that influence transcription or translation initiation and rate, and stability and/or mobility of the transcript or polypeptide product. Regulatory regions include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, and other regulatory regions that can reside within coding sequences, such as secretory signals, Nuclear Localization Sequences (NLS) and protease cleavage sites.

As used herein, "operably linked" means incorporated into a genetic construct so that expression control sequences effectively control expression of a coding sequence of interest. A coding sequence is "operably linked" and "under the control" of expression control sequences in a cell when RNA polymerase is able to transcribe the coding sequence into RNA, which if an mRNA, then can be translated into the protein encoded by the coding sequence. Thus, a regulatory region can modulate, e.g., regulate, facilitate or drive, transcription in the plant cell, plant, or plant tissue in which it is desired to express a modified target nucleic acid.

A promoter is an expression control sequence composed of a region of a DNA molecule, typically within 100 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically comprises at least a core (basal) promoter. A promoter also may include at least one control element such as an upstream element. Such elements include upstream activation regions (UARs) and, optionally, other DNA sequences that affect transcription of a polynucleotide such as a synthetic upstream element.

The choice of promoters to be included depends upon several factors, including, but not limited to, efficiency, selectability, inducibility, desired expression level, and cell or tissue specificity. For example, tissue-, organ- and cell-specific promoters that confer transcription only or predominantly in a particular tissue, organ, and cell type, respectively, can be used. In some embodiments, promoters specific to vegetative tissues such as the stem, parenchyma, ground meristem, vascular bundle, cambium, phloem, cortex, shoot apical meristem, lateral shoot meristem, root apical meristem, lateral root meristem, leaf primordium, leaf mesophyll, or leaf epidermis can be suitable regulatory regions. In some embodiments, promoters that are essentially specific to seeds ("seed-preferential promoters") can be useful. Seed-specific promoters can promote transcription of an operably linked nucleic acid in endosperm and cotyledon tissue during seed development. Alternatively, constitutive promoters can promote transcription of an operably linked nucleic acid in most or all tissues of a plant, throughout plant development. Other classes of promoters include, but are not limited to, inducible promoters, such as promoters that confer transcription in response to external stimuli such as chemical agents, developmental stimuli, or environmental stimuli.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Non-limiting examples of promoters that can be included in the nucleic acid constructs provided herein include the cauliflower mosaic virus (CaMV) 35S transcription initiation region, the 1' or 2' promoters derived from T-DNA of *Agrobacterium tumefaciens*, promoters from a maize leaf-specific gene described by Busk ((1997) *Plant J.* 11:1285-1295), kn1-related genes from maize and other species, and transcription initiation regions from various plant genes such as the maize ubiquitin-1 promoter.

A 5' untranslated region (UTR) is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA message stability or translation attenuation. Examples of 3' UTRs include, but are not limited to polyadenylation signals and transcription termination sequences. A polyadenylation region at the 3'-end of a coding region can also be operably linked to a coding sequence. The polyadenylation region can be derived from the natural gene, from various other plant genes, or from an *Agrobacterium* T-DNA.

The vectors provided herein also can include, for example, origins of replication, and/or scaffold attachment regions (SARs). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

By "delivery vector" or "delivery vectors" is intended any delivery vector which can be used in the presently described methods to put into cell contact or deliver inside cells or subcellular compartments agents/chemicals and molecules (proteins or nucleic acids). It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present document includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentivirus vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. Said lentiviral vectors can be "non-integrative" or "integrative".

By "integrative lentiviral vectors (or LV)", is meant such vectors as non limiting example, that are able to integrate the genome of a target cell.

At the opposite by "non integrative lentiviral vectors (or NILV)" is meant efficient gene delivery vectors that do not integrate the genome of a target cell through the action of the virus integrase.

One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors. A vector according to the present document comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracyclin, rifampicin or ampicillin resistance in *E. coli*. Preferably said vectors are expression vectors, wherein a sequence encoding a polypeptide of interest is placed under control of appropriate transcriptional and translational control elements to permit production or synthesis of said polypeptide. Therefore, said polynucleotide is comprised in an expression cassette. More particularly, the vector comprises a replication origin, a promoter operatively linked to said encoding polynucleotide, a ribosome binding site, a RNA-splicing site (when genomic DNA is used), a polyadenylation site and a transcription termination site. It also can comprise an enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

Inducible promoters may be induced by pathogens or stress, more preferably by stress like cold, heat, UV light, or high ionic concentrations (reviewed in Potenza et al. (2004) *In vitro Cell Dev Biol* 40:1-22). Inducible promoter may be induced by chemicals [reviewed in Moore et al. (2006); Padidam (2003); Wang et al. (2003); and Zuo and Chua (2000)].

Delivery vectors and vectors can be associated or combined with any cellular permeabilization techniques such as sonoporation or electroporation or derivatives of these techniques.

It will be understood that more than one regulatory region may be present in a recombinant polynucleotide, e.g., introns, enhancers, upstream activation regions, and inducible elements.

Recombinant nucleic acid constructs can include a polynucleotide sequence inserted into a vector suitable for transformation of cells (e.g., plant cells or animal cells). Recombinant vectors can be made using, for example, standard recombinant DNA techniques (see, e.g., Sambrook et al. (1989) *Molecular Cloning: A Laboratory Manual*, 2nd ed., Cold Spring Harbor Laboratory, Cold Spring Harbor, N.Y.).

A recombinant nucleic acid sequence as described herein can integrate into the genome of a cell via illegitimate (i.e., random, non-homologous, non site-specific) recombination, or a recombinant nucleic acid sequence as described herein can be adapted to integrate into the genome of a cell via homologous recombination. Nucleic acid sequences adapted for integration via homologous recombination are flanked on both sides with sequences that are similar or identical to endogenous target nucleotide sequences, which facilitates integration of the recombinant nucleic acid at the particular site(s) in the genome containing the endogenous target nucleotide sequences. Nucleic acid sequences adapted for integration via homologous recombination also can include a recognition site for a sequence-specific nuclease. Alternatively, the recognition site for a sequence-specific nuclease can be located in the genome of the cell to be transformed. Donor nucleic acid sequences as described below typically are adapted for integration via homologous recombination.

In some embodiments, a nucleic acid encoding a selectable marker also can be adapted to integrate via homologous recombination, and thus can be flanked on both sides with sequences that are similar or identical to endogenous sequences within the plant genome (e.g., endogenous sequences at the site of cleavage for a sequence-specific nuclease). In some cases, nucleic acid containing coding sequence for a selectable marker also can include a recognition site for a sequence-specific nuclease. In these embodiments, the recognition site for the sequence-specific nuclease can be the same as or different from that contained within the donor nucleic acid sequence (i.e., can be recognized by the same nuclease as the donor nucleic acid sequence, or recognized by a different nuclease than the donor nucleic acid sequence).

In some cases, a recombinant nucleic acid sequence can be adapted to integrate into the genome of a cell via site-specific recombination. As used herein, "site-specific" recombination refers to recombination that occurs when a nucleic acid sequence is targeted to a particular site(s) within a genome not by homology between sequences in the recombinant nucleic acid and sequences in the genome, but rather by the action of recombinase enzymes that recognize specific nucleic acid sequences and catalyze the reciprocal exchange of DNA strands between these sites. Site-specific recombination thus refers to the enzyme-mediated cleavage and ligation of two defined nucleotide sequences. Any suitable site-specific recombination system can be used, including, for example, the Cre-lox system or the FLP-FRT system. In such embodiments, a nucleic acid encoding a recombinase enzyme may be introduced into a cell in addition to a donor nucleotide sequence and a nuclease-encoding sequence, and in some cases, a selectable marker sequence. See, e.g., U.S. Pat. No. 4,959,317.

Sequence-Specific Endonucleases

Sequence-specific nucleases and recombinant nucleic acids encoding the sequence-specific endonucleases are provided herein. The sequence-specific endonucleases can include TAL effector DNA binding domains and endonuclease domains. Thus, nucleic acids encoding such sequence-specific endonucleases can include a nucleotide sequence from a sequence-specific TAL effector linked to a nucleotide sequence from a nuclease.

TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors also can be engineered and generated for the purpose of binding to particular nucleotide sequences, as described herein.

Fused to the TAL effector-encoding nucleic acid sequences are sequences encoding a nuclease or a portion of a nuclease, typically a nonspecific cleavage domain from a type II restriction endonuclease such as FokI (Kim et al. (1996) *Proc. Natl. Acad. Sci. USA* 93:1156-1160). Other useful endonucleases may include, for example, HhaI, HindIII, NoI, BbvCI, EcoRI, BglI, and AlwI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN as provided herein can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence. A nucleotide sequence encoding the desired TALEN can be inserted into any suitable expression vector, and can be linked to one or more expression control sequences. For example, a nuclease coding sequence can be operably linked to a promoter sequence that will lead to constitutive expression of the endonuclease in the species of plant to be transformed. Alternatively, an endonuclease coding sequence can be operably linked to a promoter sequence that will lead to conditional expression (e.g., expression under certain nutritional conditions). For example, a cauliflower mosaic virus 35S promoter can be used for constitutive expression. Other constitutive promoters include, without limitation, the nopaline synthase promoter, the ubiquitin promoter, and the actin promoter. In some embodiments, an artificial estrogen-induced promoter for can be used conditional expression, and high levels of transcription can be achieved when a plant is exposed to estrogen. Other conditional promoters that can be used include, for example, heat-inducible heat shock gene promoters, and light-regulated promoters such as that from the gene encoding the large subunit of ribulose bisphosphate carboxylase.

For purposes of therapy, the TAL effector-DNA modifying enzyme of the present document and a pharmaceutically acceptable excipient are administered in a therapeutically effective amount. Such a combination is said to be administered in a "therapeutically effective amount" if the amount administered is physiologically significant. An agent is physiologically significant if its presence results in a detectable change in the physiology of the recipient. In the present context, an agent is physiologically significant if its presence results in a decrease in the severity of one or more symptoms of the targeted disease and in a genome correction of the lesion or abnormality. Vectors comprising targeting DNA and/or nucleic acid encoding a TAL effector-DNA modifying enzyme can be introduced into a cell by a variety of methods (e.g., injection, direct uptake, projectile bombardment, liposomes, electroporation). TAL effector-DNA modifying enzymes can be stably or transiently expressed into cells using expression vectors. Techniques of expression in eukaryotic cells are well known to those in the art. (See *Current Protocols in Human Genetics*: Chapter 12 "Vectors For Gene Therapy" and Chapter 13 "Delivery Systems for Gene Therapy").

In one further aspect of the present document, the TAL effector-DNA modifying enzyme is substantially non-immunogenic, i.e., engender little or no adverse immunological response. A variety of methods for ameliorating or eliminating deleterious immunological reactions of this sort can be used. In a preferred embodiment, the TAL effector-DNA modifying enzyme is substantially free of N-formyl methionine. Another way to avoid unwanted immunological reactions is to conjugate TAL effector-DNA modifying enzyme to polyethylene glycol ("PEG") or polypropylene glycol ("PPG") (preferably of 500 to 20,000 daltons average molecular weight (MW)). Conjugation with PEG or PPG, as described by Davis et al. (U.S. Pat. No. 4,179,337) for example, can provide non-immunogenic, physiologically active, water soluble TAL effector-DNA modifying enzyme conjugates with anti-viral activity. Similar methods also using a polyethylene-polypropylene glycol copolymer are described in Saifer et al. (U.S. Pat. No. 5,006,333).

Donor Vectors

Also provided herein are recombinant nucleic acids including donor nucleotide sequences. A donor nucleotide sequence can include a variant sequence having one or more modifications (i.e., substitutions, deletions, or insertions) with respect to a preselected target nucleotide sequence found endogenously within the genome of a cell to be transformed (also referred to herein as a "modified target nucleotide sequence"). The variant sequence within the donor nucleic acid typically is flanked on both sides with sequences that are similar or identical to the endogenous target nucleotide sequence within the cell. The flanking sequences can have any suitable length, and typically are at least 50 nucleotides in length (e.g., at least 50 nucleotides, at least 75 nucleotides, at least 100 nucleotides, at least 200 nucleotides, at least 250 nucleotides, at least 300 nucleotides, at least 500 nucleotides, at least 750 nucleotides, at least 1000 nucleotides, from about 50 to about 5000 nucleotides, from about 100 to 2500 nucleotides, from about 100 to about 1000 nucleotides, from about 100 to 500 nucleotides, from about 200 to about 500 nucleotides, or from about 250 to 400 nucleotides). Thus, homologous recombination can occur between the recombinant donor nucleic acid construct and the endogenous target on both sides of the variant sequence, such that the resulting cell's genome contains the variant sequence within the context of endogenous sequences from, for example, the same gene. A donor nucleotide sequence can be generated to target any suitable sequence within a genome. In a plant, for example, a donor nucleotide sequence can be targeted to a lipid biosynthetic gene, carbohydrate biosynthetic gene, seed storage protein gene, disease or pest resistance gene, stress tolerance gene, drought tolerance gene, or a gene that produces an antinutritional. In addition, the donor nucleotide sequence contains a recognition site for a sequence-specific nuclease, as described herein.

Selectable Markers

Some of the methods provided herein include the use of a third recombinant nucleic acid encoding a selectable or screenable marker. A nucleotide sequence encoding a polypeptide that results in a selectable trait can be incorporated into an expression vector containing one or more expression control sequences. For example, an expression vector can include sequence encoding a selectable marker operably linked to a promoter sequence that will lead to constitutive expression in the plant cell to be transformed. Suitable selectable markers can include, without limitation, polypeptides conferring resistance to an antibiotic such as kanamycin, G418, bleomycin, ampicillin, or hygromycin, or an herbicide such as glufosinate, chlorosulfuron, or phosphinothricin.

In embodiments for use in plants, for example, a selectable marker can confer resistance to an herbicide that inhibits the growing point or meristem, such as an imidazolinone or a sulfonylurea. Exemplary polypeptides in this category code for mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides for resistance to glyphosate (sold under the trade name Roundup®) also are suitable for use in plants. See, for example, U.S. Pat. Nos. 4,940,835 and 4,769,061. U.S. Pat. No. 5,554,798 discloses transgenic glyphosate resistant maize plants, in which resistance is conferred by an altered 5-enolpyruvyl-3-phosphoshikimate (EPSP) synthase. Such polypeptides can confer resistance to glyphosate herbicidal compositions including, without limitation, glyphosate salts such as the trimethylsulphonium salt, the isopropylamine salt, the sodium salt, the potassium salt and the ammonium salt. See, e.g., U.S. Pat. Nos. 6,451,735 and 6,451,732.

Polypeptides for resistance to phosphono compounds such as glufosinate ammonium or phosphinothricin, and pyridinoxy or phenoxy propionic acids and cyclohexones also are suitable. See, for example, European Publication No. 0 242 246, as well as U.S. Pat. Nos. 5,879,903, 5,276,268, and 5,561,236.

Other herbicides include those that inhibit photosynthesis, such as triazine and benzonitrile (nitrilase). See, e.g., U.S. Pat. No. 4,810,648. Other herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Patent Publication No. 20010016956 and U.S. Pat. No. 6,084,155.

In some embodiments, a recombinant nucleic acid encoding a selectable marker can be adapted to integrate into the genome of a cell (e.g., a plant cell or an animal cell) by site-specific recombination. For example, a sequence encoding a selectable marker can be flanked by recognition sequences for a recombinase such as, e.g., Cre or FLP. In other embodiments, a recombinant nucleic acid encoding a selectable marker can be adapted for integration into a plant genome by homologous recombination. In such nucleic acids, the sequence encoding the selectable marker can be flanked by sequences that are similar or identical to endogenous nucleotide sequences found within the genome of the plant cell into which the recombinant nucleic acid is to be introduced. At least one of the endogenous sequences can be at the cleavage site for a sequence-specific nuclease. The nucleic acid encoding the selectable marker also can contain a recognition site for a sequence-specific nuclease. The nuclease can be the same sequence-specific nuclease as that which is targeted to the donor nucleotide sequence, or a sequence-specific nuclease that is different from that targeted to the donor nucleotide sequence. In still other embodiments, a recombinant nucleic acid encoding a selectable marker can be adapted for integration into the genome of a plant cell by illegitimate recombination. Such nucleic acids typically lack the flanking sequences and nuclease recognition sites that are contained within nucleic acids adapted for homologous or site-specific recombination as described herein.

Methods

One or more of the constructs provided herein can be used to transform cells and/or a DNA modifying enzyme can be introduced into cells, such that a genetically modified organism (e.g., a plant or an animal) is generated. Thus, genetically modified organisms and cells containing the nucleic acids and/or polypeptides described herein also are provided. In some embodiments, a transformed cell has a recombinant nucleic acid construct integrated into its genome, i.e., can be stably transformed. Stably transformed cells typically retain the introduced nucleic acid sequence with each cell division. A construct can integrate in a homologous manner, such that a nucleotide sequence endogenous to the transformed cell is replaced by the construct, where the construct contains a sequence that corresponds to the endogenous sequence, but that contains one or more modifications with respect to the endogenous sequence. It is noted that while a plant or animal containing such a modified endogenous sequence may be termed a "genetically modified organism" (GMO) herein, the modified endogenous sequence is not considered a transgene. A construct also can integrate in an illegitimate manner, such that it integrates randomly into the genome of the transformed cell.

Alternatively, a cell can be transiently transformed, such that the construct is not integrated into its genome. For example, a plasmid vector containing a TALEN coding sequence can be introduced into a cell, such that the TALEN coding sequence is expressed but the vector is not stably integrated in the genome. Transiently transformed cells typically lose some or all of the introduced nucleic acid construct with each cell division, such that the introduced nucleic acid cannot be detected in daughter cells after sufficient number of cell divisions. Nevertheless, expression of the TALEN coding sequence is sufficient to achieve homologous recombination between a donor sequence and an endogenous target sequence. Both transiently transformed and stably transformed cells can be useful in the methods described herein.

With particular respect to genetically modified plant cells, cells used in the methods described herein can constitute part or all of a whole plant. Such plants can be grown in a manner suitable for the species under consideration, either in a growth chamber, a greenhouse, or in a field. Genetically modified plants can be bred as desired for a particular purpose, e.g., to introduce a recombinant nucleic acid into other lines, to transfer a recombinant nucleic acid to other species or for further selection of other desirable traits. Alternatively, genetically modified plants can be propagated vegetatively for those species amenable to such techniques. Progeny includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. Seeds produced by a genetically modified plant can be grown and then selfed (or outcrossed and selfed) to obtain seeds homozygous for the nucleic acid construct.

Genetically modified cells (e.g., plant cells or animal cells) can be grown in suspension culture, or tissue or organ culture, if desired. For the purposes of the methods provided herein, solid and/or liquid tissue culture techniques can be used. When using solid medium, cells can be placed directly onto the medium or can be placed onto a filter film that is then placed in contact with the medium. When using liquid medium, cells can be placed onto a floatation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

A cell can be transformed with one recombinant nucleic acid construct or with a plurality (e.g., 2, 3, 4, or 5) of recombinant nucleic acid constructs. If multiple constructs are utilized, they can be transformed simultaneously or sequentially. Techniques for transforming a wide variety of species are known in the art. The polynucleotides and/or recombinant vectors described herein can be introduced into the genome of a host using any of a number of known methods, including electroporation, microinjection, and biolistic methods. Alternatively, polynucleotides or vectors can be combined with suitable T-DNA flanking regions and introduced into a conventional *Agrobacterium tumefaciens* host vector. Such *Agrobacterium tumefaciens*-mediated transformation techniques, including disarming and use of binary vectors, are well known in the art. Other gene transfer and transformation techniques include protoplast transformation through calcium or PEG, electroporation-mediated uptake of naked DNA, liposome-mediated transfection, electroporation, viral vector-mediated transformation, and microprojectile bombardment (see, e.g., U.S. Pat. Nos. 5,538,880, 5,204,253, 5,591,616, and 6,329,571). If a plant cell or tissue culture is used as the recipient tissue for transformation, plants can be regenerated from transformed cultures using techniques known to those skilled in the art.

In some embodiments, a DNA modifying enzyme (e.g., a TALEN) can be directly introduced into a cell. For example, a polypeptide can be introduced into a cell by mechanical injection, by delivery via a bacterial type III secretion system, by electroporation, or by *Agrobacterium* mediated transfer. See, e.g., Vergunst et al. (2000) *Science* 290:979-982 for a discussion of the *Agrobacterium* VirB/D4 transport system, and its use to mediate transfer of a nucleoprotein T complex into plant cells.

With further respect to plants, the polynucleotides, vectors and polypeptides described herein can be introduced into a number of monocotyledonous and dicotyledonous plants and plant cell systems, including dicots such as safflower, alfalfa, soybean, coffee, amaranth, rapeseed (high erucic acid and canola), peanut or sunflower, as well as monocots such as oil palm, sugarcane, banana, sudangrass, corn, wheat, rye, barley, oat, rice, millet, or *sorghum*. Also suitable are gymnosperms such as fir and pine.

Thus, the methods described herein can be utilized with dicotyledonous plants belonging, for example, to the orders *Magniolales, Illiciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violates, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales,* and *Asterales*. The methods described herein also can be utilized with monocotyledonous plants such as those belonging to the orders *Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales,* and *Orchidales*, or with plants belonging to *Gymnospermae*, e.g., *Pinales, Ginkgoales, Cycadales* and *Gnetales*.

The methods can be used over a broad range of plant species, including species from the dicot genera *Atropa, Alseodaphne, Anacardium, Arachis, Beilschmiedia, Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vitis,* and *Vigna*; the monocot genera *Allium, Andropogon, Aragrostis, Asparagus, Avena, Cynodon, Elaeis, Festuca, Festulolium, Heterocallis, Hordeum, Lemna, Lolium, Musa, Oryza, Panicum, Pannesetum, Phleum, Poa, Secale, Sorghum, Triticum,* and *Zea*; or the gymnosperm genera *Abies, Cunninghamia, Picea, Pinus,* and *Pseudotsuga*.

A transformed cell, callus, tissue, or plant can be identified and isolated by selecting or screening the engineered cells for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known. Polynucleotides that are stably incorporated into plant cells can be introduced into other plants using, for example, standard breeding techniques.

In the context of the present document, "eukaryotic cells" refer to a fungal, yeast, plant or animal cell or a cell line derived from the organisms listed below and established for in vitro culture. More preferably, the fungus can be of the genus *Aspergillus, Penicillium, Acremonium, Trichoderma, Chrysoporium, Mortierella, Kluyveromyces* or *Pichia*. More preferably, the fungus can be of the species *Aspergillus niger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kluyveromyces lactis, Pichia pastoris* or *Pichia ciferrii*.

The plant can be of the genus *Arabidospis, Nicotiana, Solanum, Lactuca, Brassica, Oryza, Asparagus, Pisum, Medicago, Zea, Hordeum, Secale, Triticum, Capsicum, Cucumis, Cucurbita, Citrullis, Citrus,* or *Sorghum*. More preferably, the plant can be of the species *Arabidospis thaliana, Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisum sativum, Medicago sativa, Zea mays, Hordeum vulgare, Secale cereal, Triticum aestivum, Triticum durum, Capsicum sativus, Cucurbita pepo, Citrullus lanatus, Cucumis melo, Citrus aurantifolia, Citrus maxima, Citrus medica,* or *Citrus reticulata*.

The animal cell can be of the genus *Homo, Rattus, Mus, Sus, Bos, Danio, Canis, Felis, Equus, Salmo, Oncorhynchus, Gallus, Meleagris, Drosophila,* or *Caenorhabditis*; more preferably, the animal cell can be of the species *Homo sapiens, Rattus norvegicus, Mus musculus, Sus scrofa, Bos taurus, Danio rerio, Canis lupus, Felis catus, Equus caballus, Oncorhynchus mykiss, Gallus gallus,* or *Meleagris gallopavo*; the animal cell can be a fish cell from *Salmo salar*, Teleost fish or zebrafish species as non-limiting examples. The animal cell also can be an insect cell from *Drosophila melanogaster* as a non-limiting example; the animal cell can also be a worm cell from *Caenorhabditis elegans* as a non-limiting example.

In the present document, the cell can be a plant cell, a mammalian cell, a fish cell, an insect cell or cell lines derived from these organisms for in vitro cultures or primary cells taken directly from living tissue and established for in vitro culture. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present document to provide cell line models to produce, express, quantify, detect, study a gene or a protein of interest; these models can also be used to screen biologically active molecules of interest in research and production in various fields such as chemical, biofuels, therapeutics and agronomy as non-limiting examples.

The present document also provides methods for harnessing the sequence-specific DNA binding domains within TAL effectors to, for example, alter the genetic material within cells, to modulate gene expression, and to target pathogenic sequences in, e.g., anti-viral therapies. For example, in some embodiments, the present document provides methods for modifying cellular genetic material. In some embodiments, the methods include introducing a polypeptide containing a TAL effector DNA binding domain, or a nucleic acid encoding such a polypeptide, into a cell. The TAL effector DNA binding domain can be fused to all or a portion of a DNA modifying enzyme (e.g., an endonuclease). In some embodiments, the methods include introducing two or more recombinant nucleic acids into a cell. A first recombinant nucleic acid contains a donor nucleotide sequence that includes one or more modifications (i.e., substitutions, deletions, or insertions) with respect to a corresponding, preselected target nucleotide sequence found in the cell. The donor nucleotide sequence can undergo homologous recombination with the endogenous target nucleotide sequence, such that the endogenous sequence or a portion thereof is replaced with the donor sequence or a portion thereof. The target nucleotide sequence typically includes a recognition site for a sequence-specific TALEN. In some cases, a target nucleotide sequence can include recognition sites for two or more distinct TALENs (e.g., two opposed target sequences that are distinct, such that TALENs having distinct DNA sequence binding specificity can be used). In such cases, the specificity of DNA cleavage can be increased as compared to cases in which only one target sequence (or multiple copies of the same target sequence) is used.

A second recombinant nucleic acid contains a nucleotide sequence encoding a sequence specific TALEN that binds to the recognition site in the target nucleotide sequence. In some cases, the donor nucleotide sequence and the nucleotide sequence encoding the sequence-specific nuclease can be contained in the same nucleic acid construct. Alternatively, the donor nucleotide sequence and the TALEN coding sequence can be contained in separate constructs, or the TALEN polypeptide can be produced and introduced directly into a cell.

In some embodiments, a third recombinant nucleic acid containing a nucleotide sequence encoding a selectable marker also may be used. The second and third recombinant nucleic acids may undergo recombination with endogenous sequences and thus integrate into the genome of the cell. These recombination events can be illegitimate (i.e., random), or they can occur through homologous recombination or through site-specific recombination. The recombinant nucleic acids can be simultaneously or sequentially transformed into the cell, and can be linearized prior to transformation.

When the cell is a plant cell, the methods provided herein can further include steps such as generating a plant containing the transformed cell, generating progeny of the plant, selecting or screening for plants expressing the selectable marker (if included), generating progeny of the selected plants, and testing the plants (e.g., tissue, seed, precursor cells, or whole plants) or progeny of the plants for recombination at the target nucleotide sequence. In some cases, the methods can include out-crossing the selected plants to remove the selectable marker, and/or screening the selected or out-crossed plants for the absence of the sequence-specific nuclease.

In some embodiments, the present document provides methods for modifying the genetic material of a cell, e.g., a prokaryotic cell, an animal cell, or a plant cell. The methods can include introducing into the cell a first recombinant nucleic acid containing a modified target nucleotide sequence that includes one or more modifications in nucleotide sequence with respect to a corresponding target nucleotide sequence present in the cell, as well as a recognition site for a sequence-specific TALEN, and a second recombinant nucleic acid containing a nucleotide sequence encoding the sequence-specific TALEN. When the cell is a plant cell, a plant containing the cell can be generated, and cells, seed, or tissue obtained from the plant (or progeny thereof) can be analyzed for recombination at the target nucleotide sequence. The first and second recombinant nucleic acids can be simultaneously or serially transformed into the cell, and one or both may be linearized prior to transformation. In some cases, the first and second recombinant nucleic acids can be present in the same construct.

In some cases, the method also can include introducing into the cell a third recombinant nucleic acid containing a nucleotide sequence encoding a selectable marker, and determining whether the cell, an organism generated from the cell, or progeny thereof expresses the selectable marker. The method further can include screening the cell, the organism or progeny thereof for the absence of the selectable marker. The nucleotide sequence encoding the selectable marker may or may not be flanked on both sides by nucleotide sequences that are similar or identical to nucleotide sequences endogenous to the cell at the site of cleavage for a second sequence-specific nuclease, or by recognition sites for a sequence-specific recombinase. In some cases, the method also can include the step of out-crossing the organism. Progeny of the out-cross can be screened for the absence of the selectable marker.

The present document also provides methods for modifying the genetic material of a cell (e.g., a plant cell or an animal cell), comprising providing a cell containing a target DNA sequence, e.g., a chromosomal, mitochondrial, or chloroplast sequence, in which it is desired to have homologous recombination occur, providing a TALEN that contains a DNA modifying enzyme domain (e.g., an endonuclease domain) and a TAL effector domain having a plurality of TAL effector repeats that, in combination, bind to a specific nucleotide sequence within the target DNA sequence, providing a nucleic acid containing a sequence homologous to at least a portion of the target DNA, and contacting the target DNA sequence in the cell with the TAL endonuclease such that both strands of a nucleotide sequence within or adjacent to the target DNA sequence in the cell are cleaved. Such cleavage can enhance the frequency of homologous recombination at the target DNA sequence. The target DNA sequence can be endogenous to the cell. The methods can include introducing into the cell a vector containing a cDNA encoding the TAL endonuclease, and expressing a TAL endonuclease protein in the cell. In some cases, the TAL endonuclease protein itself can be introduced into the cell, for example, by mechanical injection, by delivery via a bacterial type III secretion system, by electroporation, or by *Agrobacterium* mediated transfer.

The methods described herein can be used in a variety of situations. In agriculture, for example, methods described herein are useful to facilitate homologous recombination at a target site can be used to remove a previously integrated transgene (e.g., a herbicide resistance transgene) from a plant line, variety, or hybrid. The methods described herein also can be used to modify an endogenous gene such that the enzyme encoded by the gene confers herbicide resistance, e.g., modification of an endogenous 5-enolpyruvyl shikimate-3-phosphate (EPSP) synthase gene such that the modified enzyme confers resistance to glyphosate herbicides. As another example, the methods described herein are useful to facilitate homologous recombination at regulatory regions for one or more endogenous genes in a plant or mammal metabolic pathway (e.g., fatty acid biosynthesis), such that expression of such genes is modified in a desired manner. The methods described herein are useful to facilitate homologous recombination in an animal (e.g., a rat or a mouse) in one or more endogenous genes of interest involved in, as non-limiting examples, metabolic and internal signaling pathways such as those encoding cell-surface markers, genes identified as being linked to a particular disease, and any genes known to be responsible for a particular phenotype of an animal cell.

The present document also provides methods for designing sequence-specific TAL effectors capable of interacting with particular DNA sequences (e.g., TALENs capable of cleaving DNA at specific locations). The methods can include identifying a target nucleotide sequence (e.g., an endogenous chromosomal sequence, a mitochondrial DNA sequence, or a chloroplast DNA sequence) at which it is desired to have TAL effector binding (e.g., a sequence adjacent to a second nucleotide sequence at which it is desired to introduce a double-stranded cut), and designing a sequence specific TAL effector that contains a plurality of DNA binding repeats that, in combination, bind to the target sequence. As described herein, TAL effectors include a number of imperfect repeats that determine the specificity with which they interact with DNA. Each repeat binds to a single base, depending on the particular di-amino acid sequence at residues 12 and 13 of the repeat. Thus, by engineering the repeats within a TAL effector (e.g., using standard techniques or the techniques described herein), particular DNA sites can be targeted. Such engineered TAL effectors can be used, for example, as transcription factors targeted to particular DNA sequences. A diagram of a generic TAL effector is shown in FIG. 1A, with the repeat region indicated by open boxes, and the RVD in the representative repeat sequence (SEQ ID NO:1) underlined.

Examples of RVDs and their corresponding target nucleotides are shown in Table 1A (See, also, PCT Publication No. WO2010/079430).

TABLE 1A

| RVD | Nucleotide |
| --- | --- |
| HD | C |
| NG | T |
| NI | A |
| NN | G or A |
| NS | A or C or G |
| N* | C or T |
| HG | T |
| H* | T |
| IG | T |

*Denotes a gap in the repeat sequence corresponding to a lack of an amino acid residue at the second position of the RVD.

Other RVDs and their corresponding target nucleotides are shown in Table 1B.

TABLE 1B

| RVD | Nucleotide |
| --- | --- |
| HA | C |
| ND | C |
| NK | G |
| HI | C |

TABLE 1B-continued

| RVD | Nucleotide |
| --- | --- |
| HN | G |
| NA | G |
| SN | G or A |
| YG | T |

When it is desired to have sequence-specific DNA cleavage, for example, a sequence-specific TALEN can be designed to contain (a) a plurality of DNA binding repeat domains that, in combination, bind to the endogenous chromosomal nucleotide sequence, and (b) an endonuclease that generates a double-stranded cut at the second nucleotide sequence. Such sequence-specific DNA cleavage can be useful to enhance homologous recombination, as described herein. Other uses for TALENs include, for example, as therapeutics against viruses. TALENs can be engineered to target particular viral sequences, cleaving the viral DNA and reducing or abolishing virulence.

The materials and methods provided herein can be used to modify the sequence of a particular gene in a targeted manner. A gene may contain a plurality of sequences to which an engineered TAL effector could be targeted. As described herein, however, certain target sequences may be more effectively targeted. For example, as set forth in Example 9, sequences having particular characteristics may be more effectively targeted by TAL effectors. Thus, the methods provided herein can include identifying target sequences that meet particular criteria. These include sequences that: i) have a minimum length of 15 bases and an orientation from 5' to 3' with a T immediately preceding the site at the 5' end; ii) do not have a T in the first (5') position or an A in the second position; iii) end in T at the last (3') position and do not have a G at the next to last position; and iv) have a base composition of 0-63% A, 11-63% C, 0-25% G, and 2-42% T.

Since TALENs as described herein generally work as dimers, some embodiments of the methods provided herein can include identifying a first genomic nucleotide sequence and a second genomic nucleotide sequence in a cell, wherein the first and second nucleotide sequences meet at least one of the criteria set forth above and are separated by 15-18 bp. In some cases, one TALEN polypeptide can bind to each nucleotide sequences, and the endonuclease contained in the TALEN can cleave within the 15-18 bp spacer.

The present document also provides methods for generating genetically modified animals into which a desired nucleic acid has been introduced. Such methods can include obtaining a cell containing an endogenous chromosomal target DNA sequence into which it is desired to introduce the nucleic acid, introducing into the cell a TALEN to generate a double-stranded cut within the endogenous chromosomal target DNA sequence, introducing into the cell an exogenous nucleic acid containing a sequence homologous to at least a portion of the endogenous chromosomal target DNA, where the introduction is done under conditions that permit homologous recombination to occur between the exogenous nucleic acid and the endogenous chromosomal target DNA, and generating an animal from the primary cell in which homologous recombination has occurred. The homologous nucleic acid can include, e.g., a nucleotide sequence that disrupts a gene after homologous recombination, a nucleotide sequence that replaces a gene after homologous recombination, a nucleotide sequence that introduces a point mutation into a gene after homologous recombination, or a nucleotide sequence that introduces a regulatory site after homologous recombination.

The methods provided herein also can be used to generate genetically modified plants in which a desired nucleic acid has been introduced. Such methods can include obtaining a plant cell containing an endogenous target DNA sequence into which it is desired to introduce the nucleic acid, introducing a TALEN to generate a double-stranded cut within the endogenous target DNA sequence, introducing into the plant cell an exogenous nucleic acid containing a sequence homologous to at least a portion of the endogenous target DNA, where the introducing is under conditions that permit homologous recombination to occur between the exogenous nucleic acid and the endogenous target DNA, and generating a plant from the plant cell in which homologous recombination has occurred.

The DNA in cells generated by the TALEN-facilitated homologous recombination methods provided herein is modified, as compared to cells that have not undergone such methods, and cells containing the modified DNA are referred to as "genetically modified." It is noted, however, that organisms containing such cells may not be considered GMO for regulatory purposes, since such a modification involves a homologous recombination and not random integration of a transgene. Thus, using the TALEN-facilitated methods described herein to generate genetic modifications may be advantageous in that, for example, standard regulatory procedures along with their associated time and cost may be avoided.

Other methods of targeted genetic recombination, as provided herein, can include introducing into a cell (e.g., a plant cell, insect cell, teleost fish cell, or animal cell) a nucleic acid molecule encoding a TALEN targeted to a selected DNA target sequence, inducing expression of the TALEN within the cell, and identifying a recombinant cell in which the selected DNA target sequence exhibits a mutation (e.g., a deletion of genetic material, an insertion of genetic material, or both a deletion and an insertion of genetic material). A donor DNA also can be introduced into the cell.

In some embodiments, a monomeric TALEN can be used. TALENs as described herein typically function as dimers across a bipartite recognition site with a spacer, such that two TAL effector domains are each fused to a catalytic domain of the FokI restriction enzyme, the DNA recognition sites for each resulting TALEN are separated by a spacer sequence, and binding of each TALEN monomer to the recognition site allows FokI to dimerize and create a double-strand break within the spacer (see, e.g., Moscou and Bogdanove (2009) *Science* 326:1501). Monomeric TALENs also can be constructed, however, such that single TAL effectors are fused to a nuclease that does not require dimerization to function. One such nuclease, for example, is a single-chain variant of FokI in which the two monomers are expressed as a single polypeptide (Minczuk et al. (2008) *Nucleic Acids Res.* 36:3926-3938). Other naturally occurring or engineered monomeric nucleases also can serve this role. The DNA recognition domain used for a monomeric TALEN can be derived from a naturally occurring TAL effector. Alternatively, the DNA recognition domain can be engineered to recognize a specific DNA target. Engineered single-chain TALENs may be easier to construct and deploy, as they require only one engineered DNA recognition domain.

In some embodiments, a dimeric DNA sequence-specific nuclease can be generated using two different DNA binding domains (e.g., one TAL effector binding domain and one binding domain from another type of molecule). As set forth above, the TALENs described herein typically function as dimers across a bipartite recognition site with a spacer. This nuclease architecture also can be used for target-specific nucleases generated from, for example, one TALEN monomer and one zinc finger nuclease monomer. In such cases, the DNA recognition sites for the TALEN and zinc finger nuclease monomers can be separated by a spacer of appropriate length. Binding of the two monomers can allow FokI to dimerize and create a double-strand break within the spacer sequence. DNA binding domains other than zinc fingers, such as homeodomains, myb repeats or leucine zippers, also can be fused to FokI and serve as a partner with a TALEN monomer to create a functional nuclease.

In some embodiments, a TAL effector can be used to target other protein domains (e.g., non-nuclease protein domains) to specific nucleotide sequences. For example, a TAL effector can be linked to a protein domain from, without limitation, a DNA interacting enzyme (e.g., a methylase, a topoisomerase, an integrase, a transposase, or a ligase), a transcription activators or repressor, or a protein that interacts with or modifies other proteins such as histones. Applications of such TAL effector fusions include, for example, creating or modifying epigenetic regulatory elements, making site-specific insertions, deletions, or repairs in DNA, controlling gene expression, and modifying chromatin structure.

In some embodiments, the spacer of the target sequence can be selected or varied to modulate TALEN specificity and activity. The results presented herein for TALENs that function as dimers across a bipartite recognition site with a spacer demonstrate that TALENs can function over a range of spacer lengths, and that the activity of TALENs varies with spacer length. See, e.g., Example 6 below. The flexibility in spacer length indicates that spacer length can be chosen to target particular sequences (e.g., in a genome) with high specificity. Further, the variation in activity observed for different spacer lengths indicates that spacer length can be chosen to achieve a desired level of TALEN activity.

In some embodiments, TALEN activity can be modulated by varying the number and composition of repeats within the DNA binding domain(s). As described in Example 7 herein, for example, a PthXo1-based TALEN showed greater activity than an AvrBs3-based TALEN. PthXo1 differs from AvrBs3 both in the number and RVD composition of its repeats. In addition, the naturally occurring DNA recognition sites for these proteins differ in their divergence from the respective recognition sequences predicted based on the TAL effector DNA cipher described by Moscou and Bogdanove (supra). Further, several custom TALENs of the same length (12 RVDs) but with differing RVD composition differed in their activity, and a 13 RVD custom TALEN had higher activity than a 12 RVD custom TALEN. Thus, not only can TALENs be engineered to recognize a DNA sequence of interest, but (1) the number of repeats can be varied to modulate activity, (2) different binding sites can be selected to achieve different levels of activity, and (3) the composition of RVDs and their fit to the target site (according to the cipher) can be varied to modulate TALEN activity.

When the TALEN is in a heterodimeric form, for instance with two different monomers including each a TAL effector domain and a FokI nuclease catalytic domain, the RVDs can be found in equivalent number in each of the two TAL effector domains, or each domain can display different numbers of RVDs. For instance, if a total of 22 RVDs is used to bind DNA in a particular heterodimeric TALEN, 11 repeats can be found in each of the two TAL effector domains; alternatively, 10 repeats can be found in one of the two TAL effector domains and 12 in the other. The present document also encompasses TALEN with DNA modifying enzyme domain which functions as a monomer. In this case, all the RVDs can be found in a single TAL effector domain, which is fused to the monomeric enzyme. In this case, in order to have efficient binding, the number of RVDs must be equivalent to the total number of RVDs that would be found in an equivalent dimeric TALEN. For example, instead of having 10 repeats on two different TAL effector domains (as in the case for a dimeric TALEN), one would have 20 repeats in a single TAL effector domain (as in the case for a monomeric TALEN).

In a further aspect, the total number of repeats within the dimeric or monomeric TALEN is at least 14. In another further aspect, the total number of repeats within the dimeric or monomeric TALEN is at least 20. In another further aspect, the total number of repeats within the dimeric or monomeric TALEN is at least 24. In another further aspect, the total number of repeats within the dimeric or monomeric TALEN is at least 30.

This patent application also provides methods for generating TAL effector proteins having enhanced targeting capacity for a target DNA. The methods can include, for example, generating a nucleic acid encoding a TAL effector that has a DNA binding domain with a plurality of DNA binding repeats, each repeat containing a RVD that determines recognition of a base pair in the target DNA, where each DNA binding repeat is responsible for recognizing one base pair in the target DNA. As described in Example 12 below, relaxing the requirement for T at position −1 of the binding site may enhance the targeting capacity for engineered TAL effector proteins. Thus, generating a TAL effector encoding nucleic acid can include incorporating a nucleic acid encoding a variant 0th DNA binding repeat sequence with specificity for A, C, or G, thus eliminating the requirement for T at position −1 of the binding site.

In addition, methods are provided herein for generating TAL effectors having enhanced targeting capacity for a target DNA. Such methods can include generating a nucleic acid encoding a TAL effector that comprises DNA binding domain having a plurality of DNA binding repeats, each repeat containing a RVD that determines recognition of a base pair in the target DNA. As described in Example 12 below, the specificity of NN (the most common RVD that recognizes G) appears to be generally weak and can vary with context, but certain RVDs may have enhanced specificity for G. Thus, methods provided herein can include using alternate RVDs that may have more robust specificity for G. For example, one or more RVDs selected from the group consisting of RN, R*, NG, NH, KN, K*, NA, NT, DN, D*, NL, NM, EN, E*, NV, NC, QN, Q*, NR, NP, HN, H*, NK, NY, SN, S*, ND, NR, TN, T*, NE, NF, YN, Y*, and NQ can be used, where the asterisk indicates a gap at the second position of the RVD.

Articles of Manufacture

The present document also provides articles of manufacture containing, for example, nucleic acid molecules encoding TALENs, TALEN polypeptides, compositions containing such nucleic acid molecules or polypeptides, or TAL endonuclease engineered cell lines. Such items can be used, for example, as research tools, or therapeutically.

In some embodiments, an article of manufacture can include seeds from plants generated using methods provided herein. The seeds can be conditioned using means known in the art and packaged using packaging material well known in the art to prepare an article of manufacture. A package of seed can have a label e.g., a tag or label secured to the packaging material, a label printed on the packaging material or a label inserted within the package. The label can indicate that the seeds contained within the package can produce a crop of genetically modified plants, and can described the traits that are altered by the genetic modification, relative to unmodified plants.

Other Definitions

Amino acid residues or subunits in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

The term "DNA modifying enzyme" refers to any protein which is capable of modifying the genetic material of a cell, whatever the level of DNA modification (cleavage, covalent interaction, water-mediated interaction . . . ). DNA-interacting proteins (e.g., a methylase, a topoisomerase, an integrase, a transposase, or a ligase), transcription activators or repressor, other proteins such as histones, and nucleases are intended to be included in the meaning of "DNA modifying enzyme". When comprised in a TAL effector-DNA modifying enzyme the DNA modifying enzyme is referred as the DNA modifying enzyme domain.

The term "nuclease" is intended to include exonucleases and endonucleases.

The term "endonuclease" refers to any wild-type or variant enzyme capable of catalyzing the hydrolysis (cleavage) of bonds between nucleic acids within a DNA or RNA molecule, preferably a DNA molecule. Non-limiting examples of endonucleases include type II restriction endonucleases such as FokI, HhaI, HindIII, NotI, BbvCI, EcoRI, BglI, and AlwI. Endonucleases comprise also rare-cutting endonucleases when having typically a polynucleotide recognition site of about 12-45 base pairs (bp) in length, more preferably of 14-45 bp. Rare-cutting endonucleases significantly increase HR by inducing DNA double-strand breaks (DSBs) at a defined locus (Rouet, Smih et al. 1994; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005) or a chemical endonuclease (Eisenschmidt, Lanio et al. 2005; Arimondo, Thomas et al. 2006; Simon, Cannata et al. 2008). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present document. Examples of such endonuclease include I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, I-MsoI.

The endonucleases according to the present document can be part of a Transcription Activator-Like (TAL) effector endonuclease (TALEN).

By "TALEN" is intended a protein comprising a Transcription Activator-like (TAL) effector binding domain and an endonuclease domain, the fusion of both domains resulting in a "monomeric TALEN". Some monomeric TALEN can be functional per se and others require dimerization with another monomeric TALEN. The dimerization can result in a homodimeric TALEN when both monomeric TALEN are identical or can result in a heterodimeric TALEN when monomeric TALEN are different. Two monomeric TALEN are different when, for example, their RVDs numbers are different, and/or when the content (i.e. amino acid sequence) of at least one RVD is different. By "TAL effector-DNA modifying enzyme" is intended a protein comprising a Transcription Activator-Like effector binding domain and a DNA-modifying enzyme domain.

By "variant" is intended a "variant" protein, i.e. an protein that does not naturally exist in nature and that is obtained by genetic engineering or by random mutagenesis, i.e. an engineered protein. This variant protein can for example be obtained by substitution of at least one residue in the amino acid sequence of a wild-type, naturally-occurring, protein with a different amino acid. Said substitution(s) can for example be introduced by site-directed mutagenesis and/or by random mutagenesis.

By "cell" or "cells" is intended any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state to which they refer.

By "homologous" is intended a sequence with enough identity to another one to lead to homologous recombination between sequences, more particularly having at least 95% identity, preferably 97% identity and more preferably 99%.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

by "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

The term "gene of interest" refers to any nucleotide sequence encoding a known or putative gene product.

As used herein, the term "locus" is the specific physical location of a DNA sequence (e.g. of a gene) on a chromosome. The term "locus" usually refers to the specific physical location of a target sequence on a chromosome.

By "fusion protein" is intended the result of a well-known process in the art consisting in the joining of two or more genes which originally encode for separate proteins, the translation of said "fusion gene" resulting in a single polypeptide with functional properties derived from each of the original proteins.

By "catalytic domain" is intended the protein domain or module of an enzyme containing the active site of said enzyme; by active site is intended the part of said enzyme at which catalysis of the substrate occurs. Enzymes, but also their catalytic domains, are classified and named according to the reaction they catalyze. The Enzyme Commission number (EC number) is a numerical classification scheme for enzymes, based on the chemical reactions they catalyze (World Wide Web at chem.qmul.ac.uk/iubmb/enzyme/). In the scope of the present document, any catalytic domain can be used as a partner and be fused to a TAL effector domain to generate a chimeric fusion protein resulting in a TAL effector-DNA modifying enzyme. Non-limiting examples of such catalytic domains can be those of MmeI, EsaSSII, CstMI, NucA, EndA *Escherichia coli*, NucM, EndA *Streptococcus pneumonia*, SNase *Staphylococcus aureus*, SNase *Staphylococcus hyicus*, SNase *shigella flexneri*, *Bacillus subtilis* yncB, EndodeoxyribonucleaseI Enterobacteria phage T7, EndoG bovine, ttSmr DNA mismatch repair protein mutS, cleavage domain of Metnase.

The practice of the subject matter disclosed herein will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Current Protocols in Molecular Biology* (Ausubel, 2000, Wiley and son Inc, Library of Congress, USA); *Molecular Cloning: A Laboratory Manual*, Third Edition, (Sambrook et al, 2001, Cold Spring Harbor, N.Y.: Cold Spring Harbor Laboratory Press); *Oligonucleotide Synthesis* (M. J. Gait ed., 1984); U.S. Pat. No. 4,683,195; *Nucleic Acid Hybridization* (Harries and Higgins eds. 1984); *Transcription and Translation* (Hames and Higgins eds. 1984); *Culture of Animal Cells* (Freshney, Alan R. Liss, Inc., 1987); Immobilized Cells and Enzymes (IRL Press, 1986); Perbal, *A Practical Guide to Molecular Cloning* (1984); the series, *Methods in Enzymology* (Abelson and Simon, eds.-in-chief, Academic Press, Inc., New York), specifically, Vols. 154 and 155 (Wu et al. eds.) and Vol. 185, "Gene Expression Technology" (Goeddel, ed.); *Gene Transfer Vectors For Mammalian Cells* (Miller and Calos eds., 1987, Cold Spring Harbor Laboratory); *Immunochemical Methods in Cell and Molecular Biology* (Mayer and Walker, eds., Academic Press, London, 1987); *Handbook of Experimental Immunology*, Vols. I-IV (Weir and Blackwell, eds., 1986); and *Manipulating the Mouse Embryo*, (Cold Spring Harbor Laboratory Press, Cold Spring Harbor, N.Y., 1986).

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, the invention being further described in the following examples, which do not limit the scope of the invention described in the claims unless otherwise specified.

EXAMPLES

Example 1—A Cipher Governs TAL Effector-DNA Recognition

To determine whether there is a one-to-one, linear correspondence between RVDs and contiguous nucleotides in the TAL target site, the predicted promoter region (i.e., the 1,000 bp immediately preceding the annotated translational start site) of the known target gene for each of ten TAL effectors was scanned with the TAL effector RVD sequence for alignments that minimized entropy (randomness) in RVD-nucleotide associations. The following formula was used to quantify entropy, where R is the set of RVDs for the effector, D is the set of four nucleotides (A, C, G, T), and $f_{i,j}$ represents the observed frequency with which the $i_{th}$ RVD associates with the $j_{th}$ nucleotide:

$$\sum_{i \in R} \sum_{j \in D} \max_j(f_i) - f_{i,j}$$

Multiple low entropy sites were present in each promoter. For effector AvrBs3, however, only one mapped to the 54 bp upa20 promoter fragment identified previously as sufficient and necessary for activation, and it coincided with the UPA box common to genes directly activated by AvrBs3 (Kay et al., supra). Also, for effectors PthXo1 and AvrXa27, only one site each overlapped a polymorphism between the activated and non-activated alleles of their respective targets, Os8N3 and Xa27. Across the alignments at these three sites, RVD-nucleotide associations were consistent, so the remaining alignments were selected based on those associations, resulting in exactly one site per TAL effector-target pair (FIG. 1B and Table 2). Each site is preceded by a T (FIG. 1D).

To assess the specificity conferred by the RVD-nucleotide associations, a weight matrix was first generated based on the frequencies of all RVD-nucleotide associations observed across the ten minimal entropy TAL effector-target site alignments (FIG. 1B). The weight matrix was then used to scan the promoter region, the 1,000 bp preceding the translational start, of each nonredundant gene model in rice, Oryza sativa spp. japonica cv. Nipponbare (Osa1, Release 6.0, rice.plantbiology.msu.edu) for best matches to the five TAL effectors of the rice pathogen Xanthomonas oryzae (AvrXa27, PthXo1, PthXo6, PthXo7, and Tal1c). For AvrXa27, the sequence upstream of Xa27 (GenBank accession AY986492) was included. This upstream sequence is not present in Nipponbare. Observed association frequencies were weighted at 90% and the remaining 10% was distributed equally to frequencies of all possible associations. Alignments were ranked using a weight matrix score (y axis), taken as a negative log of the frequency score derived from the RVD-nucleotide association frequencies in FIG. 1B. Thus, the lower the score, the better the match. For PthXo1, PthXo6, PthXo7, and Tal1c, the experimentally identified target gene was the best or nearly best match. Better matches were not preceded by a T, were not represented on the microarray used to identify the target, or lacked introns and EST evidence. Scanning the reverse complement promoter sequences yielded no better scoring alignments than the forward sites for the known targets. This result does not imply that TAL effectors bind to the positive strand, but indicates that they function in a forward orientation relative to the positive strand. The known target of the fifth effector, AvrXa27, is the disease resistance gene Xa27 (Gu et al., supra). The poorer rank for this match (5,368) may reflect a calibrated, or recent and sub-optimal host adaptation. Better scoring sites likely comprise genes targeted by AvrXa27 for pathogenesis.

Using the weight matrix again, ten additional alignments were obtained by scanning all rice promoters with 40 additional *X. oryzae* TAL effectors and retaining the best alignments for which the downstream gene was activated during infection based on public microarray data (PLEXdb.org, accession OS3) (Table 3). As with the initial set, a T precedes each site, and no reverse-strand sites scored better. The RVD-nucleotide association frequencies of the total 20 alignments are shown in FIG. 1C. They constitute a strikingly simple cipher.

The RVD-nucleotide frequencies in the expanded set of 20 TAL effector nucleotide alignments were used to generate a new weight matrix, and a computational script was written in Python v2.5 (www.python.org). The script can be used to scan any collection of DNA sequences for matches to a particular TAL effector, with a user-definable weight factor for observed vs. unobserved RVD-nucleotide associations. See Moscou and Bogdanove (supra).

There is some degeneracy in the cipher. Strong associations may represent anchors that account for most of the binding affinity, with weak associations providing a measure of flexibility. Alternatively, neighbor effects may be involved. The latter possibility was investigated by determining the nucleotide association frequencies of every RVD conditioned on the RVD to either side and comparing them to the total observed frequencies—in other words, by sorting the RVD-nucleotide pairings according to the neighbor RVD to the left or right, and comparing the relative frequencies of each pair thus sorted with the overall frequency for that pair. The frequencies of the RVD-nucleotide associations sorted by neighbor did not deviate significantly from the total observed frequencies, suggesting that the associations are context independent.

Sequences flanking the 20 target sites revealed no conserved nucleotides except the T at −1, but they tend to be C-rich following the site and G-poor throughout (FIG. 1D). With few exceptions, sites begin within 60 bp upstream of the annotated transcriptional start, and none are closer than 87 bp to the translational start (Table 2 and Table 3). Additional rules governing RVD/nucleotide associations are described in Examples 4 and 5.

Given these results, prediction of TAL effector targets in a genome and construction of targets de novo are now possible. The ability to predict sites will expedite identification of host genes important in disease. The ability to construct targets holds promise for designing durable resistance genes that are responsive to conserved or multiple TAL effectors. Customizing TAL effectors for arbitrary gene activation or targeting of fused proteins for DNA modification also is possible, as described herein.

TABLE 2

Predicted target site features for experimentally identified TAL effector-target pairs

| TAL effector | Source | RVDs | Target gene | TcS | TATA box | TlS |
|---|---|---|---|---|---|---|
| AvrXa27[1] | *Xanthomonas oryzae* pv. *oryzae* PXO99[A] | 17 | Xa27 (rice) | 27 | −7 | 87 |
| AvrBs3[2] | *X. campestris* pv. *vesicatoria* | 18 | Bs3 (pepper) | 59 | 1 | 123 |

TABLE 2-continued

Predicted target site features for experimentally identified TAL effector-target pairs

| TAL effector | Source | RVDs | Target gene | TcS | TATA box | TIS |
|---|---|---|---|---|---|---|
| AvrBs3[3] | X. campestris pv. vesicatoria | 18 | UPA20 (pepper) | 72 | 1 | 150 |
| AvrBs3Δrep16[4,5] | Modified AvrBs3 | 14 | Bs3-E (pepper) | 85 | 1 | 136 |
| AvrBs3Δrep109[4] | Modified AvrBs3 | 15 | Bs3 (pepper) | 59 | 1 | 123 |
| AvrHah1[6] | X. gardneri | 14 | Bs3 (pepper) | 59 | 1 | 121 |
| PthXo1[7] | X. oryzae pv. oryzae PXO99[A] | 24 | Os8N3 (rice) | 79 | 46 | 251 |
| PthXo6[8] | X. oryzae pv. oryzae PXO99[A] | 23 | OsTFX1 (rice) | 31 | −780 | 136 |
| PthXo7[8] | X. oryzae pv. oryzae PXO99[A] | 22 | OsTFIIAγ1 (rice) | 333 | 44 | 469 |
| Tal1c | X. oryzae pv. - oryzicola BLS256 | 16 | OsHEN1 (rice) | 10 | −265 | 217 |

RVDs, repeat-variable diresidues; TcS, annotated transcriptional start site; TIS, translational start site. Locations are relative to the 5' end of the target site.
[1]Gu et al., supra
[2]Kay et al. (2007) Science 318: 648
[3]Römer et al. (2007) Science 318: 645
[4]Herbers et al. (1992) Nature 356: 172
[5]Römer et al. (2009) Plant Physiol.
[6]Schornack et al. (2008) New Phytologist 179: 546
[7]Yang et al. (2006) Proc. Natl. Acad. Sci. USA 103: 10503
[8]Sugio et al. (2007) Proc. Natl. Acad. Sci. USA

TABLE 3

Xanthomonas oryzae TAL effector candidate targets in rice activated during infection.

| Effector | Strain | RVDs | Rice locus | r | TcS | TATA box | TIS | q | Fold change |
|---|---|---|---|---|---|---|---|---|---|
| Tal1c | BLS256 | 16 | OsHen1 | 1 | 10 | −265 | 217 | 0.01 | 3.3 |
| Tal2c | BLS256 | 27 | Os03g03034 | 15 | −16 | −145 | 143 | 0.01 | 5.2 |
| Tal2d | BLS256 | 16 | Os04g49194 | 9 | 27 | n.p. | 102 | 3.9E−07 | 29.7 |
| Tal3b | BLS256 | 18 | Os05g27590 | 42 | 34 | −1 | 104 | 3.4E−08 | 8.5 |
| Tal4a | BLS256 | 26 | Os03g37840 | 1 | 152 | 221 | 363 | 2.2E−04 | 2.6 |
| Tal4b | BLS256 | 14 | Os09g32100 | 72 | 68 | n.p. | 271 | 8.0E−03 | 3.6 |
| Tal4c | BLS256 | 23 | Os06g37080 | 18 | 31 | n.p. | 151 | 2.7E−10 | 17.1 |
| Tal6 | BLS256 | 20 | Os07g47790 | 16 | −15 | −70 | 93 | 3.6E−02 | 21.6 |
| PthXo1 | PXO99[A] | 24 | Os8N3 | 1 | 79 | 46 | 251 | 1.0E−08 | 84.2 |
| PthXo6 | PXO99[A] | 23 | OsTFX1 | 2 | 31 | −780 | 136 | 3.5E−03 | 2.8 |
| PthXo7 | PXO99[A] | 22 | OsTFIIAγ1 | 7 | 333 | 44 | 469 | 1.6E−06 | 4.5 |
| Tal9a | PXO99[A] | 20 | OsHen1 | 1 | 44 | −3 | 93 | 0.13 | 8.2 |
| Tal7a/8a | PXO99[A] | 18 | Os01g68740 | 2 | 32 | −197 | 102 | 1.8E−01 | 1.7 |
| Tal7b/8b | PXO99[A] | 20 | Os01g40290 | 57 | −2 | −276 | 206 | 1.8E−01 | 1.7 |

RVDs, repeat-variable diresidues; r, rank out of 58,918 gene models scanned, based on the RVD weight matrix score; TcS, annotated transcriptional start site; n.p., not present; TIS, translational start site. Locations are relative to the 5' end of the target site. q values are for a comparison to mock across five time points up to 96 hours after inoculation, replicated four times; fold change given is at 96 hours (PLEXdb, accession OS3).

Example 2—TALENs can Function in Yeast

Plasmid Construction:

The protein coding sequence of the TAL effector, AvrBs3, was obtained by digestion from a plasmid with BamHI. A DNA fragment encoding principally the repeat domain was excised with SphI. The amino acid sequence of AvrBs3 can be found under GENBANK Accession No. P14727 and SEQ ID NO:12 (FIG. 3), and the nucleic acid sequence under Accession No. X16130 and SEQ ID NO:13 (FIG. 4). In FIG. 4, the BamHI and SphI sites are in bold and underlined. The AvrBs3 BamHI and SphI fragments were cloned into the nuclease expression vector pDW1789_TAL (FIG. 5) adjacent to sequences encoding the FokI nuclease domain. To clone the AvrBs3 target site into the target reporter plasmid, two complementary DNA oligos, containing two AvrBs3 recognition sites arranged in an inverted orientation with an 18 bp spacer sequence in between, were synthesized with BglII and SpeI overhangs at the 5' and 3' ends, respectively. Other reporter plasmids were made that had recognition sites with spacer lengths of 6, 9, 12 and 15 bp. The annealed DNA oligos were cloned into the reporter plasmid, pCP5 (FIG. 6), which was digested with BglII and SpeI.

Yeast Assay:

The target reporter plasmids were transformed into the yeast strain YPH499 (a MAT a strain), and transformants were selected on synthetic complete medium lacking tryptophan (SC—W). The TALEN expression plasmids were transformed into YPH500 (a MAT a strain); and transformants were plated on SC medium lacking histidine (SC—H). Yeast colonies carrying the target reporter plasmid and colonies carrying the TALEN expression plasmid were cultured overnight at 30° C. in liquid SC—W and SC—H media, respectively. The cultures were adjusted to the same $OD_{600}$, and 200 µl of each were mixed into 200 µl YPD medium. The mixture was incubated at 30° C. for 4 hours to allow the two types of yeast strain to mate. The mixed culture was spun down and resuspended in 5 ml SC—W—H media at 30 C overnight or until the $OD_{600}$ reaches a range of 0.5-1. The cells were harvested and quantitative β-galactosidase assays were performed as described (Townsend et al. (2009) Nature 459:442-445).

Figure 7:
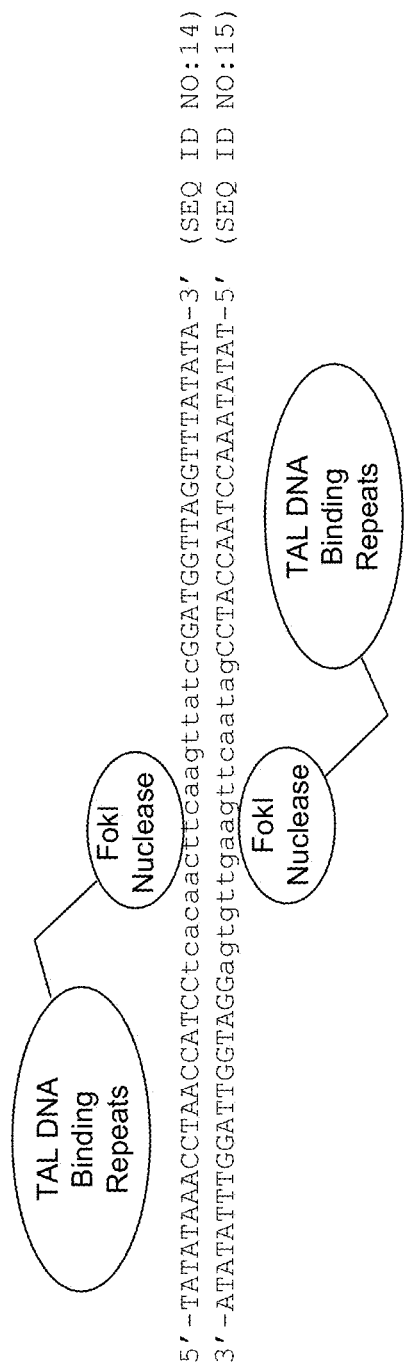
FIG. 7 is a diagram of the schematic architecture of TAL nucleases. The recognition sites of TAL DNA binding domain are represented as capital letters, while the spacer sequence is indicated in lowercase.

Results:

The TAL-FokI fusion is a site-specific nuclease consisting of the TAL DNA recognition domain and the non-specific FokI DNA cleavage domain. The TAL DNA recognition domain can be engineered to bind different DNA sequences. As described in Example 1 herein, the DNA recognition specificity for TAL effectors, a novel class of DNA binding domain, has been deciphered. In particular, the DNA binding domain of TAL effectors contain a various number of tandem, 34-amino acid repeats, which can recognize and bind to specific DNA sequences. Amino acid sequences of the repeats are conserved except for two adjacent highly variable residues at positions 12 and 13 of the repeats. These positions together specify individual nucleotides in the DNA binding site, one repeat to one nucleotide. The architecture of the TALENs is illustrated in FIG. 7. The TALENs function as dimers, with each monomer composed of engineered TAL DNA recognition repeats fused to a non-specific cleavage domain from the FokI endonuclease. The DNA recognition repeats can be engineered to bind target DNA sequences within a genome of interest. TAL nuclease monomers bind to one of two DNA half-sites that are separated by a spacer sequence. This spacing allows the FokI monomers to dimerize and create a double-strand DNA break (DSB) in the spacer sequence between the half-sites.

Figure 5:
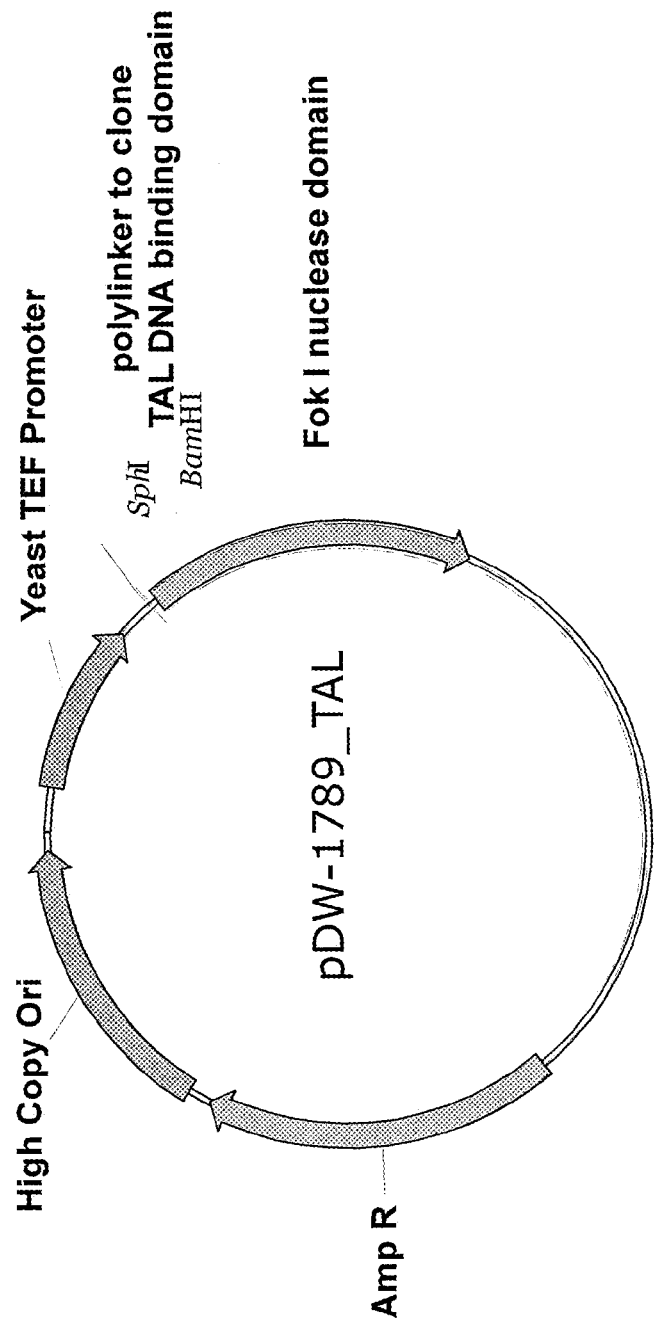
FIG. 5 is a map of a TAL nuclease expression vector.
Figure 6:
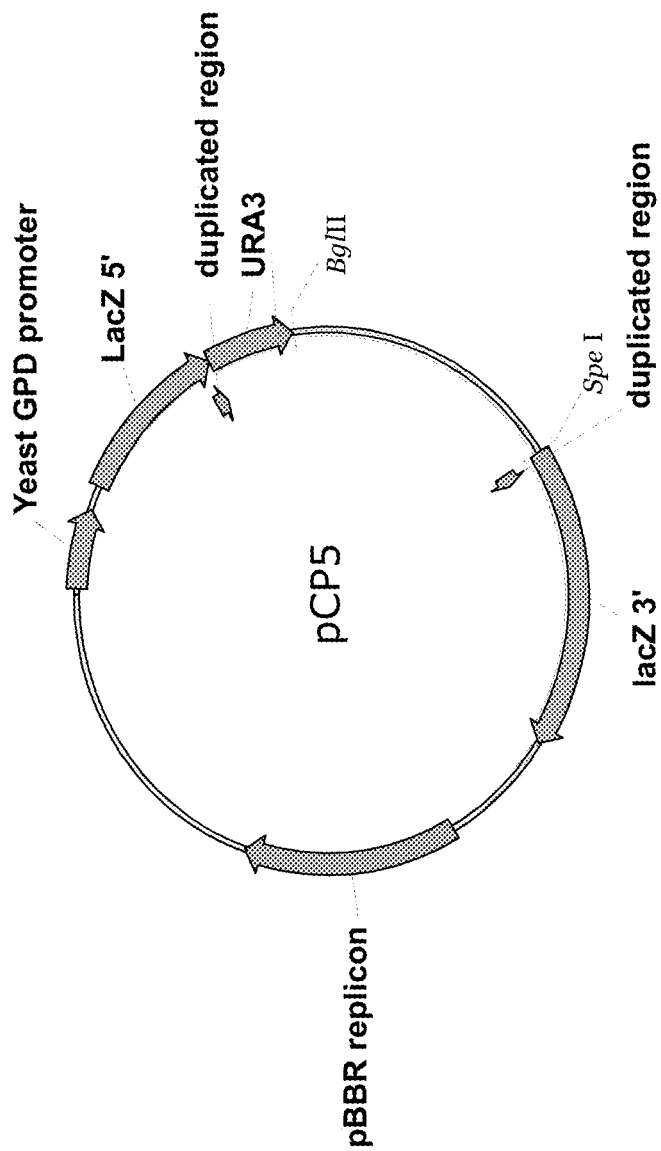
FIG. 6 is a map of a target reporter plasmid.

To explore the potential of the TAL effector DNA recognition domain, experiments were conducted to determine whether native TAL effectors can function as nucleases when fused with the FokI nuclease domain. The yeast-based assay was carried out by using a TAL nuclease expression construct and a target reporter construct. As illustrated in FIG. 5, the backbone of the nuclease expression construct contains a FokI nuclease domain and an N-terminal nuclear localization signal (NLS) under control of the yeast TEF1 promoter. Several restriction sites are located between the FokI nuclease domain and the NLS motif to facilitate cloning of various TAL effectors. The target reporter construct has a disrupted lacZ reporter gene with a 125 bp duplication of coding sequence as shown in FIG. 6. The duplication flanks a URA3 gene and a target sequence (composed of two half sites and a spacer sequence) recognized by TAL DNA binding domains. If the TALEN binds and generates DNA double-strand breaks (DSBs) at the target site, such breaks, in yeast, are repaired predominantly by homologous recombination between the duplicated lacZ sequences through single strand annealing (Haber (1995) Bioessays 17:609). Recombination results in reconstitution of a functional lacZ gene and loss of URA3 (conferring 5-fluoroorotic acid resistance). Relative cleavage activity of TALENs was measured by determining lacZ enzyme activity.

Figure 9:
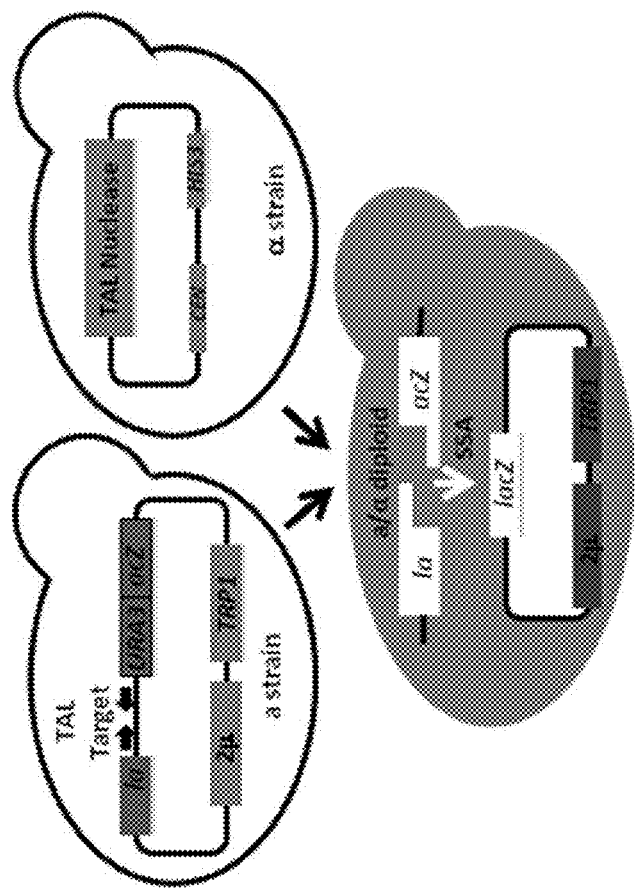
FIG. 9 is a diagram showing a scheme for a yeast assay to test TAL effectiveness.
Figure 10:
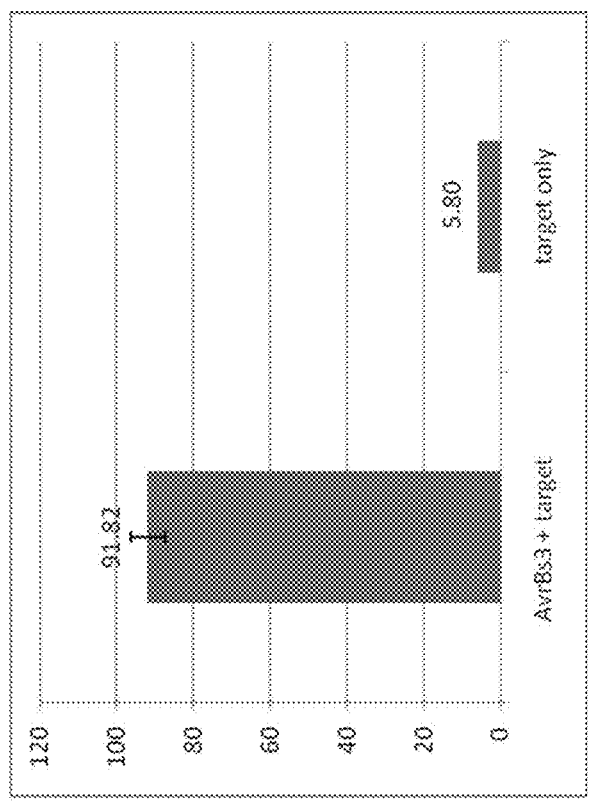
FIG. 10 is a graph plotting yeast assay results of AvrBs3 TAL nuclease.

In these studies, a native TAL effector, AvrBs3, which had a central nuclease repeat region as set forth in SEQ ID NO:3 (FIG. 8) was cloned into the nuclease expression vector, and the AvrBs3 target sites (two binding sites arranged in an inverted orientation) with an 18 bp spacer sequence were cloned into the target reporter vector. The yeast assay was performed using the scheme shown in FIG. 9 and described above. The results showed that the lacZ activity from yeast cells transformed with both the AvrBs3 nuclease plasmid and the target reporter plasmid was significantly higher (15.8-fold higher) than the control yeast cells that contained only the target reporter plasmid (FIG. 10). No activity was observed with nuclease fusions made with only the SphI fragment that encodes predominantly the repeat domain. This indicated that sequences other than the DNA binding domain are required for TALEN activity. Reporter plasmids with spacer lengths of 6 and 9 bp also failed to show activity, indicating that the space between the two binding sites is critical to allow FokI to dimerize. These data indicate that the AvrBs3 TAL nuclease can function as a site-specific nuclease that cleaves its cognate target sequence in yeast.

Example 3—Modular Assembly of TAL Effector Repeats for Customized TALENs

Figure 11:
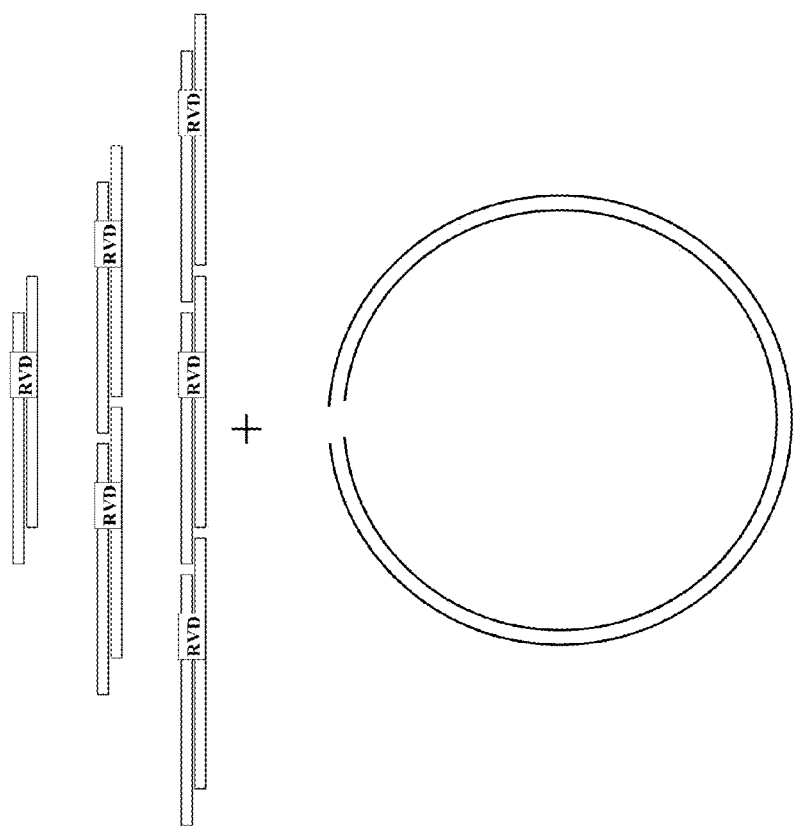
FIG. 11 is a diagram showing a schematic representation of single, double, or triple AsvBs3 repeat modules and a cloning vector.

Complementary oligonucleotides corresponding to the 102 basepairs of each of four individual TAL effector repeats, each specifying a different nucleotide, are synthesized, annealed and cloned into a high copy bacterial cloning vector, individually and in combinations of 2 and 3 repeats in all permutations to yield 4 single, 16 double, and 64 triple repeat modules using standard restriction digestion and ligation techniques (e.g., as illustrated in FIG. 11). The desired TAL effector coding sequence is assembled by introducing the appropriate modules sequentially into a Gateway-ready high copy bacterial cloning vector containing a truncated form of the tal1c gene that lacks the central repeat region except for the characteristic final half repeat. For example, an 18 repeat TAL effector coding sequence can be assembled by sequentially introducing 5 triple modules and 1 double module into the truncated tal1c vector.

Example 4—A System for Modular Assembly of TAL Effector Repeats

Plasmids and methods were developed for generating custom TAL effector-encoding genes. The functional specificity of TAL effectors is determined by the RVDs in the repeats, as described herein; other polymorphisms in the repeats and elsewhere in the proteins are rare and inconsequential with regard to functional specificity. Thus, custom TAL effector genes were generated by replacing the repeat region of an arbitrary TAL effector gene with repeats containing the desired RVDs. The repeat sequences outside the RVDs matched a consensus sequence (see below). DNA fragments encoding TAL effector repeats were sequentially assembled into modules encoding one, two, or three repeats, and the modules were cloned into a TAL effector gene from which the original repeats were removed. Each encoded repeat, with the exception of the last (half) repeat, had the sequence LTPDQVVAIASXXGGKQALETVQRLLPVLC-QDHG (SEQ ID NO:18; FIG. 12A). The last (half) repeat had the sequence LTPDQVVAIASXXGGKQALES (SEQ ID NO:20; FIG. 12B). In both sequences, "XX" indicates the location of the RVD. The RVDs used in the modular repeats were NI, HD, NN, and NG, which specify binding to A, C, G, and T, respectively. In the experiments described below, the tal1c gene of Xanthomonas oryzae pv. oryzicola strain BLS256, with its repeats removed, was used as the "backbone" for building custom TAL effector genes.

The method described herein included five components: (1) generation of single repeat starter plasmids; (2) generation of single repeat module plasmids; (3) generation of multiple repeat modules; (4) generation of a complete set of one-, two-, and three-repeat module plasmids; and (5) assembly of custom TAL effector coding sequences.

Figure 13:
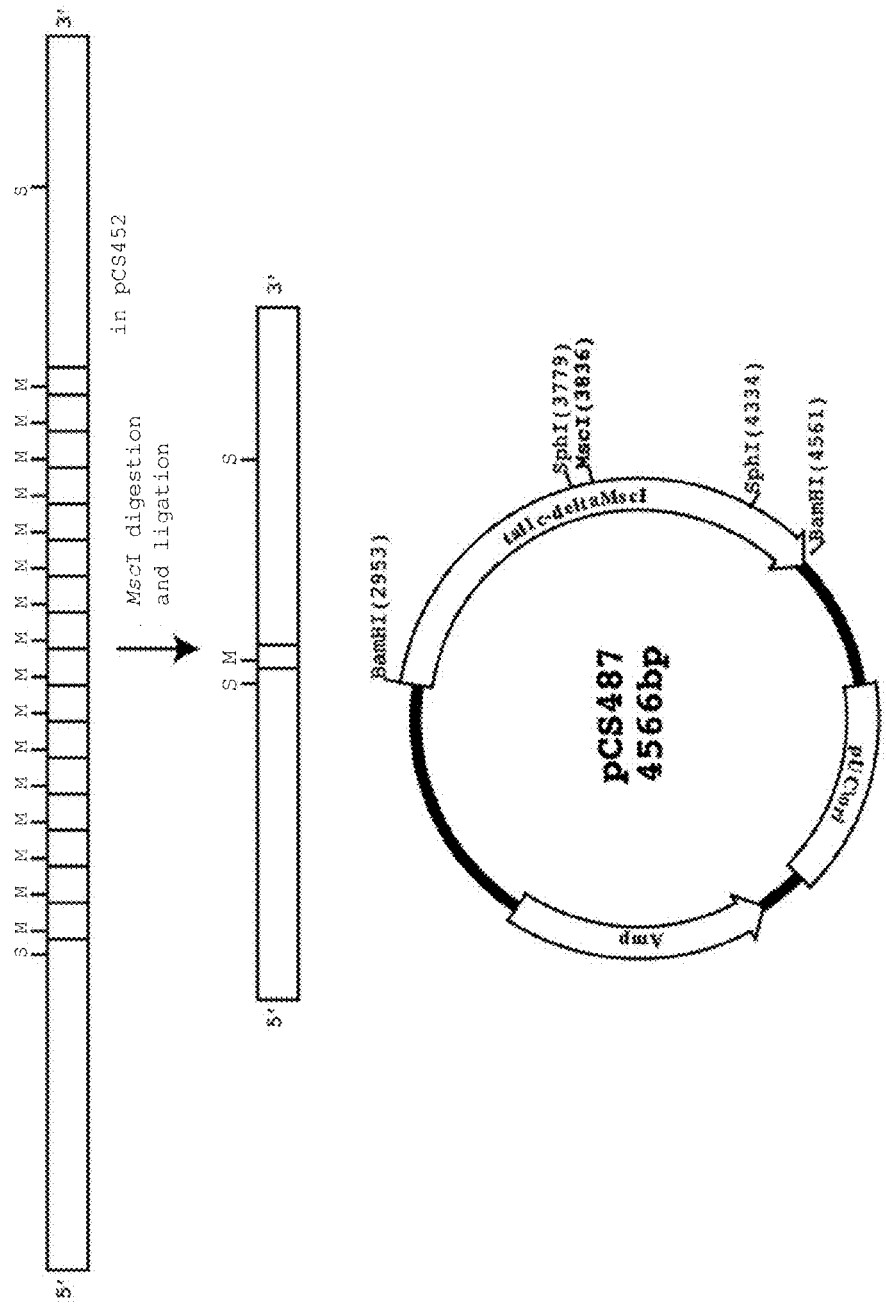
FIG. 13 is a schematic depicting the tal1c gene and the process by which the repeat region was reduced to a single, truncated repeat, resulting in pCS487, also shown. M, MscI site; S, SphI site.

To generate single repeat starter plasmids, the tal1c gene was digested with MscI and religated to remove the entire repeat region except for the first part of the first repeat and the last part of the last, truncated repeat, resulting in the plasmid designated pCS487 (FIG. 13). The resulting gene encoded the RVD NI and, like most TAL effector genes, contained two SphI sites that flanked the repeat region. The gene contained no XhoI site.

Figure 14:
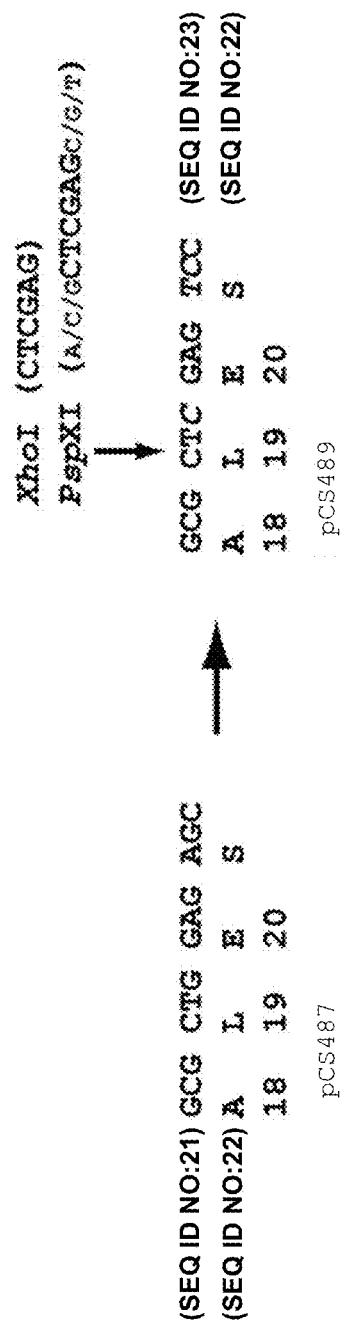
FIG. 14 is a schematic depicting introduction of a translationally silent mutation at the end of the original truncated repeat in pCS487 to create a PspXI and XhoI site, yielding pCS489. Sequences of codons 18-21 in the original repeat (SEQ ID NO:6) and the mutated repeat (SEQ ID NO:8) are shown. The encoded amino acid sequence (SEQ ID NO:7) was not changed by the mutation. The mutated nucleotides are italicized.

Next, a translationally silent mutation was introduced into pCS487 to create a unique PspXI site, which encompasses a unique XhoI site centered on codons 19 and 20. The mutation is depicted in FIG. 14, which shows the original and altered nucleotide sequences for codons 18-21 (SEQ ID NO:21 and SEQ ID NO:23, respectively), both of which encode the amino acid sequence ALES (SEQ ID NO:22). The resulting plasmid was designated pCS489.

Figure 15:
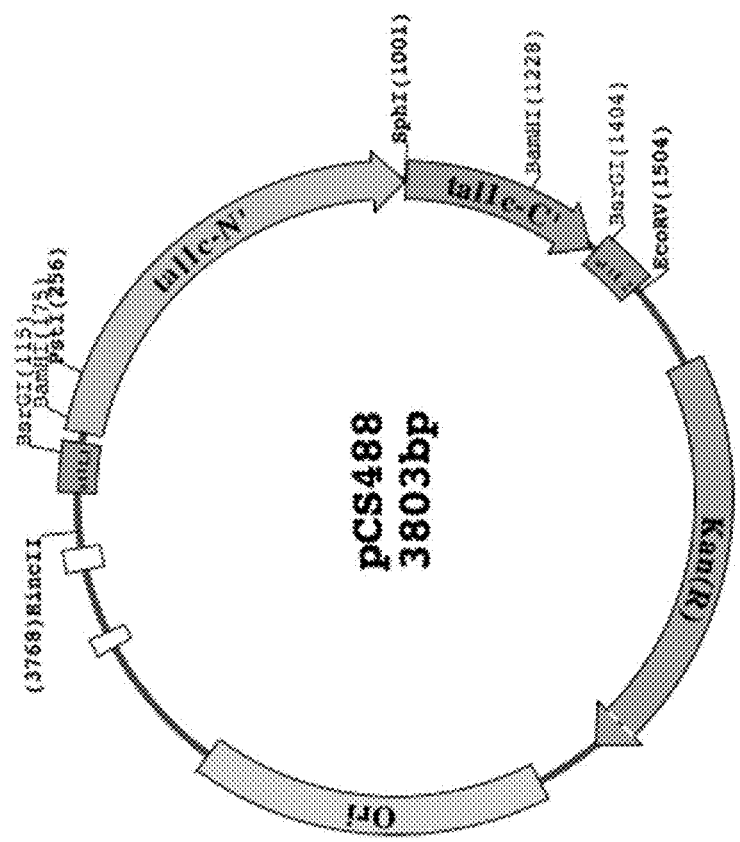
FIG. 15 is a map of pCS488, which is a kanamycin resistant plasmid encoding only the N- and C-terminal portions of tal1c, without the repeat region, in the Gateway entry vector pENTR-D (Invitrogen, Carlsbad, Calif.).
Figure 16:
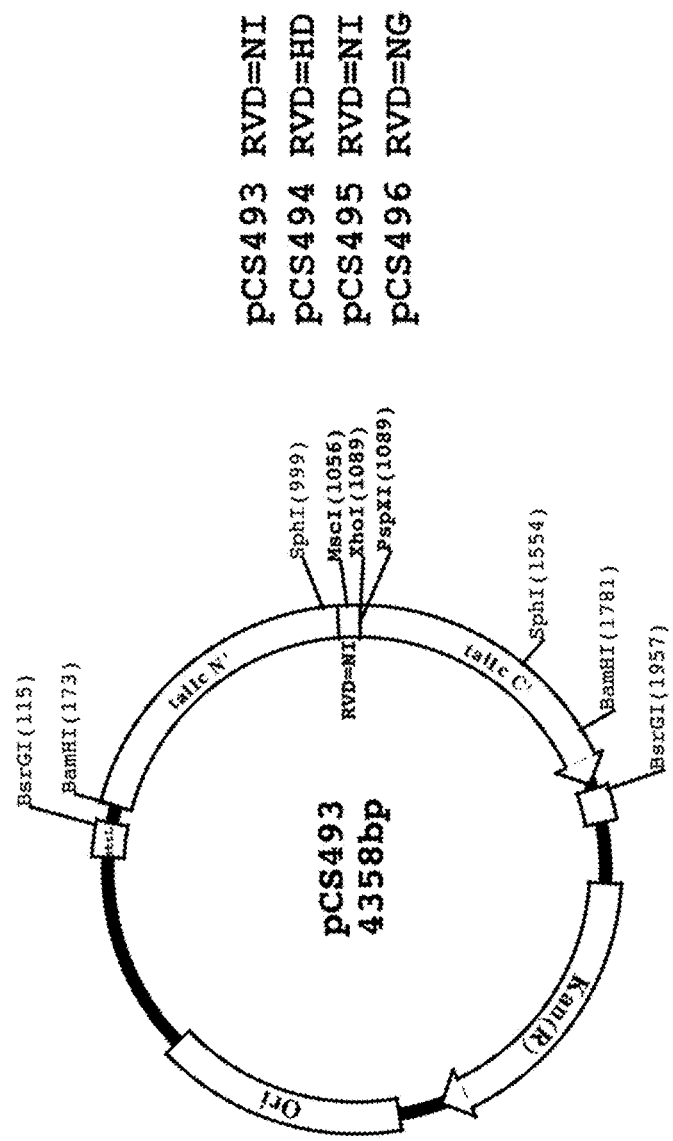
FIG. 16 is a map of the single repeat starter plasmid designated pCS493, which encodes a repeat having the RVD NI. Three other plasmids, designated pCS494, pCS495, and pCS496, were identical except for the RVDs they encode (given at right).

By further mutagenesis, three additional constructs were generated with the RVDs HD, NN, and NG, to create the plasmids designated pCS490, pCS491, and pCS492, respectively. The SphI fragment encompassing the modified repeat region was transferred from pCS489, pCS490, pCS491, and pCS492 to the kanamycin resistant plasmid designated pCS488 (FIG. 15), which encoded only the N- and C-terminal portions of tal1c, without the repeat region, in the Gateway entry vector pENTR-D (Invitrogen, Carlsbad, Calif.). This transfer resulted in the single repeat starter plasmids designated pCS493 (FIG. 16), pCS494, pCS495, and pCS496, respectively. The PspXI/XhoI site in the truncated repeat remained unique in these plasmids. The TAL effector gene in pCS488 and each of its derivatives was preceded by Shine-Dalgarno and Kozak sequences for efficient translation in prokaryotes and eukaryotes, respectively.

Single repeat module plasmids were then constructed. One plasmid was generated for each of the four chosen RVDs (NI, HD, NN, and NG). Each plasmid had a 5' compatible cohesive end that reconstituted a XhoI but not a PspXI site when ligated into a PspXI site, and a 3' compatible cohesive end that reconstituted both a XhoI and a PspXI site. The plasmids were generated by cloning annealed synthetic, complementary oligonucleotides with overhangs (FIG. 17A) into the PspXI/XhoI site of pBluescript SK-, resulting in plasmids designated pCS502 (FIG. 17B), pCS503, pCS504, and pCS505, respectively. Each plasmid allowed for introduction of additional repeats at the 3' end of the single repeat module at the unique reconstituted PspXI site, or for excision of the repeat module using the reconstituted XhoI sites.

Figure 18:
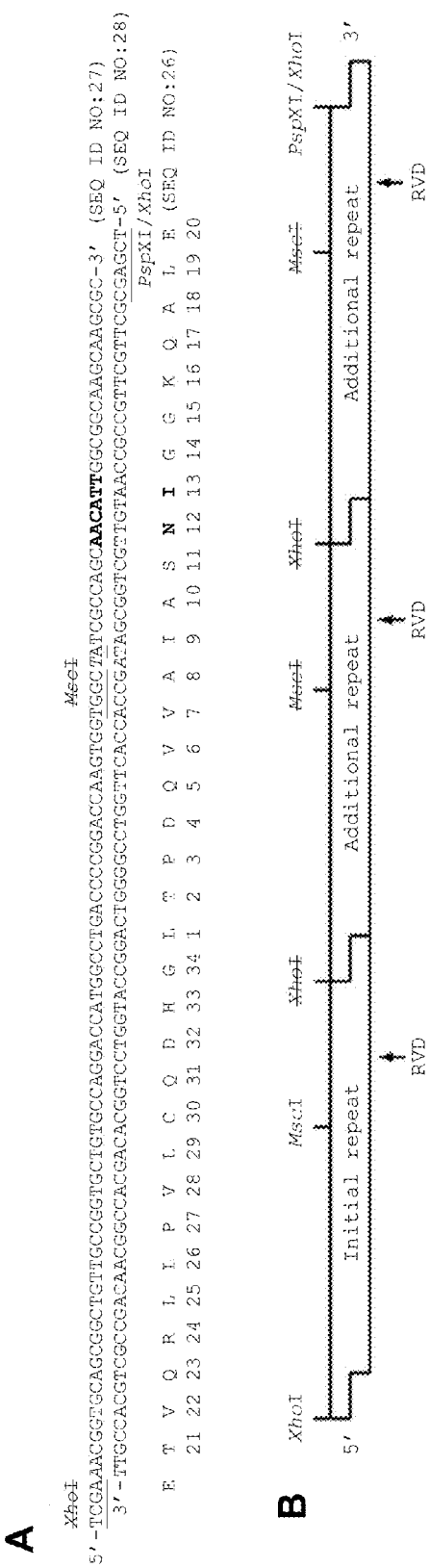
FIG. 18A depicts nucleotide and encoded amino acid sequences for a single repeat module with RVD NI, in which nucleotide substitutions (italicized) prevent reconstitution of the XhoI site at the 5' end following ligation into a PspXI/XhoI site and destroy the internal MscI site. The RVD and its encoding nucleotides are in bold type. Three additional repeat modules were constructed that are identical to that shown except for the RVD encoding sequences, which encode HD, NI, and NG, respectively.
FIG. 18B is a schematic of a three repeat module assembled by sequentially ligating additional repeat modules into a single repeat module plasmid. The MscI site in the first repeat and the PspXI site at the 3' end remain unique, and the entire module is flanked by two XhoI sites.

Additional single repeat modules, one each for NI, HD, NN, and NG, were generated. Each had a 5' compatible cohesive end that did not reconstitute a PspXI or XhoI site when ligated into a PspXI site, a 3' compatible cohesive end that reconstituted both the XhoI and a PspXI site, and a translationally silent nucleotide substitution that destroyed the internal MscI site (FIG. 18A). These modules were generated by annealing synthetic, complementary oligonucleotides with overhangs. Ligating any of these additional single repeat modules into the unique PspXI/XhoI site of a single repeat module plasmid (pCS502, pCS503, pCS504, or pCS505) resulted in no new XhoI site at the 5' junction, but restoration of the unique 3' PspXI/XhoI site, so the resulting plasmids could be linearized for introduction of more additional repeats by cutting with PspXI. Reiteration of this process resulted in modules containing multiple repeats (FIG. 18B). Further, each entire multiple repeat module could be excised using XhoI. Because the MscI site was destroyed in the additional single repeat modules, the MscI site in the initial repeat remained unique, and was useful to check orientation upon subsequent subcloning of the multiple repeat module.

Additional single repeat modules were cloned iteratively into the single repeat module plasmids to generate, along with the single repeat module plasmids, a complete set of all possible one-, two-, and three-repeat modules, for a total of 84 plasmids designated pCS502 through pCS585 (FIG. 19). Modules containing more than three repeats (e.g., four, five, six, seven, eight, nine, ten, or more than ten repeats) are generated in the same manner.

A method was then devised to assemble any sequence of repeats into the tal1c "backbone" to generate a custom TAL effector gene. The method included the following steps, which also are depicted in FIG. 20:

(1) Choose a single repeat starter plasmid with the first desired repeat (pCS493, pCS494, pCS495, or pCS495, encoding RVD NI, HD, NN, or NG, respectively);

(2) linearize the plasmid with PspXI;

(3) isolate the module for the next repeat(s) from the appropriate module plasmid (pCS502 through pCS585) using XhoI;

(4) ligate;

(5) check orientation by digestion with MscI and confirm sequence from the 3' end using a vector based primer; and (6) repeat steps 2-5 until all repeats are assembled.

Example 5—Library of Plasmids for Modular Assembly of TALENs

Assembly of TALEN repeats as described herein (e.g., using the steps depicted in FIG. 20) results in numerous intermediate plasmids containing increasing numbers of repeats. Each of these plasmids is stored such that a library of plasmids for modular assembly of TALENs (pMATs) is generated. For example, FIGS. 21A and 21B depict the assembly of repeat modules in construction of TAL endonucleases that will target the nucleotide sequences shown. In FIG. 21A, repeat modules from plasmids designated pCS519, pCS524, pCS537, pCS551, pCS583, and pCS529 are sequentially added to the sequence in the starter plasmid designated pCS493, resulting in plasmids designated pMAT55, pMAT56, pMAT57, pMAT58, pMAT59, and pMAT60. In FIG. 21B, repeat modules from plasmids designated pCS530, pCS533, pCS522, and pCS541 are sequentially added to the sequence in the plasmid designated pMAT1, resulting in plasmids designated pMAT61, pMAT62, pMAT63, and pMAT64.

Example 6—Generation and Testing of Customized TALENs

Figure 22:
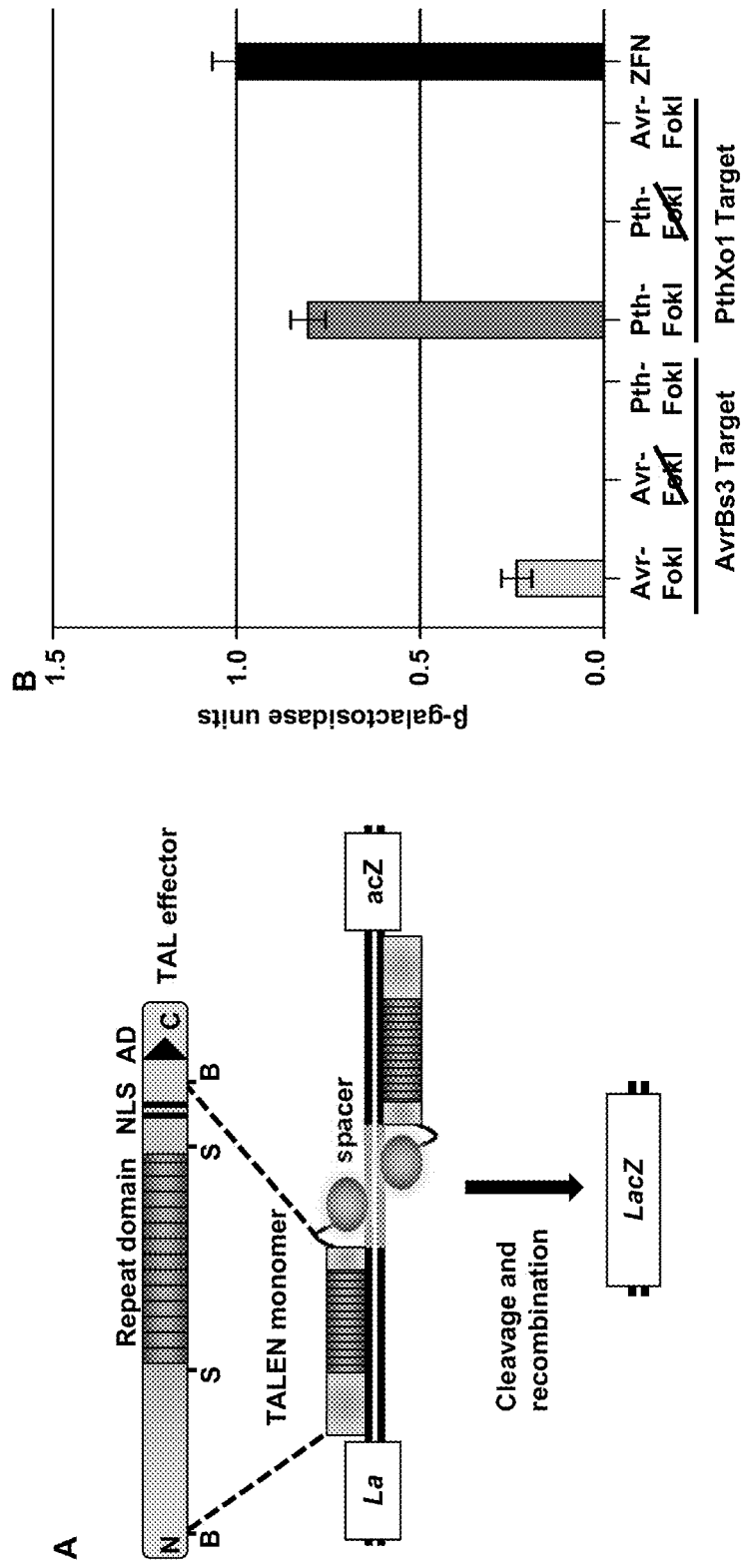
FIG. 22A is a schematic of a TAL effector protein. BamHI fragments (denoted by B's) were fused to the catalytic domain of the FokI endonuclease to create TALENs. N, N-terminus; NLS, nuclear localization signal; B, BamHI site, AD, acidic activation domain.
FIG. 22B is a graph plotting activity of TALENs constructed with TAL effectors AvrBs3 and PthXo1. Avr-FokI, AvrBs3 TALEN; Pth-FokI, PthXo1 TALEN, Avr-FokI and Pth-FokI, AvrBs3 and PthXo1 fusions to a catalytically inactive version of FokI (Bitinaite et al. (1998) *Proc. Natl. Acad. Sci. USA* 95:10570-10575); ZFN, zinc finger nuclease containing the Zif268 DNA binding domain (Porteus and Baltimore (2003) *Science* 300:763).

The TAL DNA recognition domain was used to create TALENs that recognize and cleave particular DNA targets (FIG. 22A), using the system described in Examples 4 and 5. To assess TALEN function, a yeast assay was adapted in which LacZ activity serves as an indicator of DNA cleavage (Townsend et al., supra). In this assay, a target plasmid and a TALEN expression plasmid are brought together in the same cell by mating. The target plasmid has a lacZ reporter gene with a 125-bp duplication of coding sequence. The duplication flanks a target site recognized by a given TALEN. When a double-strand DNA break occurs at the target site, it is repaired through single-strand annealing between the duplicated sequences, which creates a functional lacZ gene whose expression can be measured using standard β-galactosidase assays that provide a quantifiable readout (FIG. 22A). This assay has been demonstrated to be a good predictor of the ability of a ZFN to create chromosomal mutations by NHEJ or to stimulate homologous recombination for gene editing in higher eukaryotes (Townsend et al., supra; and Zhang et al. (2010) Proc. Natl. Acad. Sci. USA 107:12028-12033).

Two well characterized TAL effectors were used—AvrBs3 from the pepper pathogen Xanthomonas campestris pv. vesicatoria and PthXo1 from the rice pathogen X. oryzae pv. oryzae (Bonas et al. (1989) Mol. Gen. Genet. 218:127-136; and Yang et al. (2006) Proc. Natl. Acad. Sci. USA 103:10503-10508). The amino acid sequence of AvrBs3 can be found under GENBANK Accession No. P14727 and SEQ ID NO:12 (FIG. 3), and the nucleic acid sequence under Accession No. X16130 and SEQ ID NO:13 (FIG. 4). The amino acid sequence of PthXo1 can be found under GENBANK Accession No. ACD58243 and SEQ ID NO:31 (FIG. 23), and the nucleic acid sequence under Accession No. CP000967, gene ID 6305128, and SEQ ID NO:32 (FIG. 24). The amino acid sequence of PthXo1 under GENBANK Accession No. ACD58243 is truncated at the N-terminus due to a misannotation of the start codon. The complete sequence is presented in FIG. 23.

Figure 25:
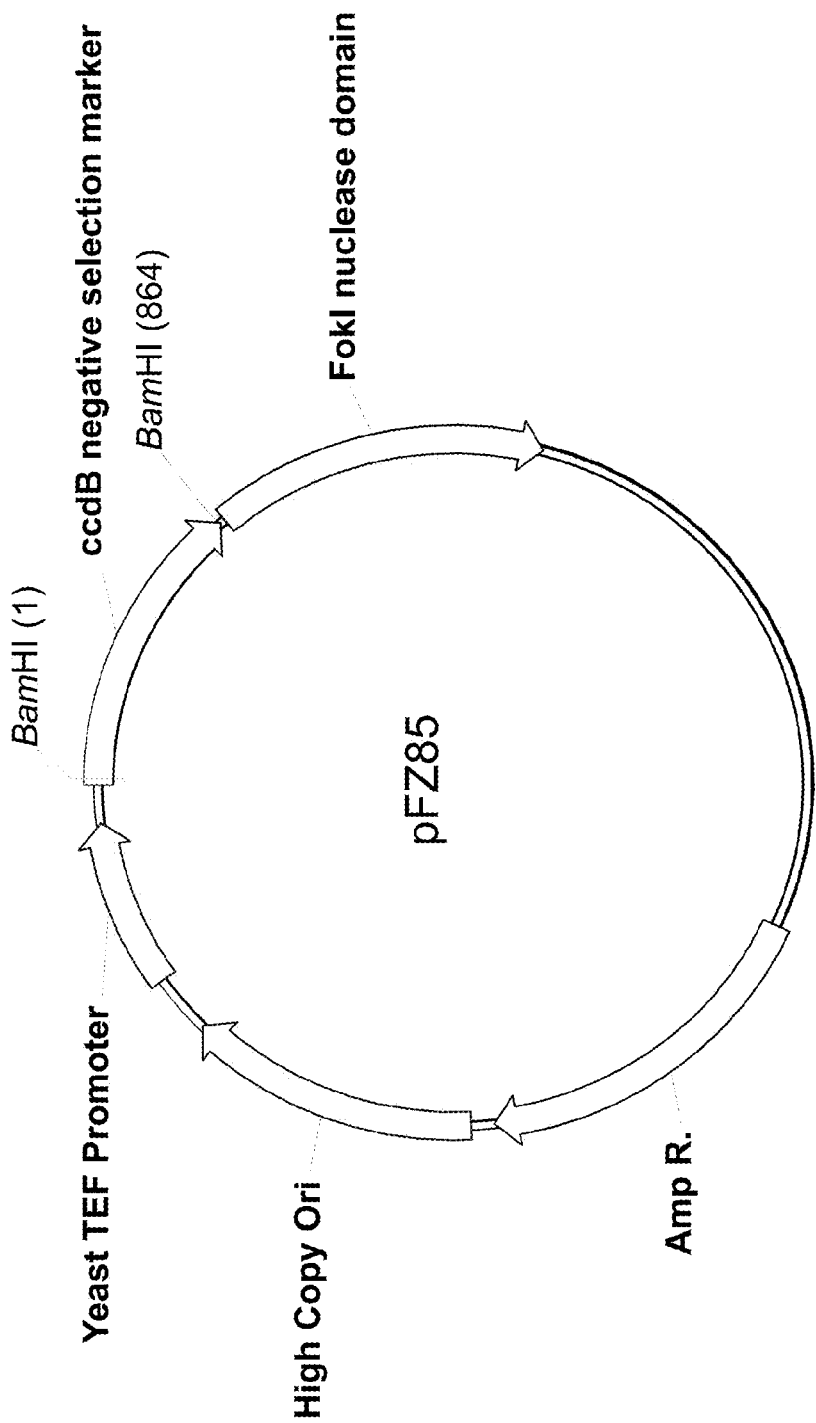
FIG. 25 is a diagram of the pFZ85 vector.

The repeat domains of both AvrBs3 and PthXo1 are encoded entirely within a conserved SphI fragment (FIGS. 4 and 24). Both TAL effector-encoding genes also have a BamHI restriction fragment that encompasses the coding sequence for the repeat domain and 287 amino acids prior and 231 amino acids after (FIGS. 4 and 24; see, also, FIG. 22A). Absent from the BamHI fragment is the TAL effector transcriptional activation domain. Both the SphI fragments and the BamHI fragments were fused to a DNA fragment encoding FokI that is present in the nuclease expression vector pFZ85 (FIG. 25). The fusion proteins between FokI nuclease and the BamHI fragments encoded by AvrBs3 and PthXo1 are given in FIGS. 26 and 27; SEQ ID NOS:33 and 34.

The FokI monomers must dimerize in order to cleave, but the appropriate spacer length between the two DNA recognition sites was unclear. For ZFNs, in which the zinc finger array is separated from FokI by a 4-7 amino acid linker, the typical spacer between the two recognition sites is 5-7 bp (Handel et al. (2009) Mol. Ther. 17:104-111). Since, for example, 235 amino acids separate the repeat domain from FokI in the BamHI TALEN constructs used herein, a variety of spacer lengths for both the BamHI and SphI constructs (6, 9, 12, 15, and 18 bp) were used. As a positive control, a well-characterized zinc finger nuclease with a DNA binding domain derived from the mouse transcription factor Zif268 (Porteus and Baltimore (2003) Science 300:763) was used. As negative controls, the TAL effector domains were fused to a catalytically inactive FokI variant or tested against non-cognate DNA targets.

Haploid cell types containing either TALEN expression or target plasmid in 200 μl of overnight culture were mated in YPD medium at 30° C. After 4 hours, the YPD medium was replaced with 5 ml of selective medium and incubated overnight at 30° C. Mated cultures were lysed, ONPG substrate added, and absorbance read at 415 nm using a 96-well plate reader (Townsend et al., supra). β-galactosidase levels were calculated as a function of substrate cleavage velocity. The results obtained with target reporter constructs that had a 15 bp spacer separating the two recognition sites are shown in FIG. 22B. All nuclease expression constructs derived from the SphI fragment, which encoded principally the repeat array, failed to show activity, indicating that amino acid sequences in addition to those in the repeat array are required for function (FIG. 22B). Robust activity, however, was observed for both the AvrBs3 and the PthXo1 TALENs derived from the BamHI fragment (FIG. 22B). The activity of the PthXo1 TALEN approximated that of the ZFN positive control. The activity required the functional FokI domain and was specific for the DNA target recognized by a given TALEN.

Figure 28:
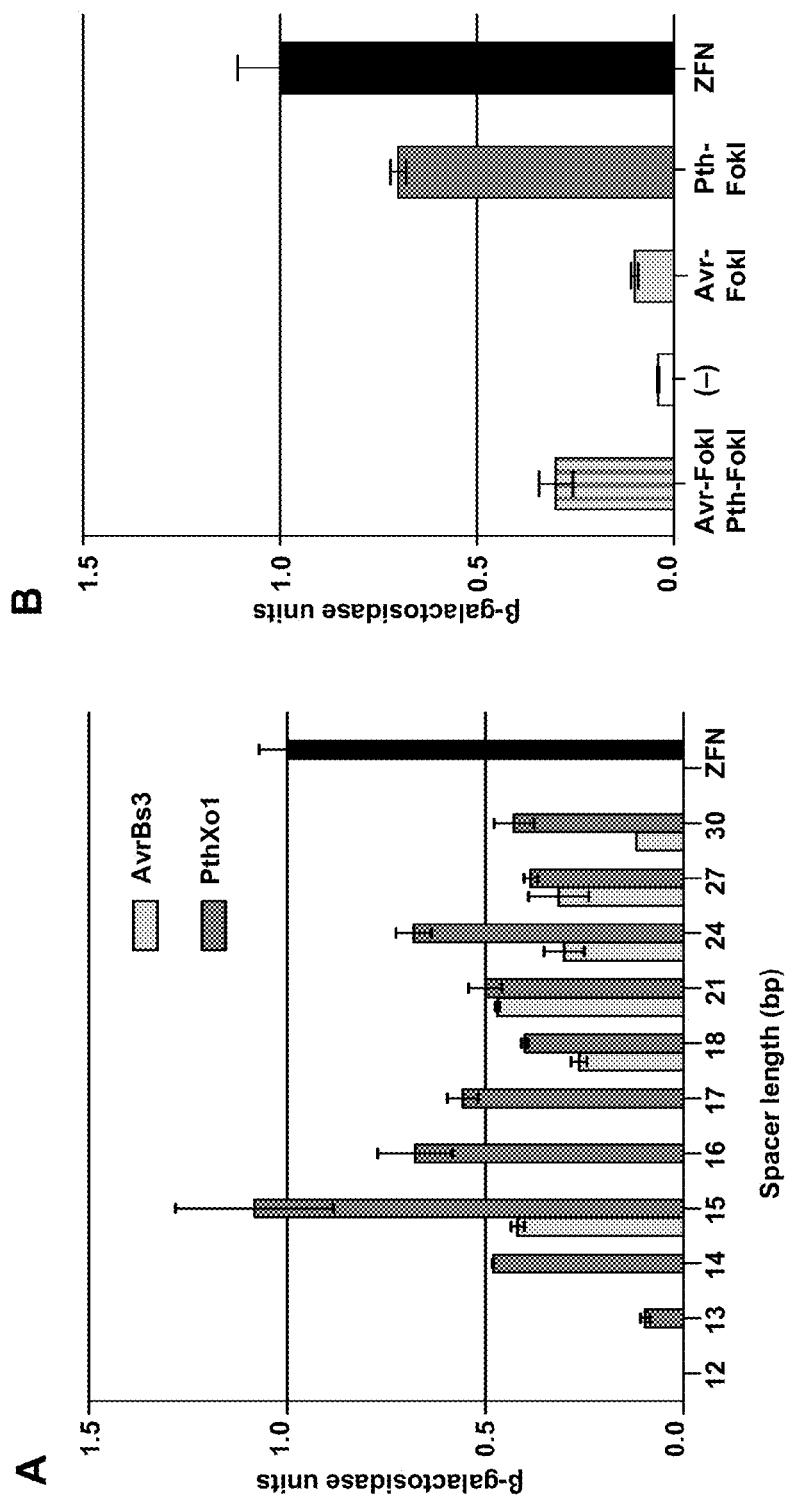
FIG. 28A is a graph plotting activity of AvrBs3 and PthXo1 TALENS on targets with different spacer lengths. ZFN, Zif268-derived zinc finger nuclease.
FIG. 28B is a graph plotting activity of a heterodimeric TALEN. Activity in yeast containing PthXo1-FokI and AvrBs3-FokI expression vectors and a plasmid with a target consisting of recognition sites for each, in head to tail orientation separated by 15 bp is shown (Avr-FokI, Pth-FokI). Also shown for reference is activity of AvrBs3 (Avr-FokI) and PthXo1 (Pth-FokI) TALENS individually and Zif268 (ZFN) on their respective targets. As a negative control, a yeast culture with only the target site plasmid for Avr-FokI, Pth-FokI was assayed for LacZ activity (denoted as (−)).

Experiments also were conducted to test various distances between the TAL effector binding sites (11 length variants between 12 and 30 bp), in order to identify spacer lengths that enable FokI to dimerize most efficiently (FIG. 28A). Both enzymes showed two spacer length optima—one at 15 bp and the other at either 21 bp (AvrBs3) or 24 bp (PthXo1). For PthXo1, activity was observed for all tested spacer lengths 13 bp and longer. Some spacer lengths for AvrBs3 showed no activity, however, suggesting that spacer length is critical for certain TALENs.

The above experiments tested activity of homodimeric TALENs, which bind two identical recognition sequences placed in opposition on either side of the spacer. Since such palindromic sites are unlikely to occur naturally in genomic targets, experiments were conducted to test whether TALENs could function as heterodimers. AvrBs3 and PthXo1 recognition sites were placed in head to tail orientation on either side of a 15 bp spacer. Activity of AvrBs3 and PthXo1 TALENS individually and Zif268 on their respective targets was measured as controls. As a negative control, a yeast culture with only the target site plasmid for the heterodimeric site was assayed for LacZ activity. The resulting activity of the heterodimeric TALEN approximated an average of the activities observed with the two homodimeric enzymes (FIG. 28B).

To test whether repeat domains can be assembled to target TALENs to arbitrary chromosomal sequences, two genes were chosen that were previously targeted for mutagenesis with ZFNs-ADH1 from Arabidopsis and gridlock from zebrafish (Foley et al. (2009) PLoS One 4:e4348; and Zhang et al., supra). A search was conducted for 12-13 bp sequences in the coding regions that were preceded by a 5' T and with a nucleotide composition similar to that of TAL effector binding sites identified by Moscou and Bogdanove (supra). In ADH1 and gridlock, such sites occurred on average every 7-9 bp. Four 12 bp sites were selected in ADH1 (at positions 360, 408, 928, and 975 of the chromosomal gene sequence) and one 13 bp site in gridlock (at position 2356 of the chromosomal gene sequence; FIG. 29A). TAL effector repeat domains were constructed to recognize these targets, using the most abundant RVDs from native TAL effectors (NI for A, HD for C, NN for G, and NG for T). To construct custom TALENs, repeats with these RVDs were synthesized individually and assembled into modules of one, two, or three repeats as described in Examples 4 and 5. These modules were ligated sequentially into a derivative of the tal1c gene (Moscou and Bogdanove, supra) from which the original repeats had been removed, and BamHI fragments from these engineered TAL effectors were fused to sequences encoding the catalytic domain of FokI in pFZ85 (FIG. 25). Five custom TALENs targeted to ADH1 from Arabidopsis and the zebrafish gridlock gene were created.

The resulting custom TALENs were tested in the yeast assay as homodimeric TALENs (that is, the identical DNA binding site was duplicated in inverse orientation on either side of a 16-18 bp spacer), although it is noted that heterodimeric TALENs would need to be constructed to direct cleavage at naturally occurring DNA targets. Spacer lengths were chosen based on the distance closest to 15 bp from the 3' end of the next neighboring (and opposing) candidate site. Sixteen by spacers were used for ADH1-360-12, ADH1-408-12r, and 18 bp spacers for ADH1-928-12, ADH1-975-12r, and gridlock-2356-13r. The yeast assay was performed as described above.

Figure 29B:
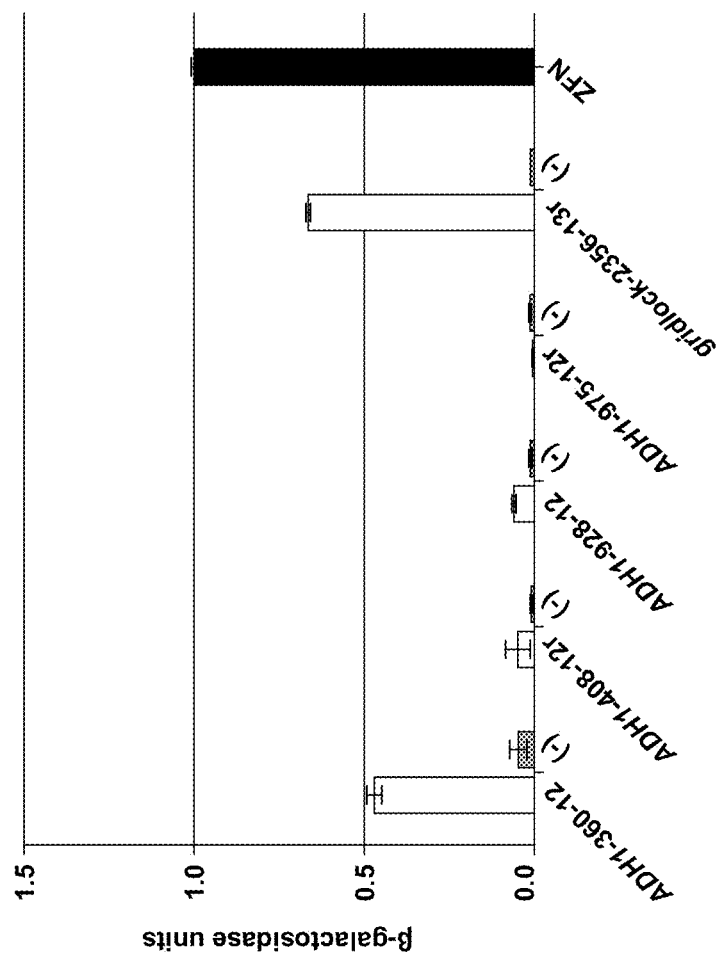
FIG. 29B is a graph plotting the activity of custom TALENs. (−), negative control with target site plasmids only; ZFN, zinc finger nuclease positive control.

Robust nuclease activity was observed for the ADH1-360-12 and gridlock-2356-13r TALEN (FIG. 29B). The ADH1-928-12 TALEN had modest activity that was nonetheless significantly above the negative controls. For each TALEN that gave positive results, nuclease activity was specific to the cognate target. These results indicate that novel, functional TALENs can be created by assembly of customized repeat domains.

Figure 30:
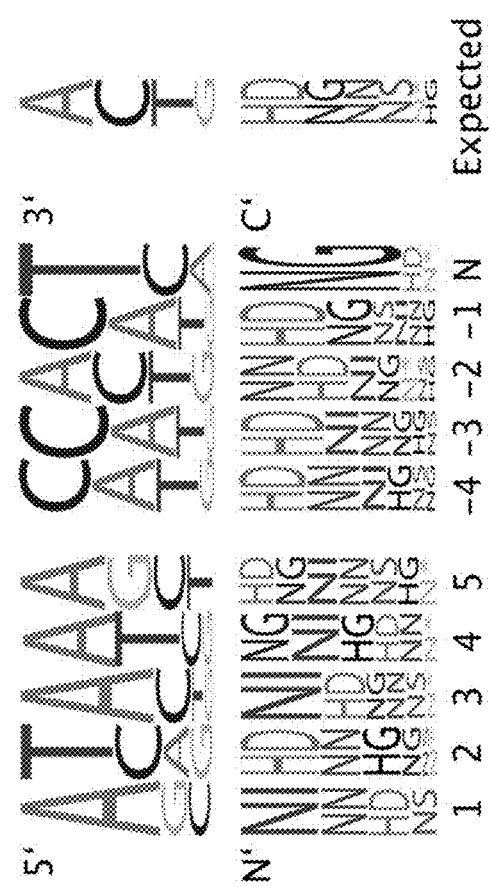
FIG. 30 is a depiction of the nucleotide and RVD frequencies at the termini of 20 target and TAL effector pairs.

Example 7—Naturally Occurring Target and TAL Effector Pairs Show Overall and Positional Bias in Nucleotide and RVD Composition The 20 paired targets and TAL effectors analyzed by Moscou and Bogdanove (supra) were evaluated for overall composition bias and for positional effects on nucleotide or RVD frequencies. It was observed that sites (on the positive strand) were generally A- and C-rich, and G-poor. The average percent A was 31±16% (1 standard deviation). The average percent C was 37±13%. The average percent G was 9±8%, and the average percent T was 22±10%. Since the alignments vary in length, the analysis of positional effects was restricted to the five positions on each end. Strikingly, bias in the target sequences was apparent for A and against T at positions 1 and 3, and for T at position N and possibly 2. G was particularly rare at position N−1. This bias was reflected by matching RVDs in the effectors, with NI being most common at positions 1 and 3, no NG at position 1, nearly always NG at position N, and rarely NN at position N−1 (FIG. 30).

Figure 31:
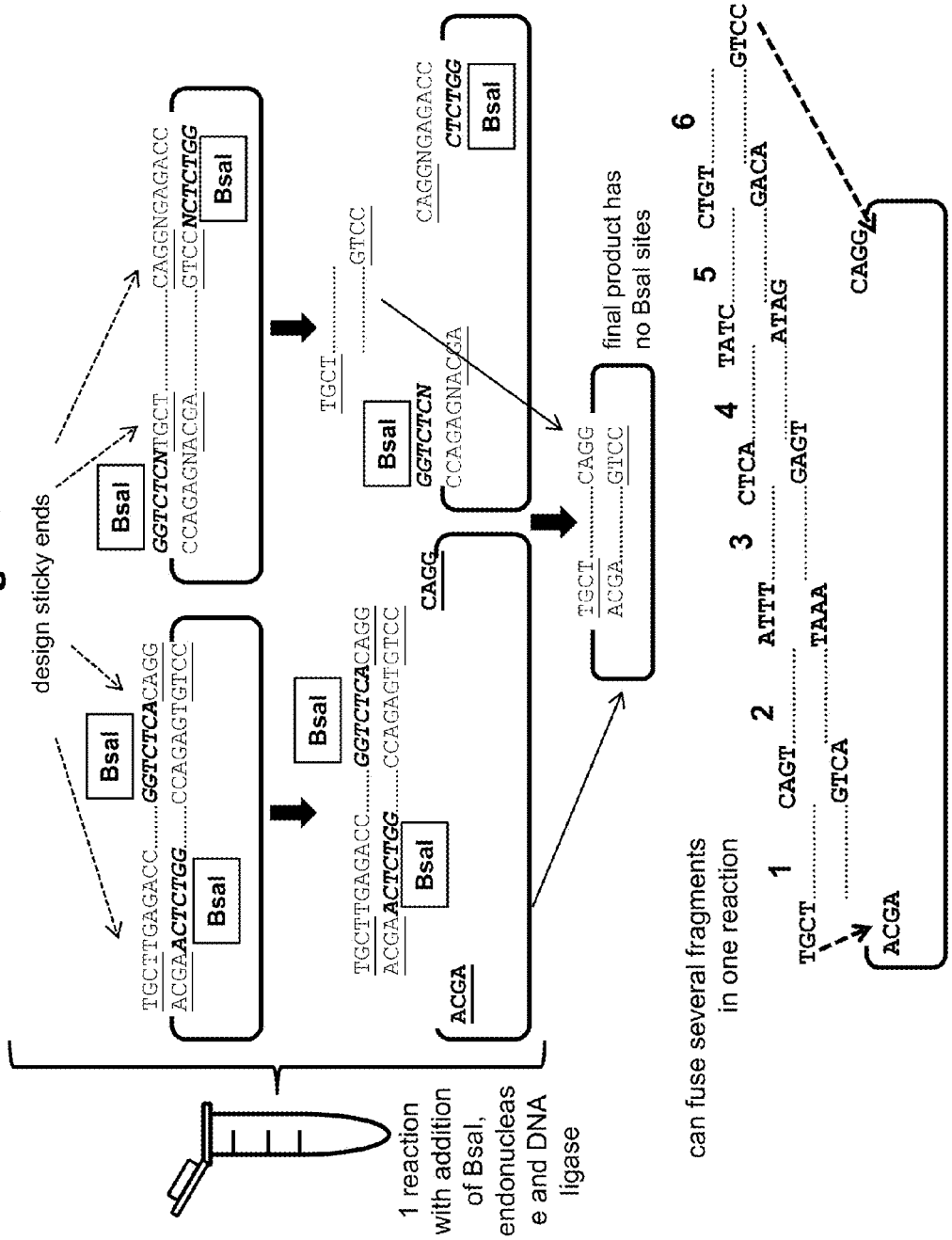
FIG. 31 is a schematic of the Golden Gate cloning system [Engler et al. (2008) *PLoS One* 3:e3647; and Engler et al. (2009) *PLoS One* 4:e5553].

Example 8—Method and Reagents for Rapid Assembly and Cloning of Custom TAL Effector Repeat Arrays The Golden Gate cloning method [Engler et al. (2008), supra; and Engler et al. (2009), supra] employs the ability of Type IIS restriction endonucleases (e.g. BsaI) to cut outside their recognition sites to create custom overhangs for ordered ligation of multiple DNA fragments simultaneously. Using this method, several DNA fragments can be fused into an array in a specific order and cloned into a desired destination vector in a single reaction (FIG. 31).

A method and reagents for assembling custom TAL effector repeat encoding arrays were developed based on the Golden Gate system. When BsaI sites are positioned on either side of a TAL effector repeat coding sequence, cleavage releases a repeat fragment flanked by 4-bp overhangs. Because the cleavage site is not sequence-specific, by staggering, repeat clones can be released with ordered, complementary overhangs (sticky ends), enabling the ordered assembly of multi-repeat arrays.

Figure 32A:
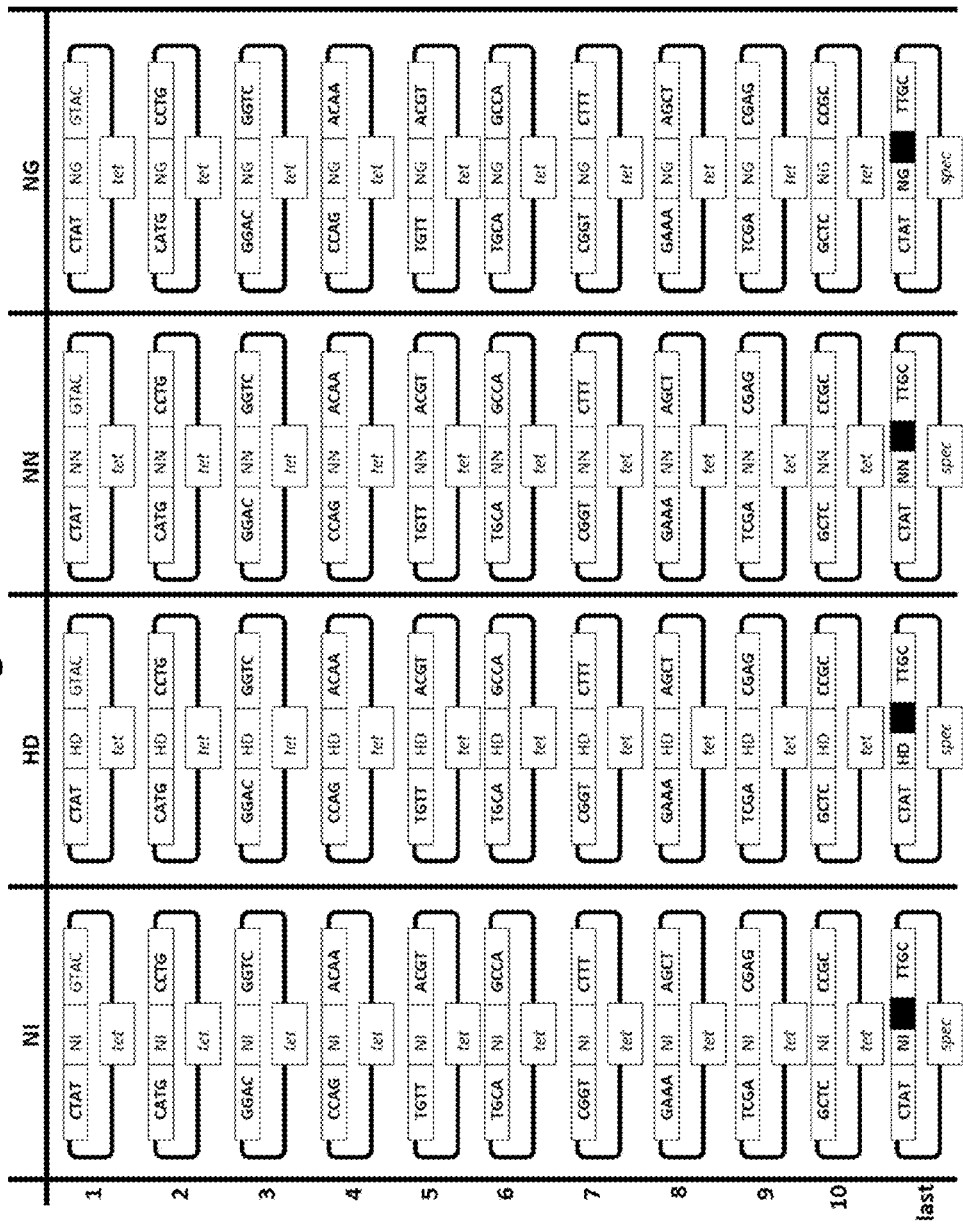
FIGS. 32A and 32B depict a set of 58 plasmids for assembly and cloning of custom TAL effector repeat encoding arrays using the Golden Gate cloning approach as described herein. Tet, tetracycline resistance gene, a marker for plasmid selection; spec, spectinomycin resistance gene, a marker for plasmid selection; amp, ampicillin resistance gene, a marker for plasmid selection.
Figure 32B:
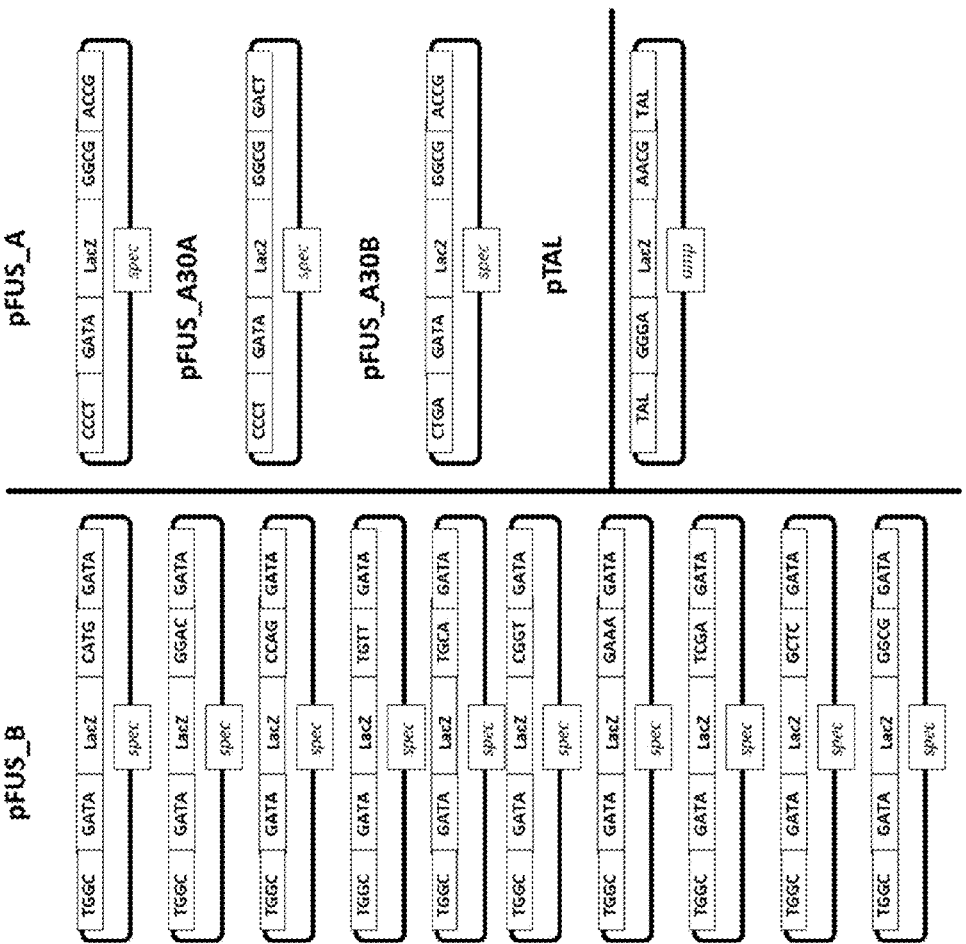

A library of 58 plasmids (FIGS. 32A and 32B) was generated to allow the simultaneous assembly of up to 10 repeat units into "subarrays," followed by simultaneous assembly of one, two, or three of these subarrays together with a final truncated repeat into a complete, custom array. Ten staggered sets of four fragments, each fragment in a set encoding a repeat module with a different one of the four most common RVDs, HD, NG, NI, and NN, were synthesized and cloned into a vector carrying the tetracycline resistance gene, for a total of 40 plasmids. Four more fragments that encoded the terminal truncated TAL effector repeat of 20 amino acids, each fragment encoding a different one of the four most common RVDs, were synthesized and cloned into a different vector carrying the spectinomycin resistance gene to yield four more plasmids, designated as "last repeat plasmids," FIG. 32A). All fragments in the staggered sets are flanked by BsaI sites in the vector so that cleavage with BsaI releases the fragments with different sticky ends that allow for assembly in the appropriate order; that is, i.e. the overhang at the 3' end of a fragment for repeat module 1 is complementary only to the overhang at the 5' end of the fragment for repeat module 2, the overhang at the 3' end of repeat module 2 is complementary only to the overhang at the 5' end of repeat module 3, and so on. The fragments in the last repeat plasmids are flanked by sites for a different Type IIS restriction endonuclease, Esp3I. Fourteen additional plasmids, described following, were constructed as destination vectors to receive assembled subarrays.

Figure 33:
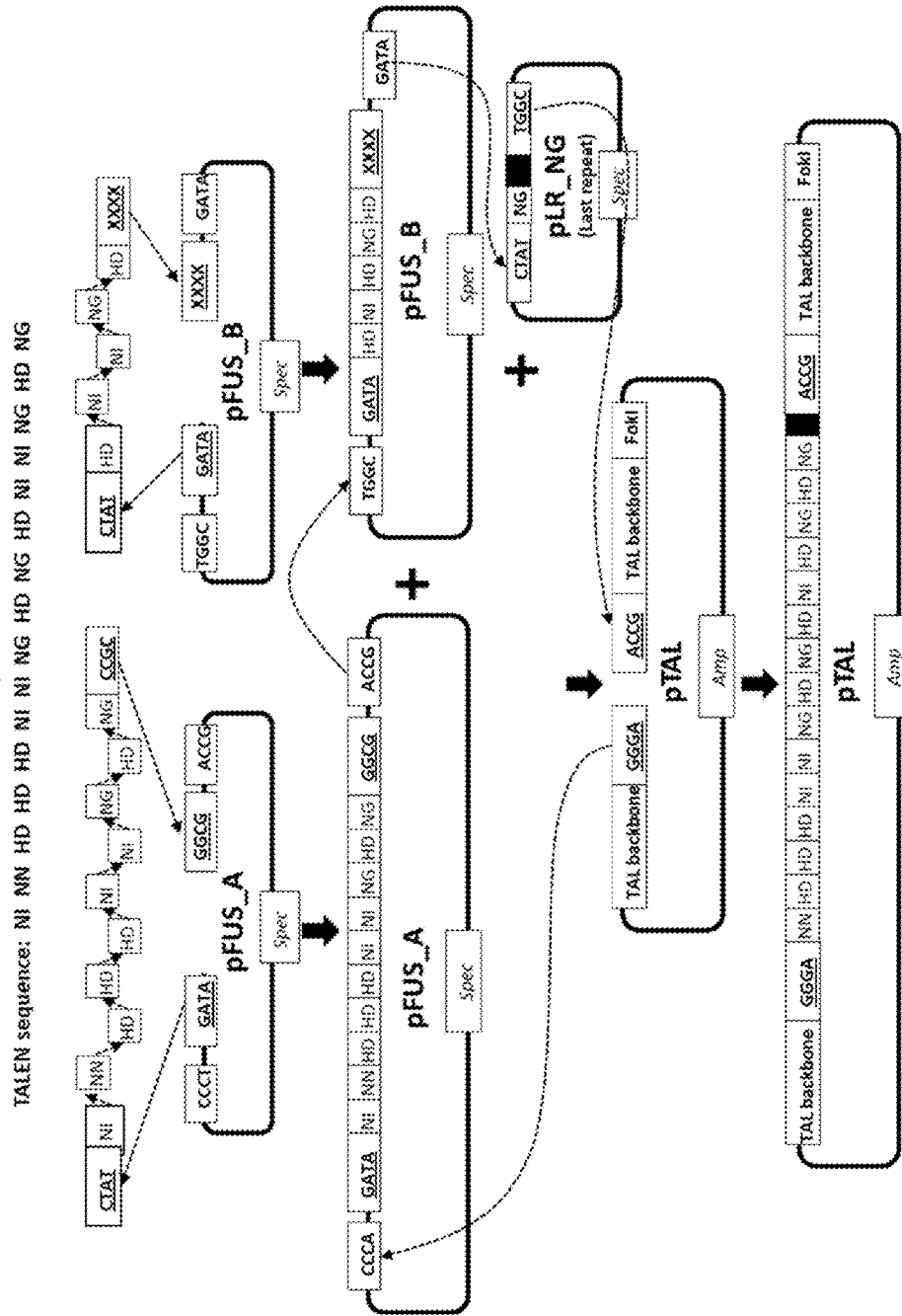
FIG. 33 is a schematic of a method for assembly and cloning of custom TAL effector repeat encoding arrays by the Golden Gate approach using the set of plasmids shown in FIG. 32. For illustration purposes, assembly of an arbitrary repeat array is shown. spec, spectinomycin resistance gene, a marker for plasmid selection; amp, ampicillin resistance gene, a marker for plasmid selection.

The first destination vector, plasmid pFUS_A was constructed to receive the first subarray of 10 repeats to be assembled into a final array of 21 or fewer repeats (counting the final, truncated repeat). pFUS_A was constructed such that cleavage by BsaI creates an overhang on one side complementary to the overhang at the 5' end of the first repeat module and an overhang at the other side complementary to the overhang at the 3' end of the 10th repeat module. To receive a second subarray of 10 or fewer repeats to be assembled into such a final array, destination vector plasmids pFUS_B1, pFUS_B2, pFUS_B3, pFUS_B4, pFUS_B5, pFUS_B6, pFUS_B7, pFUS_B8, pFUS_B9, and pFUS_B10 were constructed that when cleaved by BsaI have overhangs respectively complementary to the overhang at the 5' end of the first repeat module and the 3' end of the repeat module for the corresponding numbered position (e.g., the pFUS_B6 overhang for the 3' end of the subarray matches the overhang of the four repeat module fragments for position 6). Arrays cloned in pFUS_A and the pFUS_B series of plasmids are flanked by Esp3I sites in the vector and when released by digestion with Esp3I the arrays have unique complementary overhangs that allow for them to be ligated in order along with a final truncated repeat fragment into destination vector pTAL, which encodes a TALEN missing the repeat region. pTAL was constructed so that cleavage with Esp3I allows insertion of the repeat array at the correct location and in the correct orientation by virtue of an overhang at one end that is complementary to the overhang at the 5' end of the first ten repeat subarray and an overhang at the other end complementary to the overhang at the 3' end of the final truncated repeat fragment (FIG. 33).

The final two destination vector plasmids, pFUS_A30A and pFUS_A30B were constructed to receive the first and second ten repeat subarrays to be assembled into a final array of 22-31 repeats. pFUS_A30A and pFUS_A30B were constructed such that digestion with Esp3I releases the arrays with the appropriate complementary overhangs such that the arrays can be ligated in order along with a third array from a pFUS_B vector and a final truncated repeat fragment from a last repeat plasmid, released similarly by digestion with Esp3I, into pTAL (FIG. 32).

All destination vectors have the LacZ gene cloned in between the Type IIS restriction endonuclease sites, allowing for blue-white screening for recombinants. Except for pTAL, which carries a gene for ampicillin resistance, all the destination vectors carry a gene for spectinomycin resistance.

To rapidly construct a custom TAL effector repeat array using these reagents, the following method was established. In the first step, the appropriate individual RVD module plasmids for the necessary subarrays of ten or fewer repeats are mixed together with the appropriate destination vector in one tube. T4 DNA ligase and BsaI endonuclease are added and the reaction is incubated in a PCR machine for 10 cycles of 5 minutes at 37° C. and 10 minutes at 16° C., the respective optimal temperatures for the two enzymes. The reaction mixture is then treated with the PLASMID-SAFE™ nuclease to hydrolyze all linear dsDNA fragments in order to prevent cloning of shorter, incomplete arrays by in vivo recombination, and then the mixture is used to transform chemically competent E. coli cells. The resulting recombinant plasmids are isolated and the correct constructs confirmed. Then, in the second step, the confirmed plasmids from the first step are mixed together with the appropriate last repeat plasmid and pTAL, and the digestion and ligation reaction cycle carried out as in the first step. Finally, the reaction products are introduced into E. coli, and the full length, final array construct is isolated and confirmed. The protocol can be completed by one person within a week's time.

Expression constructs for TALENS 85, 102 and 117 in Table 4A, as well as TALENS HPRT-3254-17 and HPRT-3286-20r, described in Example 14 below, were made using the method and reagents described in this example.

Repeat arrays cloned in pTAL are subcloned readily into other TAL effector gene contexts using the conserved SphI restriction endonuclease sites that flank the repeat region.

Example 9—Custom TALEN Data Show Initial Support for "Rules" and a Correlation Between RVD Number and Activity Example 6 describes experiments conducted to engineer the TALEN DNA binding domain so that it can recognize unique DNA sequences. As described, these custom TAL-ENs recognized sites in the Arabidopsis ADH1 and zebrafish gridlock genes. Additional custom TAL effector DNA binding domains were engineered to recognize not only sites in these genes, but also in the TT4 gene from Arabidopsis, and telomerase from zebrafish (Foley et al., supra; and Zhang et al., supra). These custom TALENs were made using the methods described in Examples 3, 4 and 8. In engineering the custom TALENs, the observed compositional and positional biases were adopted as design principles or "rules." First, a search was conducted for sequences in the coding regions that were preceded by a 5' T and at least 15 bp in length, and that had a nucleotide composition consistent with the averages noted above. Specifically, only those sites with 0-63% A, 11-63% C, 0-25% G, and 2-42% T were selected. Such sites occurred on average every 7-9 bp. Sites were then selected that conformed to the observed positional biases described above. From this set, two pairs of binding sites in each gene were identified that were 15-19 bp in length and separated by 15-18 bp, so that binding of the engineered TALENs would allow FokI to dimerize. The modular assembly methods (Examples 3 and 4) generated partial length constructs.

Figure 35:
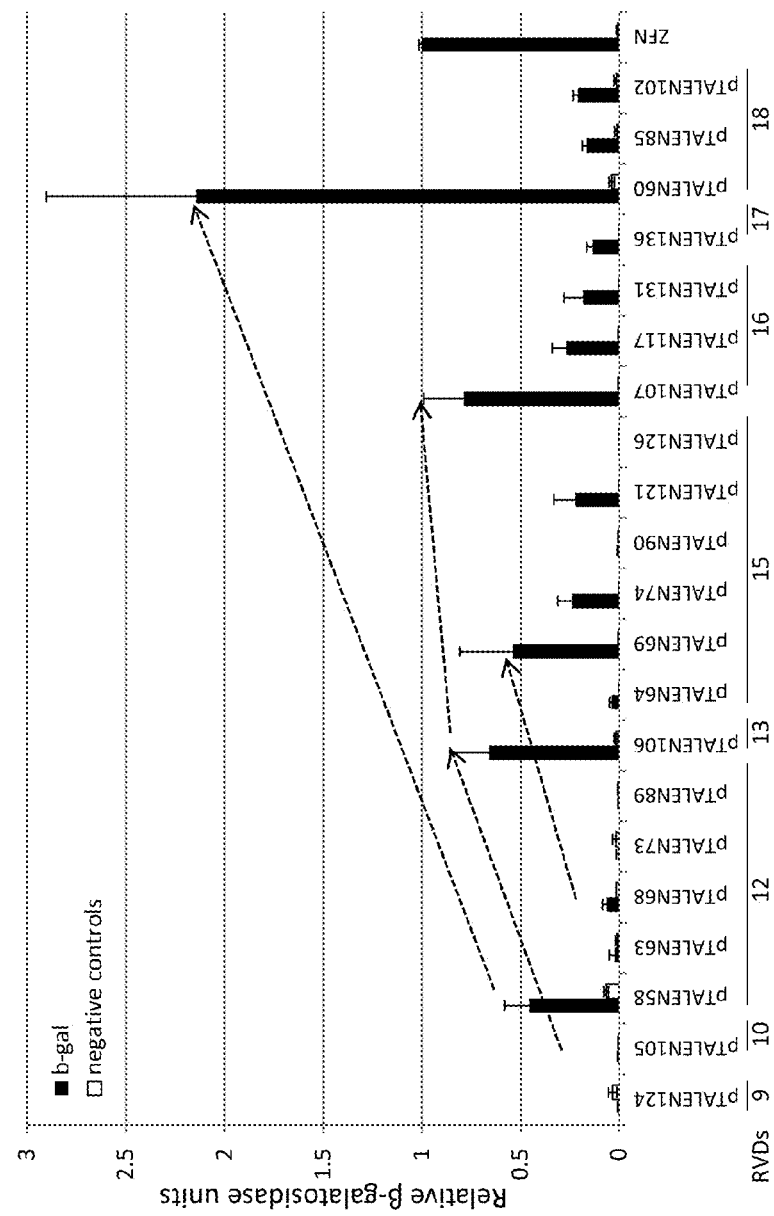
FIG. 35 is a graph plotting TALEN activity as measured by the yeast assay using custom TALEN monomers of increasing length (9-, 10-, 12-, 13-, 15-, 16-, 17-, or 18 mers). The TALENs were targeted to *Arabidopsis* and zebrafish genes, as indicated.

In total, 21 intermediate and full length TALENs designed to target 16 nucleotide sequences, each with an array of nine repeats or longer. The amino acid sequences of these TAL-ENs are provided in FIGS. 34A-34U (SEQ ID NOS:35-55). These 21 TALENs were tested for their ability to cleave DNA using the yeast assay described in Examples 2 and 6. Activity data are shown in FIG. 35 and summarized in Table 4A.

Some of the intermediate, partial length TALENs correspond to targets that break the rules for nucleotide composition and terminal T. Table 4A shows length, conformity to these two rules, and activity relative to that of ZFN268 for each TALEN. The results reveal a general trend that increasing the length of the RVD array increases activity of the resulting TALEN. This suggests that there is a minimal number of RVDs that are needed before a DNA target can be recognized in vivo. Further, conformity to the rules appears to be important. Of the six TALENs showing no detectable activity, two violated the target composition rule, two did not end in NG, and another broke both rules (one obeyed both rules). Three of the eight TALENs with activity less than 25% of ZFN268 violated one of the rules, and one of four TALENs with activity 25-50% of ZFN268 did not have an RVD sequence ending in NG. It is noted that TALENs with activity 50% or greater than that of ZFN268 obeyed all the rules, and for TALENs of the same length, rule breakers generally had less activity than obedient arrays. Consistent with the overall trend regarding length, even for intermediates that broke no rules, the corresponding full length TALENs had higher activity (Table 4A and FIG. 35). Variation in spacer length due to TALEN length differences on the same target may have contributed to this observation, but some range of spacer lengths is tolerated (Christian et al., supra).

Some complexities in the data were apparent. For example, activity varied among obedient TALENs of the same length, some short arrays had moderately high activity, and some long arrays that were obedient had little or no activity (Table 4B). Nonetheless, the results provided support for the conclusions that 1) generally a greater number of repeats results in greater activity, and 2) conformity to composition and positional bias rules is important for activity. Therefore, the following design principles were derived.

TAL effector binding sites are designed to be a minimum of 15 bases long and oriented from 5' to 3' with a T immediately preceding the site at the 5' end.

A site may not have a T in the first (5') position or an A in the second position.

A site must end in T (3'), and may not have a G at the next to last position.

The base composition of the site must fall within specified ranges (average±two standard deviations): A 0-63%, C 11-63%, G 0-25%, and T 2-42%.

TABLE 4A

Activity, conformity to rules, and length of TALENs tested in the yeast assay.

| Gene | TALEN | Names from Christian et al. (supra) | RVDs | Activity | % GATC | Ends in NG | RVD sequence[1] |
|---|---|---|---|---|---|---|---|
| telomerase | 124 | | 9 | — | N | Y | HD NN NN NG NG NG NN HD NG |

TABLE 4A-continued

Activity, conformity to rules, and length of TALENs tested in the yeast assay.

| Gene | TALEN | Names from Christian et al. (supra) | RVDs | Activity | % GATC | Ends in NG | RVD sequence[1] |
|---|---|---|---|---|---|---|---|
| gridlock | 105 | | 10 | + | N | N | NI HD HD HD HD NG HD NG HD HD |
| ADH1 | 58 | ADH1-360-12 | 12 | ++ | Y | N | NI NG HD NI NI NN NI NG NG HD NG HD |
| ADH1 | 63 | ADH1-408-12r | 12 | − | Y | N | HD HD HD NI NN NI NI NN NG NI NI NI |
| ADH1 | 68 | ADH1-928-12 | 12 | + | Y | Y | HD HD NN NN NI NG NN HD NG HD HD NG |
| ADH1 | 73 | ADH1-975-12r | 12 | − | N | N | NI NN NI HD NI NI NI HD HD NI HD NI |
| TT4 | 89 | | 12 | − | Y | N | NN NN HD NI HD NG NN HD NG NI NI HD |
| gridlock | 106 | gridlock-2356-13r | 13 | ++ | Y | Y | NI HD HD HD HD NG HD NG HD HD NN HD NG |
| ADH1 | 64 | | 15 | + | Y | Y | HD HD HD NI NN NI NI NN NG NI NI NI HD NI NG |
| ADH1 | 69 | | 15 | +++ | Y | Y | ND ND NN NN NI NG NN HD NG HD HD NG HD NG NG |
| ADH1 | 74 | | 15 | ++ | Y | Y | NI NN NI HD NI NI NI HD HD NI HD NI NI HD NG |
| TT4 | 90 | | 15 | − | Y | Y | NN NN HD NI HD NG NN HD NG NI NI HD HD HD NG |
| telomerase | 121 | | 15 | + | Y | Y | HD NG NG NN NG HD HD NN HD NI NG NN NI NG NG |
| telomerase | 126 | | 15 | − | N | Y | HD NN NN NG NG NG NN HD NG NI NG HD NN NG NG |
| gridlock | 107 | | 16 | ++++ | Y | Y | NI HD HD HD HD NG HD NG HD HD NN HD NG NG HD NG |
| gridlock | 117 | | 16 | ++ | Y | Y | HD HD HD NN NN NI NI NN HD HD NN NI HD NN HD NG |
| telomerase | 131 | | 16 | + | Y | Y | NI NG NG HD HD HD HD NI HD NN NI NN HD NG HD NG |
| telomerase | 136 | | 17 | + | N | Y | NI NN NI HD NI NN NN NI NI NN NG NN NN NI NN HD NG |

TABLE 4A-continued

Activity, conformity to rules, and length of TALENs tested in the yeast assay.

| Gene | TALEN | Names from Christian et al. (supra) | RVDs | Activity | % GATC | Ends in NG | RVD sequence[1] |
|---|---|---|---|---|---|---|---|
| ADH1 | 60 | | 18 | +++++ | Y | Y | NI NG HD NI NI NN NI HG NG HD NG HD NG NG HD NI HD NG |
| TT4 | 85 | | 18 | + | Y | Y | NI HD NG HD HD NN HD HD NG NN NI NI NN HD NI HD NI NG |
| gridlock | 102 | | 18 | + | Y | N | NN NN HD NG HD NI HD HD NG NI HD NI NI HD NN NI HD NI |

[1]Target sequences tested consist of inverted repeats of the corresponding nucleotide sequence, where HD, NG, NI, and NN correspond to C, T, A, and G, respectively, separated by a spacer sequence of 16-18 bp.

TABLE 4B

Excerpt of Table 4A, sorted by activity level

| RVDs | Activity | % GATC | Ends in NG |
|---|---|---|---|
| 9 | − | n | y |
| 12 | − | y | n |
| 12 | − | n | n |
| 12 | − | y | n |
| 15 | − | y | y |
| 15 | − | n | y |
| 10 | + | n | n |
| 12 | + | y | y |
| 15 | + | y | y |
| 15 | + | y | y |
| 16 | + | y | y |
| 17 | + | n | y |
| 18 | + | y | y |
| 18 | + | y | n |
| 12 | ++ | y | n |
| 13 | ++ | y | y |
| 15 | ++ | y | y |
| 16 | ++ | y | y |
| 15 | +++ | y | y |
| 16 | ++++ | y | y |
| 18 | +++++ | y | y |

Figure 36:
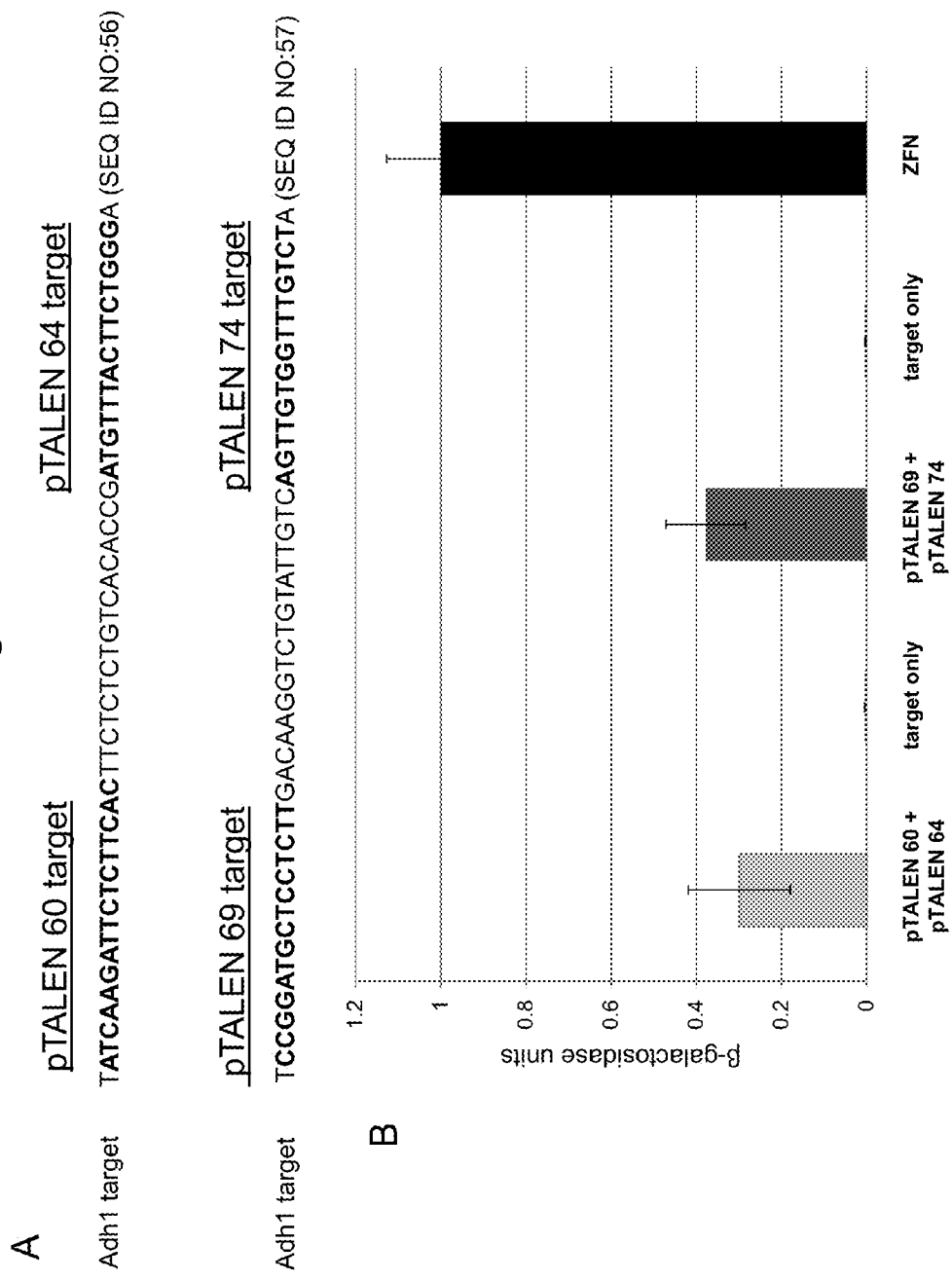
FIG. 36A is a diagram showing two different DNA target sequences from the *Arabidopsis* ADH1 gene that are targeted by two TALEN pairs.
FIG. 36B is a graph plotting yeast assay data for functional TALEN pairs that target the *Arabidopsis* ADH1 gene.

Example 10—Heterodimeric TALEN Pairs Cleave their Intended Naturally Occurring Target Sequences in the Yeast Assay The data in Examples 2, 6 and 9 demonstrate that custom TALENs can be engineered to recognize novel target DNA sequences. The yeast activity data for the custom TALENs was gathered using individual TALEN monomers that recognized a homodimeric target site. That is, the target sequence of the TALEN was duplicated in inverse orientation on either side of a 15-18 bp spacer. Cleavage of endogenous chromosomal sequences, however, generally would require that two different custom TALENs recognize two different sequences on either side of a spacer. As described in Example 6, this ability was demonstrated for the AvrBs3 and PthXo1 TALENS together using a corresponding chimeric target site in the yeast assay. We tested whether two different custom TALENs could recognize and cleave a naturally occurring DNA sequence. Using the yeast assay described in Example 2, custom TALENs designed to cleave two different target sequences in the *Arabidopsis* ADH1 gene were assayed for activity on these targets. The DNA sequences of the target sites and the corresponding TALENs are shown in FIG. 36A. The amino acid sequences of the TALENs are provided in FIG. 34. The beta-galactosidase activity obtained in the yeast assay is plotted in the graph shown in FIG. 36B. The activity of the TALENs on their naturally occurring target sequence was significantly above the negative controls, indicating that TALENs can be engineered to recognize and cleave endogenous target DNA sequences.

Figure 37:
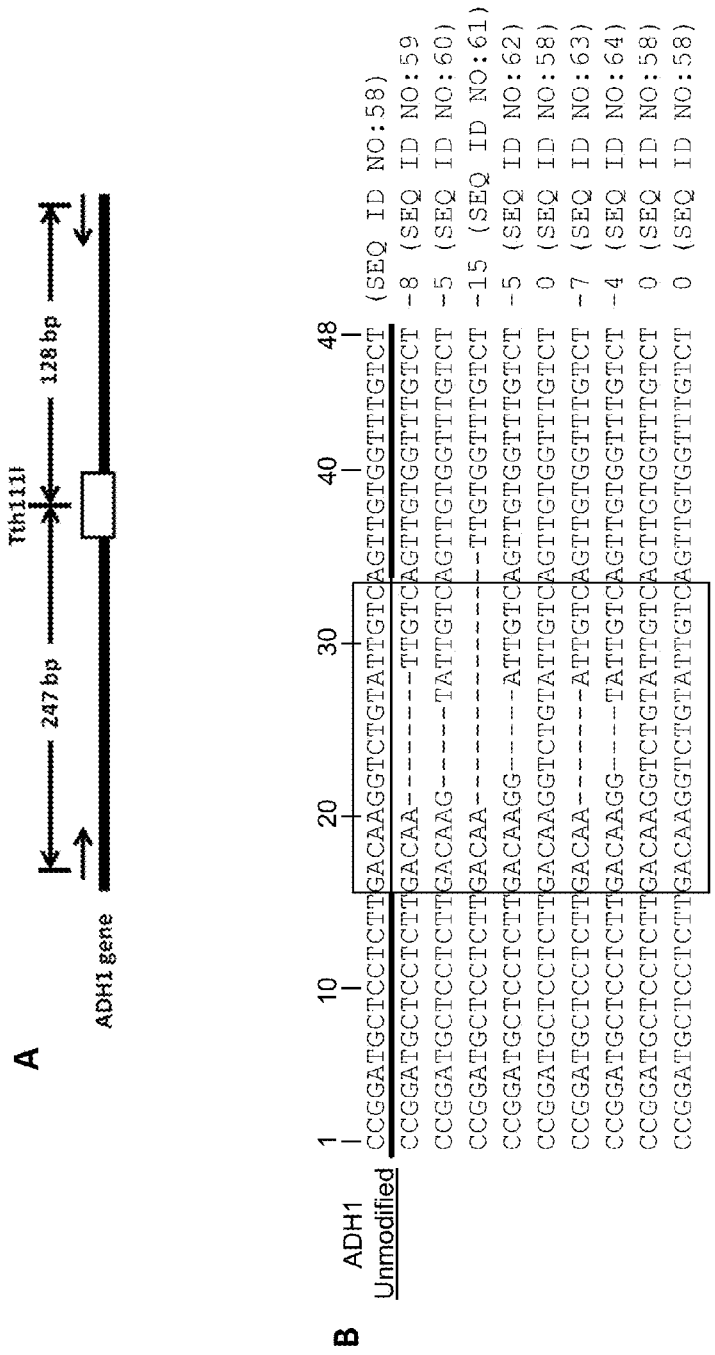
FIG. 37A is a schematic of a restriction endonuclease assay used to detect TALEN-induced mutations in *Arabidopsis* protoplasts.
FIG. 37B shows the sequences of nine clones from undigested DNA in the restriction endonuclease assay. Six of the clones have mutations introduced by non-homologous end joining (NHEJ).

Example 11—TALENs Cleave Native Genes in *Arabidopsis* and Introduce Mutations by Imprecise Non-Homologous End-Joining One of the active TALEN pairs designed to recognize a target sequence in the *Arabidopsis* ADH1 gene was tested to determine whether it can bind, cleave and mutate chromosomal DNA. Each of the individual ADH1 TALENs comprising this pair (pTALENs 69 and 74) was cloned into the plant expression vector pFZ14, which places the TALENs under the control of the constitutive 35S promoter (Zhang et al., supra). The resulting constructs were then introduced into *Arabidopsis* protoplasts by electroporation. After 48 hours, genomic DNA was isolated and digested with Tth111I. A Tth111I cleavage site is located in the spacer sequence between the two TALEN recognition sites (FIG. 37A). Cleavage of the chromosomal DNA by the TALEN would be expected to introduce mutations by imprecise non-homologous end joining (NHEJ), which would result in failure to cleave by Tth111I. A 375 bp fragment encompassing the TALEN recognition site was then PCR amplified. The PCR product was digested again with Tth111I to remove most of the remaining genomic DNA that was not modified by TALEN-mediated NHEJ. The digestion products were then run on an agarose gel. An uncleaved PCR product was observed, and such uncleaved PCR products are diagnostic of nuclease activity (in this case TALEN activity) at the endogenous target sequence (Zhang et al., supra). The uncut DNA was cloned and analyzed by DNA sequencing. The sequencing of nine independent clones revealed that six carried mutations introduced by NHEJ (FIG. 37B). Thus, TALENS cleave endogenous chromosomal loci and introduce DNA double strand breaks and mutations.

Example 12—Enhancing Targeting Capacity

At the core of the TAL effector DNA cipher, the four most common RVDs each have apparent one-to-one specificity for the four nucleotides, based on association frequencies. This is markedly so for HD, NG, and NI, but less so for NN (FIG. 1C). NN associates most frequently with G, but almost as commonly with A, and sometimes with C or T. For a randomly assembled TAL effector with NN at four locations in a 13 RVD sequence, having G at all corresponding positions in an artificial target gave the best activity (Boch et al. (2009) Science 326:1509-1512). A reduced but did not abolish activity, and C and T eliminated detectable activity. A drastic loss of activity was observed when C, T, or A was substituted for G at just the first position in the binding site for the 24 RVD effector PthXo1, which is an NN (Romer et al. (2010) New Phytol. 187:1048-1057). This was in contrast, however, to the observation that the much shorter AvrHah1 (14 RVDs) begins with an NN that aligns with A, and the 23 RVD effector PthXo6 has three NNs in a row at positions 4-6 that each align with A, yet both of these proteins are highly active (see, Schornack et al. (2008) New Phytol. 179:546-556; and Romer et al., supra). Thus the specificity of NN for G appears to be generally weak and can vary with context.

The observed invariance of the thymine immediately preceding TAL effector target sites is a requirement for several effectors [Boch et al., supra; Romer et al., supra; and Romer et al. (2009) Plant Physiol. 150:1697-1712]. The amino acid sequence immediately preceding the repeat region in TAL effectors, which is highly conserved (FIG. 38A), shares significant similarity with the repeat, both in amino acid sequence and in predicted secondary structure (FIG. 38B and Bodganove et al. (2010) Curr. Opin. Plant Biol. 13:394-401). It was hypothesized that this sequence, termed the "0$^{th}$" repeat, is the basis for the requirement for T at position −1 of the binding site, and that residues in the RVD-analogous position (FIG. 38B) specify the nucleotide.

Based on these findings, it was hypothesized that by incorporating repeats with high specificity for G, and by relaxing the requirement for T at −1, targeting capacity for engineered TAL effector proteins can be enhanced. Experiments were initiated to test novel and rare RVDs for more robust specificity for G than NN displays, and to replace the RVD-analogous residues of the 0$^{th}$ repeat with common RVDs.

Novel and Rare RVDs for Robust Specificity for G:

The modules disclosed above (see, e.g., Example 4) used four particular RVDs (NI, HD, NN, and NG) to specify binding to the four nucleotide bases (A, C, G, and T, respectively). Repeats containing other RVDs also may be useful, and may have increased specificity and/or affinity for the four bases as compared to NI, HD, NN, and NG. Toward improving specificity for G, several repeats encoding novel and rare RVDs were constructed. The rare RVDs NK, HN, and NA associated with G, suggesting that N may be important as one or the other of the residues (FIG. 1C). Thus, a broad set of derivatives encoding repeats having the RVDs shown in Table 5 were constructed. The left column lists RVDs having a polar amino acid (R, K, D, E, Q, H, S, T, or Y) at position 12 and N at position 13. The right columns list combinations of N in the first position with any of 17 other amino acids (G, L, V, R, K, D, E, Q, H, T, M, C, P, Y, W, or F) in the second position of the RVD. To account for the possibility of greater specificity without N, repeats also were made with a polar amino acid (R, K, D, E, Q, H, S, T, or Y) at position 12 and a gap (*) at position 13 (middle column).

Novel artificial RVDs are tested for function in a quantitative reporter gene based assay for transcriptional activation activity of TAL effectors, such as a GUS or dual luciferase reporter based, Agrobacterium-mediated transient expression assay in Nicotiana benthamiana, or in the lacZ reporter based TALEN assay in Saccharomyces cerevisiae, described above (see, e.g., Example 2) Repeat modules containing RVDs to be tested are incorporated into a TAL effector or TALEN with measurable and sub-saturation levels of activity, and the resulting proteins are tested for differences in activity on a set of DNA targets with integrated permutations of all four nucleotides at corresponding positions. In particular, beginning with the PthXo1 variant(s) minimally active in the in planta and yeast assays and responsive to mismatches at three added repeats, TALENs containing each of the novel and rare repeats (in homomeric threes) are tested in vivo against targets with G at each of the corresponding positions. For any that show increased activity, the assays are repeated with targets permutated to the other nucleotides at those positions, to ascertain specificity.

TABLE 5

| RVDs to be tested[a] | | | |
|---|---|---|---|
| Polar + N | Polar* | | N + all |
| RN | R* | NG | NH |
| KN | K* | NA | NT |
| DN | D* | NL | NM |
| EN | E* | NV | NC |
| QN | Q* | NR | NP |
| HN | H* | NK | NY |
| SN | S* | ND | NW |
| TN | T* | NE | NF |
| YN | Y* | NQ | |

[a]N*, NG, and NS nt association frequencies are known. An asterisk represents a gap corresponding to the 2$^{nd}$ position in the RVD (i.e., the 13$^{th}$ position of the consensus repeat sequence).

Common RVD Substitutions for the RVD-Analogous Position of the 0$^{th}$ Repeat to Relax Specificity of Tat Position −1:

Secondary structure predictions and alignment of the 0$^{th}$ repeat and repeat consensus sequences suggested that positions occupied by KR* (asterisk denotes a gap) in the 0$^{th}$ repeat were analogous to the RVD and were therefore the residues that specify the T at −1. Variants of PthXo1 with substitutions of HD, NG, NI, and NN for KR and separately for R* were constructed in the Tal1c "backbone" construct described above. Activities of these variants are compared to the wild type effector in the in planta and yeast assays using targets with corresponding nucleotides at position −1, namely, C, T, A, and G, respectively. Additional variants of PthXo1 are constructed that have S, the residue at position 11 of the consensus repeat sequence, substituted for the K at position 11 of the 0$^{th}$ repeat. And other variants are constructed that have this substitution combined with a substitution of K, the residue at position 16 of the consensus repeat sequence, for the V at position 15 of the 0$^{th}$ repeat (Table 6). A proximal TATA box for TAL effector activity may be included. In addition, PthXo1 is useful for this experiment because unlike AvrBs3, for which the T at −1 appears to be part of a TATA box, the TATA box closest to the PthXo1 binding site is 46 bp downstream and would not be perturbed by modifications at −1.

If the above modifications do not result in enhanced targeting for G or increased ability to target sequences preceded by nucleotides other than T, then a more comprehensive set of artificial RVDs are tested for G specificity, and substitutions other than the common RVDs are tested for the 0th repeat.

TABLE 6

$0^{th}$ repeat constructs to be made and tested for specificity for targets with A, C, G, or T at the -1 position

| Native $0^{th}$ repeat sequence (specifies T at -1) | Substitution specifying T | Substitution specifying A | Substitution specifying C | Substitution specifying G |
|---|---|---|---|---|
| ... KIA* KRGGV ... (74)† | ... KIA* NGGGV ... (75) | ... KIA* NIGGV ... (76) | ... KIA* HDGGV ... (77) | ...KIA* NNGGV ... (78) |
| ... KIA* KRGGV ... (79) | ... KIA<u>S</u> NGGGV ... (80) | ... KIA<u>S</u> NIGGV ... (81) | ... KIA<u>S</u> HDGGV ... (82) | ...KIA<u>S</u> NNGGV ... (83) |
| ... KIAKR* GGV ... (84) | ... KIAK NGGGV ... (85) | ... KIAK NIGGV ... (86) | ... KIAK HDGGV ... (87) | ...KIAK NNGGV ... (88) |
| ... KIA* KRGGV ... (89) | ... KIA<u>S</u> NGGG<u>K</u> ... (90) | ... KIA<u>S</u> NIGG<u>K</u> ... (91) | ... KIA<u>S</u> HDGG<u>K</u> ... (92) | ...KIA<u>S</u> NNGG<u>K</u> ... (93) |

Candidate and substituted RVDs are bold. Other substitutions or modifications are underlined. Asterisks denote a gap relative to the consensus repeat sequence.
†SEQ ID NO:

Example 13—Novel Predicted Nucleotide Specific RVDs

It was observed that when the RVDs listed in Tables 1A and 1B were grouped by the second amino acid residue in the RVD (i.e., the $13^{th}$ in the overall repeat), there was a near perfect correlation of that amino acid with the nucleotide(s) specified by the RVD, irrespective of the amino acid at the first position of the RVD (Table 7). Thus, RVDs ending in a gap (denoted by an asterisk) specify C or T, or T; RVDs ending in D specify C; RVDs ending in G specify T; and RVDs ending in N specify G or A, or G. It also was observed that amino acids at position 1 of the RVD were either H, I, N, S, or Y. These observations suggested that RVD specificity is determined by the residue in the second position, independent of whether the residue at the first position is H, I, N, S, or Y. Therefore, specificities were predicted for several novel (i.e., yet unobserved) RVDs that combine residues observed at the second position with residues H, I, S, N, or Y at the first position. Thus, I*, S*, and Y* were predicted to specify C or T, or T; ID, SD, and YD were predicted to specify C; SG was predicted to specify T: and IN and YN were predicted to specify G or A, or G. Also, although there was only one instance of K at the second position, based on the observed specificity of NK, it was predicted that HK, IK, SK, and YK specify G.

These novel RVDs are tested and compared to existing RVDs for function and specificity in quantitative TAL effector and TALEN activity assays as described in Examples 2 and 11.

TABLE 7[1]

RVDs grouped and ordered by their second residue

| $1^{st}$ residue | $2^{nd}$ residue | Nucleotide |
|---|---|---|
| N | * | C or T |
| H | * | T |
| H | A | C |
| N | A | G |
| H | D | C |
| N | D | C |
| H | G | T |
| I | G | T |
| N | G | T |
| Y | G | T |
| N | I | A |
| H | I | C |
| N | K | G |
| H | N | G |
| S | N | G or A |
| N | N | G or A[1] |
| N | S | A or C or G[1] |

[1] An asterisk denotes a gap.
RVD groups with like specificities are boxed in thick lines.

Figure 39:
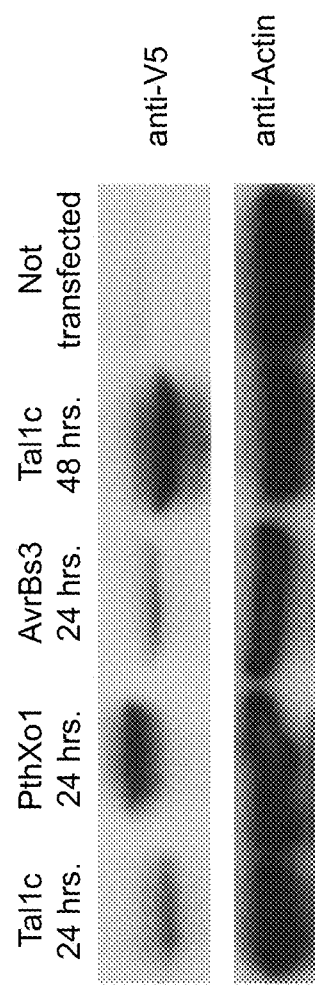
FIG. 39 shows a western blot of total protein isolated from human embryonic kidney 293T cells transfected with plasmids encoding V5-tagged TAL effector proteins AvrBs3, PthXo1, and Tal1c, as indicated, following immunodetection using a mouse-antiV5 antibody. Immunolabeled actin is shown as a control for equivalent loading in each lane.

Example 14—Custom TALENs Cleave Endogenous Targets in Animal Cells and Introduce Mutations by Imprecise Non-Homologous End Joining To test whether TALENs could be used for targeted mutagenesis in animal cells, first, expression of TAL effectors AvrBs3, PthXo1, and Tal1c was tested in human embryonic kidney (HEK) 293T cells. The stop codon was removed from the AvrBs3, PthXo1, and Tal1c encoding genes and the genes were subcloned into mammalian expression vector pcDNA3.2/V5-DEST (Invitrogen, Carlsbad, Calif.) in frame with the downstream sequence in that vector that encodes the V5 epitope for protein immunodetection. pcDNA3.2/V5-DEST places the TAL effector gene under the control of the constitutive human cytomegalovirus (CMV) promoter. HEK 293T cells were transfected using Lipofectamine 2000 (Invitrogen) with the resulting plasmids individually, and after 24 hours, total proteins were isolated from each transfected batch of cells and subjected to polyacrylamide gel electrophoresis, western blotting and immunolabeling using a mouse anti-V5 antibody. The labeled proteins were detected with a goat anti-mouse antibody-horse radish peroxidase conjugate using the SuperSignal Weat Pico Chemiluminescent kit (ThermoScientific, Inc.). Equivalent loading was confirmed by immunolabeling and detection of actin. Each TAL effector protein was detectably expressed with no apparent degradation (FIG. 39).

Figure 41A:
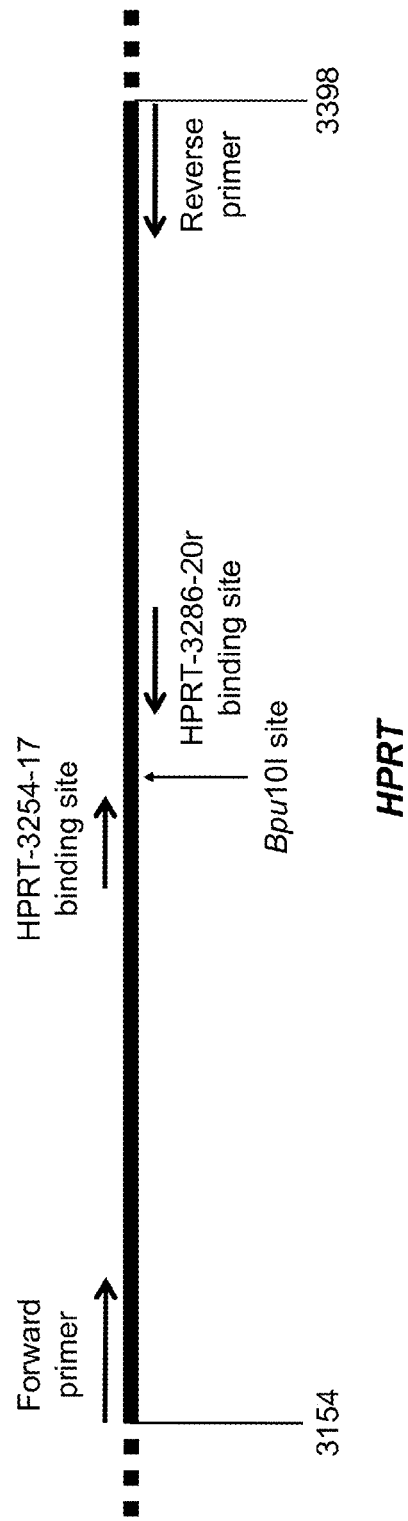
FIG. 41A is a schematic showing the TALEN-targeted site in the human chromosomal HPRT gene. Binding sites for the HPRT-3254-17 and HPRT-3286-20r TALENs, the Bpu10I site in the spacer between those sites, and the primer sites for amplification of the region are indicated. Coordinates at the bottom give distance in base pairs from the first nucleotide of the coding sequence.
Figure 41B:
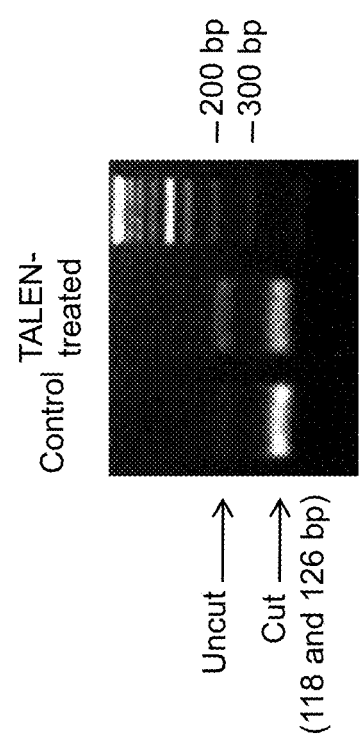
FIG. 41B shows the results of Bpu10I digestion of products of PCR amplification of the region shown in FIG. 41A using genomic DNA isolated from TALEN-treated and untreated cells as templates. Genomic DNA was digested with Bpu10I prior to amplification. DNA fragments were separated by agarose gel electrophoresis and visualized using ethidium bromide.

Next, a pair of TALENs were designed as described in Example 9 to target a sequence in the endogenous human HPRT gene, and named HPRT-3254-17 and HPRT-3286-20r (FIG. 40A and FIG. 40B). Plasmids pTALEN141 encoding HPRT-3254-17 and plasmid pTALEN142 encoding HPRT-3286-20r were constructed using the Golden Gate cloning-based method and reagents described in Example 8. The TALEN genes were then subcloned into the mammalian expression vector pcDNA3.1(−) (Invitrogen, Inc.), which places them under control of the constitutive CMV promoter, yielding plasmids pTALEN141M and pTALEN 142M. HEK 293T cells were then transfected with both pTALEN141M and pTALEN142M together and separately with pcDNA3.1(−) as a negative control. After 72 hours, genomic DNA was isolated and digested with restriction endonuclease Bpu10I. A Bpu10I site exists within the spacer that separates the HPRT-3254-17 and HPRT-3286-20r binding sites in HPRT (FIG. 41A). Following Bpu10I digestion, PCR was used to amplify a 244 bp fragment spanning the TALEN-targeted site from both the TALEN-treated and the control samples. The expected fragment was amplified from both samples, indicating that Bpu10I digestion of the genomic DNA had been incomplete. Subsequent digestion of the PCR products with Bpu10I, however, resulted in complete cleavage of the product amplified from the control sample, but incomplete cleavage of the product from the TALEN treated sample (FIG. 41B). The presence of cleavage-resistant PCR product in the TALEN-treated sample provides evidence that the endogenous Bpu10I site was mutated in vivo as a result of imperfect repair by non-homologous end joining of a TALEN-mediated double strand break at the intended target in HPRT. Thus, TALENs can be used for targeted mutagenesis in mammalian cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for modifying the genetic material of a cell, comprising:
   (a) providing a cell containing a target DNA sequence; and
   (b) introducing a transcription activator-like (TAL) effector endonuclease into the cell, the TAL effector endonuclease comprising:
      (i) a FokI endonuclease domain that can cleave double stranded DNA, and
      (ii) a TAL effector domain comprising a plurality of TAL effector repeat sequences that, in combination, bind to a specific nucleotide sequence in the target DNA sequence,
   such that the TAL effector endonuclease cleaves the target DNA sequence within or adjacent to the specific nucleotide sequence in the cell or progeny thereof.

2. The method of claim 1, further comprising introducing into the cell a nucleic acid comprising a sequence homologous to at least a portion of the target DNA sequence, such that homologous recombination occurs between the target DNA sequence and the nucleic acid.

3. The method of claim 1, wherein the cell is a eukaryotic cell.

4. The method of claim 1, wherein the cell is a plant cell.

5. The method of claim 4, wherein the plant cell is a protoplast.

6. The method of claim 1, wherein the target DNA is chromosomal DNA.

7. The method of claim 1, wherein the introducing comprises transfecting the cell with a nucleic acid encoding the TAL effector endonuclease.

8. The method of claim 1, wherein the introducing comprises mechanically injecting the TAL effector endonuclease into the cell as a protein.

9. The method of claim 1, wherein the introducing comprises delivering the TAL effector endonuclease into the cell as a protein by means of the bacterial type III secretion system.

10. The method of claim 1, wherein the introducing comprises introducing the TAL effector endonuclease into the cell as a protein by electroporation.

11. The method of claim 1, wherein the TAL effector domain that binds to a specific nucleotide sequence within the target DNA sequence comprises 15 or more DNA binding repeats.

12. The method of claim 11, wherein each DNA binding repeat comprises a repeat variable-diresidue (RVD) that determines recognition of a base pair in the target DNA sequence, wherein each DNA binding repeat is responsible for recognizing one base pair in the target DNA sequence, and wherein the RVD comprises one or more of:
   HD for recognizing C;
   NG for recognizing T;
   NI for recognizing A;
   NN for recognizing G;
   NS for recognizing A;
   HG for recognizing T;
   IG for recognizing T;
   NK for recognizing G;
   HA for recognizing C;
   ND for recognizing C;
   HI for recognizing C;
   HN for recognizing G; and
   NA for recognizing G.

13. A method for generating a genetically modified organism, comprising:
   (a) providing a cell capable of generating an organism and containing a target DNA sequence in its genome;
   (b) introducing a TAL effector endonuclease into the cell, the TAL effector endonuclease comprising:
      (i) a FokI endonuclease domain that can cleave double stranded DNA, and
      (ii) a TAL effector domain comprising a plurality of TAL effector repeat sequences that, in combination, bind to a specific nucleotide sequence in the target DNA sequence,
   such that the TAL effector endonuclease cleaves the target DNA sequence within or adjacent to the specific nucleotide sequence in the cell, or progeny thereof, and introduces a genetic modification to the genome of the cell or progeny thereof; and
   (c) generating a genetically modified organism from the cell or progeny resulting from step (b), wherein the organism comprises the genetic modification in its genome.

14. The method of claim 13, wherein cell is a plant cell and the organism is a plant.

15. The method of claim 14, wherein the method further comprises obtaining seeds from the plant.

* * * * *

SEQUENCE LISTING

```
<160> NUMBER OF SEQ ID NOS: 107

<210> SEQ ID NO 1
<211> LENGTH: 34
<212> TYPE: PRT
<213> ORGANISM: Artificial Sequence
<220> FEATURE:
<223> OTHER INFORMATION: synthetic peptide

<400> SEQUENCE: 1

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 2
<211> LENGTH: 17
<212> TYPE: DNA
<213> ORGANISM: Artificial Sequence
<220> FEATURE:
<223> OTHER INFORMATION: target sequence

<400> SEQUENCE: 2
agaagaagag acccata                                                  17

<210> SEQ ID NO 3
<211> LENGTH: 18
<212> TYPE: DNA
<213> ORGANISM: Artificial Sequence
<220> FEATURE:
<223> OTHER INFORMATION: target sequence

<400> SEQUENCE: 3
```

```
atataaacct aaccatcc                                           18

<210> SEQ ID NO 4
<211> LENGTH: 18
<212> TYPE: DNA
<213> ORGANISM: Artificial Sequence
<220> FEATURE:
<223> OTHER INFORMATION: target sequence

<400> SEQUENCE: 4
atataaacct gacccttt                                           18

<210> SEQ ID NO 5
<211> LENGTH: 14
<212> TYPE: DNA
<213> ORGANISM: Artificial Sequence
<220> FEATURE:
<223> OTHER INFORMATION: target sequence

<400> SEQUENCE: 5
atataaacct ctct                                               14

<210> SEQ ID NO 6
<211> LENGTH: 15
<212> TYPE: DNA
<213> ORGANISM: Artificial Sequence
<220> FEATURE:
<223> OTHER INFORMATION: target sequence

<400> SEQUENCE: 6
atataaacct aacca                                              15

<210> SEQ ID NO 7
<211> LENGTH: 14
<212> TYPE: DNA
<213> ORGANISM: Artificial Sequence
<220> FEATURE:
<223> OTHER INFORMATION: target sequence

<400> SEQUENCE: 7
ataaacctaa ccat                                               14

<210> SEQ ID NO 8
<211> LENGTH: 24
<212> TYPE: DNA
<213> ORGANISM: Artificial Sequence
<220> FEATURE:
<223> OTHER INFORMATION: target sequence

<400> SEQUENCE: 8
gcatctcccc ctactgtaca ccac                                    24

<210> SEQ ID NO 9
<211> LENGTH: 23
<212> TYPE: DNA
<213> ORGANISM: Artificial Sequence
<220> FEATURE:
<223> OTHER INFORMATION: target sequence

<400> SEQUENCE: 9
ataaaaggcc ctcaccaacc cat                                     23

<210> SEQ ID NO 10
<211> LENGTH: 22
<212> TYPE: DNA
```

```
<213> ORGANISM: Artificial Sequence
<220> FEATURE:
<223> OTHER INFORMATION: target sequence

<400> SEQUENCE: 10
ataatcccca aatcccctcc tc                                              22

<210> SEQ ID NO 11
<211> LENGTH: 16
<212> TYPE: DNA
<213> ORGANISM: Artificial Sequence
<220> FEATURE:
<223> OTHER INFORMATION: target sequence

<400> SEQUENCE: 11
ccccctcgct tccctt                                                     16

<210> SEQ ID NO 12
<211> LENGTH: 1164
<212> TYPE: PRT
<213> ORGANISM: Xanthomonas euvesicatoria

<400> SEQUENCE: 12

Met Asp Pro Ile Arg Ser Arg Thr Pro Ser Pro Ala Arg Glu Leu Leu
 1               5                  10                  15

Pro Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Gly Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270
```

```
Glu Ala Val His Ala Trp Arg Asn Ala Leu Thr Gly Ala Pro Leu Asn
            275                 280                 285

Leu Thr Pro Glu Gln Val Val Ala Ile Ala Ser His Asp Gly Gly Lys
290                 295                 300

Gln Ala Leu Glu Thr Val Gln Arg Leu Leu Pro Val Leu Cys Gln Ala
305                 310                 315                 320

His Gly Leu Thr Pro Gln Gln Val Val Ala Ile Ala Ser Asn Gly Gly
                325                 330                 335

Gly Lys Gln Ala Leu Glu Thr Val Gln Arg Leu Leu Pro Val Leu Cys
            340                 345                 350

Gln Ala His Gly Leu Thr Pro Gln Gln Val Val Ala Ile Ala Ser Asn
            355                 360                 365

Ser Gly Gly Lys Gln Ala Leu Glu Thr Val Gln Arg Leu Leu Pro Val
370                 375                 380

Leu Cys Gln Ala His Gly Leu Thr Pro Glu Gln Val Val Ala Ile Ala
385                 390                 395                 400

Ser Asn Gly Gly Gly Lys Gln Ala Leu Glu Thr Val Gln Arg Leu Leu
                405                 410                 415

Pro Val Leu Cys Gln Ala His Gly Leu Thr Pro Glu Gln Val Val Ala
                420                 425                 430

Ile Ala Ser Asn Ile Gly Gly Lys Gln Ala Leu Glu Thr Val Gln Ala
            435                 440                 445

Leu Leu Pro Val Leu Cys Gln Ala His Gly Leu Thr Pro Glu Gln Val
        450                 455                 460

Val Ala Ile Ala Ser Asn Ile Gly Gly Lys Gln Ala Leu Glu Thr Val
465                 470                 475                 480

Gln Ala Leu Leu Pro Val Leu Cys Gln Ala His Gly Leu Thr Pro Glu
                485                 490                 495

Gln Val Val Ala Ile Ala Ser Asn Ile Gly Gly Lys Gln Ala Leu Glu
                500                 505                 510

Thr Val Gln Ala Leu Leu Pro Val Leu Cys Gln Ala His Gly Leu Thr
        515                 520                 525

Pro Glu Gln Val Val Ala Ile Ala Ser His Asp Gly Gly Lys Gln Ala
530                 535                 540

Leu Glu Thr Val Gln Arg Leu Leu Pro Val Leu Cys Gln Ala His Gly
545                 550                 555                 560

Leu Thr Pro Glu Gln Val Val Ala Ile Ala Ser His Asp Gly Gly Lys
                565                 570                 575

Gln Ala Leu Glu Thr Val Gln Arg Leu Leu Pro Val Leu Cys Gln Ala
            580                 585                 590

His Gly Leu Thr Pro Gln Gln Val Val Ala Ile Ala Ser Asn Gly Gly
        595                 600                 605

Gly Lys Gln Ala Leu Glu Thr Val Gln Arg Leu Leu Pro Val Leu Cys
610                 615                 620

Gln Ala His Gly Leu Thr Pro Glu Gln Val Val Ala Ile Ala Ser Asn
625                 630                 635                 640

Ser Gly Gly Lys Gln Ala Leu Glu Thr Val Gln Ala Leu Leu Pro Val
                645                 650                 655

Leu Cys Gln Ala His Gly Leu Thr Pro Glu Gln Val Val Ala Ile Ala
                660                 665                 670

Ser Asn Ser Gly Gly Lys Gln Ala Leu Glu Thr Val Gln Arg Leu Leu
            675                 680                 685

Pro Val Leu Cys Gln Ala His Gly Leu Thr Pro Glu Gln Val Val Ala
```

```
                690                 695                 700
Ile Ala Ser His Asp Gly Gly Lys Gln Ala Leu Glu Thr Val Gln Arg
705                 710                 715                 720

Leu Leu Pro Val Leu Cys Gln Ala His Gly Leu Thr Pro Glu Gln Val
                725                 730                 735

Val Ala Ile Ala Ser His Asp Gly Gly Lys Gln Ala Leu Glu Thr Val
                740                 745                 750

Gln Arg Leu Leu Pro Val Leu Cys Gln Ala His Gly Leu Thr Pro Glu
        755                 760                 765

Gln Val Val Ala Ile Ala Ser His Asp Gly Gly Lys Gln Ala Leu Glu
        770                 775                 780

Thr Val Gln Arg Leu Leu Pro Val Leu Cys Gln Ala His Gly Leu Thr
785                 790                 795                 800

Pro Gln Gln Val Val Ala Ile Ala Ser Asn Gly Gly Arg Pro Ala
                805                 810                 815

Leu Glu Thr Val Gln Arg Leu Leu Pro Val Leu Cys Gln Ala His Gly
        820                 825                 830

Leu Thr Pro Glu Gln Val Val Ala Ile Ala Ser His Asp Gly Gly Lys
        835                 840                 845

Gln Ala Leu Glu Thr Val Gln Arg Leu Leu Pro Val Leu Cys Gln Ala
        850                 855                 860

His Gly Leu Thr Pro Gln Gln Val Val Ala Ile Ala Ser Asn Gly Gly
865                 870                 875                 880

Gly Arg Pro Ala Leu Glu Ser Ile Val Ala Gln Leu Ser Arg Pro Asp
                885                 890                 895

Pro Ala Leu Ala Ala Leu Thr Asn Asp His Leu Val Ala Leu Ala Cys
                900                 905                 910

Leu Gly Gly Arg Pro Ala Leu Asp Ala Val Lys Lys Gly Leu Pro His
        915                 920                 925

Ala Pro Ala Leu Ile Lys Arg Thr Asn Arg Arg Ile Pro Glu Arg Thr
        930                 935                 940

Ser His Arg Val Ala Asp His Ala Gln Val Val Arg Val Leu Gly Phe
945                 950                 955                 960

Phe Gln Cys His Ser His Pro Ala Gln Ala Phe Asp Asp Ala Met Thr
                965                 970                 975

Gln Phe Gly Met Ser Arg His Gly Leu Leu Gln Leu Phe Arg Arg Val
        980                 985                 990

Gly Val Thr Glu Leu Glu Ala Arg Ser Gly Thr Leu Pro Pro Ala Ser
        995                 1000                1005

Gln Arg Trp Asp Arg Ile Leu Gln Ala Ser Gly Met Lys Arg Ala Lys
        1010                1015                1020

Pro Ser Pro Thr Ser Thr Gln Thr Pro Asp Gln Ala Ser Leu His Ala
1025                1030                1035                1040

Phe Ala Asp Ser Leu Glu Arg Asp Leu Asp Ala Pro Ser Pro Met His
                1045                1050                1055

Glu Gly Asp Gln Thr Arg Ala Ser Ser Arg Lys Arg Ser Arg Ser Asp
                1060                1065                1070

Arg Ala Val Thr Gly Pro Ser Ala Gln Gln Ser Phe Glu Val Arg Val
        1075                1080                1085

Pro Glu Gln Arg Asp Ala Leu His Leu Pro Leu Ser Trp Arg Val Lys
        1090                1095                1100

Arg Pro Arg Thr Ser Ile Gly Gly Gly Leu Pro Asp Pro Gly Thr Pro
1105                1110                1115                1120
```

Thr Ala Ala Asp Leu Ala Ala Ser Ser Thr Val Met Arg Glu Gln Asp
            1125                1130                1135

Glu Asp Pro Phe Ala Gly Ala Ala Asp Asp Phe Pro Ala Phe Asn Glu
        1140                1145                1150

Glu Glu Leu Ala Trp Leu Met Glu Leu Leu Pro Gln
        1155                1160

<210> SEQ ID NO 13
<211> LENGTH: 4366
<212> TYPE: DNA
<213> ORGANISM: Xanthomonas euvesicatoria

<400> SEQUENCE: 13
gaattcaagg tgtcaaaaag cgataggcgg aattatagat gtacttgtat gaacttatca 60
acgccagttt agtgaacggg ttcgacaaag cgaaaccaac acccaggcgc gaaagccttg 120
cgccgcaatg ctttccggca atgtgaccca gggcattgac cgaaacggcg taggaatttc 180
ggaacacgac ggtaggggaa tgctctaccg cccggctacg caaaagcact ctcgcctgcc 240
agacgcgcca ctgcgtggaa ttggccgtta tgtccgctgg cggcctcgcc gccgtagtgc 300
ttgcagcgca gccttgaatg atcgaacatc aaacatcact gtttgatagg tcgatcatga 360
catcgcccat ttcgagggtc ggcagggatt cgtgtaaaaa acagccaaaa gtgagctaac 420
tcgctgtcag cacagaaatt tttcacaacc ttctgccgat cctccatgcg ggtccgtgat 480
cgccttcatg tctgcgcctc accctggtcg tcgagggttg ccaggatcac ccgaagttgt 540
gtactgccat gcggcctcgg aagctatgta ggaaccacag accgctagtc tggaggcgac 600
catgtaaaga ggtatgcctg atggatccca ttcgttcgcg cacaccaagt cctgcccgcg 660
agcttctgcc cggaccccaa cccgatgggg ttcagccgac tgcagatcgt ggggtgtctc 720
cgcctgccgg cggccccctg gatggcttgc ccgctcggcg gacgatgtcc cggacccggc 780
tgccatctcc ccctgccccc tcacctgcgt tctcggcggg cagcttcagt gacctgttac 840
gtcagttcga tccgtcactt tttaatacat cgctttttga ttcattgcct cccttcggcg 900
ctcaccatac agaggctgcc acaggcgagt gggatgaggt gcaatcgggt ctgcgggcag 960
ccgacgcccc cccacccacc atgcgcgtgg ctgtcactgc cgcgcggccg ccgcgcgcca 1020
agccggcgcc gcgacgacgt gctgcgcaac cctccgacgc ttcgccggcc gcgcaggtgg 1080
atctacgcac gctcggctac agccagcagc aacaggagaa gatcaaaccg aaggttcgtt 1140
cgacagtggc gcagcaccac gaggcactgg tcggccatgg gtttacacac gcgcacatcg 1200
ttgcgctcag ccaacacccg gcagcgttag ggaccgtcgc tgtcaagtat caggacatga 1260
tcgcagcgtt gccagaggcg acacacgaag cgatcgttgg cgtcggcaaa cagtggtccg 1320
gcgcacgcgc tctggaggcc ttgctcacgg tggcgggaga gttgagaggt ccaccgttac 1380
agttggacac aggccaactt ctcaagattg caaaacgtgg cggcgtgacc gcagtggagg 1440
cagtgcatgc atggcgcaat gcactgacgg gtgcccccct gaacctgacc ccggagcagg 1500
tggtggccat cgccagccac gatggcggca agcaggcgct ggagacggtg cagcggctgt 1560
tgccggtgct gtgccaggcc catggcctga ccccgcagca ggtggtggcc atcgccagca 1620
atggcggtgg caagcaggcg ctggagacgg tgcagcggct gttgccggtg ctgtgccagg 1680
cccatggcct gaccccgcag caggtggtgg ccatcgccag caatagcggt ggcaagcagg 1740
cgctggagac ggtgcagcgg ctgttgccgg tgctgtgcca ggcccatggc ctgaccccgg 1800
agcaggtggt ggccatcgcc agcaatggcg gtggcaagca ggcgctggag acggtgcagc 1860

```
ggctgttgcc ggtgctgtgc caggcccatg gcctgacccc ggagcaggtg gtggccatcg      1920
ccagcaatat tggtggcaag caggcgctgg agacggtgca gcggctgttg ccggtgctgt      1980
gccaggccca tggcctgacc ccggagcagg tggtggccat cgccagcaat attggtggca      2040
agcaggcgct ggagacggtg caggcgctgt tgccggtgct gtgccaggcc atggcctga      2100 ccccggagca ggtggtggcc atcgccagca atattggtgg caagcaggcg ctggagacgg      2160
tgcaggcgct gttgccggtg ctgtgccagg cccatggcct gaccccggag caggtggtgg      2220
ccatcgccag ccacgatggc ggcaagcagg cgctggagac ggtgcagcgg ctgttgccgg      2280
tgctgtgcca ggcccatggc ctgaccccgg agcaggtggt ggccatcgcc agccacgatg      2340
gcggcaagca ggcgctggag acggtgcagc ggctgttgcc ggtgctgtgc caggcccatg      2400
gcctgacccc gcagcaggtg gtggccatcg ccagcaatgg cggtggcaag caggcgctgg      2460
agacggtgca gcggctgttg ccggtgctgt gccaggccca tggcctgacc ccggagcagg      2520
tggtggccat cgccagcaat agcggtggca agcaggcgct ggagacggtg caggcgctgt      2580
tgccggtgct gtgccaggcc catggcctga ccccggagca ggtggtggcc atcgccagca      2640
atagcggtgg caagcaggcg ctggagacgg tgcagcggct gttgccggtg ctgtgccagg      2700
cccatggcct gaccccggag caggtggtgg ccatcgccag ccacgatggc ggcaagcagg      2760
cgctggagac ggtgcagcgg ctgttgccgg tgctgtgcca ggcccatggc ctgaccccgg      2820
agcaggtggt ggccatcgcc agccacgatg gcggcaagca ggcgctggag acggtgcagc      2880
ggctgttgcc ggtgctgtgc caggcccatg gcctgacccc ggagcaggtg gtggccatcg      2940
ccagccacga tggcggcaag caggcgctgg agacggtgca gcggctgttg ccggtgctgt      3000
gccaggccca tggcctgacc ccgcagcagg tggtggccat cgccagcaat ggcggcggca      3060
ggccggcgct ggagacggtg cagcggctgt tgccggtgct gtgccaggcc catggcctga      3120
ccccggagca ggtggtggcc atcgccagcc acgatggcgg caagcaggcg ctggagacgg      3180
tgcagcggct gttgccggtg ctgtgccagg cccatggcct gaccccgcag caggtggtgg      3240
ccatcgccag caatggcggc ggcaggccgc gctggagag cattgttgcc cagttatctc      3300
gccctgatcc ggcgttggcc gcgttgacca acgaccacct cgtcgccttg gcctgcctcg      3360
gcggacgtcc tgcgctggat gcagtgaaaa agggattgcc gcacgcgccg gccttgatca      3420
aaagaaccaa tcgccgtatt cccgaacgca catcccatcg cgttgccgac cacgcgcaag      3480
tggttcgcgt gctgggtttt ttccagtgcc actcccaccc agcgcaagca tttgatgacg      3540
ccatgacgca gttcgggatg agcaggcacg ggttgttaca gctctttcgc agagtgggcg      3600
tcaccgaact cgaagcccgc agtggaacgc tccccccagc ctcgcagcgt gggaccgta      3660 tcctccaggc atcagggatg aaaagggcca accgtcccc tacttcaact caaacgccgg      3720
atcaggcgtc tttgcatgca ttcgccgatt cgctggagcg tgaccttgat gcgcctagcc      3780
caatgcacga gggagatcag acgcgggcaa gcagccgtaa acgtcccga tcggatcgtg      3840 ctgtcaccgg tccctccgca cagcaatcgt tcgaggtgcg cgttcccgaa cagcgcgatg      3900
cgctgcattt gccctcagt tggagggtaa aacgcccgcg taccagtatc gggggcggcc      3960
tcccggatcc tggtacgccc acggctgccg acctggcagc gtccagcacc gtgatgcggg      4020
aacaagatga ggacccctcc gcagggggcag cggatgattt cccggcattc aacgaagagg      4080
agctcgcatg gttgatggag ctattgcctc agtgaggctc agtcggtgac tacctgagcg      4140
tcggcaggga ttggtgtaag taacctttac tgacagcgag ttagcccact tttggctgtt      4200
```

-continued

```
ttttacacaa atccctgcct cccctctggt tgcaccacac ccgtacacca agcgcggcgg   4260
cgaagcaggc accgagtggt tccgctgcgg tgttgcgttc cctaaccagg gcggtggcta   4320
tacgctcaag ctgcgcaccg tcccggtggc gatcgacgac gaaatg                  4366

<210> SEQ ID NO 14
<211> LENGTH: 56
<212> TYPE: DNA
<213> ORGANISM: Artificial Sequence
<220> FEATURE:
<223> OTHER INFORMATION: target sequence

<400> SEQUENCE: 14
tatataaacc taaccatcct cacaacttca agttatcgga tggttaggtt tatata         56

<210> SEQ ID NO 15
<211> LENGTH: 56
<212> TYPE: DNA
<213> ORGANISM: Artificial Sequence
<220> FEATURE:
<223> OTHER INFORMATION: target sequence

<400> SEQUENCE: 15
tatataaacc taaccatccg ataacttgaa gttgtgagga tggttaggtt tatata         56

<210> SEQ ID NO 16
<211> LENGTH: 1373
<212> TYPE: PRT
<213> ORGANISM: Xanthomonas euvesicatoria

<400> SEQUENCE: 16

Met Asp Pro Ile Arg Ser Arg Thr Pro Ser Pro Ala Arg Glu Leu Leu
1               5                   10                  15

Pro Gly Pro Gln Pro Asp Arg Val Gln Pro Thr Ala Asp Arg Gly Gly
            20                  25                  30

Ala Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Gly Ser Phe Ser Asp Leu Leu Arg Gln Phe Asp Pro Ser Leu
65                  70                  75                  80

Leu Asp Thr Ser Leu Leu Asp Ser Met Pro Ala Val Gly Thr Pro His
                85                  90                  95

Thr Ala Ala Ala Pro Ala Glu Cys Asp Glu Val Gln Ser Gly Leu Arg
            100                 105                 110

Ala Ala Asp Asp Pro Pro Pro Thr Val Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Gly Ser Thr Val
                165                 170                 175

Ala Gln His His Glu Ala Leu Val Gly His Gly Phe Thr His Ala His
            180                 185                 190

Ile Val Ala Leu Ser Arg His Pro Ala Ala Leu Gly Thr Val Ala Val
        195                 200                 205

Lys Tyr Gln Asp Met Ile Ala Ala Leu Pro Glu Ala Thr His Glu Asp
    210                 215                 220
```

```
Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
            245                 250                 255

Thr Gly Gln Leu Val Lys Ile Ala Lys Arg Gly Gly Val Thr Ala Val
                260                 265                 270

Glu Ala Val His Ala Ser Arg Asn Ala Leu Thr Gly Ala Pro Leu Asn
            275                 280                 285

Leu Thr Pro Ala Gln Val Val Ala Ile Ala Ser Asn Asn Gly Gly Lys
            290                 295                 300

Gln Ala Leu Glu Thr Val Gln Arg Leu Leu Pro Val Leu Cys Gln Ala
305                 310                 315                 320

His Gly Leu Thr Pro Ala Gln Val Val Ala Ile Ala Ser His Asp Gly
                325                 330                 335

Gly Lys Gln Ala Leu Glu Thr Met Gln Arg Leu Leu Pro Val Leu Cys
            340                 345                 350

Gln Ala His Gly Leu Pro Pro Asp Gln Val Val Ala Ile Ala Ser Asn
            355                 360                 365

Ile Gly Gly Lys Gln Ala Leu Glu Thr Val Gln Arg Leu Leu Pro Val
370                 375                 380

Leu Cys Gln Ala His Gly Leu Thr Pro Asp Gln Val Val Ala Ile Ala
385                 390                 395                 400

Ser His Gly Gly Gly Lys Gln Ala Leu Glu Thr Val Gln Arg Leu Leu
            405                 410                 415

Pro Val Leu Cys Gln Ala His Gly Leu Thr Pro Asp Gln Val Val Ala
            420                 425                 430

Ile Ala Ser His Asp Gly Gly Lys Gln Ala Leu Glu Thr Val Gln Arg
            435                 440                 445

Leu Leu Pro Val Leu Cys Gln Ala His Gly Leu Thr Pro Asp Gln Val
            450                 455                 460

Val Ala Ile Ala Ser Asn Gly Gly Gly Lys Gln Ala Leu Glu Thr Val
465                 470                 475                 480

Gln Arg Leu Leu Pro Val Leu Cys Gln Ala His Gly Leu Thr Pro Asp
                485                 490                 495

Gln Val Val Ala Ile Ala Ser Asn Gly Gly Lys Gln Ala Leu Glu Thr
            500                 505                 510

Val Gln Arg Leu Leu Pro Val Leu Cys Gln Ala His Gly Leu Thr Pro
            515                 520                 525

Asp Gln Val Val Ala Ile Ala Ser His Asp Gly Gly Lys Gln Ala Leu
530                 535                 540

Glu Thr Val Gln Arg Leu Leu Pro Val Leu Cys Gln Thr His Gly Leu
545                 550                 555                 560

Thr Pro Ala Gln Val Val Ala Ile Ala Ser His Asp Gly Gly Lys Gln
            565                 570                 575

Ala Leu Glu Thr Val Gln Gln Leu Leu Pro Val Leu Cys Gln Ala His
            580                 585                 590

Gly Leu Thr Pro Asp Gln Val Val Ala Ile Ala Ser Asn Ile Gly Gly
            595                 600                 605

Lys Gln Ala Leu Ala Thr Val Gln Arg Leu Leu Pro Val Leu Cys Gln
            610                 615                 620

Ala His Gly Leu Thr Pro Asp Gln Val Val Ala Ile Ala Ser Asn Gly
625                 630                 635                 640
```

```
Gly Gly Lys Gln Ala Leu Glu Thr Val Gln Arg Leu Leu Pro Val Leu
                645                 650                 655
Cys Gln Ala His Gly Leu Thr Pro Asp Gln Val Val Ala Ile Ala Ser
            660                 665                 670
Asn Gly Gly Lys Gln Ala Leu Glu Thr Val Gln Arg Leu Leu Pro
        675                 680                 685
Val Leu Cys Gln Ala His Gly Leu Thr Gln Val Gln Val Val Ala Ile
    690                 695                 700
Ala Ser Asn Ile Gly Gly Lys Gln Ala Leu Glu Thr Val Gln Arg Leu
705                 710                 715                 720
Leu Pro Val Leu Cys Gln Ala His Gly Leu Thr Pro Ala Gln Val Val
                725                 730                 735
Ala Ile Ala Ser His Asp Gly Gly Lys Gln Ala Leu Glu Thr Val Gln
            740                 745                 750
Arg Leu Leu Pro Val Leu Cys Gln Ala His Gly Leu Thr Pro Asp Gln
        755                 760                 765
Val Val Ala Ile Ala Ser Asn Gly Gly Gly Lys Gln Ala Leu Glu Thr
    770                 775                 780
Val Gln Arg Leu Leu Pro Val Leu Cys Gln Ala His Gly Leu Thr Gln
785                 790                 795                 800
Glu Gln Val Val Ala Ile Ala Ser Asn Asn Gly Gly Lys Gln Ala Leu
                805                 810                 815
Glu Thr Val Gln Arg Leu Leu Pro Val Leu Cys Gln Ala His Gly Leu
            820                 825                 830
Thr Pro Asp Gln Val Val Ala Ile Ala Ser Asn Gly Gly Gly Lys Gln
        835                 840                 845
Ala Leu Glu Thr Val Gln Arg Leu Leu Pro Val Leu Cys Gln Ala His
    850                 855                 860
Gly Leu Thr Pro Ala Gln Val Val Ala Ile Ala Ser Asn Ile Gly Gly
865                 870                 875                 880
Lys Gln Ala Leu Glu Thr Val Gln Arg Leu Leu Pro Val Leu Cys Gln
                885                 890                 895
Asp His Gly Leu Thr Leu Ala Gln Val Val Ala Ile Ala Ser Asn Ile
            900                 905                 910
Gly Gly Lys Gln Ala Leu Glu Thr Val Gln Arg Leu Leu Pro Val Leu
        915                 920                 925
Cys Gln Ala His Gly Leu Thr Gln Asp Gln Val Val Ala Ile Ala Ser
    930                 935                 940
Asn Ile Gly Gly Lys Gln Ala Leu Glu Thr Val Gln Arg Leu Leu Pro
945                 950                 955                 960
Val Leu Cys Gln Asp His Gly Leu Thr Pro Asp Gln Val Val Ala Ile
                965                 970                 975
Ala Ser Asn Ile Gly Gly Lys Gln Ala Leu Glu Thr Val Gln Arg Leu
            980                 985                 990
Leu Pro Val Leu Cys Gln Asp His Gly Leu Thr Leu Asp Gln Val Val
        995                 1000                1005
Ala Ile Ala Ser Asn Gly Gly Lys Gln Ala Leu Glu Thr Val Gln Arg
    1010                1015                1020
Leu Leu Pro Val Leu Cys Gln Asp His Gly Leu Thr Pro Asp Gln Val
1025                1030                1035                1040
Val Ala Ile Ala Ser Asn Ser Gly Gly Lys Gln Ala Leu Glu Thr Val
                1045                1050                1055
Gln Arg Leu Leu Pro Val Leu Cys Gln Asp His Gly Leu Thr Pro Asn
```

Gln Val Val Ala Ile Ala Ser Asn Gly Gly Lys Gln Ala Leu Glu Ser
          1075                1080                1085

Ile Val Ala Gln Leu Ser Arg Pro Asp Pro Ala Leu Ala Ala Leu Thr
    1090                1095                1100

Asn Asp His Leu Val Ala Leu Ala Cys Leu Gly Gly Arg Pro Ala Met
1105                1110                1115                1120

Asp Ala Val Lys Lys Gly Leu Pro His Ala Pro Glu Leu Ile Arg Arg
              1125                1130                1135

Val Asn Arg Arg Ile Gly Glu Arg Thr Ser His Arg Val Ala Asp Tyr
          1140                1145                1150

Ala Gln Val Val Arg Val Leu Glu Phe Phe Gln Cys His Ser His Pro
          1155                1160                1165

Ala Tyr Ala Phe Asp Glu Ala Met Thr Gln Phe Gly Met Ser Arg Asn
    1170                1175                1180

Gly Leu Val Gln Leu Phe Arg Arg Val Gly Val Thr Glu Leu Glu Ala
1185                1190                1195                1200

Arg Gly Gly Thr Leu Pro Pro Ala Ser Gln Arg Trp Asp Arg Ile Leu
              1205                1210                1215

Gln Ala Ser Gly Met Lys Arg Ala Lys Pro Ser Pro Thr Ser Ala Gln
          1220                1225                1230

Thr Pro Asp Gln Ala Ser Leu His Ala Phe Ala Asp Ser Leu Glu Arg
          1235                1240                1245

Asp Leu Asp Ala Pro Ser Pro Met His Glu Gly Asp Gln Thr Gly Ala
          1250                1255                1260

Ser Ser Arg Lys Arg Ser Arg Ser Asp Arg Ala Val Thr Gly Pro Ser
1265                1270                1275                1280

Ala Gln His Ser Phe Glu Val Arg Val Pro Gln Arg Asp Ala Leu
          1285                1290                1295

His Leu Pro Leu Ser Trp Arg Val Lys Arg Pro Arg Thr Arg Ile Gly
          1300                1305                1310

Gly Gly Leu Pro Asp Pro Gly Thr Pro Ile Ala Ala Asp Leu Ala Ala
          1315                1320                1325

Ser Ser Thr Val Met Trp Glu Gln Asp Ala Ala Pro Phe Ala Gly Ala
          1330                1335                1340

Ala Asp Asp Phe Pro Ala Phe Asn Glu Glu Leu Ala Trp Leu Met
1345                1350                1355                1360

Glu Leu Leu Pro Gln Ser Gly Ser Val Gly Gly Thr Ile
          1365                1370

<210> SEQ ID NO 17
<211> LENGTH: 102
<212> TYPE: DNA
<213> ORGANISM: Artificial Sequence
<220> FEATURE:
<223> OTHER INFORMATION: synthetic oligonucleotide

<400> SEQUENCE: 17
ctgaccccgg cacaggtggt ggccatcgcc agcmaygayg gcggcaagca ggcgctggag    60
acggtgcagc ggctgttgcc ggtgctgtgc caggaccatg gc                      102

<210> SEQ ID NO 18
<211> LENGTH: 34
<212> TYPE: PRT
<213> ORGANISM: Artificial Sequence
<220> FEATURE:

<223> OTHER INFORMATION: synthetic peptide

<400> SEQUENCE: 18

Leu Thr Pro Ala Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 19
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 19
ctgaccccgg cacaggtggt ggccatcgcc agcmaygayg cggcaagca ggcgctcgag    60 agc                                                                63

<210> SEQ ID NO 20
<211> LENGTH: 21
<212> TYPE: PRT
<213> ORGANISM: Artificial Sequence
<220> FEATURE:
<223> OTHER INFORMATION: synthetic peptide

<400> SEQUENCE: 20

Leu Thr Pro Ala Gln Val Val Ala Ile Ala Ser His Asp Gly Gly Lys
1               5                   10                  15

Gln Ala Leu Glu Ser
            20

<210> SEQ ID NO 21
<211> LENGTH: 12
<212> TYPE: DNA
<213> ORGANISM: Xanthomonas oryzae

<400> SEQUENCE: 21
gcgctggaga gc                                                      12

<210> SEQ ID NO 22
<211> LENGTH: 4
<212> TYPE: PRT
<213> ORGANISM: Xanthomonas oryzae

<400> SEQUENCE: 22

Ala Leu Glu Ser
1

<210> SEQ ID NO 23
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 23
gcgctcgagt cc                                                      12

<210> SEQ ID NO 24
<211> LENGTH: 102
<212> TYPE: DNA

```
<213> ORGANISM: Artificial Sequence
<220> FEATURE:
<223> OTHER INFORMATION: synthetic oligonucleotide

<400> SEQUENCE: 24
tcgagacggt gcagcggctg ttgccggtgc tgtgccagga ccatggcctg accccggacc    60
aagtggtggc catcgccagc aacattggcg gcaagcaagc gc                      102

<210> SEQ ID NO 25
<211> LENGTH: 102
<212> TYPE: DNA
<213> ORGANISM: Artificial Sequence
<220> FEATURE:
<223> OTHER INFORMATION: synthetic oligonucleotide

<400> SEQUENCE: 25
tcgagcgctt gcttgccgcc aatgttgctg gcgatggcca ccacttggtc cggggtcagg    60
ccatggtcct ggcacagcac cggcaacagc cgctgcaccg tc                      102

<210> SEQ ID NO 26
<211> LENGTH: 35
<212> TYPE: PRT
<213> ORGANISM: Artificial Sequence
<220> FEATURE:
<223> OTHER INFORMATION: synthetic peptide

<400> SEQUENCE: 26

Glu Thr Val Gln Arg Leu Leu Pro Val Leu Cys Gln Asp His Gly Leu
 1               5                  10                  15

Thr Pro Asp Gln Val Val Ala Ile Ala Ser Asn Ile Gly Gly Lys Gln
            20                  25                  30

Ala Leu Glu
        35

<210> SEQ ID NO 27
<211> LENGTH: 102
<212> TYPE: DNA
<213> ORGANISM: Artificial Sequence
<220> FEATURE:
<223> OTHER INFORMATION: synthetic oligonucleotide

<400> SEQUENCE: 27
tcgaaacggt gcagcggctg ttgccggtgc tgtgccagga ccatggcctg accccggacc    60
aagtggtggc tatcgccagc aacattggcg gcaagcaagc gc                      102

<210> SEQ ID NO 28
<211> LENGTH: 102
<212> TYPE: DNA
<213> ORGANISM: Artificial Sequence
<220> FEATURE:
<223> OTHER INFORMATION: synthetic oligonucleotide

<400> SEQUENCE: 28
tcgagcgctt gcttgccgcc aatgttgctg gcgatagcca ccacttggtc cggggtcagg    60
ccatggtcct ggcacagcac cggcaacagc cgctgcaccg tt                      102

<210> SEQ ID NO 29
<211> LENGTH: 18
<212> TYPE: DNA
<213> ORGANISM: Artificial Sequence
<220> FEATURE:
<223> OTHER INFORMATION: target sequence
```

```
<400> SEQUENCE: 29
atcaagattc tcttcact                                                   18

<210> SEQ ID NO 30
<211> LENGTH: 15
<212> TYPE: DNA
<213> ORGANISM: Artificial Sequence
<220> FEATURE:
<223> OTHER INFORMATION: target sequence

<400> SEQUENCE: 30
cccagaagta aacat                                                      15

<210> SEQ ID NO 31
<211> LENGTH: 598
<212> TYPE: PRT
<213> ORGANISM: Xanthomonas oryzae

<400> SEQUENCE: 31
```

Leu Thr Pro Gl

```
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ser Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser Asn Ser Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu Thr Val Gln Arg Leu Leu Pro Val Leu Cys Gln Ala His Gly
    530                 535                 540

Leu Thr Pro Glu Gln Val Val Ala Ile Ala Ser His Asp Gly Gly Lys
545                 550                 555                 560

Gln Ala Leu Glu Thr Val Gln Arg Leu Leu Pro Val Leu Cys Gln Ala
                565                 570                 575

His Gly Leu Thr Pro Gln Gln Val Val Ala Ile Ala Ser Asn Gly Gly
            580                 585                 590

Gly Arg Pro Ala Leu Glu
        595

<210> SEQ ID NO 32
<211> LENGTH: 4122
<212> TYPE: DNA
<213> ORGANISM: Xanthomonas oryzae

<400> SEQUENCE: 32
atggatccca ttcgttcgcg cacgccaagt cctgcccgcg agcttctgcc cggaccccaa      60
ccggataggg ttcagccgac tgcagatcgg gggggggctc cgcctgctgg cggccccctg     120
gatggcttgc ccgctcggcg gacgatgtcc cggacccggc tgccatctcc ccctgcgccc     180
tcgcctgcgt tctcggcggg cagcttcagc gatctgctcc gtcagttcga tccgtcgctt     240
cttgatacat cgcttcttga ttcgatgcct gccgtcggca cgccgcatac agcggctgcc     300
ccagcagagt gcgatgaggt gcaatcgggt ctgcgtgcag ccgatgaccc gccacccacc     360
```

```
gtgcgtgtcg ctgtcactgc cgcgcggccg ccgcgcgcca agccggcccc gcgacggcgt      420
gcggcgcaac cctccgacgc ttcgccggcc gcgcaggtgg atctacgcac gctcggctac      480
agtcagcagc agcaagagaa gatcaaaccg aaggtgggtt cgacagtggc gcagcaccac      540
gaggcactgg tgggccatgg gtttacacac gcgcacatcg ttgcgctcag ccgacacccg      600
gcagcgttag ggaccgtcgc tgtcaagtat caggacatga tcgcggcgtt accagaggcg      660
acacacgaag acatcgttgg tgtcggcaaa cagtggtccg gcgcacgcgc cctgcaggcc      720
ttgctcacgg tggcgggaga gttgagaggt ccaccgttac agttggacac aggccaactt      780
gtcaagattg caaaacgtgg cggcgtgacc gcagtggagg cagtgcatgc atcgcgcaat      840
gcactgacgg gtgcccccct gaacctgacc ccggcacagg tggtggccat cgccagcaat      900
aacggtggca agcaggcgct ggagacggtg cagcggctgt tgccggtgct gtgccaggcc      960
catggcctga ccccggcgca ggtggtggcc atcgccagcc acgatggcgg caagcaggca     1020
ctggagacga tgcagcggct gttgccggtg ctgtgccagg cccatggcct gcccccggac     1080
caggtggtgg ccatcgccag caatattggc ggcaagcagg cgctggagac ggtgcagcgg     1140
ctgttgccgg tgctctgcca ggcccatggc ctgaccccgg accaggtggt ggccatcgcc     1200
agccatggcg gcggcaagca ggcgctggag acggtgcagc ggctgttgcc ggtgctctgc     1260
caggcccatg gcctgacccc ggaccaggtg gtggccatcg ccagccacga tggcggcaag     1320
caggcgctgg agacggtgca gcggctgttg ccggtgctgt gccaggccca tggcctgacc     1380
ccggaccagg tggtggccat cgccagcaat ggcggcggca agcaggcgct ggagacggtg     1440
cagcggctgt tgccggtgct gtgccaggcc catggtctga ccccggacca ggtggtggcc     1500
atcgccagca atggcggcaa gcaggcgctg gagacggtgc agcggctgtt gccggtgctg     1560
tgccaggccc atggcctgac cccggaccag gtggtggcca tcgccagcca cgatggcggc     1620
aagcaggcgc tggagacggt gcagcggctg ttgccggtgc tgtgccagac ccatggtctg     1680
accccggcgc aggtggtggc catcgccagc acgatggcg gcaagcaggc gctggagacg      1740
gtgcagcagc tgttgccggt gctgtgccag gcccatggcc tgaccccgga ccaggtggtg     1800
gccatcgcca gcaatattgg cggcaagcag gcgctagcga cggtgcagcg gctgttgccg     1860
gtgctgtgcc aagcccatgg cctgaccccg gaccaggtgg tggccatcgc cagcaatggc     1920
ggcggcaagc aggcgctgga gacggtgcag cggctgttgc cggtgctgtg ccaggcccat     1980
ggcctgaccc cggaccaggt ggtggccatc gccagcaatg gcggcggcaa gcaggcgctg     2040
gagacggtgc agcggctgtt gccggtgctg tgccaggccc atggtctgac ccaggtgcag     2100
gtggtggcca tcgccagcaa tattggcggc aagcaggcgc tggagacggt gcagcggctg     2160
ttgccggtgc tgtgccaggc ccatggcctg accccggcgc aggtggtggc catcgccagc     2220
cacgatggcg gcaagcaggc gctggagacg gtgcagcggc tgttgccggt gctgtgccag     2280
gcccatggcc tgaccccgga ccaagtggtg gccatcgcca gcaatggcgg cggcaagcag     2340
gcgctggaga cggtgcagcg gctgttgccg gtgctgtgcc aggcccatgg cctgacccag     2400
gagcaggtgg tggccatcgc cagcaataac ggcggcaagc aggcgctgga gacggtgcag     2460
cggctgttgc cggtgctgtg ccaggcccat ggcctgaccc cggaccaggt ggtggccatc     2520
gccagcaatg gcggcggcaa gcaggcgctg gagacggtgc agcggctgtt gccggtgctg     2580
tgccaggccc atggtctgac cccggcgcag gtggtggcca tcgccagcaa tattggcggc     2640
aagcaggcgc tggagacggt gcagcggctg ttgccggtgc tgtgccagga ccatggcctg     2700
accctggcgc aggtggtggc catcgccagc aatattggcg gcaagcaggc gctggagacg     2760
```

```
gtgcagcggc tgttgccggt gctgtgccag gcacatggcc tgacccagga ccaggtggtg      2820
gccatcgcca gcaatattgg cggcaagcag gcgctggaga cggtgcagcg gctgttgccg      2880
gtgctgtgcc aggaccatgg cctgaccccg gaccaggtcg tggccatcgc cagcaatatt      2940
ggcggcaagc aggcgctgga gacggtgcag cggctgttgc cggtgctgtg ccaggaccat      3000
ggcctgaccc tggaccaggt ggtggccatc gccagcaatg gcggcaagca ggcgctggag      3060
acggtgcagc ggctgttgcc ggtgctgtgc caggaccatg gactgacccc ggaccaggtc      3120
gtggccatcg ccagcaatag tggcggcaag caggcgctgg agacggtgca gcggctgttg      3180
ccggtgctgt gccaggacca tggcctgacc ccgaaccagg tggtggccat cgccagcaat      3240
ggcggcaagc aggcgctgga gagcattgtt gcccagttat ctcgccctga tccggcgttg      3300
gccgcgttga ccaacgacca cctcgtcgcc ttggcctgcc tcggcggacg tcctgccatg      3360
gatgcagtga aaagggatt gccgcacgcg ccggaattga tcagaagagt caatcgccgt      3420
attggcgaac gcacgtccca tcgcgttgcc gactacgcgc aagtggttcg cgtgctggag      3480 ttttccagt gccactccca cccagcgtac gcatttgatg aggccatgac gcagttcggg      3540
atgagcagga acgggttggt acagctcttt cgcagagtgg gcgtcaccga actcgaagcc      3600
cgcggtggaa cgctcccccc agcctcgcag cgttgggacc gtatcctcca ggcatcaggg      3660
atgaaaaggg ccaaaccgtc ccctacttca gctcaaacac cggatcaggc gtctttgcat      3720
gcattcgccg attcgctgga gcgtgacctt gatgcgccta gcccaatgca cgagggagat      3780
cagacagggg caagcagccg taaacggtcc cgatcggatc gtgctgtcac cggcccctcc      3840
gcacagcact ctttcgaggt gcgcgttccc gaacagcgcg atgcgctgca tttgcccctc      3900
agctggaggg taaaacgccc gcgtaccagg atcgggggcg gcctcccgga tcctggtacg      3960
cccatcgctg ccgacctggc agcgtccagc accgtgatgt gggaacaaga tgcggccccc      4020
ttcgcagggg cagcggatga tttcccggca ttcaacgaag aggagctcgc atggttgatg      4080
gagctattgc ctcagtcagg ctcagtcgga gggacgatct ga                        4122
```

<210> SEQ ID NO 33
<211> LENGTH: 1341
<212> TYPE: PRT
<213> ORGANISM: Artificial Sequence
<220> FEATURE:
<223> OTHER INFORMATION: synthetic peptide

<400> SEQUENCE: 33

```
Met Ala Ser Ser Pro Lys Lys Arg Lys Val Ser Trp Lys Asp
  1               5                  10                  15

Ala Ser Gly Trp Ser Arg Met His Ala Asp Pro Ile Arg Ser Arg Thr
                 20                  25                  30

Pro Ser Pro Ala Arg Glu Leu Leu Pro Gly Pro Gln Pro Asp Gly Val
             35                  40                  45

Gln Pro Thr Ala Asp Arg Gly Val Ser Pro Ala Gly Gly Pro Leu
         50                  55                  60

Asp Gly Leu Pro Ala Arg Arg Thr Met Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
```

```
            115                 120                 125
Asp Glu Val Gln Ser Gly Leu Arg Ala Ala Asp Ala Pro Pro Thr
    130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Glu Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Gly Gly Lys Gln Ala Leu Glu Thr Val
        355                 360                 365

Gln Arg Leu Leu Pro Val Leu Cys Gln Ala His Gly Leu Thr Pro Gln
370                 375                 380

Gln Val Val Ala Ile Ala Ser Asn Ser Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Ala Leu Leu Pro Val Leu Cys Gln Ala
465                 470                 475                 480

His Gly Leu Thr Pro Glu Gln Val Val Ala Ile Ala Ser Asn Ile Gly
                485                 490                 495

Gly Lys Gln Ala Leu Glu Thr Val Gln Ala Leu Leu Pro Val Leu Cys
            500                 505                 510

Gln Ala His Gly Leu Thr Pro Glu Gln Val Val Ala Ile Ala Ser Asn
        515                 520                 525

Ile Gly Gly Lys Gln Ala Leu Glu Thr Val Gln Ala Leu Leu Pro Val
    530                 535                 540
```

```
Leu Cys Gln Ala His Gly Leu Thr Pro Glu Gln Val Val Ala Ile Ala
545                 550                 555                 560

Ser His Asp Gly Gly Lys Gln Ala Leu Glu Thr Val Gln Arg Leu Leu
            565                 570                 575

Pro Val Leu Cys Gln Ala His Gly Leu Thr Pro Glu Gln Val Val Ala
                580                 585                 590

Ile Ala Ser His Asp Gly Gly Lys Gln Ala Leu Glu Thr Val Gln Arg
            595                 600                 605

Leu Leu Pro Val Leu Cys Gln Ala His Gly Leu Thr Pro Gln Gln Val
610                 615                 620

Val Ala Ile Ala Ser Asn Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser Asn Ser Gly Gly Lys Gln Ala Leu Glu
                660                 665                 670

Thr Val Gln Ala Leu Leu Pro Val Leu Cys Gln Ala His Gly Leu Thr
            675                 680                 685

Pro Glu Gln Val Val Ala Ile Ala Ser Asn Ser Gly Gly Lys Gln Ala
690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser His Asp Gly Gly Lys
                725                 730                 735

Gln Ala Leu Glu Thr Val Gln Arg Leu Leu Pro Val Leu Cys Gln Ala
            740                 745                 750

His Gly Leu Thr Pro Glu Gln Val Val Ala Ile Ala Ser His Asp Gly
            755                 760                 765

Gly Lys Gln Ala Leu Glu Thr Val Gln Arg Leu Leu Pro Val Leu Cys
        770                 775                 780

Gln Ala His Gly Leu Thr Pro Glu Gln Val Val Ala Ile Ala Ser His
785                 790                 795                 800

Asp Gly Gly Lys Gln Ala Leu Glu Thr Val Gln Arg Leu Leu Pro Val
                805                 810                 815

Leu Cys Gln Ala His Gly Leu Thr Pro Gln Gln Val Val Ala Ile Ala
                820                 825                 830

Ser Asn Gly Gly Gly Arg Pro Ala Leu Glu Thr Val Gln Arg Leu Leu
            835                 840                 845

Pro Val Leu Cys Gln Ala His Gly Leu Thr Pro Glu Gln Val Val Ala
            850                 855                 860

Ile Ala Ser His Asp Gly Gly Lys Gln Ala Leu Glu Thr Val Gln Arg
865                 870                 875                 880

Leu Leu Pro Val Leu Cys Gln Ala His Gly Leu Thr Pro Gln Gln Val
                885                 890                 895

Val Ala Ile Ala Ser Asn Gly Gly Gly Arg Pro Ala Leu Glu Ser Ile
                900                 905                 910

Val Ala Gln Leu Ser Arg Pro Asp Pro Ala Leu Ala Ala Leu Thr Asn
            915                 920                 925

Asp His Leu Val Ala Leu Ala Cys Leu Gly Gly Arg Pro Ala Leu Asp
            930                 935                 940

Ala Val Lys Lys Gly Leu Pro His Ala Pro Ala Leu Ile Lys Arg Thr
945                 950                 955                 960
```

```
Asn Arg Arg Ile Pro Glu Arg Thr Ser His Arg Val Ala Asp His Ala
            965                 970                 975

Gln Val Val Arg Val Leu Gly Phe Phe Gln Cys His Ser His Pro Ala
        980                 985                 990

Gln Ala Phe Asp Asp Ala Met Thr Gln Phe Gly Met Ser Arg His Gly
    995                1000                1005

Leu Leu Gln Leu Phe Arg Arg Val Gly Val Thr Glu Leu Glu Ala Arg
1010                1015                1020

Ser Gly Thr Leu Pro Pro Ala Ser Gln Arg Trp Asp Arg Ile Leu Gln
1025                1030                1035                1040

Ala Ser Gly Met Lys Arg Ala Lys Pro Ser Pro Thr Ser Thr Gln Thr
            1045                1050                1055

Pro Asp Gln Ala Ser Leu His Ala Phe Ala Asp Ser Leu Glu Arg Asp
        1060                1065                1070

Leu Asp Ala Pro Ser Pro Met His Glu Gly Asp Gln Thr Arg Ala Ser
    1075                1080                1085

Ser Arg Lys Arg Ser Arg Ser Asp Arg Ala Val Thr Gly Pro Ser Ala
        1090                1095                1100

Gln Gln Ser Phe Glu Val Arg Val Pro Glu Gln Arg Asp Ala Leu His
1105                1110                1115                1120

Leu Pro Leu Ser Trp Arg Val Lys Arg Pro Arg Thr Ser Ile Gly Gly
                1125                1130                1135

Gly Leu Pro Asp Pro Ile Ser Arg Ser Gln Leu Val Lys Ser Glu Leu
            1140                1145                1150

Glu Glu Lys Lys Ser Glu Leu Arg His Lys Leu Lys Tyr Val Pro His
        1155                1160                1165

Glu Tyr Ile Glu Leu Ile Glu Ile Ala Arg Asn Ser Thr Gln Asp Arg
    1170                1175                1180

Ile Leu Glu Met Lys Val Met Glu Phe Phe Met Lys Val Tyr Gly Tyr
1185                1190                1195                1200

Arg Gly Lys His Leu Gly Gly Ser Arg Lys Pro Asp Gly Ala Ile Tyr
                1205                1210                1215

Thr Val Gly Ser Pro Ile Asp Tyr Gly Val Ile Val Asp Thr Lys Ala
            1220                1225                1230

Tyr Ser Gly Gly Tyr Asn Leu Pro Ile Gly Gln Ala Asp Glu Met Gln
        1235                1240                1245

Arg Tyr Val Glu Glu Asn Gln Thr Arg Asn Lys His Ile Asn Pro Asn
    1250                1255                1260

Glu Trp Trp Lys Val Tyr Pro Ser Ser Val Thr Glu Phe Lys Phe Leu
1265                1270                1275                1280

Phe Val Ser Gly His Phe Lys Gly Asn Tyr Lys Ala Gln Leu Thr Arg
                1285                1290                1295

Leu Asn His Ile Thr Asn Cys Asn Gly Ala Val Leu Ser Val Glu Glu
            1300                1305                1310

Leu Leu Ile Gly Gly Glu Met Ile Lys Ala Gly Thr Leu Thr Leu Glu
        1315                1320                1325

Glu Val Arg Arg Lys Phe Asn Asn Gly Glu Ile Asn Phe
    1330                1335                1340

<210> SEQ ID NO 34
<211> LENGTH: 1542
<212> TYPE: PRT
<213> ORGANISM: Artificial Sequence
<220> FEATURE:
<223> OTHER INFORMATION: synthetic peptide
```

<400> SEQUENCE: 34

```
Met Ala Ser Ser Pro Pro Lys Lys Arg Lys Val Ser Trp Lys Asp
 1               5                  10                  15

Ala Ser Gly Trp Ser Arg Met His Ala Asp Pro Ile Arg Pro Arg
            20                  25                  30

Pro Ser Pro Ala Arg Glu Leu Leu Pro Gly Pro Gln Pro Asp Arg Val
        35                  40                  45

Gln Pro Thr Ala Asp Arg Gly Val Ser Ala Pro Ala Gly Ser Pro Leu
 50                  55                  60

Asp Gly Leu Pro Ala Arg Arg Thr Val Ser Arg Thr Arg Leu Pro Ser
 65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
                100                 105                 110

Met Pro Ala Val Gly Thr Pro His Thr Ala Ala Ala Pro Ala Glu Trp
            115                 120                 125

Asp Glu Ala Gln Ser Ala Leu Arg Ala Ala Asp Asp Pro Pro Pro Thr
130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
            195                 200                 205

Gly His Gly Phe Thr His Ala His Ile Val Ala Leu Ser Gln His Pro
210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
            275                 280                 285

Lys Arg Gly Gly Val Thr Ala Met Glu Ala Val His Ala Ser Arg Asn
290                 295                 300

Ala Leu Thr Gly Ala Pro Leu Asn Leu Thr Pro Ala Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Ala Gln Val
                340                 345                 350

Val Ala Ile Ala Ser His Asp Gly Gly Lys Gln Ala Leu Glu Thr Met
            355                 360                 365

Gln Arg Leu Leu Pro Val Leu Cys Gln Ala His Gly Leu Pro Pro Asp
            370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Ala His Gly Leu Thr
```

```
                405                 410                 415
Pro Asp Gln Val Val Ala Ile Ala Ser His Gly Gly Lys Gln Ala
            420                 425                 430

Leu Glu Thr Val Gln Arg Leu Leu Pro Val Leu Cys Gln Ala His Gly
        435                 440                 445

Leu Thr Pro Asp Gln Val Val Ala Ile Ala Ser His Asp Gly Gly Lys
450                 455                 460

Gln Ala Leu Glu Thr Val Gln Arg Leu Leu Pro Val Leu Cys Gln Ala
465                 470                 475                 480

His Gly Leu Thr Pro Asp Gln Val Val Ala Ile Ala Ser Asn Gly Gly
            485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Ser Asn
            515                 520                 525

Gly Gly Lys Gln Ala Leu Glu Thr Val Gln Arg Leu Leu Pro Val Leu
            530                 535                 540

Cys Gln Ala His Gly Leu Thr Pro Asp Gln Val Val Ala Ile Ala Ser
545                 550                 555                 560

His Asp Gly Gly Lys Gln Ala Leu Glu Thr Val Gln Arg Leu Leu Pro
                565                 570                 575

Val Leu Cys Gln Thr His Gly Leu Thr Pro Ala Gln Val Val Ala Ile
            580                 585                 590

Ala Ser His Asp Gly Gly Lys Gln Ala Leu Glu Thr Val Gln Gln Leu
            595                 600                 605

Leu Pro Val Leu Cys Gln Ala His Gly Leu Thr Pro Asp Gln Val Val
        610                 615                 620

Ala Ile Ala Ser Asn Ile Gly Gly Lys Gln Ala Leu Ala Thr Val Gln
625                 630                 635                 640

Arg Leu Leu Pro Val Leu Cys Gln Ala His Gly Leu Thr Pro Asp Gln
                645                 650                 655

Val Val Ala Ile Ala Ser Asn Gly Gly Gly Lys Gln Ala Leu Glu Thr
            660                 665                 670

Val Gln Arg Leu Leu Pro Val Leu Cys Gln Ala His Gly Leu Thr Pro
        675                 680                 685

Asp Gln Val Val Ala Ile Ala Ser Asn Gly Gly Gly Lys Gln Ala Leu
        690                 695                 700

Glu Thr Val Gln Arg Leu Leu Pro Val Leu Cys Gln Ala His Gly Leu
705                 710                 715                 720

Thr Gln Val Gln Val Val Ala Ile Ala Ser Asn Ile Gly Gly Lys Gln
            725                 730                 735

Ala Leu Glu Thr Val Gln Arg Leu Leu Pro Val Leu Cys Gln Ala His
            740                 745                 750

Gly Leu Thr Pro Ala Gln Val Val Ala Ile Ala Ser His Asp Gly Gly
            755                 760                 765

Lys Gln Ala Leu Glu Thr Val Gln Arg Leu Leu Pro Val Leu Cys Gln
        770                 775                 780

Ala His Gly Leu Thr Pro Asp Gln Val Val Ala Ile Ala Ser Asn Gly
785                 790                 795                 800

Gly Gly Lys Gln Ala Leu Glu Thr Val Gln Arg Leu Leu Pro Val Leu
            805                 810                 815

Cys Gln Ala His Gly Leu Thr Gln Glu Gln Val Val Ala Ile Ala Ser
            820                 825                 830
```

-continued

```
Asn Asn Gly Gly Lys Gln Ala Leu Glu Thr Val Gln Arg Leu Leu Pro
        835                 840                 845

Val Leu Cys Gln Ala His Gly Leu Thr Pro Asp Gln Val Val Ala Ile
    850                 855                 860

Ala Ser Asn Gly Gly Lys Gln Ala Leu Glu Thr Val Gln Arg Leu
865                 870                 875                 880

Leu Pro Val Leu Cys Gln Ala His Gly Leu Thr Pro Ala Gln Val Val
            885                 890                 895

Ala Ile Ala Ser Asn Ile Gly Gly Lys Gln Ala Leu Glu Thr Val Gln
                900                 905                 910

Arg Leu Leu Pro Val Leu Cys Gln Asp His Gly Leu Thr Leu Ala Gln
            915                 920                 925

Val Val Ala Ile Ala Ser Asn Ile Gly Gly Lys Gln Ala Leu Glu Thr
    930                 935                 940

Val Gln Arg Leu Leu Pro Val Leu Cys Gln Ala His Gly Leu Thr Gln
945                 950                 955                 960

Asp Gln Val Val Ala Ile Ala Ser Asn Ile Gly Gly Lys Gln Ala Leu
                965                 970                 975

Glu Thr Val Gln Arg Leu Leu Pro Val Leu Cys Gln Asp His Gly Leu
            980                 985                 990

Thr Pro Asp Gln Val Val Ala Ile Ala Ser Asn Ile Gly Gly Lys Gln
            995                 1000                1005

Ala Leu Glu Thr Val Gln Arg Leu Leu Pro Val Leu Cys Gln Asp His
        1010                1015                1020

Gly Leu Thr Leu Asp Gln Val Val Ala Ile Ala Ser Asn Gly Gly Lys
1025                1030                1035                1040

Gln Ala Leu Glu Thr Val Gln Arg Leu Leu Pro Val Leu Cys Gln Asp
                1045                1050                1055

His Gly Leu Thr Pro Asp Gln Val Val Ala Ile Ala Ser Asn Ser Gly
            1060                1065                1070

Gly Lys Gln Ala Leu Glu Thr Val Gln Arg Leu Leu Pro Val Leu Cys
1075                1080                1085

Gln Asp His Gly Leu Thr Pro Asn Gln Val Val Ala Ile Ala Ser Asn
    1090                1095                1100

Gly Gly Lys Gln Ala Leu Glu Ser Ile Val Ala Gln Leu Ser Arg Pro
1105                1110                1115                1120

Asp Pro Ala Leu Ala Ala Leu Thr Asn Asp His Leu Val Ala Leu Ala
            1125                1130                1135

Cys Leu Gly Gly Arg Pro Ala Met Asp Ala Val Lys Lys Gly Leu Pro
            1140                1145                1150

His Ala Pro Glu Leu Ile Arg Arg Val Asn Arg Arg Ile Gly Glu Arg
            1155                1160                1165

Thr Ser His Arg Val Ala Asp Tyr Ala Gln Val Val Arg Val Leu Glu
    1170                1175                1180

Phe Phe Gln Cys His Ser His Pro Ala Tyr Ala Phe Asp Glu Ala Met
1185                1190                1195                1200

Thr Gln Phe Gly Met Ser Arg Asn Gly Leu Val Gln Leu Phe Arg Arg
            1205                1210                1215

Val Gly Val Thr Glu Leu Glu Ala Arg Gly Gly Thr Leu Pro Pro Ala
            1220                1225                1230

Ser Gln Arg Trp Asp Arg Ile Leu Gln Ala Ser Gly Met Lys Arg Ala
            1235                1240                1245
```

-continued

```
Lys Pro Ser Pro Thr Ser Ala Gln Thr Pro Asp Gln Ala Ser Leu His
    1250                1255                1260

Ala Phe Ala Asp Ser Leu Glu Arg Asp Leu Asp Ala Pro Ser Pro Met
1265                1270                1275                1280

His Glu Gly Asp Gln Thr Arg Ala Ser Arg Lys Arg Ser Arg Ser
                1285                1290                1295

Asp Arg Ala Val Thr Gly Pro Ser Ala Gln Gln Ala Val Glu Val Arg
            1300                1305                1310

Val Pro Glu Gln Arg Asp Ala Leu His Leu Pro Leu Ser Trp Arg Val
            1315                1320                1325

Lys Arg Pro Arg Thr Arg Ile Trp Gly Gly Leu Pro Asp Pro Ile Ser
    1330                1335                1340

Arg Ser Gln Leu Val Lys Ser Glu Leu Glu Glu Lys Ser Glu Leu
1345                1350                1355                1360

Arg His Lys Leu Lys Tyr Val Pro His Glu Tyr Ile Glu Leu Ile Glu
            1365                1370                1375

Ile Ala Arg Asn Ser Thr Gln Asp Arg Ile Leu Glu Met Lys Val Met
            1380                1385                1390

Glu Phe Phe Met Lys Val Tyr Gly Tyr Arg Gly Lys His Leu Gly Gly
            1395                1400                1405

Ser Arg Lys Pro Asp Gly Ala Ile Tyr Thr Val Gly Ser Pro Ile Asp
    1410                1415                1420

Tyr Gly Val Ile Val Asp Thr Lys Ala Tyr Ser Gly Gly Tyr Asn Leu
1425                1430                1435                1440

Pro Ile Gly Gln Ala Asp Glu Met Gln Arg Tyr Val Glu Glu Asn Gln
            1445                1450                1455

Thr Arg Asn Lys His Ile Asn Pro Asn Glu Trp Trp Lys Val Tyr Pro
            1460                1465                1470

Ser Ser Val Thr Glu Phe Lys Phe Leu Phe Val Ser Gly His Phe Lys
    1475                1480                1485

Gly Asn Tyr Lys Ala Gln Leu Thr Arg Leu Asn His Ile Thr Asn Cys
    1490                1495                1500

Asn Gly Ala Val Leu Ser Val Glu Glu Leu Leu Ile Gly Gly Glu Met
1505                1510                1515                1520

Ile Lys Ala Gly Thr Leu Thr Leu Glu Glu Val Arg Arg Lys Phe Asn
            1525                1530                1535

Asn Gly Glu Ile Asn Phe
            1540

<210> SEQ ID NO 35
<211> LENGTH: 1035
<212> TYPE: PRT
<213> ORGANISM: Artificial Sequence
<220> FEATURE:
<223> OTHER INFORMATION: synthetic peptide

<400> SEQUENCE: 35

Met Ala Ser Ser Pro Pro Lys Lys Lys Arg Lys Val Ser Trp Lys Asp
  1               5                  10                  15

Ala Ser Gly Trp Ser Arg Met His Ala Asp Pro Ile Arg Pro Arg Arg
            20                  25                  30

Pro Ser Pro Ala Arg Glu Leu Leu Pro Gly Pro Gln Pro Asp Arg Val
        35                  40                  45

Gln Pro Thr Ala Asp Arg Gly Val Ser Ala Pro Ala Gly Ser Pro Leu
    50                  55                  60
```

```
Asp Gly Leu Pro Ala Arg Arg Thr Val Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Pro Ala Glu Trp
        115                 120                 125

Asp Glu Ala Gln Ser Ala Leu Arg Ala Ala Asp Pro Pro Thr
130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
    290                 295                 300

Ala Leu Thr Gly Ala Pro Leu Asn Leu Thr Pro Ala Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Asn Asn Gly Lys Gln Ala Leu Glu Thr Val
        355                 360                 365

Gln Arg Leu Leu Pro Val Leu Cys Gln Asp His Gly Leu Thr Pro Asp
370                 375                 380

Gln Val Val Ala Ile Ala Asn Asn Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser Asn Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Gly Gly
```

```
                    485                 490                 495
Gly Lys Gln Ala Leu Glu Thr Val Gln Arg Leu Leu Pro Val Leu Cys
                500                 505                 510

Gln Asp His Gly Leu Thr Pro Asp Gln Val Val Ala Ile Ala Asn Asn
            515                 520                 525

Asn Gly Gly Lys Gln Ala Leu Glu Thr Val Gln Arg Leu Leu Pro Val
        530                 535                 540

Leu Cys Gln Asp His Gly Leu Thr Pro Asp Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser Asn Gly Gly Gly Lys Gln Ala Leu Glu Ser Ile Val Ala
        595                 600                 605

Gln Leu Ser Arg Arg Asp Pro Ala Leu Ala Ala Leu Thr Asn Asp His
    610                 615                 620

Leu Val Ala Leu Ala Cys Leu Gly Gly Arg Pro Ala Leu Asp Ala Val
625                 630                 635                 640

Lys Lys Gly Leu Pro His Ala Pro Glu Phe Ile Arg Arg Val Asn Arg
                645                 650                 655

Arg Ile Ala Glu Arg Thr Ser His Arg Val Ala Asp Tyr Ala His Val
            660                 665                 670

Val Arg Val Leu Glu Phe Phe Gln Cys His Ser His Pro Ala His Ala
        675                 680                 685

Phe Asp Glu Ala Met Thr Gln Phe Gly Met Ser Arg His Gly Leu Val
690                 695                 700

Gln Leu Phe Arg Arg Val Gly Val Thr Glu Phe Glu Ala Arg Tyr Gly
705                 710                 715                 720

Thr Leu Pro Pro Ala Ser Gln Arg Trp Asp Arg Ile Leu Gln Ala Ser
                725                 730                 735

Gly Met Lys Arg Ala Lys Pro Ser Pro Thr Ser Ala Gln Thr Pro Asp
            740                 745                 750

Gln Thr Ser Leu His Ala Phe Ala Asp Ser Leu Glu Arg Asp Leu Asp
        755                 760                 765

Ala Pro Ser Pro Met His Glu Gly Asp Gln Thr Arg Ala Ser Ser Arg
    770                 775                 780

Lys Arg Ser Arg Ser Asp Arg Ala Val Thr Gly Pro Ser Ala Gln Gln
785                 790                 795                 800

Ala Val Glu Val Arg Val Pro Glu Gln Arg Asp Ala Leu His Leu Pro
                805                 810                 815

Leu Ser Trp Arg Val Lys Arg Pro Arg Thr Arg Ile Trp Gly Gly Leu
            820                 825                 830

Pro Asp Pro Ile Ser Arg Ser Gln Leu Val Lys Ser Glu Leu Glu Glu
        835                 840                 845

Lys Lys Ser Glu Leu Arg His Lys Leu Lys Tyr Val Pro His Glu Tyr
    850                 855                 860

Ile Glu Leu Ile Glu Ile Ala Arg Asn Ser Thr Gln Asp Arg Ile Leu
865                 870                 875                 880

Glu Met Lys Val Met Glu Phe Phe Met Lys Val Tyr Gly Tyr Arg Gly
                885                 890                 895

Lys His Leu Gly Gly Ser Arg Lys Pro Asp Gly Ala Ile Tyr Thr Val
            900                 905                 910
```

```
Gly Ser Pro Ile Asp Tyr Gly Val Ile Val Asp Thr Lys Ala Tyr Ser
        915                 920                 925

Gly Gly Tyr Asn Leu Pro Ile Gly Gln Ala Asp Glu Met Gln Arg Tyr
    930                 935                 940

Val Glu Glu Asn Gln Thr Arg Asn Lys His Ile Asn Pro Asn Glu Trp
945                 950                 955                 960

Trp Lys Val Tyr Pro Ser Ser Val Thr Glu Phe Lys Phe Leu Phe Val
                965                 970                 975

Ser Gly His Phe Lys Gly Asn Tyr Lys Ala Gln Leu Thr Arg Leu Asn
                980                 985                 990

His Ile Thr Asn Cys Asn Gly Ala Val Leu Ser Val Glu Glu Leu Leu
            995                1000                1005

Ile Gly Gly Glu Met Ile Lys Ala Gly Thr Leu Thr Leu Glu Glu Val
    1010                1015                1020

Arg Arg Lys Phe Asn Asn Gly Glu Ile Asn Phe
1025                1030                1035

<210> SEQ ID NO 36
<211> LENGTH: 1069
<212> TYPE: PRT
<213> ORGANISM: Artificial Sequence
<220> FEATURE:
<223> OTHER INFORMATION: synthetic peptide

<400> SEQUENCE: 36

Met Ala Ser Ser Pro Pro Lys Lys Lys Arg Lys Val Ser Trp Lys Asp
  1               5                  10                  15

Ala Ser Gly Trp Ser Arg Met His Ala Asp Pro Ile Arg Pro Arg Arg
             20                  25                  30

Pro Ser Pro Ala Arg Glu Leu Leu Pro Gly Pro Gln Pro Asp Arg Val
         35                  40                  45

Gln Pro Thr Ala Asp Arg Gly Val Ser Ala Pro Ala Gly Ser Pro Leu
     50                  55                  60

Asp Gly Leu Pro Ala Arg Arg Thr Val Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240
```

```
Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
    290                 295                 300

Ala Leu Thr Gly Ala Pro Leu Asn Leu Thr Pro Ala Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Asp His Gly Leu Thr Pro Asp
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser His Asp Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser His Asp Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser His
        515                 520                 525

Asp Gly Gly Lys Gln Ala Leu Glu Thr Val Gln Arg Leu Leu Pro Val
    530                 535                 540

Leu Cys Gln Asp His Gly Leu Thr Pro Asp Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Asp His Gly Leu Thr Pro Asp Gln Val
    610                 615                 620

Val Ala Ile Ala Ser His Asp Gly Gly Lys Gln Ala Leu Glu Ser Ile
625                 630                 635                 640

Val Ala Gln Leu Ser Arg Arg Asp Pro Ala Leu Ala Ala Leu Thr Asn
                645                 650                 655
```

-continued

```
Asp His Leu Val Ala Leu Ala Cys Leu Gly Arg Pro Ala Leu Asp
            660                 665                 670

Ala Val Lys Lys Gly Leu Pro His Ala Pro Glu Phe Ile Arg Arg Val
        675                 680                 685

Asn Arg Arg Ile Ala Glu Arg Thr Ser His Arg Val Ala Asp Tyr Ala
        690                 695                 700

His Val Val Arg Val Leu Glu Phe Phe Gln Cys His Ser His Pro Ala
705                 710                 715                 720

His Ala Phe Asp Glu Ala Met Thr Gln Phe Gly Met Ser Arg His Gly
                725                 730                 735

Leu Val Gln Leu Phe Arg Arg Val Gly Val Thr Glu Phe Glu Ala Arg
            740                 745                 750

Tyr Gly Thr Leu Pro Pro Ala Ser Gln Arg Trp Asp Arg Ile Leu Gln
        755                 760                 765

Ala Ser Gly Met Lys Arg Ala Lys Pro Ser Pro Thr Ser Ala Gln Thr
        770                 775                 780

Pro Asp Gln Thr Ser Leu His Ala Phe Ala Asp Ser Leu Glu Arg Asp
785                 790                 795                 800

Leu Asp Ala Pro Ser Pro Met His Glu Gly Asp Gln Thr Arg Ala Ser
                805                 810                 815

Ser Arg Lys Arg Ser Arg Ser Asp Arg Ala Val Thr Gly Pro Ser Ala
            820                 825                 830

Gln Gln Ala Val Glu Val Arg Val Pro Glu Gln Arg Asp Ala Leu His
        835                 840                 845

Leu Pro Leu Ser Trp Arg Val Lys Arg Pro Arg Thr Arg Ile Trp Gly
850                 855                 860

Gly Leu Pro Asp Pro Ile Ser Arg Ser Gln Leu Val Lys Ser Glu Leu
865                 870                 875                 880

Glu Glu Lys Lys Ser Glu Leu Arg His Lys Leu Lys Tyr Val Pro His
                885                 890                 895

Glu Tyr Ile Glu Leu Ile Glu Ile Ala Arg Asn Ser Thr Gln Asp Arg
            900                 905                 910

Ile Leu Glu Met Lys Val Met Glu Phe Phe Met Lys Val Tyr Gly Tyr
        915                 920                 925

Arg Gly Lys His Leu Gly Gly Ser Arg Lys Pro Asp Gly Ala Ile Tyr
930                 935                 940

Thr Val Gly Ser Pro Ile Asp Tyr Gly Val Ile Val Asp Thr Lys Ala
945                 950                 955                 960

Tyr Ser Gly Gly Tyr Asn Leu Pro Ile Gly Gln Ala Asp Glu Met Gln
                965                 970                 975

Arg Tyr Val Glu Glu Asn Gln Thr Arg Asn Lys His Ile Asn Pro Asn
            980                 985                 990

Glu Trp Trp Lys Val Tyr Pro Ser Ser Val Thr Glu Phe Lys Phe Leu
        995                 1000                1005

Phe Val Ser Gly His Phe Lys Gly Asn Tyr Lys Ala Gln Leu Thr Arg
        1010                1015                1020

Leu Asn His Ile Thr Asn Cys Asn Gly Ala Val Leu Ser Val Glu Glu
1025                1030                1035                1040

Leu Leu Ile Gly Gly Glu Met Ile Lys Ala Gly Thr Leu Thr Leu Glu
                1045                1050                1055

Glu Val Arg Arg Lys Phe Asn Asn Gly Glu Ile Asn Phe
            1060                1065
```

<210> SEQ ID NO 37
<211> LENGTH: 1137
<212> TYPE: PRT
<213> ORGANISM: Artificial Sequence
<220> FEATURE:
<223> OTHER INFORMATION: synthetic peptide

<400> SEQUENCE: 37

```
Met Ala Ser Ser Pro Lys Lys Arg Lys Val Ser Trp Lys Asp
 1               5                  10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
        50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Pro Pro Pro Thr
130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
    290                 295                 300

Ala Leu Thr Gly Ala Pro Leu Asn Leu Thr Pro Ala Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser Asn Gly Gly Lys Gln Ala Leu Glu Thr Val
        355                 360                 365

Gln Arg Leu Leu Pro Val Leu Cys Gln Asp His Gly Leu Thr Pro Asp
```

```
            370                 375                 380
Gln Val Val Ala Ile Ala Ser His Asp Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Ile Gly Gly Lys Gln Ala
                420                 425                 430

Leu Glu Thr Val Gln Arg Leu Leu Pro Val Leu Cys Gln Asp His Gly
            435                 440                 445

Leu Thr Pro Asp Gln Val Val Ala Ile Ala Ser Asn Ile Gly Gly Lys
        450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Asn Asn Asn Gly
                485                 490                 495

Gly Lys Gln Ala Leu Glu Thr Val Gln Arg Leu Leu Pro Val Leu Cys
                500                 505                 510

Gln Asp His Gly Leu Thr Pro Asp Gln Val Val Ala Ile Ala Ser Asn
            515                 520                 525

Ile Gly Gly Lys Gln Ala Leu Glu Thr Val Gln Arg Leu Leu Pro Val
        530                 535                 540

Leu Cys Gln Asp His Gly Leu Thr Pro Asp Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
                580                 585                 590

Ile Ala Ser Asn Gly Gly Gly Lys Gln Ala Leu Glu Thr Val Gln Arg
            595                 600                 605

Leu Leu Pro Val Leu Cys Gln Asp His Gly Leu Thr Pro Asp Gln Val
        610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Gly Gly Gly Lys Gln Ala Leu Glu
                660                 665                 670

Thr Val Gln Arg Leu Leu Pro Val Leu Cys Gln Asp His Gly Leu Thr
            675                 680                 685

Pro Asp Gln Val Val Ala Ile Ala Ser His Asp Gly Gly Lys Gln Ala
        690                 695                 700

Leu Glu Ser Ile Val Ala Gln Leu Ser Arg Arg Asp Pro Ala Leu Ala
705                 710                 715                 720

Ala Leu Thr Asn Asp His Leu Val Ala Leu Ala Cys Leu Gly Gly Arg
                725                 730                 735

Pro Ala Leu Asp Ala Val Lys Lys Gly Leu Pro His Ala Pro Glu Phe
                740                 745                 750

Ile Arg Arg Val Asn Arg Arg Ile Ala Glu Arg Thr Ser His Arg Val
            755                 760                 765

Ala Asp Tyr Ala His Val Val Arg Val Leu Glu Phe Phe Gln Cys His
        770                 775                 780

Ser His Pro Ala His Ala Phe Asp Glu Ala Met Thr Gln Phe Gly Met
785                 790                 795                 800
```

Ser Arg His Gly Leu Val Gln Leu Phe Arg Arg Val Gly Val Thr Glu
            805                 810                 815

Phe Glu Ala Arg Tyr Gly Thr Leu Pro Pro Ala Ser Gln Arg Trp Asp
            820                 825                 830

Arg Ile Leu Gln Ala Ser Gly Met Lys Arg Ala Lys Pro Ser Pro Thr
            835                 840                 845

Ser Ala Gln Thr Pro Asp Gln Thr Ser Leu His Ala Phe Ala Asp Ser
            850                 855                 860

Leu Glu Arg Asp Leu Asp Ala Pro Ser Pro Met His Glu Gly Asp Gln
865                 870                 875                 880

Thr Arg Ala Ser Ser Arg Lys Arg Ser Arg Ser Asp Arg Ala Val Thr
            885                 890                 895

Gly Pro Ser Ala Gln Gln Ala Val Glu Val Arg Val Pro Glu Gln Arg
            900                 905                 910

Asp Ala Leu His Leu Pro Leu Ser Trp Arg Val Lys Arg Pro Arg Thr
            915                 920                 925

Arg Ile Trp Gly Gly Leu Pro Asp Pro Ile Ser Arg Ser Gln Leu Val
            930                 935                 940

Lys Ser Glu Leu Glu Glu Lys Ser Glu Leu Arg His Lys Leu Lys
945                 950                 955                 960

Tyr Val Pro His Glu Tyr Ile Glu Leu Ile Glu Ile Ala Arg Asn Ser
            965                 970                 975

Thr Gln Asp Arg Ile Leu Glu Met Lys Val Met Glu Phe Phe Met Lys
            980                 985                 990

Val Tyr Gly Tyr Arg Gly Lys His Leu Gly Gly Ser Arg Lys Pro Asp
            995                 1000                1005

Gly Ala Ile Tyr Thr Val Gly Ser Pro Ile Asp Tyr Gly Val Ile Val
        1010                1015                1020

Asp Thr Lys Ala Tyr Ser Gly Gly Tyr Asn Leu Pro Ile Gly Gln Ala
1025                1030                1035                1040

Asp Glu Met Gln Arg Tyr Val Glu Glu Asn Gln Thr Arg Asn Lys His
                1045                1050                1055

Ile Asn Pro Asn Glu Trp Trp Lys Val Tyr Pro Ser Ser Val Thr Glu
                1060                1065                1070

Phe Lys Phe Leu Phe Val Ser Gly His Phe Lys Gly Asn Tyr Lys Ala
                1075                1080                1085

Gln Leu Thr Arg Leu Asn His Ile Thr Asn Cys Asn Gly Ala Val Leu
            1090                1095                1100

Ser Val Glu Glu Leu Leu Ile Gly Gly Glu Met Ile Lys Ala Gly Thr
1105                1110                1115                1120

Leu Thr Leu Glu Glu Val Arg Arg Lys Phe Asn Asn Gly Glu Ile Asn
                1125                1130                1135

Phe

<210> SEQ ID NO 38
<211> LENGTH: 1137
<212> TYPE: PRT
<213> ORGANISM: Artificial Sequence
<220> FEATURE:
<223> OTHER INFORMATION: synthetic peptide

<400> SEQUENCE: 38

Met Ala Ser Ser Pro Pro Lys Lys Lys Arg Lys Val Ser Trp Lys Asp
1               5                   10                  15

```
Ala Ser Gly Trp Ser Arg Met His Ala Asp Pro Ile Arg Pro Arg Arg
            20                  25                  30

Pro Ser Pro Ala Arg Glu Leu Leu Pro Gly Pro Gln Pro Asp Arg Val
        35                  40                  45

Gln Pro Thr Ala Asp Arg Gly Val Ser Ala Pro Ala Gly Ser Pro Leu
50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Pro Ala Glu Trp
        115                 120                 125

Asp Glu Ala Gln Ser Ala Leu Arg Ala Asp Asp Pro Pro Thr
        130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
290                 295                 300

Ala Leu Thr Gly Ala Pro Leu Asn Leu Thr Pro Ala Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Asp His Gly Leu Thr Pro Asp
370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Ile Gly Gly Lys Gln Ala
            420                 425                 430

Leu Glu Thr Val Gln Arg Leu Leu Pro Val Leu Cys Gln Asp His Gly
```

-continued

```
            435                 440                 445
Leu Thr Pro Asp Gln Val Val Ala Ile Ala Asn Asn Gly Gly Lys
450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Ile Gly
                485                 490                 495

Gly Lys Gln Ala Leu Glu Thr Val Gln Arg Leu Leu Pro Val Leu Cys
                500                 505                 510

Gln Asp His Gly Leu Thr Pro Asp Gln Val Val Ala Ile Ala Ser Asn
            515                 520                 525

Ile Gly Gly Lys Gln Ala Leu Glu Thr Val Gln Arg Leu Leu Pro Val
        530                 535                 540

Leu Cys Gln Asp His Gly Leu Thr Pro Asp Gln Val Val Ala Ile Ala
545                 550                 555                 560

Asn Asn Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser Asn Gly Gly Lys Gln Ala Leu Glu Thr Val Gln Arg
        595                 600                 605

Leu Leu Pro Val Leu Cys Gln Asp His Gly Leu Thr Pro Asp Gln Val
610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Ile Gly Gly Lys Gln Ala Leu Glu
                660                 665                 670

Thr Val Gln Arg Leu Leu Pro Val Leu Cys Gln Asp His Gly Leu Thr
            675                 680                 685

Pro Asp Gln Val Val Ala Ile Ala Ser Asn Ile Gly Gly Lys Gln Ala
        690                 695                 700

Leu Glu Ser Ile Val Ala Gln Leu Ser Arg Arg Asp Pro Ala Leu Ala
705                 710                 715                 720

Ala Leu Thr Asn Asp His Leu Val Ala Leu Ala Cys Leu Gly Gly Arg
                725                 730                 735

Pro Ala Leu Asp Ala Val Lys Lys Gly Leu Pro His Ala Pro Glu Phe
                740                 745                 750

Ile Arg Arg Val Asn Arg Arg Ile Ala Glu Arg Thr Ser His Arg Val
            755                 760                 765

Ala Asp Tyr Ala His Val Val Arg Val Leu Glu Phe Phe Gln Cys His
        770                 775                 780

Ser His Pro Ala His Ala Phe Asp Glu Ala Met Thr Gln Phe Gly Met
785                 790                 795                 800

Ser Arg His Gly Leu Val Gln Leu Phe Arg Arg Val Gly Val Thr Glu
                805                 810                 815

Phe Glu Ala Arg Tyr Gly Thr Leu Pro Pro Ala Ser Gln Arg Trp Asp
                820                 825                 830

Arg Ile Leu Gln Ala Ser Gly Met Lys Arg Ala Lys Pro Ser Pro Thr
            835                 840                 845

Ser Ala Gln Thr Pro Asp Gln Ser Leu His Ala Phe Ala Asp Ser
        850                 855                 860
```

```
Leu Glu Arg Asp Leu Asp Ala Pro Ser Pro Met His Glu Gly Asp Gln
865                 870                 875                 880

Thr Arg Ala Ser Ser Arg Lys Arg Ser Arg Ser Asp Arg Ala Val Thr
                885                 890                 895

Gly Pro Ser Ala Gln Gln Ala Val Glu Val Arg Val Pro Glu Gln Arg
            900                 905                 910

Asp Ala Leu His Leu Pro Leu Ser Trp Arg Val Lys Arg Pro Arg Thr
            915                 920                 925

Arg Ile Trp Gly Gly Leu Pro Asp Pro Ile Ser Arg Ser Gln Leu Val
930                 935                 940

Lys Ser Glu Leu Glu Lys Lys Ser Glu Leu Arg His Lys Leu Lys
945                 950                 955                 960

Tyr Val Pro His Glu Tyr Ile Glu Leu Ile Glu Ile Ala Arg Asn Ser
                965                 970                 975

Thr Gln Asp Arg Ile Leu Glu Met Lys Val Met Glu Phe Phe Met Lys
            980                 985                 990

Val Tyr Gly Tyr Arg Gly Lys His Leu Gly Ser Arg Lys Pro Asp
                995                 1000                1005

Gly Ala Ile Tyr Thr Val Gly Ser Pro Ile Asp Tyr Gly Val Ile Val
    1010                1015                1020

Asp Thr Lys Ala Tyr Ser Gly Gly Tyr Asn Leu Pro Ile Gly Gln Ala
1025                1030                1035                1040

Asp Glu Met Gln Arg Tyr Val Glu Gly Asn Gln Thr Arg Asn Lys His
            1045                1050                1055

Ile Asn Pro Asn Glu Trp Trp Lys Val Tyr Pro Ser Ser Val Thr Glu
            1060                1065                1070

Phe Lys Phe Leu Phe Val Ser Gly His Phe Lys Gly Asn Tyr Lys Ala
            1075                1080                1085

Gln Leu Thr Arg Leu Asn His Ile Thr Asn Cys Asn Gly Ala Val Leu
            1090                1095                1100

Ser Val Glu Glu Leu Leu Ile Gly Gly Glu Met Ile Lys Ala Gly Thr
1105                1110                1115                1120

Leu Thr Leu Glu Glu Val Arg Arg Lys Phe Asn Asn Gly Glu Ile Asn
                1125                1130                1135

Phe

<210> SEQ ID NO 39
<211> LENGTH: 1137
<212> TYPE: PRT
<213> ORGANISM: Artificial Sequence
<220> FEATURE:
<223> OTHER INFORMATION: synthetic peptide

<400> SEQUENCE: 39

Met Ala Ser Ser Pro Pro Lys Lys Lys Arg Lys Val Ser Trp Lys Asp
1               5                   10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Gln Pro Asp Arg Val
            35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Arg Thr Arg Leu Pro Ser
65                  70                  75                  80
```

-continued

```
Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Pro Ala Glu Trp
        115                 120                 125

Asp Glu Ala Gln Ser Ala Leu Arg Ala Asp Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
            195                 200                 205

Gly His Gly Phe Thr His Ala His Ile Val Ala Leu Ser Gln His Pro
        210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
                260                 265                 270

Arg Gly Pro Pro Leu Gln Leu Asp Thr Gly Gln Leu Val Lys Ile Ala
            275                 280                 285

Lys Arg Gly Gly Val Thr Ala Met Glu Ala Val His Ala Ser Arg Asn
290                 295                 300

Ala Leu Thr Gly Ala Pro Leu Asn Leu Thr Pro Ala Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser His Asp Gly Gly Lys Gln Ala Leu Glu Thr Val
            355                 360                 365

Gln Arg Leu Leu Pro Val Leu Cys Gln Asp His Gly Leu Thr Pro Asp
370                 375                 380

Gln Val Val Ala Ile Ala Asn Asn Asn Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Asn Asn Asn Gly Gly Lys Gln Ala
            420                 425                 430

Leu Glu Thr Val Gln Arg Leu Leu Pro Val Leu Cys Gln Asp His Gly
            435                 440                 445

Leu Thr Pro Asp Gln Val Val Ala Ile Ala Ser Asn Ile Gly Gly Lys
        450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Gly Gly
                485                 490                 495

Gly Lys Gln Ala Leu Glu Thr Val Gln Arg Leu Leu Pro Val Leu Cys
```

-continued

```
            500                 505                 510
Gln Asp His Gly Leu Thr Pro Asp Gln Val Ala Ile Ala Asn Asn
            515                 520                 525
Asn Gly Gly Lys Gln Ala Leu Glu Thr Val Gln Arg Leu Leu Pro Val
        530                 535                 540
Leu Cys Gln Asp His Gly Leu Thr Pro Asp Gln Val Val Ala Ile Ala
545                 550                 555                 560
Ser His Asp Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
                580                 585                 590
Ile Ala Ser Asn Gly Gly Lys Gln Ala Leu Glu Thr Val Gln Arg
            595                 600                 605
Leu Leu Pro Val Leu Cys Gln Asp His Gly Leu Thr Pro Asp Gln Val
            610                 615                 620
Val Ala Ile Ala Ser His Asp Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Ser His Asp Gly Gly Lys Gln Ala Leu Glu
                660                 665                 670
Thr Val Gln Arg Leu Leu Pro Val Leu Cys Gln Asp His Gly Leu Thr
            675                 680                 685
Pro Asp Gln Val Val Ala Ile Ala Ser Asn Gly Gly Lys Gln Ala
            690                 695                 700
Leu Glu Ser Ile Val Ala Gln Leu Ser Arg Arg Asp Pro Ala Leu Ala
705                 710                 715                 720
Ala Leu Thr Asn Asp His Leu Val Ala Leu Ala Cys Leu Gly Gly Arg
                725                 730                 735
Pro Ala Leu Asp Ala Val Lys Lys Gly Leu Pro His Ala Pro Glu Phe
                740                 745                 750
Ile Arg Arg Val Asn Arg Arg Ile Ala Glu Arg Thr Ser His Arg Val
            755                 760                 765
Ala Asp Tyr Ala His Val Val Arg Val Leu Glu Phe Phe Gln Cys His
            770                 775                 780
Ser His Pro Ala His Ala Phe Asp Glu Ala Met Thr Gln Phe Gly Met
785                 790                 795                 800
Ser Arg His Gly Leu Val Gln Leu Phe Arg Arg Val Gly Val Thr Glu
                805                 810                 815
Phe Glu Ala Arg Tyr Gly Thr Leu Pro Pro Ala Ser Gln Arg Trp Asp
                820                 825                 830
Arg Ile Leu Gln Ala Ser Gly Met Lys Arg Ala Lys Pro Ser Pro Thr
            835                 840                 845
Ser Ala Gln Thr Pro Asp Gln Thr Ser Leu His Ala Phe Ala Asp Ser
            850                 855                 860
Leu Glu Arg Asp Leu Asp Ala Pro Ser Pro Met His Glu Gly Asp Gln
865                 870                 875                 880
Thr Arg Ala Ser Ser Arg Lys Arg Ser Arg Ser Asp Arg Ala Val Thr
                885                 890                 895
Gly Pro Ser Ala Gln Gln Ala Val Glu Val Arg Val Pro Glu Gln Arg
                900                 905                 910
Asp Ala Leu His Leu Pro Leu Ser Trp Arg Val Lys Arg Pro Arg Thr
            915                 920                 925
```

Arg Ile Trp Gly Gly Leu Pro Asp Pro Ile Ser Arg Ser Gln Leu Val
            930                 935                 940

Lys Ser Glu Leu Glu Glu Lys Lys Ser Glu Leu Arg His Lys Leu Lys
945                 950                 955                 960

Tyr Val Pro His Glu Tyr Ile Glu Leu Ile Glu Ile Ala Arg Asn Ser
                965                 970                 975

Thr Gln Asp Arg Ile Leu Glu Met Lys Val Met Glu Phe Phe Met Lys
            980                 985                 990

Val Tyr Gly Tyr Arg Gly Lys His Leu Gly Gly Ser Arg Lys Pro Asp
        995                1000                1005

Gly Ala Ile Tyr Thr Val Gly Ser Pro Ile Asp Tyr Gly Val Ile Val
        1010                1015                1020

Asp Thr Lys Ala Tyr Ser Gly Gly Tyr Asn Leu Pro Ile Gly Gln Ala
1025                1030                1035                1040

Asp Glu Met Gln Arg Tyr Val Glu Glu Asn Gln Thr Arg Asn Lys His
            1045                1050                1055

Ile Asn Pro Asn Glu Trp Trp Lys Val Tyr Pro Ser Ser Val Thr Glu
            1060                1065                1070

Phe Lys Phe Leu Phe Val Ser Gly His Phe Lys Gly Asn Tyr Lys Ala
            1075                1080                1085

Gln Leu Thr Arg Leu Asn His Ile Thr Asn Cys Asn Gly Ala Val Leu
            1090                1095                1100

Ser Val Glu Glu Leu Leu Ile Gly Gly Glu Met Ile Lys Ala Gly Thr
1105                1110                1115                1120

Leu Thr Leu Glu Glu Val Arg Arg Lys Phe Asn Asn Gly Glu Ile Asn
            1125                1130                1135

Phe

<210> SEQ ID NO 40
<211> LENGTH: 1137
<212> TYPE: PRT
<213> ORGANISM: Artificial Sequence
<220> FEATURE:
<223> OTHER INFORMATION: synthetic peptide

<400> SEQUENCE: 40

Met Ala Ser Ser Pro Pro Lys Lys Lys Arg Lys Val Ser Trp Lys Asp
  1               5                  10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
        50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Asp Pro Pro Pro Thr
    130                 135                 140

-continued

```
Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
            165                 170                 175

Val Asp Leu Arg Thr Leu Gly Tyr Ser Gln Gln Gln Glu Lys Ile
            180                 185                 190

Lys Pro Lys Val Arg Ser Thr Val Ala Gln His His Glu Ala Leu Val
            195                 200                 205

Gly His Gly Phe Thr His Ala His Ile Val Ala Leu Ser Gln His Pro
            210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
            245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
            275                 280                 285

Lys Arg Gly Gly Val Thr Ala Met Glu Ala Val His Ala Ser Arg Asn
290                 295                 300

Ala Leu Thr Gly Ala Pro Leu Asn Leu Thr Pro Ala Gln Val Val Ala
305                 310                 315                 320

Ile Ala Ser Asn Ile Gly Gly Lys Gln Ala Leu Glu Thr Val Gln Arg
            325                 330                 335

Leu Leu Pro Val Leu Cys Gln Asp His Gly Leu Thr Pro Asp Gln Val
            340                 345                 350

Val Ala Ile Ala Asn Asn Asn Gly Gly Lys Gln Ala Leu Glu Thr Val
            355                 360                 365

Gln Arg Leu Leu Pro Val Leu Cys Gln Asp His Gly Leu Thr Pro Asp
            370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Asp His Gly Leu Thr
            405                 410                 415

Pro Asp Gln Val Val Ala Ile Ala Ser His Asp Gly Gly Lys Gln Ala
            420                 425                 430

Leu Glu Thr Val Gln Arg Leu Leu Pro Val Leu Cys Gln Asp His Gly
            435                 440                 445

Leu Thr Pro Asp Gln Val Val Ala Ile Ala Ser Asn Ile Gly Gly Lys
            450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Ile Gly
            485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser Asn
            515                 520                 525

Ile Gly Gly Lys Gln Ala Leu Glu Thr Val Gln Arg Leu Leu Pro Val
            530                 535                 540

Leu Cys Gln Asp His Gly Leu Thr Pro Asp Gln Val Val Ala Ile Ala
545                 550                 555                 560

Ser His Asp Gly Gly Lys Gln Ala Leu Glu Thr Val Gln Arg Leu Leu
```

```
                565                 570                 575
Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
            595                 600                 605

Leu Leu Pro Val Leu Cys Gln Asp His Gly Leu Thr Pro Asp Gln Val
        610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser His Asp Gly Gly Lys Gln Ala Leu Glu
                660                 665                 670

Thr Val Gln Arg Leu Leu Pro Val Leu Cys Gln Asp His Gly Leu Thr
            675                 680                 685

Pro Asp Gln Val Val Ala Ile Ala Ser Asn Ile Gly Gly Lys Gln Ala
        690                 695                 700

Leu Glu Ser Ile Val Ala Gln Leu Ser Arg Arg Asp Pro Ala Leu Ala
705                 710                 715                 720

Ala Leu Thr Asn Asp His Leu Val Ala Leu Ala Cys Leu Gly Gly Arg
                725                 730                 735

Pro Ala Leu Asp Ala Val Lys Lys Gly Leu Pro His Ala Pro Glu Phe
                740                 745                 750

Ile Arg Arg Val Asn Arg Arg Ile Ala Glu Arg Thr Ser His Arg Val
            755                 760                 765

Ala Asp Tyr Ala His Val Val Arg Val Leu Glu Phe Phe Gln Cys His
        770                 775                 780

Ser His Pro Ala His Ala Phe Asp Glu Ala Met Thr Gln Phe Gly Met
785                 790                 795                 800

Ser Arg His Gly Leu Val Gln Leu Phe Arg Arg Val Gly Val Thr Glu
                805                 810                 815

Phe Glu Ala Arg Tyr Gly Thr Leu Pro Pro Ala Ser Gln Arg Trp Asp
            820                 825                 830

Arg Ile Leu Gln Ala Ser Gly Met Lys Arg Ala Lys Pro Ser Pro Thr
        835                 840                 845

Ser Ala Gln Thr Pro Asp Gln Thr Ser Leu His Ala Phe Ala Asp Ser
        850                 855                 860

Leu Glu Arg Asp Leu Asp Ala Pro Ser Pro Met His Glu Gly Asp Gln
865                 870                 875                 880

Thr Arg Ala Ser Ser Arg Lys Arg Ser Arg Ser Asp Arg Ala Val Thr
                885                 890                 895

Gly Pro Ser Ala Gln Gln Ala Val Glu Val Arg Val Pro Glu Gln Arg
            900                 905                 910

Asp Ala Leu His Leu Pro Leu Ser Trp Arg Val Lys Arg Pro Arg Thr
        915                 920                 925

Arg Ile Trp Gly Gly Leu Pro Asp Pro Ile Ser Arg Ser Gln Leu Val
        930                 935                 940

Lys Ser Glu Leu Glu Glu Lys Ser Glu Leu Arg His Lys Leu Lys
945                 950                 955                 960

Tyr Val Pro His Glu Tyr Ile Glu Leu Ile Glu Ile Ala Arg Asn Ser
                965                 970                 975

Thr Gln Asp Arg Ile Leu Glu Met Lys Val Met Glu Phe Phe Met Lys
            980                 985                 990
```

Val Tyr Gly Tyr Arg Gly Lys His Leu Gly Ser Arg Lys Pro Asp
        995                 1000                1005

Gly Ala Ile Tyr Thr Val Gly Ser Pro Ile Asp Tyr Gly Val Ile Val
        1010                1015                1020

Asp Thr Lys Ala Tyr Ser Gly Gly Tyr Asn Leu Pro Ile Gly Gln Ala
1025                1030                1035                1040

Asp Glu Met Gln Arg Tyr Val Glu Glu Asn Gln Thr Arg Asn Lys His
            1045                1050                1055

Ile Asn Pro Asn Glu Trp Trp Lys Val Tyr Pro Ser Ser Val Thr Glu
            1060                1065                1070

Phe Lys Phe Leu Phe Val Ser Gly His Phe Lys Gly Asn Tyr Lys Ala
        1075                1080                1085

Gln Leu Thr Arg Leu Asn His Ile Thr Asn Cys Asn Gly Ala Val Leu
        1090                1095                1100

Ser Val Glu Glu Leu Leu Ile Gly Gly Glu Met Ile Lys Ala Gly Thr
1105                1110                1115                1120

Leu Thr Leu Glu Glu Val Arg Arg Lys Phe Asn Asn Gly Glu Ile Asn
            1125                1130                1135

Phe

<210> SEQ ID NO 41
<211> LENGTH: 1137
<212> TYPE: PRT
<213> ORGANISM: Artificial Sequence
<220> FEATURE:
<223> OTHER INFORMATION: synthetic peptide

<400> SEQUENCE: 41

Met Ala Ser Ser Pro Lys Lys Lys Arg Lys Val Ser Trp Lys Asp
1               5                   10                  15

Ala Ser Gly Trp Ser Arg Met His Ala Asp Pro Ile Arg Pro Arg
            20                  25                  30

Pro Ser Pro Ala Arg Glu Leu Leu Pro Gly Pro Gln Pro Asp Arg Val
        35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

```
Gly His Gly Phe Thr His Ala His Ile Val Ala Leu Ser Gln His Pro
    210                 215                 220
Ala Ala Leu Gly Thr Val Ala Val Thr Tyr Gln His Ile Ile Thr Ala
225                 230                 235                 240
Leu Pro Glu Ala Thr His Glu Asp Ile Val Gly Val Gly Lys Gln Trp
                245                 250                 255
Ser Gly Ala Arg Ala Leu Glu Ala Leu Leu Thr Asp Ala Gly Glu Leu
                260                 265                 270
Arg Gly Pro Pro Leu Gln Leu Asp Thr Gly Gln Leu Val Lys Ile Ala
            275                 280                 285
Lys Arg Gly Gly Val Thr Ala Met Glu Ala Val His Ala Ser Arg Asn
290                 295                 300
Ala Leu Thr Gly Ala Pro Leu Asn Leu Thr Pro Ala Gln Val Val Ala
305                 310                 315                 320
Ile Ala Asn Asn Asn Gly Gly Lys Gln Ala Leu Glu Thr Val Gln Arg
                325                 330                 335
Leu Leu Pro Val Leu Cys Gln Asp His Gly Leu Thr Pro Asp Gln Val
            340                 345                 350
Val Ala Ile Ala Asn Asn Asn Gly Gly Lys Gln Ala Leu Glu Thr Val
        355                 360                 365
Gln Arg Leu Leu Pro Val Leu Cys Gln Asp His Gly Leu Thr Pro Asp
370                 375                 380
Gln Val Val Ala Ile Ala Ser His Asp Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser Asn Ile Gly Gly Lys Gln Ala
            420                 425                 430
Leu Glu Thr Val Gln Arg Leu Leu Pro Val Leu Cys Gln Asp His Gly
        435                 440                 445
Leu Thr Pro Asp Gln Val Val Ala Ile Ala Ser His Asp Gly Gly Lys
450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser Asn Gly Gly
                485                 490                 495
Gly Lys Gln Ala Leu Glu Thr Val Gln Arg Leu Leu Pro Val Leu Cys
            500                 505                 510
Gln Asp His Gly Leu Thr Pro Asp Gln Val Val Ala Ile Ala Asn Asn
        515                 520                 525
Asn Gly Gly Lys Gln Ala Leu Glu Thr Val Gln Arg Leu Leu Pro Val
530                 535                 540
Leu Cys Gln Asp His Gly Leu Thr Pro Asp Gln Val Val Ala Ile Ala
545                 550                 555                 560
Ser His Asp Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
            580                 585                 590
Ile Ala Ser Asn Gly Gly Gly Lys Gln Ala Leu Glu Thr Val Gln Arg
        595                 600                 605
Leu Leu Pro Val Leu Cys Gln Asp His Gly Leu Thr Pro Asp Gln Val
610                 615                 620

Val Ala Ile Ala Ser Asn Ile Gly Gly Lys Gln Ala Leu Glu Thr Val
```

```
            625                 630                 635                 640
        Gln Arg Leu Leu Pro Val Leu Cys Gln Asp His Gly Leu Thr Pro Asp
                        645                 650                 655
        Gln Val Val Ala Ile Ala Ser Asn Ile Gly Gly Lys Gln Ala Leu Glu
                        660                 665                 670
        Thr Val Gln Arg Leu Leu Pro Val Leu Cys Gln Asp His Gly Leu Thr
                    675                 680                 685
        Pro Asp Gln Val Val Ala Ile Ala Ser His Asp Gly Gly Lys Gln Ala
                690                 695                 700
        Leu Glu Ser Ile Val Ala Gln Leu Ser Arg Arg Asp Pro Ala Leu Ala
        705                 710                 715                 720
        Ala Leu Thr Asn Asp His Leu Val Ala Leu Ala Cys Leu Gly Gly Arg
                        725                 730                 735
        Pro Ala Leu Asp Ala Val Lys Lys Gly Leu Pro His Ala Pro Glu Phe
                        740                 745                 750
        Ile Arg Arg Val Asn Arg Arg Ile Ala Glu Arg Thr Ser His Arg Val
                    755                 760                 765
        Ala Asp Tyr Ala His Val Val Arg Val Leu Glu Phe Phe Gln Cys His
                770                 775                 780
        Ser His Pro Ala His Ala Phe Asp Glu Ala Met Thr Gln Phe Gly Met
        785                 790                 795                 800
        Ser Arg His Gly Leu Val Gln Leu Phe Arg Arg Val Gly Val Thr Glu
                        805                 810                 815
        Phe Glu Ala Arg Tyr Gly Thr Leu Pro Pro Ala Ser Gln Arg Trp Asp
                        820                 825                 830
        Arg Ile Leu Gln Ala Ser Gly Met Lys Arg Ala Lys Pro Ser Pro Thr
                    835                 840                 845
        Ser Ala Gln Thr Pro Asp Gln Thr Ser Leu His Ala Phe Ala Asp Ser
                850                 855                 860
        Leu Glu Arg Asp Leu Asp Ala Pro Ser Pro Met His Glu Gly Asp Gln
        865                 870                 875                 880
        Thr Arg Ala Ser Ser Arg Lys Arg Ser Arg Ser Asp Arg Ala Val Thr
                        885                 890                 895
        Gly Pro Ser Ala Gln Gln Ala Val Glu Val Arg Val Pro Glu Gln Arg
                        900                 905                 910
        Asp Ala Leu His Leu Pro Leu Ser Trp Arg Val Lys Arg Pro Arg Thr
                    915                 920                 925
        Arg Ile Trp Gly Gly Leu Pro Asp Pro Ile Ser Arg Ser Gln Leu Val
                930                 935                 940
        Lys Ser Glu Leu Glu Glu Lys Lys Ser Glu Leu Arg His Lys Leu Lys
        945                 950                 955                 960
        Tyr Val Pro His Glu Tyr Ile Glu Leu Ile Glu Ile Ala Arg Asn Ser
                        965                 970                 975
        Thr Gln Asp Arg Ile Leu Glu Met Lys Val Met Glu Phe Phe Met Lys
                    980                 985                 990
        Val Tyr Gly Tyr Arg Gly Lys His Leu Gly Gly Ser Arg Lys Pro Asp
                995                 1000                1005
        Gly Ala Ile Tyr Thr Val Gly Ser Pro Ile Asp Tyr Gly Val Ile Val
                1010                1015                1020
        Asp Thr Lys Ala Tyr Ser Gly Gly Tyr Asn Leu Pro Ile Gly Gln Ala
        1025                1030                1035                1040
        Asp Glu Met Gln Arg Tyr Val Glu Glu Asn Gln Thr Arg Asn Lys His
                        1045                1050                1055
```

```
Ile Asn Pro Asn Glu Trp Trp Lys Val Tyr Pro Ser Ser Val Thr Glu
            1060                1065                1070

Phe Lys Phe Leu Phe Val Ser Gly His Phe Lys Gly Asn Tyr Lys Ala
        1075                1080                1085

Gln Leu Thr Arg Leu Asn His Ile Thr Asn Cys Asn Gly Ala Val Leu
    1090                1095                1100

Ser Val Glu Glu Leu Leu Ile Gly Gly Glu Met Ile Lys Ala Gly Thr
1105                1110                1115                1120

Leu Thr Leu Glu Glu Val Arg Arg Lys Phe Asn Asn Gly Glu Ile Asn
                1125                1130                1135

Phe

<210> SEQ ID NO 42
<211> LENGTH: 1171
<212> TYPE: PRT
<213> ORGANISM: Artificial Sequence
<220> FEATURE:
<223> OTHER INFORMATION: synthetic peptide

<400> SEQUENCE: 42

Met Ala Ser Ser Pro Lys Lys Arg Lys Val Ser Trp Lys Asp
 1               5                  10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
    115                 120                 125

Asp Glu Ala Gln Ser Ala Leu Arg Ala Ala Asp Asp Pro Pro Pro Thr
130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
    195                 200                 205

Gly His Gly Phe Thr His Ala His Ile Val Ala Leu Ser Gln His Pro
210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270
```

```
Arg Gly Pro Pro Leu Gln Leu Asp Thr Gly Gln Leu Val Lys Ile Ala
            275                 280                 285
Lys Arg Gly Gly Val Thr Ala Met Glu Ala Val His Ala Ser Arg Asn
290                 295                 300
Ala Leu Thr Gly Ala Pro Leu Asn Leu Thr Pro Ala Gln Val Val Ala
305                 310                 315                 320
Ile Ala Ser Asn Ile Gly Gly Lys Gln Ala Leu Glu Thr Val Gln Arg
                325                 330                 335
Leu Leu Pro Val Leu Cys Gln Asp His Gly Leu Thr Pro Asp Gln Val
                340                 345                 350
Val Ala Ile Ala Ser His Asp Gly Gly Lys Gln Ala Leu Glu Thr Val
                355                 360                 365
Gln Arg Leu Leu Pro Val Leu Cys Gln Asp His Gly Leu Thr Pro Asp
370                 375                 380
Gln Val Val Ala Ile Ala Ser His Asp Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser His Asp Gly Gly Lys Gln Ala
                420                 425                 430
Leu Glu Thr Val Gln Arg Leu Leu Pro Val Leu Cys Gln Asp His Gly
                435                 440                 445
Leu Thr Pro Asp Gln Val Val Ala Ile Ala Ser His Asp Gly Gly Lys
                450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser Asn Gly Gly
                485                 490                 495
Gly Lys Gln Ala Leu Glu Thr Val Gln Arg Leu Leu Pro Val Leu Cys
                500                 505                 510
Gln Asp His Gly Leu Thr Pro Asp Gln Val Val Ala Ile Ala Ser His
                515                 520                 525
Asp Gly Gly Lys Gln Ala Leu Glu Thr Val Gln Arg Leu Leu Pro Val
530                 535                 540
Leu Cys Gln Asp His Gly Leu Thr Pro Asp Gln Val Val Ala Ile Ala
545                 550                 555                 560
Ser Asn Gly Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
                580                 585                 590
Ile Ala Ser His Asp Gly Gly Lys Gln Ala Leu Glu Thr Val Gln Arg
                595                 600                 605
Leu Leu Pro Val Leu Cys Gln Asp His Gly Leu Thr Pro Asp Gln Val
            610                 615                 620
Val Ala Ile Ala Ser His Asp Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Asn Asn Asn Gly Gly Lys Gln Ala Leu Glu
                660                 665                 670
Thr Val Gln Arg Leu Leu Pro Val Leu Cys Gln Asp His Gly Leu Thr
                675                 680                 685
Pro Asp Gln Val Val Ala Ile Ala Ser His Asp Gly Gly Lys Gln Ala
```

```
            690             695             700
Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Gly Gly Gly Lys
            725                 730                 735

Gln Ala Leu Glu Ser Ile Val Ala Gln Leu Ser Arg Arg Asp Pro Ala
            740                 745                 750

Leu Ala Ala Leu Thr Asn Asp His Leu Val Ala Leu Ala Cys Leu Gly
            755                 760                 765

Gly Arg Pro Ala Leu Asp Ala Val Lys Lys Gly Leu Pro His Ala Pro
770                 775                 780

Glu Phe Ile Arg Arg Val Asn Arg Arg Ile Ala Glu Arg Thr Ser His
785                 790                 795                 800

Arg Val Ala Asp Tyr Ala His Val Val Arg Val Leu Glu Phe Phe Gln
                805                 810                 815

Cys His Ser His Pro Ala His Ala Phe Asp Glu Ala Met Thr Gln Phe
                820                 825                 830

Gly Met Ser Arg His Gly Leu Val Gln Leu Phe Arg Arg Val Gly Val
            835                 840                 845

Thr Glu Phe Glu Ala Arg Tyr Gly Thr Leu Pro Pro Ala Ser Gln Arg
            850                 855                 860

Trp Asp Arg Ile Leu Gln Ala Ser Gly Met Lys Arg Ala Lys Pro Ser
865                 870                 875                 880

Pro Thr Ser Ala Gln Thr Pro Asp Gln Thr Ser Leu His Ala Phe Ala
                885                 890                 895

Asp Ser Leu Glu Arg Asp Leu Asp Ala Pro Ser Pro Met His Glu Gly
            900                 905                 910

Asp Gln Thr Arg Ala Ser Ser Arg Lys Arg Ser Arg Ser Asp Arg Ala
            915                 920                 925

Val Thr Gly Pro Ser Ala Gln Gln Ala Val Glu Val Arg Val Pro Glu
            930                 935                 940

Gln Arg Asp Ala Leu His Leu Pro Leu Ser Trp Arg Val Lys Arg Pro
945                 950                 955                 960

Arg Thr Arg Ile Trp Gly Gly Leu Pro Asp Pro Ile Ser Arg Ser Gln
                965                 970                 975

Leu Val Lys Ser Glu Leu Glu Glu Lys Ser Glu Leu Arg His Lys
            980                 985                 990

Leu Lys Tyr Val Pro His Glu Tyr Ile Glu Leu Ile Glu Ile Ala Arg
            995                 1000                1005

Asn Ser Thr Gln Asp Arg Ile Leu Glu Met Lys Val Met Glu Phe Phe
            1010                1015                1020

Met Lys Val Tyr Gly Tyr Arg Gly Lys His Leu Gly Gly Ser Arg Lys
1025                1030                1035                1040

Pro Asp Gly Ala Ile Tyr Thr Val Gly Ser Pro Ile Asp Tyr Gly Val
                1045                1050                1055

Ile Val Asp Thr Lys Ala Tyr Ser Gly Gly Tyr Asn Leu Pro Ile Gly
            1060                1065                1070

Gln Ala Asp Glu Met Gln Arg Tyr Val Glu Glu Asn Gln Thr Arg Asn
            1075                1080                1085

Lys His Ile Asn Pro Asn Glu Trp Trp Lys Val Tyr Pro Ser Ser Val
            1090                1095                1100

Thr Glu Phe Lys Phe Leu Phe Val Ser Gly His Phe Lys Gly Asn Tyr
1105                1110                1115                1120
```

-continued

```
Lys Ala Gln Leu Thr Arg Leu Asn His Ile Thr Asn Cys Asn Gly Ala
            1125                1130                1135

Val Leu Ser Val Glu Glu Leu Leu Ile Gly Gly Glu Met Ile Lys Ala
        1140                1145                1150

Gly Thr Leu Thr Leu Glu Glu Val Arg Arg Lys Phe Asn Asn Gly Glu
        1155                1160                1165

Ile Asn Phe
    1170

<210> SEQ ID NO 43
<211> LENGTH: 1239
<212> TYPE: PRT
<213> ORGANISM: Artificial Sequence
<220> FEATURE:
<223> OTHER INFORMATION: synthetic peptide

<400> SEQUENCE: 43

Met Ala Ser Ser Pro Pro Lys Lys Arg Lys Val Ser Trp Lys Asp
 1               5                  10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Gly Ser Pro Leu
    50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
    290                 295                 300
```

```
Ala Leu Thr Gly Ala Pro Leu Asn Leu Thr Pro Ala Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Asp His Gly Leu Thr Pro Asp
370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Ile Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Asn Asn Asn Gly Gly Lys
450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Ile Gly
                485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser Asn
        515                 520                 525

Ile Gly Gly Lys Gln Ala Leu Glu Thr Val Gln Arg Leu Leu Pro Val
530                 535                 540

Leu Cys Gln Asp His Gly Leu Thr Pro Asp Gln Val Val Ala Ile Ala
545                 550                 555                 560

Asn Asn Asn Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser Asn Gly Gly Lys Gln Ala Leu Glu Thr Val Gln Arg
        595                 600                 605

Leu Leu Pro Val Leu Cys Gln Asp His Gly Leu Thr Pro Asp Gln Val
610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Ile Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Ser Asn Ile Gly Gly Lys Gln Ala
690                 695                 700

Leu Glu Thr Val Gln Arg Leu Leu Pro Val Leu Cys Gln Asp His Gly
705                 710                 715                 720
```

```
Leu Thr Pro Asp Gln Val Val Ala Ile Ala Ser His Asp Gly Gly Lys
            725                 730                 735

Gln Ala Leu Glu Thr Val Gln Arg Leu Leu Pro Val Leu Cys Gln Asp
        740                 745                 750

His Gly Leu Thr Pro Asp Gln Val Val Ala Ile Ala Ser Asn Ile Gly
    755                 760                 765

Gly Lys Gln Ala Leu Glu Thr Val Gln Arg Leu Leu Pro Val Leu Cys
770                 775                 780

Gln Asp His Gly Leu Thr Pro Asp Gln Val Val Ala Ile Ala Ser Asn
785                 790                 795                 800

Gly Gly Gly Lys Gln Ala Leu Glu Ser Ile Val Ala Gln Leu Ser Arg
                805                 810                 815

Arg Asp Pro Ala Leu Ala Ala Leu Thr Asn Asp His Leu Val Ala Leu
            820                 825                 830

Ala Cys Leu Gly Gly Arg Pro Ala Leu Asp Ala Val Lys Lys Gly Leu
        835                 840                 845

Pro His Ala Pro Glu Phe Ile Arg Arg Val Asn Arg Arg Ile Ala Glu
    850                 855                 860

Arg Thr Ser His Arg Val Ala Asp Tyr Ala His Val Val Arg Val Leu
865                 870                 875                 880

Glu Phe Phe Gln Cys His Ser His Pro Ala His Ala Phe Asp Glu Ala
                885                 890                 895

Met Thr Gln Phe Gly Met Ser Arg His Gly Leu Val Gln Leu Phe Arg
            900                 905                 910

Arg Val Gly Val Thr Glu Phe Glu Ala Arg Tyr Gly Thr Leu Pro Pro
        915                 920                 925

Ala Ser Gln Arg Trp Asp Arg Ile Leu Gln Ala Ser Gly Met Lys Arg
    930                 935                 940

Ala Lys Pro Ser Pro Thr Ser Ala Gln Thr Pro Asp Gln Thr Ser Leu
945                 950                 955                 960

His Ala Phe Ala Asp Ser Leu Glu Arg Asp Leu Asp Ala Pro Ser Pro
                965                 970                 975

Met His Glu Gly Asp Gln Thr Arg Ala Ser Ser Arg Lys Arg Ser Arg
            980                 985                 990

Ser Asp Arg Ala Val Thr Gly Pro Ser Ala Gln Gln Ala Val Glu Val
        995                 1000                1005

Arg Val Pro Glu Gln Arg Asp Ala Leu His Leu Pro Leu Ser Trp Arg
    1010                1015                1020

Val Lys Arg Pro Arg Thr Arg Ile Trp Gly Gly Leu Pro Asp Pro Ile
1025                1030                1035                1040

Ser Arg Ser Gln Leu Val Lys Ser Glu Leu Glu Glu Lys Lys Ser Glu
                1045                1050                1055

Leu Arg His Lys Leu Lys Tyr Val Pro His Glu Tyr Ile Glu Leu Ile
            1060                1065                1070

Glu Ile Ala Arg Asn Ser Thr Gln Asp Arg Ile Leu Glu Met Lys Val
        1075                1080                1085

Met Glu Phe Phe Met Lys Val Tyr Gly Tyr Arg Gly Lys His Leu Gly
    1090                1095                1100

Gly Ser Arg Lys Pro Asp Gly Ala Ile Tyr Thr Val Gly Ser Pro Ile
1105                1110                1115                1120

Asp Tyr Gly Val Ile Val Asp Thr Lys Ala Tyr Ser Gly Gly Tyr Asn
                1125                1130                1135

Leu Pro Ile Gly Gln Ala Asp Glu Met Gln Arg Tyr Val Glu Glu Asn
```

```
                     1140               1145                1150
Gln Thr Arg Asn Lys His Ile Asn Pro Asn Glu Trp Trp Lys Val Tyr
            1155               1160                1165

Pro Ser Ser Val Thr Glu Phe Lys Phe Leu Phe Val Ser Gly His Phe
        1170                1175                1180

Lys Gly Asn Tyr Lys Ala Gln Leu Thr Arg Leu Asn His Ile Thr Asn
1185                1190                1195                1200

Cys Asn Gly Ala Val Leu Ser Val Glu Glu Leu Leu Ile Gly Gly Glu
                1205                1210                1215

Met Ile Lys Ala Gly Thr Leu Thr Leu Glu Glu Val Arg Arg Lys Phe
            1220                1225                1230

Asn Asn Gly Glu Ile Asn Phe
            1235

<210> SEQ ID NO 44
<211> LENGTH: 1239
<212> TYPE: PRT
<213> ORGANISM: Artificial Sequence
<220> FEATURE:
<223> OTHER INFORMATION: synthetic peptide

<400> SEQUENCE: 44

Met Ala Ser Ser Pro Pro Lys Lys Arg Lys Val Ser Trp Lys Asp
 1               5                  10                  15

Ala Ser Gly Trp Ser Arg Met His Ala Asp Pro Ile Arg Pro Arg Arg
             20                  25                  30

Pro Ser Pro Ala Arg Glu Leu Leu Pro Gly Pro Gln Pro Asp Arg Val
         35                  40                  45

Gln Pro Thr Ala Asp Arg Gly Val Ser Ala Pro Ala Gly Ser Pro Leu
     50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                 85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
```

```
                260                 265                 270
Arg Gly Pro Pro Leu Gln Leu Asp Thr Gly Gln Leu Val Lys Ile Ala
            275                 280                 285
Lys Arg Gly Gly Val Thr Ala Met Glu Ala Val His Ala Ser Arg Asn
        290                 295                 300
Ala Leu Thr Gly Ala Pro Leu Asn Leu Thr Pro Ala Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Asp His Gly Leu Thr Pro Asp Gln Val
            340                 345                 350
Val Ala Ile Ala Ser His Asp Gly Gly Lys Gln Ala Leu Glu Thr Val
        355                 360                 365
Gln Arg Leu Leu Pro Val Leu Cys Gln Asp His Gly Leu Thr Pro Asp
    370                 375                 380
Gln Val Val Ala Ile Ala Asn Asn Asn Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Asn Asn Asn Gly Gly Lys Gln Ala
            420                 425                 430
Leu Glu Thr Val Gln Arg Leu Leu Pro Val Leu Cys Gln Asp His Gly
        435                 440                 445
Leu Thr Pro Asp Gln Val Val Ala Ile Ala Ser Asn Ile Gly Gly Lys
    450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser Asn Gly Gly
                485                 490                 495
Gly Lys Gln Ala Leu Glu Thr Val Gln Arg Leu Leu Pro Val Leu Cys
            500                 505                 510
Gln Asp His Gly Leu Thr Pro Asp Gln Val Val Ala Ile Ala Asn Asn
        515                 520                 525
Asn Gly Gly Lys Gln Ala Leu Glu Thr Val Gln Arg Leu Leu Pro Val
    530                 535                 540
Leu Cys Gln Asp His Gly Leu Thr Pro Asp Gln Val Val Ala Ile Ala
545                 550                 555                 560
Ser His Asp Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
            580                 585                 590
Ile Ala Ser Asn Gly Gly Gly Lys Gln Ala Leu Glu Thr Val Gln Arg
        595                 600                 605
Leu Leu Pro Val Leu Cys Gln Asp His Gly Leu Thr Pro Asp Gln Val
    610                 615                 620
Val Ala Ile Ala Ser His Asp Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Ser His Asp Gly Gly Lys Gln Ala Leu Glu
            660                 665                 670
Thr Val Gln Arg Leu Leu Pro Val Leu Cys Gln Asp His Gly Leu Thr
        675                 680                 685
```

```
Pro Asp Gln Val Val Ala Ile Ala Ser Asn Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser His Asp Gly Lys
                725                 730                 735

Gln Ala Leu Glu Thr Val Gln Arg Leu Leu Pro Val Leu Cys Gln Asp
            740                 745                 750

His Gly Leu Thr Pro Asp Gln Val Val Ala Ile Ala Ser Asn Gly Gly
        755                 760                 765

Gly Lys Gln Ala Leu Glu Thr Val Gln Arg Leu Leu Pro Val Leu Cys
    770                 775                 780

Gln Asp His Gly Leu Thr Pro Asp Gln Val Val Ala Ile Ala Ser Asn
785                 790                 795                 800

Gly Gly Gly Lys Gln Ala Leu Glu Ser Ile Val Ala Gln Leu Ser Arg
                805                 810                 815

Arg Asp Pro Ala Leu Ala Ala Leu Thr Asn Asp His Leu Val Ala Leu
            820                 825                 830

Ala Cys Leu Gly Gly Arg Pro Ala Leu Asp Ala Val Lys Lys Gly Leu
        835                 840                 845

Pro His Ala Pro Glu Phe Ile Arg Arg Val Asn Arg Arg Ile Ala Glu
    850                 855                 860

Arg Thr Ser His Arg Val Ala Asp Tyr Ala His Val Val Arg Val Leu
865                 870                 875                 880

Glu Phe Phe Gln Cys His Ser His Pro Ala His Ala Phe Asp Glu Ala
                885                 890                 895

Met Thr Gln Phe Gly Met Ser Arg His Gly Leu Val Gln Leu Phe Arg
            900                 905                 910

Arg Val Gly Val Thr Glu Phe Glu Ala Arg Tyr Gly Thr Leu Pro Pro
        915                 920                 925

Ala Ser Gln Arg Trp Asp Arg Ile Leu Gln Ala Ser Gly Met Lys Arg
    930                 935                 940

Ala Lys Pro Ser Pro Thr Ser Ala Gln Thr Pro Asp Gln Thr Ser Leu
945                 950                 955                 960

His Ala Phe Ala Asp Ser Leu Glu Arg Asp Leu Asp Ala Pro Ser Pro
                965                 970                 975

Met His Glu Gly Asp Gln Thr Arg Ala Ser Ser Arg Lys Arg Ser Arg
            980                 985                 990

Ser Asp Arg Ala Val Thr Gly Pro Ser Ala Gln Gln Ala Val Glu Val
        995                 1000                1005

Arg Val Pro Glu Gln Arg Asp Ala Leu His Leu Pro Leu Ser Trp Arg
    1010                1015                1020

Val Lys Arg Pro Arg Thr Arg Ile Trp Gly Gly Leu Pro Asp Pro Ile
1025                1030                1035                1040

Ser Arg Ser Gln Leu Val Lys Ser Glu Leu Glu Lys Lys Ser Glu
                1045                1050                1055

Leu Arg His Lys Leu Lys Tyr Val Pro His Glu Tyr Ile Glu Leu Ile
            1060                1065                1070

Glu Ile Ala Arg Asn Ser Thr Gln Asp Arg Ile Leu Glu Met Lys Val
        1075                1080                1085

Met Glu Phe Phe Met Lys Val Tyr Gly Tyr Arg Gly Lys His Leu Gly
    1090                1095                1100
```

Gly Ser Arg Lys Pro Asp Gly Ala Ile Tyr Thr Val Gly Ser Pro Ile
1105                1110                1115                1120

Asp Tyr Gly Val Ile Val Asp Thr Lys Ala Tyr Ser Gly Gly Tyr Asn
            1125                1130                1135

Leu Pro Ile Gly Gln Ala Asp Glu Met Gln Arg Tyr Val Glu Glu Asn
            1140                1145                1150

Gln Thr Arg Asn Lys His Ile Asn Pro Asn Glu Trp Trp Lys Val Tyr
        1155                1160                1165

Pro Ser Ser Val Thr Glu Phe Lys Phe Leu Phe Val Ser Gly His Phe
        1170                1175                1180

Lys Gly Asn Tyr Lys Ala Gln Leu Thr Arg Leu Asn His Ile Thr Asn
1185                1190                1195                1200

Cys Asn Gly Ala Val Leu Ser Val Glu Glu Leu Leu Ile Gly Gly Glu
            1205                1210                1215

Met Ile Lys Ala Gly Thr Leu Thr Leu Glu Glu Val Arg Arg Lys Phe
            1220                1225                1230

Asn Asn Gly Glu Ile Asn Phe
        1235

<210> SEQ ID NO 45
<211> LENGTH: 1239
<212> TYPE: PRT
<213> ORGANISM: Artificial Sequence
<220> FEATURE:
<223> OTHER INFORMATION: synthetic peptide

<400> SEQUENCE: 45

Met Ala Ser Ser Pro Pro Lys Lys Lys Arg Lys Val Ser Trp Lys Asp
1               5                   10                  15

Ala Ser Gly Trp Ser Arg Met His Ala Asp Pro Ile Arg Pro Arg Arg
            20                  25                  30

Pro Ser Pro Ala Arg Glu Leu Leu Pro Gly Pro Gln Pro Asp Arg Val
        35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

```
Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
            245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
            275                 280                 285

Lys Arg Gly Gly Val Thr Ala Met Glu Ala Val His Ala Ser Arg Asn
290                 295                 300

Ala Leu Thr Gly Ala Pro Leu Asn Leu Thr Pro Ala Gln Val Val Ala
305                 310                 315                 320

Ile Ala Ser Asn Ile Gly Gly Lys Gln Ala Leu Glu Thr Val Gln Arg
            325                 330                 335

Leu Leu Pro Val Leu Cys Gln Asp His Gly Leu Thr Pro Asp Gln Val
            340                 345                 350

Val Ala Ile Ala Asn Asn Asn Gly Gly Lys Gln Ala Leu Glu Thr Val
            355                 360                 365

Gln Arg Leu Leu Pro Val Leu Cys Gln Asp His Gly Leu Thr Pro Asp
370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Asp His Gly Leu Thr
            405                 410                 415

Pro Asp Gln Val Val Ala Ile Ala Ser His Asp Gly Gly Lys Gln Ala
            420                 425                 430

Leu Glu Thr Val Gln Arg Leu Leu Pro Val Leu Cys Gln Asp His Gly
            435                 440                 445

Leu Thr Pro Asp Gln Val Val Ala Ile Ala Ser Asn Ile Gly Gly Lys
450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Ile Gly
            485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser Asn
            515                 520                 525

Ile Gly Gly Lys Gln Ala Leu Glu Thr Val Gln Arg Leu Leu Pro Val
530                 535                 540

Leu Cys Gln Asp His Gly Leu Thr Pro Asp Gln Val Val Ala Ile Ala
545                 550                 555                 560

Ser His Asp Gly Gly Lys Gln Ala Leu Glu Thr Val Gln Arg Leu Leu
            565                 570                 575

Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
            595                 600                 605

Leu Leu Pro Val Leu Cys Gln Asp His Gly Leu Thr Pro Asp Gln Val
            610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
```

```
                    645                 650                 655
Gln Val Val Ala Ile Ala Ser His Asp Gly Gly Lys Gln Ala Leu Glu
                660                 665                 670

Thr Val Gln Arg Leu Leu Pro Val Leu Cys Gln Asp His Gly Leu Thr
            675                 680                 685

Pro Asp Gln Val Val Ala Ile Ala Ser Asn Ile Gly Gly Lys Gln Ala
690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Ile Gly Gly Lys
                725                 730                 735

Gln Ala Leu Glu Thr Val Gln Arg Leu Leu Pro Val Leu Cys Gln Asp
            740                 745                 750

His Gly Leu Thr Pro Asp Gln Val Val Ala Ile Ala Ser His Asp Gly
        755                 760                 765

Gly Lys Gln Ala Leu Glu Thr Val Gln Arg Leu Leu Pro Val Leu Cys
770                 775                 780

Gln Asp His Gly Leu Thr Pro Asp Gln Val Val Ala Ile Ala Ser Asn
785                 790                 795                 800

Gly Gly Gly Lys Gln Ala Leu Glu Ser Ile Val Ala Gln Leu Ser Arg
                805                 810                 815

Arg Asp Pro Ala Leu Ala Ala Leu Thr Asn Asp His Leu Val Ala Leu
            820                 825                 830

Ala Cys Leu Gly Gly Arg Pro Ala Leu Asp Ala Val Lys Lys Gly Leu
        835                 840                 845

Pro His Ala Pro Glu Phe Ile Arg Arg Val Asn Arg Arg Ile Ala Glu
    850                 855                 860

Arg Thr Ser His Arg Val Ala Asp Tyr Ala His Val Val Arg Val Leu
865                 870                 875                 880

Glu Phe Phe Gln Cys His Ser His Pro Ala His Ala Phe Asp Glu Ala
                885                 890                 895

Met Thr Gln Phe Gly Met Ser Arg His Gly Leu Val Gln Leu Phe Arg
            900                 905                 910

Arg Val Gly Val Thr Glu Phe Glu Ala Arg Tyr Gly Thr Leu Pro Pro
        915                 920                 925

Ala Ser Gln Arg Trp Asp Arg Ile Leu Gln Ala Ser Gly Met Lys Arg
    930                 935                 940

Ala Lys Pro Ser Pro Thr Ser Ala Gln Thr Pro Asp Gln Thr Ser Leu
945                 950                 955                 960

His Ala Phe Ala Asp Ser Leu Glu Arg Asp Leu Asp Ala Pro Ser Pro
                965                 970                 975

Met His Glu Gly Asp Gln Thr Arg Ala Ser Ser Arg Lys Arg Ser Arg
            980                 985                 990

Ser Asp Arg Ala Val Thr Gly Pro Ser Ala Gln Gln Ala Val Glu Val
        995                 1000                1005

Arg Val Pro Glu Gln Arg Asp Ala Leu His Leu Pro Leu Ser Trp Arg
    1010                1015                1020

Val Lys Arg Pro Arg Thr Arg Ile Trp Gly Gly Leu Pro Asp Pro Ile
1025                1030                1035                1040

Ser Arg Ser Gln Leu Val Lys Ser Glu Leu Glu Glu Lys Lys Ser Glu
                1045                1050                1055

Leu Arg His Lys Leu Lys Tyr Val Pro His Glu Tyr Ile Glu Leu Ile
            1060                1065                1070
```

-continued

```
Glu Ile Ala Arg Asn Ser Thr Gln Asp Arg Ile Leu Glu Met Lys Val
        1075                1080                1085

Met Glu Phe Phe Met Lys Val Tyr Gly Tyr Arg Gly Lys His Leu Gly
    1090                1095                1100

Gly Ser Arg Lys Pro Asp Gly Ala Ile Tyr Thr Val Gly Ser Pro Ile
1105                1110                1115                1120

Asp Tyr Gly Val Ile Val Asp Thr Lys Ala Tyr Ser Gly Gly Tyr Asn
                1125                1130                1135

Leu Pro Ile Gly Gln Ala Asp Glu Met Gln Arg Tyr Val Glu Glu Asn
                1140                1145                1150

Gln Thr Arg Asn Lys His Ile Asn Pro Asn Glu Trp Trp Lys Val Tyr
                1155                1160                1165

Pro Ser Ser Val Thr Glu Phe Lys Phe Leu Phe Val Ser Gly His Phe
                1170                1175                1180

Lys Gly Asn Tyr Lys Ala Gln Leu Thr Arg Leu Asn His Ile Thr Asn
1185                1190                1195                1200

Cys Asn Gly Ala Val Leu Ser Val Glu Glu Leu Leu Ile Gly Gly Glu
                1205                1210                1215

Met Ile Lys Ala Gly Thr Leu Thr Leu Glu Glu Val Arg Arg Lys Phe
                1220                1225                1230

Asn Asn Gly Glu Ile Asn Phe
        1235

<210> SEQ ID NO 46
<211> LENGTH: 1239
<212> TYPE: PRT
<213> ORGANISM: Artificial Sequence
<220> FEATURE:
<223> OTHER INFORMATION: synthetic peptide

<400> SEQUENCE: 46

Met Ala Ser Ser Pro Lys Lys Lys Arg Lys Val Ser Trp Lys Asp
  1               5                  10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
        50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
                100                 105                 110

Met Pro Ala Val Gly Thr Pro His Thr Ala Ala Ala Pro Ala Glu Trp
            115                 120                 125

Asp Glu Ala Gln Ser Ala Leu Arg Ala Ala Asp Pro Pro Pro Thr
        130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
                180                 185                 190
```

```
Lys Pro Lys Val Arg Ser Thr Val Ala Gln His His Glu Ala Leu Val
            195                 200                 205

Gly His Gly Phe Thr His Ala His Ile Val Ala Leu Ser Gln His Pro
        210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
290                 295                 300

Ala Leu Thr Gly Ala Pro Leu Asn Leu Thr Pro Ala Gln Val Val Ala
305                 310                 315                 320

Ile Ala Asn Asn Asn Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Asn Asn Asn Gly Gly Lys Gln Ala Leu Glu Thr Val
        355                 360                 365

Gln Arg Leu Leu Pro Val Leu Cys Gln Asp His Gly Leu Thr Pro Asp
370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Ile Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser His Asp Gly Gly Lys
450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Asn Asn
        515                 520                 525

Asn Gly Gly Lys Gln Ala Leu Glu Thr Val Gln Arg Leu Leu Pro Val
530                 535                 540

Leu Cys Gln Asp His Gly Leu Thr Pro Asp Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser Asn Gly Gly Gly Lys Gln Ala Leu Glu Thr Val Gln Arg
        595                 600                 605
```

```
Leu Leu Pro Val Leu Cys Gln Asp His Gly Leu Thr Pro Asp Gln Val
    610                 615                 620
Val Ala Ile Ala Ser Asn Ile Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Ser Asn Ile Gly Gly Lys Gln Ala Leu Glu
            660                 665                 670
Thr Val Gln Arg Leu Leu Pro Val Leu Cys Gln Asp His Gly Leu Thr
        675                 680                 685
Pro Asp Gln Val Val Ala Ile Ala Ser His Asp Gly Gly Lys Gln Ala
    690                 695                 700
Leu Glu Thr Val Gln Arg Leu Leu Pro Val Leu Cys Gln Asp His Gly
705                 710                 715                 720
Leu Thr Pro Asp Gln Val Val Ala Ile Ala Ser His Asp Gly Gly Lys
                725                 730                 735
Gln Ala Leu Glu Thr Val Gln Arg Leu Leu Pro Val Leu Cys Gln Asp
            740                 745                 750
His Gly Leu Thr Pro Asp Gln Val Val Ala Ile Ala Ser His Asp Gly
        755                 760                 765
Gly Lys Gln Ala Leu Glu Thr Val Gln Arg Leu Leu Pro Val Leu Cys
    770                 775                 780
Gln Asp His Gly Leu Thr Pro Asp Gln Val Val Ala Ile Ala Ser Asn
785                 790                 795                 800
Gly Gly Gly Lys Gln Ala Leu Glu Ser Ile Val Ala Gln Leu Ser Arg
                805                 810                 815
Arg Asp Pro Ala Leu Ala Ala Leu Thr Asn Asp His Leu Val Ala Leu
            820                 825                 830
Ala Cys Leu Gly Gly Arg Pro Ala Leu Asp Ala Val Lys Lys Gly Leu
        835                 840                 845
Pro His Ala Pro Glu Phe Ile Arg Arg Val Asn Arg Arg Ile Ala Glu
    850                 855                 860
Arg Thr Ser His Arg Val Ala Asp Tyr Ala His Val Val Arg Val Leu
865                 870                 875                 880
Glu Phe Phe Gln Cys His Ser His Pro Ala His Ala Phe Asp Glu Ala
                885                 890                 895
Met Thr Gln Phe Gly Met Ser Arg His Gly Leu Val Gln Leu Phe Arg
            900                 905                 910
Arg Val Gly Val Thr Glu Phe Glu Ala Arg Tyr Gly Thr Leu Pro Pro
        915                 920                 925
Ala Ser Gln Arg Trp Asp Arg Ile Leu Gln Ala Ser Gly Met Lys Arg
    930                 935                 940
Ala Lys Pro Ser Pro Thr Ser Ala Gln Thr Pro Asp Gln Thr Ser Leu
945                 950                 955                 960
His Ala Phe Ala Asp Ser Leu Glu Arg Asp Leu Asp Ala Pro Ser Pro
                965                 970                 975
Met His Glu Gly Asp Gln Thr Arg Ala Ser Ser Arg Lys Arg Ser Arg
            980                 985                 990
Ser Asp Arg Ala Val Thr Gly Pro Ser Ala Gln Gln Ala Val Glu Val
        995                 1000                1005
Arg Val Pro Glu Gln Arg Asp Ala Leu His Leu Pro Leu Ser Trp Arg
    1010                1015                1020
Val Lys Arg Pro Arg Thr Arg Ile Trp Gly Gly Leu Pro Asp Pro Ile
```

```
1025                1030                1035                1040

Ser Arg Ser Gln Leu Val Lys Ser Glu Leu Glu Glu Lys Ser Glu
                1045                1050                1055

Leu Arg His Lys Leu Lys Tyr Val Pro His Glu Tyr Ile Glu Leu Ile
                1060                1065                1070

Glu Ile Ala Arg Asn Ser Thr Gln Asp Arg Ile Leu Glu Met Lys Val
            1075                1080                1085

Met Glu Phe Phe Met Lys Val Tyr Gly Tyr Arg Gly Lys His Leu Gly
            1090                1095                1100

Gly Ser Arg Lys Pro Asp Gly Ala Ile Tyr Thr Val Gly Ser Pro Ile
1105                1110                1115                1120

Asp Tyr Gly Val Ile Val Asp Thr Lys Ala Tyr Ser Gly Gly Tyr Asn
                1125                1130                1135

Leu Pro Ile Gly Gln Ala Asp Glu Met Gln Arg Tyr Val Glu Glu Asn
                1140                1145                1150

Gln Thr Arg Asn Lys His Ile Asn Pro Asn Glu Trp Trp Lys Val Tyr
                1155                1160                1165

Pro Ser Ser Val Thr Glu Phe Lys Phe Leu Phe Val Ser Gly His Phe
                1170                1175                1180

Lys Gly Asn Tyr Lys Ala Gln Leu Thr Arg Leu Asn His Ile Thr Asn
1185                1190                1195                1200

Cys Asn Gly Ala Val Leu Ser Val Glu Glu Leu Leu Ile Gly Gly Glu
                1205                1210                1215

Met Ile Lys Ala Gly Thr Leu Thr Leu Glu Glu Val Arg Arg Lys Phe
                1220                1225                1230

Asn Asn Gly Glu Ile Asn Phe
        1235

<210> SEQ ID NO 47
<211> LENGTH: 1239
<212> TYPE: PRT
<213> ORGANISM: Artificial Sequence
<220> FEATURE:
<223> OTHER INFORMATION: synthetic peptide

<400> SEQUENCE: 47

Met Ala Ser Ser Pro Pro Lys Lys Lys Arg Lys Val Ser Trp Lys Asp
 1               5                   10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
        50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
                100                 105                 110

Met Pro Ala Val Gly Thr Pro His Thr Ala Ala Ala Pro Ala Glu Trp
            115                 120                 125

Asp Glu Ala Gln Ser Ala Leu Arg Ala Ala Asp Asp Pro Pro Pro Thr
        130                 135                 140

Val Arg Val Ala Val Thr Ala Ala Arg Pro Pro Arg Ala Lys Pro Ala
```

```
             145                 150                 155                 160
Pro Arg Arg Ala Ala Gln Pro Ser Asp Ala Ser Pro Ala Ala Gln
                    165                 170                 175
Val Asp Leu Arg Thr Leu Gly Tyr Ser Gln Gln Gln Glu Lys Ile
                    180                 185                 190
Lys Pro Lys Val Arg Ser Thr Val Ala Gln His His Glu Ala Leu Val
                195                 200                 205
Gly His Gly Phe Thr His Ala His Ile Val Ala Leu Ser Gln His Pro
            210                 215                 220
Ala Ala Leu Gly Thr Val Ala Thr Tyr Gln His Ile Ile Thr Ala
225                 230                 235                 240
Leu Pro Glu Ala Thr His Glu Asp Ile Val Gly Val Lys Gln Trp
                245                 250                 255
Ser Gly Ala Arg Ala Leu Glu Ala Leu Leu Thr Asp Ala Gly Glu Leu
                260                 265                 270
Arg Gly Pro Pro Leu Gln Leu Asp Thr Gly Gln Leu Val Lys Ile Ala
                275                 280                 285
Lys Arg Gly Gly Val Thr Ala Met Glu Ala Val His Ala Ser Arg Asn
            290                 295                 300
Ala Leu Thr Gly Ala Pro Leu Asn Leu Thr Pro Ala Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Asp His Gly Leu Thr Pro Asp Gln Val
                340                 345                 350
Val Ala Ile Ala Ser Asn Gly Gly Lys Gln Ala Leu Glu Thr Val
            355                 360                 365
Gln Arg Leu Leu Pro Val Leu Cys Gln Asp His Gly Leu Thr Pro Asp
    370                 375                 380
Gln Val Val Ala Ile Ala Ser Asn Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Asn Asn Asn Gly Gly Lys Gln Ala
            420                 425                 430
Leu Glu Thr Val Gln Arg Leu Leu Pro Val Leu Cys Gln Asp His Gly
            435                 440                 445
Leu Thr Pro Asp Gln Val Val Ala Ile Ala Ser Asn Gly Gly Gly Lys
450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser His Asp Gly
                485                 490                 495
Gly Lys Gln Ala Leu Glu Thr Val Gln Arg Leu Leu Pro Val Leu Cys
                500                 505                 510
Gln Asp His Gly Leu Thr Pro Asp Gln Val Val Ala Ile Ala Ser His
            515                 520                 525
Asp Gly Gly Lys Gln Ala Leu Glu Thr Val Gln Arg Leu Leu Pro Val
            530                 535                 540
Leu Cys Gln Asp His Gly Leu Thr Pro Asp Gln Val Val Ala Ile Ala
545                 550                 555                 560
Asn Asn Asn Gly Gly Lys Gln Ala Leu Glu Thr Val Gln Arg Leu Leu
                565                 570                 575
```

```
Pro Val Leu Cys Gln Asp His Gly Leu Thr Pro Asp Gln Val Val Ala
        580                 585                 590

Ile Ala Ser His Asp Gly Gly Lys Gln Ala Leu Glu Thr Val Gln Arg
        595                 600                 605

Leu Leu Pro Val Leu Cys Gln Asp His Gly Leu Thr Pro Asp Gln Val
    610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Asn Asn Asn Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Ile Gly Gly Lys
                725                 730                 735

Gln Ala Leu Glu Thr Val Gln Arg Leu Leu Pro Val Leu Cys Gln Asp
            740                 745                 750

His Gly Leu Thr Pro Asp Gln Val Val Ala Ile Ala Ser Asn Gly Gly
        755                 760                 765

Gly Lys Gln Ala Leu Glu Thr Val Gln Arg Leu Leu Pro Val Leu Cys
    770                 775                 780

Gln Asp His Gly Leu Thr Pro Asp Gln Val Val Ala Ile Ala Ser Asn
785                 790                 795                 800

Gly Gly Gly Lys Gln Ala Leu Glu Ser Ile Val Ala Gln Leu Ser Arg
                805                 810                 815

Arg Asp Pro Ala Leu Ala Ala Leu Thr Asn Asp His Leu Val Ala Leu
            820                 825                 830

Ala Cys Leu Gly Gly Arg Pro Ala Leu Asp Ala Val Lys Lys Gly Leu
        835                 840                 845

Pro His Ala Pro Glu Phe Ile Arg Arg Val Asn Arg Arg Ile Ala Glu
    850                 855                 860

Arg Thr Ser His Arg Val Ala Asp Tyr Ala His Val Val Arg Val Leu
865                 870                 875                 880

Glu Phe Phe Gln Cys His Ser His Pro Ala His Ala Phe Asp Glu Ala
                885                 890                 895

Met Thr Gln Phe Gly Met Ser Arg His Gly Leu Val Gln Leu Phe Arg
            900                 905                 910

Arg Val Gly Val Thr Glu Phe Glu Ala Arg Tyr Gly Thr Leu Pro Pro
        915                 920                 925

Ala Ser Gln Arg Trp Asp Arg Ile Leu Gln Ala Ser Gly Met Lys Arg
    930                 935                 940

Ala Lys Pro Ser Pro Thr Ser Ala Gln Thr Pro Asp Gln Thr Ser Leu
945                 950                 955                 960

His Ala Phe Ala Asp Ser Leu Glu Arg Asp Leu Asp Ala Pro Ser Pro
                965                 970                 975

Met His Glu Gly Asp Gln Thr Arg Ala Ser Ser Arg Lys Arg Ser Arg
            980                 985                 990
```

Ser Asp Arg Ala Val Thr Gly Pro Ser Ala Gln Gln Ala Val Glu Val
            995                 1000                1005

Arg Val Pro Glu Gln Arg Asp Ala Leu His Leu Pro Leu Ser Trp Arg
        1010                1015                1020

Val Lys Arg Pro Arg Thr Arg Ile Trp Gly Gly Leu Pro Asp Pro Ile
1025                1030                1035                1040

Ser Arg Ser Gln Leu Val Lys Ser Glu Leu Glu Lys Lys Ser Glu
            1045                1050                1055

Leu Arg His Lys Leu Lys Tyr Val Pro His Glu Tyr Ile Glu Leu Ile
            1060                1065                1070

Glu Ile Ala Arg Asn Ser Thr Gln Asp Arg Ile Leu Glu Met Lys Val
            1075                1080                1085

Met Glu Phe Phe Met Lys Val Tyr Gly Tyr Arg Gly Lys His Leu Gly
            1090                1095                1100

Gly Ser Arg Lys Pro Asp Gly Ala Ile Tyr Thr Val Gly Ser Pro Ile
1105                1110                1115                1120

Asp Tyr Gly Val Ile Val Asp Thr Lys Ala Tyr Ser Gly Gly Tyr Asn
                1125                1130                1135

Leu Pro Ile Gly Gln Ala Asp Glu Met Gln Arg Tyr Val Glu Glu Asn
            1140                1145                1150

Gln Thr Arg Asn Lys His Ile Asn Pro Asn Glu Trp Trp Lys Val Tyr
            1155                1160                1165

Pro Ser Ser Val Thr Glu Phe Lys Phe Leu Phe Val Ser Gly His Phe
            1170                1175                1180

Lys Gly Asn Tyr Lys Ala Gln Leu Thr Arg Leu Asn His Ile Thr Asn
1185                1190                1195                1200

Cys Asn Gly Ala Val Leu Ser Val Glu Glu Leu Leu Ile Gly Gly Glu
            1205                1210                1215

Met Ile Lys Ala Gly Thr Leu Thr Leu Glu Glu Val Arg Arg Lys Phe
            1220                1225                1230

Asn Asn Gly Glu Ile Asn Phe
            1235

<210> SEQ ID NO 48
<211> LENGTH: 1239
<212> TYPE: PRT
<213> ORGANISM: Artificial Sequence
<220> FEATURE:
<223> OTHER INFORMATION: synthetic peptide

<400> SEQUENCE: 48

Met Ala Ser Ser Pro Lys Lys Lys Arg Lys Val Ser Trp Lys Asp
 1               5                  10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
        50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

```
Met Pro Ala Val Gly Thr Pro His Thr Ala Ala Pro Ala Glu Trp
        115                 120                 125
Asp Glu Ala Gln Ser Ala Leu Arg Ala Ala Asp Pro Pro Pro Thr
130                 135                 140
Val Arg Val Ala Val Thr Ala Ala Arg Pro Pro Arg Ala Lys Pro Ala
145                 150                 155                 160
Pro Arg Arg Arg Ala Ala Gln Pro Ser Asp Ala Ser Pro Ala Ala Gln
                165                 170                 175
Val Asp Leu Arg Thr Leu Gly Tyr Ser Gln Gln Gln Glu Lys Ile
                180                 185                 190
Lys Pro Lys Val Arg Ser Thr Val Ala Gln His His Glu Ala Leu Val
                195                 200                 205
Gly His Gly Phe Thr His Ala His Ile Val Ala Leu Ser Gln His Pro
        210                 215                 220
Ala Ala Leu Gly Thr Val Ala Val Thr Tyr Gln His Ile Ile Thr Ala
225                 230                 235                 240
Leu Pro Glu Ala Thr His Glu Asp Ile Val Gly Val Gly Lys Gln Trp
                245                 250                 255
Ser Gly Ala Arg Ala Leu Glu Ala Leu Leu Thr Asp Ala Gly Glu Leu
        260                 265                 270
Arg Gly Pro Pro Leu Gln Leu Asp Thr Gly Gln Leu Val Lys Ile Ala
        275                 280                 285
Lys Arg Gly Gly Val Thr Ala Met Glu Ala Val His Ala Ser Arg Asn
        290                 295                 300
Ala Leu Thr Gly Ala Pro Leu Asn Leu Thr Pro Ala Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Asp His Gly Leu Thr Pro Asp Gln Val
                340                 345                 350
Val Ala Ile Ala Asn Asn Asn Gly Gly Lys Gln Ala Leu Glu Thr Val
        355                 360                 365
Gln Arg Leu Leu Pro Val Leu Cys Gln Asp His Gly Leu Thr Pro Asp
        370                 375                 380
Gln Val Val Ala Ile Ala Asn Asn Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser Asn Gly Gly Lys Gln Ala
                420                 425                 430
Leu Glu Thr Val Gln Arg Leu Leu Pro Val Leu Cys Gln Asp His Gly
        435                 440                 445
Leu Thr Pro Asp Gln Val Val Ala Ile Ala Ser Asn Gly Gly Gly Lys
        450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser Asn Gly Gly
                485                 490                 495
Gly Lys Gln Ala Leu Glu Thr Val Gln Arg Leu Leu Pro Val Leu Cys
                500                 505                 510
Gln Asp His Gly Leu Thr Pro Asp Gln Val Val Ala Ile Ala Asn Asn
                515                 520                 525
Asn Gly Gly Lys Gln Ala Leu Glu Thr Val Gln Arg Leu Leu Pro Val
```

```
                    530                 535                 540
Leu Cys Gln Asp His Gly Leu Thr Pro Asp Gln Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
                580                 585                 590

Ile Ala Ser Asn Gly Gly Lys Gln Ala Leu Glu Thr Val Gln Arg
                595                 600                 605

Leu Leu Pro Val Leu Cys Gln Asp His Gly Leu Thr Pro Asp Gln Val
    610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Gly Gly Lys Gln Ala Leu Glu
                660                 665                 670

Thr Val Gln Arg Leu Leu Pro Val Leu Cys Gln Asp His Gly Leu Thr
                675                 680                 685

Pro Asp Gln Val Val Ala Ile Ala Ser His Asp Gly Gly Lys Gln Ala
690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Asn Asn Asn Gly Gly Lys
                725                 730                 735

Gln Ala Leu Glu Thr Val Gln Arg Leu Leu Pro Val Leu Cys Gln Asp
                740                 745                 750

His Gly Leu Thr Pro Asp Gln Val Val Ala Ile Ala Ser Asn Gly Gly
                755                 760                 765

Gly Lys Gln Ala Leu Glu Thr Val Gln Arg Leu Leu Pro Val Leu Cys
                770                 775                 780

Gln Asp His Gly Leu Thr Pro Asp Gln Val Val Ala Ile Ala Ser Asn
785                 790                 795                 800

Gly Gly Gly Lys Gln Ala Leu Glu Ser Ile Val Ala Gln Leu Ser Arg
                805                 810                 815

Arg Asp Pro Ala Leu Ala Ala Leu Thr Asn Asp His Leu Val Ala Leu
                820                 825                 830

Ala Cys Leu Gly Gly Arg Pro Ala Leu Asp Ala Val Lys Lys Gly Leu
                835                 840                 845

Pro His Ala Pro Glu Phe Ile Arg Arg Val Asn Arg Arg Ile Ala Glu
850                 855                 860

Arg Thr Ser His Arg Val Ala Asp Tyr Ala His Val Val Arg Val Leu
865                 870                 875                 880

Glu Phe Phe Gln Cys His Ser His Pro Ala His Ala Phe Asp Glu Ala
                885                 890                 895

Met Thr Gln Phe Gly Met Ser Arg His Gly Leu Val Gln Leu Phe Arg
                900                 905                 910

Arg Val Gly Val Thr Glu Phe Glu Ala Arg Tyr Gly Thr Leu Pro Pro
                915                 920                 925

Ala Ser Gln Arg Trp Asp Arg Ile Leu Gln Ala Ser Gly Met Lys Arg
                930                 935                 940

Ala Lys Pro Ser Pro Thr Ser Ala Gln Thr Pro Asp Gln Thr Ser Leu
945                 950                 955                 960
```

```
His Ala Phe Ala Asp Ser Leu Glu Arg Asp Leu Asp Ala Pro Ser Pro
            965                 970                 975
Met His Glu Gly Asp Gln Thr Arg Ala Ser Ser Arg Lys Arg Ser Arg
        980                 985                 990
Ser Asp Arg Ala Val Thr Gly Pro Ser Ala Gln Gln Ala Val Glu Val
    995                 1000                1005
Arg Val Pro Glu Gln Arg Asp Ala Leu His Leu Pro Leu Ser Trp Arg
    1010                1015                1020
Val Lys Arg Pro Arg Thr Arg Ile Trp Gly Gly Leu Pro Asp Pro Ile
1025                1030                1035                1040
Ser Arg Ser Gln Leu Val Lys Ser Glu Leu Glu Lys Lys Ser Glu
                1045                1050                1055
Leu Arg His Lys Leu Lys Tyr Val Pro His Glu Tyr Ile Glu Leu Ile
                1060                1065                1070
Glu Ile Ala Arg Asn Ser Thr Gln Asp Arg Ile Leu Glu Met Lys Val
            1075                1080                1085
Met Glu Phe Phe Met Lys Val Tyr Gly Tyr Arg Gly Lys His Leu Gly
        1090                1095                1100
Gly Ser Arg Lys Pro Asp Gly Ala Ile Tyr Thr Val Gly Ser Pro Ile
1105                1110                1115                1120
Asp Tyr Gly Val Ile Val Asp Thr Lys Ala Tyr Ser Gly Gly Tyr Asn
                1125                1130                1135
Leu Pro Ile Gly Gln Ala Asp Glu Met Gln Arg Tyr Val Glu Glu Asn
                1140                1145                1150
Gln Thr Arg Asn Lys His Ile Asn Pro Asn Glu Trp Trp Lys Val Tyr
            1155                1160                1165
Pro Ser Ser Val Thr Glu Phe Lys Phe Leu Phe Val Ser Gly His Phe
        1170                1175                1180
Lys Gly Asn Tyr Lys Ala Gln Leu Thr Arg Leu Asn His Ile Thr Asn
1185                1190                1195                1200
Cys Asn Gly Ala Val Leu Ser Val Glu Glu Leu Leu Ile Gly Gly Glu
                1205                1210                1215
Met Ile Lys Ala Gly Thr Leu Thr Leu Glu Glu Val Arg Arg Lys Phe
            1220                1225                1230
Asn Asn Gly Glu Ile Asn Phe
        1235

<210> SEQ ID NO 49
<211> LENGTH: 1273
<212> TYPE: PRT
<213> ORGANISM: Artificial Sequence
<220> FEATURE:
<223> OTHER INFORMATION: synthetic peptide

<400> SEQUENCE: 49

Met Ala Ser Ser Pro Pro Lys Lys Lys Arg Lys Val Ser Trp Lys Asp
 1               5                  10                  15
Ala Ser Gly Trp Ser Arg Met His Ala Asp Pro Ile Arg Pro Arg Arg
            20                  25                  30
Pro Ser Pro Ala Arg Glu Leu Leu Pro Gly Pro Gln Pro Asp Arg Val
        35                  40                  45
Gln Pro Thr Ala Asp Arg Gly Val Ser Ala Pro Ala Gly Ser Pro Leu
    50                  55                  60
Asp Gly Leu Pro Ala Arg Arg Thr Val Ser Arg Thr Arg Leu Pro Ser
65                  70                  75                  80
```

```
Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Pro Ala Glu Trp
            115                 120                 125

Asp Glu Ala Gln Ser Ala Leu Arg Ala Ala Asp Asp Pro Pro Thr
130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Glu Lys Ile
            180                 185                 190

Lys Pro Lys Val Arg Ser Thr Val Ala Gln His His Glu Ala Leu Val
195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
                260                 265                 270

Arg Gly Pro Pro Leu Gln Leu Asp Thr Gly Gln Leu Val Lys Ile Ala
                275                 280                 285

Lys Arg Gly Gly Val Thr Ala Met Glu Ala Val His Ala Ser Arg Asn
290                 295                 300

Ala Leu Thr Gly Ala Pro Leu Asn Leu Thr Pro Ala Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Asp His Gly Leu Thr Pro Asp Gln Val
                340                 345                 350

Val Ala Ile Ala Ser His Asp Gly Gly Lys Gln Ala Leu Glu Thr Val
                355                 360                 365

Gln Arg Leu Leu Pro Val Leu Cys Gln Asp His Gly Leu Thr Pro Asp
370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser His Asp Gly Gly Lys Gln Ala
                420                 425                 430

Leu Glu Thr Val Gln Arg Leu Leu Pro Val Leu Cys Gln Asp His Gly
                435                 440                 445

Leu Thr Pro Asp Gln Val Val Ala Ile Ala Ser His Asp Gly Gly Lys
                450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Gly Gly
                485                 490                 495
```

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser His
        515                 520                 525

Asp Gly Gly Lys Gln Ala Leu Glu Thr Val Gln Arg Leu Leu Pro Val
    530                 535                 540

Leu Cys Gln Asp His Gly Leu Thr Pro Asp Gln Val Val Ala Ile Ala
545                 550                 555                 560

Ser Asn Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Asp His Gly Leu Thr Pro Asp Gln Val
    610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Asn Asn Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Ser His Asp Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Gly Gly Lys
                725                 730                 735

Gln Ala Leu Glu Thr Val Gln Arg Leu Leu Pro Val Leu Cys Gln Asp
            740                 745                 750

His Gly Leu Thr Pro Asp Gln Val Val Ala Ile Ala Ser Asn Gly Gly
        755                 760                 765

Gly Lys Gln Ala Leu Glu Thr Val Gln Arg Leu Leu Pro Val Leu Cys
    770                 775                 780

Gln Asp His Gly Leu Thr Pro Asp Gln Val Val Ala Ile Ala Ser His
785                 790                 795                 800

Asp Gly Gly Lys Gln Ala Leu Glu Thr Val Gln Arg Leu Leu Pro Val
                805                 810                 815

Leu Cys Gln Asp His Gly Leu Thr Pro Asp Gln Val Val Ala Ile Ala
            820                 825                 830

Ser Asn Gly Gly Lys Gln Ala Leu Glu Ser Ile Val Ala Gln Leu
        835                 840                 845

Ser Arg Arg Asp Pro Ala Leu Ala Ala Leu Thr Asn Asp His Leu Val
    850                 855                 860

Ala Leu Ala Cys Leu Gly Gly Arg Pro Ala Leu Asp Ala Val Lys Lys
865                 870                 875                 880

Gly Leu Pro His Ala Pro Glu Phe Ile Arg Arg Val Asn Arg Arg Ile
                885                 890                 895

Ala Glu Arg Thr Ser His Arg Val Ala Asp Tyr Ala His Val Val Arg
            900                 905                 910

Val Leu Glu Phe Phe Gln Cys His Ser His Pro Ala His Ala Phe Asp

```
                915                 920                 925
Glu Ala Met Thr Gln Phe Gly Met Ser Arg His Gly Leu Val Gln Leu
        930                 935                 940

Phe Arg Arg Val Gly Val Thr Glu Phe Glu Ala Arg Tyr Gly Thr Leu
945                 950                 955                 960

Pro Pro Ala Ser Gln Arg Trp Asp Arg Ile Leu Gln Ala Ser Gly Met
                965                 970                 975

Lys Arg Ala Lys Pro Ser Pro Thr Ser Ala Gln Thr Pro Asp Gln Thr
        980                 985                 990

Ser Leu His Ala Phe Ala Asp Ser Leu Glu Arg Asp Leu Asp Ala Pro
                995                 1000                1005

Ser Pro Met His Glu Gly Asp Gln Thr Arg Ala Ser Ser Arg Lys Arg
        1010                1015                1020

Ser Arg Ser Asp Arg Ala Val Thr Gly Pro Ser Ala Gln Gln Ala Val
1025                1030                1035                1040

Glu Val Arg Val Pro Glu Gln Arg Asp Ala Leu His Leu Pro Leu Ser
                1045                1050                1055

Trp Arg Val Lys Arg Pro Arg Thr Arg Ile Trp Gly Gly Leu Pro Asp
        1060                1065                1070

Pro Ile Ser Arg Ser Gln Leu Val Lys Ser Glu Leu Glu Glu Lys Lys
                1075                1080                1085

Ser Glu Leu Arg His Lys Leu Lys Tyr Val Pro His Gly Tyr Ile Glu
        1090                1095                1100

Leu Ile Glu Ile Ala Arg Asn Ser Thr Gln Asp Arg Ile Leu Glu Met
1105                1110                1115                1120

Lys Val Met Glu Phe Phe Met Lys Val Tyr Gly Tyr Arg Gly Lys His
                1125                1130                1135

Leu Gly Gly Ser Arg Lys Pro Asp Gly Ala Ile Tyr Thr Val Gly Ser
        1140                1145                1150

Pro Ile Asp Tyr Gly Val Ile Val Asp Thr Lys Ala Tyr Ser Gly Gly
                1155                1160                1165

Tyr Asn Leu Pro Ile Gly Gln Ala Asp Glu Met Gln Arg Tyr Val Glu
        1170                1175                1180

Glu Asn Gln Thr Arg Asn Lys His Ile Asn Pro Asn Glu Trp Trp Lys
1185                1190                1195                1200

Val Tyr Pro Ser Ser Val Thr Glu Phe Lys Phe Leu Phe Val Ser Gly
                1205                1210                1215

His Phe Lys Gly Asn Tyr Lys Ala Gln Leu Thr Arg Leu Asn His Ile
        1220                1225                1230

Thr Asn Cys Asn Gly Ala Val Leu Ser Val Glu Glu Leu Leu Ile Gly
        1235                1240                1245

Gly Glu Met Ile Lys Ala Gly Thr Leu Thr Leu Glu Val Arg Arg
        1250                1255                1260

Lys Phe Asn Asn Gly Glu Ile Asn Phe
1265                1270

<210> SEQ ID NO 50
<211> LENGTH: 1273
<212> TYPE: PRT
<213> ORGANISM: Artificial Sequence
<220> FEATURE:
<223> OTHER INFORMATION: synthetic peptide

<400> SEQUENCE: 50

Met Ala Ser Ser Pro Pro Lys Lys Lys Arg Lys Val Ser Trp Lys Asp
```

-continued

```
               1               5              10              15
             Ala Ser Gly Trp Ser Arg Met His Ala Asp Pro Ile Arg Pro Arg Arg
                              20                  25                  30

Pro Ser Pro Ala Arg Glu Leu Leu Pro Gly Pro Gln Pro Asp Arg Val
                              35                  40                  45

Gln Pro Thr Ala Asp Arg Gly Val Ser Ala Pro Ala Gly Ser Pro Leu
              50                  55                  60

Asp Gly Leu Pro Ala Arg Arg Thr Val Ser Arg Thr Arg Leu Pro Ser
              65                  70                  75                  80

Pro Pro Ala Pro Ser Pro Ala Phe Ser Ala Gly Ser Phe Ser Asp Leu
                              85                  90                  95

Leu Arg Pro Phe Asp Pro Ser Leu Leu Asp Thr Ser Leu Leu Asp Ser
                             100                 105                 110

Met Pro Ala Val Gly Thr Pro His Thr Ala Ala Pro Ala Glu Trp
                             115                 120                 125

Asp Glu Ala Gln Ser Ala Leu Arg Ala Ala Asp Asp Pro Pro Thr
                 130                 135                 140

Val Arg Val Ala Val Thr Ala Ala Arg Pro Pro Arg Ala Lys Pro Ala
             145                 150                 155                 160

Pro Arg Arg Arg Ala Ala Gln Pro Ser Asp Ala Ser Pro Ala Ala Gln
                             165                 170                 175

Val Asp Leu Arg Thr Leu Gly Tyr Ser Gln Gln Gln Gln Glu Lys Ile
                             180                 185                 190

Lys Pro Lys Val Arg Ser Thr Val Ala Gln His His Glu Ala Leu Val
                             195                 200                 205

Gly His Gly Phe Thr His Ala His Ile Val Ala Leu Ser Gln His Pro
                             210                 215                 220

Ala Ala Leu Gly Thr Val Ala Val Thr Tyr Gln His Ile Ile Thr Ala
             225                 230                 235                 240

Leu Pro Glu Ala Thr His Glu Asp Ile Val Gly Val Gly Lys Gln Trp
                             245                 250                 255

Ser Gly Ala Arg Ala Leu Glu Ala Leu Leu Thr Asp Ala Gly Glu Leu
                             260                 265                 270

Arg Gly Pro Pro Leu Gln Leu Asp Thr Gly Gln Leu Val Lys Ile Ala
                             275                 280                 285

Lys Arg Gly Gly Val Thr Ala Met Glu Ala Val His Ala Ser Arg Asn
                             290                 295                 300

Ala Leu Thr Gly Ala Pro Leu Asn Leu Thr Pro Ala Gln Val Val Ala
             305                 310                 315                 320

Ile Ala Ser His Asp Gly Gly Lys Gln Ala Leu Glu Thr Val Gln Arg
                             325                 330                 335

Leu Leu Pro Val Leu Cys Gln Asp His Gly Leu Thr Pro Asp Gln Val
                             340                 345                 350

Val Ala Ile Ala Ser His Asp Gly Gly Lys Gln Ala Leu Glu Thr Val
                             355                 360                 365

Gln Arg Leu Leu Pro Val Leu Cys Gln Asp His Gly Leu Thr Pro Asp
                             370                 375                 380

Gln Val Val Ala Ile Ala Ser His Asp Gly Gly Lys Gln Ala Leu Glu
             385                 390                 395                 400

Thr Val Gln Arg Leu Leu Pro Val Leu Cys Gln Asp His Gly Leu Thr
                             405                 410                 415

Pro Asp Gln Val Val Ala Ile Ala Ser Asn Asn Gly Gly Lys Gln Ala
                             420                 425                 430
```

```
Leu Glu Thr Val Gln Arg Leu Leu Pro Val Leu Cys Gln Asp His Gly
        435                 440                 445

Leu Thr Pro Asp Gln Val Val Ala Ile Ala Ser Asn Asn Gly Gly Lys
450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Ile Gly
                485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser Asn
        515                 520                 525

Ile Gly Gly Lys Gln Ala Leu Glu Thr Val Gln Arg Leu Leu Pro Val
    530                 535                 540

Leu Cys Gln Asp His Gly Leu Thr Pro Asp Gln Val Val Ala Ile Ala
545                 550                 555                 560

Ser Asn Asn Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Asp His Gly Leu Thr Pro Asp Gln Val
    610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Asn Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Ser Asn Ile Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Gly Gly Gly Lys
                725                 730                 735

Gln Ala Leu Glu Thr Val Gln Arg Leu Leu Pro Val Leu Cys Gln Asp
            740                 745                 750

His Gly Leu Thr Pro Asp Gln Val Val Ala Ile Ala Ser Asn Asn Gly
        755                 760                 765

Gly Lys Gln Ala Leu Glu Thr Val Gln Arg Leu Leu Pro Val Leu Cys
    770                 775                 780

Gln Asp His Gly Leu Thr Pro Asp Gln Val Val Ala Ile Ala Ser His
785                 790                 795                 800

Asp Gly Gly Lys Gln Ala Leu Glu Thr Val Gln Arg Leu Leu Pro Val
                805                 810                 815

Leu Cys Gln Asp His Gly Leu Thr Pro Asp Gln Val Val Ala Ile Ala
            820                 825                 830

Ser Asn Gly Gly Gly Lys Gln Ala Leu Glu Ser Ile Val Ala Gln Leu
        835                 840                 845
```

```
Ser Arg Pro Asp Pro Ala Leu Ala Ala Leu Thr Asn Asp His Leu Val
    850                 855                 860

Ala Leu Ala Cys Leu Gly Gly Arg Pro Ala Met Asp Ala Val Lys Lys
865                 870                 875                 880

Gly Leu Pro His Ala Pro Glu Leu Ile Arg Arg Val Asn Arg Arg Ile
                885                 890                 895

Gly Glu Arg Thr Ser His Arg Val Ala Asp Tyr Ala Gln Val Val Arg
                900                 905                 910

Val Leu Glu Phe Phe Gln Cys His Ser His Pro Ala Tyr Ala Phe Asp
                915                 920                 925

Glu Ala Met Thr Gln Phe Gly Met Ser Arg Asn Gly Leu Val Gln Leu
            930                 935                 940

Phe Arg Arg Val Gly Val Thr Glu Leu Glu Ala Arg Gly Gly Thr Leu
945                 950                 955                 960

Pro Pro Ala Ser Gln Arg Trp Asp Arg Ile Leu Gln Ala Ser Gly Met
                965                 970                 975

Lys Arg Ala Lys Pro Ser Pro Thr Ser Ala Gln Thr Pro Asp Gln Ala
                980                 985                 990

Ser Leu His Ala Phe Ala Asp Ser Leu Glu Arg Asp Leu Asp Ala Pro
    995                 1000                1005

Ser Pro Met His Glu Gly Asp Gln Thr Arg Ala Ser Ser Arg Lys Arg
    1010                1015                1020

Ser Arg Ser Asp Arg Ala Val Thr Gly Pro Ser Ala Gln Gln Ala Val
1025                1030                1035                1040

Glu Val Arg Val Pro Glu Gln Arg Asp Ala Leu His Leu Pro Leu Ser
                1045                1050                1055

Trp Arg Val Lys Arg Pro Arg Thr Arg Ile Trp Gly Gly Leu Pro Asp
                1060                1065                1070

Pro Ile Ser Arg Ser Gln Leu Val Lys Ser Glu Leu Glu Glu Lys Lys
                1075                1080                1085

Ser Glu Leu Arg His Lys Leu Lys Tyr Val Pro His Gly Tyr Ile Glu
                1090                1095                1100

Leu Ile Glu Ile Ala Arg Asn Ser Thr Gln Asp Arg Ile Leu Glu Met
1105                1110                1115                1120

Lys Val Met Glu Phe Phe Met Lys Val Tyr Gly Tyr Arg Gly Lys His
                1125                1130                1135

Leu Gly Gly Ser Arg Lys Pro Asp Gly Ala Ile Tyr Thr Val Gly Ser
                1140                1145                1150

Pro Ile Asp Tyr Gly Val Ile Val Asp Thr Lys Ala Tyr Ser Gly Gly
                1155                1160                1165

Tyr Asn Leu Pro Ile Gly Gln Ala Asp Glu Met Gln Arg Tyr Val Glu
    1170                1175                1180

Glu Asn Gln Thr Arg Asn Lys His Ile Asn Pro Asn Glu Trp Trp Lys
1185                1190                1195                1200

Val Tyr Pro Ser Ser Val Thr Glu Phe Lys Phe Leu Phe Val Ser Gly
                1205                1210                1215

His Phe Lys Gly Asn Tyr Lys Ala Gln Leu Thr Arg Leu Asn His Ile
                1220                1225                1230

Thr Asn Cys Asn Gly Ala Val Leu Ser Val Glu Glu Leu Leu Ile Gly
                1235                1240                1245

Gly Glu Met Ile Lys Ala Gly Thr Leu Thr Leu Glu Glu Val Arg Arg
                1250                1255                1260

Lys Phe Asn Asn Gly Glu Ile Asn Phe
```

<210> SEQ ID NO 51
<211> LENGTH: 1273
<212> TYPE: PRT
<213> ORGANISM: Artificial Sequence
<220> FEATURE:
<223> OTHER INFORMATION: synthetic peptide

<400> SEQUENCE: 51

```
Met Ala Ser Ser Pro Pro Lys Lys Arg Lys Val Ser Trp Lys Asp
 1               5                  10                  15

Ala Ser Gly Trp Ser Arg Met His Ala Asp Pro Ile Arg Pro Arg Arg
            20                  25                  30

Pro Ser Pro Ala Arg Glu Leu Leu Pro Gly Pro Gln Pro Asp Arg Val
        35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
    290                 295                 300

Ala Leu Thr Gly Ala Pro Leu Asn Leu Thr Pro Ala Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser Asn Gly Gly Gly Lys Gln Ala Leu Glu Thr Val
```

```
              355                 360                 365
Gln Arg Leu Leu Pro Val Leu Cys Gln Asp His Gly Leu Thr Pro Asp
370                 375                 380
Gln Val Val Ala Ile Ala Ser Asn Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser His Asp Gly Gly Lys Gln Ala
                420                 425                 430
Leu Glu Thr Val Gln Arg Leu Leu Pro Val Leu Cys Gln Asp His Gly
                435                 440                 445
Leu Thr Pro Asp Gln Val Val Ala Ile Ala Ser His Asp Gly Gly Lys
            450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser His Asp Gly
                485                 490                 495
Gly Lys Gln Ala Leu Glu Thr Val Gln Arg Leu Leu Pro Val Leu Cys
                500                 505                 510
Gln Asp His Gly Leu Thr Pro Asp Gln Val Val Ala Ile Ala Ser His
            515                 520                 525
Asp Gly Gly Lys Gln Ala Leu Glu Thr Val Gln Arg Leu Leu Pro Val
530                 535                 540
Leu Cys Gln Asp His Gly Leu Thr Pro Asp Gln Val Val Ala Ile Ala
545                 550                 555                 560
Ser Asn Ile Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
                580                 585                 590
Ile Ala Ser His Asp Gly Gly Lys Gln Ala Leu Glu Thr Val Gln Arg
            595                 600                 605
Leu Leu Pro Val Leu Cys Gln Asp His Gly Leu Thr Pro Asp Gln Val
        610                 615                 620
Val Ala Ile Ala Asn Asn Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Ser Asn Ile Gly Gly Lys Gln Ala Leu Glu
                660                 665                 670
Thr Val Gln Arg Leu Leu Pro Val Leu Cys Gln Asp His Gly Leu Thr
                675                 680                 685
Pro Asp Gln Val Val Ala Ile Ala Asn Asn Gly Gly Lys Gln Ala
            690                 695                 700
Leu Glu Thr Val Gln Arg Leu Leu Pro Val Leu Cys Gln Asp His Gly
705                 710                 715                 720
Leu Thr Pro Asp Gln Val Val Ala Ile Ala Ser His Asp Gly Gly Lys
                725                 730                 735
Gln Ala Leu Glu Thr Val Gln Arg Leu Leu Pro Val Leu Cys Gln Asp
                740                 745                 750
His Gly Leu Thr Pro Asp Gln Val Val Ala Ile Ala Ser Asn Gly Gly
            755                 760                 765
Gly Lys Gln Ala Leu Glu Thr Val Gln Arg Leu Leu Pro Val Leu Cys
770                 775                 780
```

```
Gln Asp His Gly Leu Thr Pro Asp Gln Val Val Ala Ile Ala Ser His
785                 790                 795                 800

Asp Gly Gly Lys Gln Ala Leu Glu Thr Val Gln Arg Leu Leu Pro Val
            805                 810                 815

Leu Cys Gln Asp His Gly Leu Thr Pro Asp Gln Val Val Ala Ile Ala
                820                 825                 830

Ser Asn Gly Gly Gly Lys Gln Ala Leu Glu Ser Ile Val Ala Gln Leu
        835                 840                 845

Ser Arg Arg Asp Pro Ala Leu Ala Ala Leu Thr Asn Asp His Leu Val
850                 855                 860

Ala Leu Ala Cys Leu Gly Gly Arg Pro Ala Leu Asp Ala Val Lys Lys
865                 870                 875                 880

Gly Leu Pro His Ala Pro Glu Phe Ile Arg Arg Val Asn Arg Arg Ile
                885                 890                 895

Ala Glu Arg Thr Ser His Arg Val Ala Asp Tyr Ala His Val Val Arg
            900                 905                 910

Val Leu Glu Phe Phe Gln Cys His Ser His Pro Ala His Ala Phe Asp
        915                 920                 925

Glu Ala Met Thr Gln Phe Gly Met Ser Arg His Gly Leu Val Gln Leu
    930                 935                 940

Phe Arg Arg Val Gly Val Thr Glu Phe Glu Ala Arg Tyr Gly Thr Leu
945                 950                 955                 960

Pro Pro Ala Ser Gln Arg Trp Asp Arg Ile Leu Gln Ala Ser Gly Met
                965                 970                 975

Lys Arg Ala Lys Pro Ser Pro Thr Ser Ala Gln Thr Pro Asp Gln Thr
            980                 985                 990

Ser Leu His Ala Phe Ala Asp Ser Leu Glu Arg Asp Leu Asp Ala Pro
        995                 1000                1005

Ser Pro Met His Glu Gly Asp Gln Thr Arg Ala Ser Ser Arg Lys Arg
    1010                1015                1020

Ser Arg Ser Asp Arg Ala Val Thr Gly Pro Ser Ala Gln Gln Ala Val
1025                1030                1035                1040

Glu Val Arg Val Pro Glu Gln Arg Asp Ala Leu His Leu Pro Leu Ser
                1045                1050                1055

Trp Arg Val Lys Arg Pro Arg Thr Arg Ile Trp Gly Gly Leu Pro Asp
            1060                1065                1070

Pro Ile Ser Arg Ser Gln Leu Val Lys Ser Glu Leu Glu Glu Lys Lys
        1075                1080                1085

Ser Glu Leu Arg His Lys Leu Lys Tyr Val Pro His Glu Tyr Ile Glu
    1090                1095                1100

Leu Ile Glu Ile Ala Arg Asn Ser Thr Gln Asp Arg Ile Leu Glu Met
1105                1110                1115                1120

Lys Val Met Glu Phe Phe Met Lys Val Tyr Gly Tyr Arg Gly Lys His
                1125                1130                1135

Leu Gly Gly Ser Arg Lys Pro Asp Gly Ala Ile Tyr Thr Val Gly Ser
            1140                1145                1150

Pro Ile Asp Tyr Gly Val Ile Val Asp Thr Lys Ala Tyr Ser Gly Gly
        1155                1160                1165

Tyr Asn Leu Pro Ile Gly Gln Ala Asp Glu Met Gln Arg Tyr Val Glu
    1170                1175                1180

Glu Asn Gln Thr Arg Asn Lys His Ile Asn Pro Asn Glu Trp Trp Lys
1185                1190                1195                1200
```

Val Tyr Pro Ser Ser Val Thr Glu Phe Lys Phe Leu Phe Val Ser Gly
            1205                1210                1215

His Phe Lys Gly Asn Tyr Lys Ala Gln Leu Thr Arg Leu Asn His Ile
        1220                1225                1230

Thr Asn Cys Asn Gly Ala Val Leu Ser Val Glu Glu Leu Leu Ile Gly
        1235                1240                1245

Gly Glu Met Ile Lys Ala Gly Thr Leu Thr Leu Glu Glu Val Arg Arg
        1250                1255                1260

Lys Phe Asn Asn Gly Glu Ile Asn Phe
1265                1270

<210> SEQ ID NO 52
<211> LENGTH: 1307
<212> TYPE: PRT
<213> ORGANISM: Artificial Sequence
<220> FEATURE:
<223> OTHER INFORMATION: synthetic peptide

<400> SEQUENCE: 52

Met Ala Ser Ser Pro Lys Lys Arg Lys Val Ser Trp Lys Asp
1               5                   10                  15

Ala Ser Gly Trp Ser Arg Met His Ala Asp Pro Ile Arg Pro Arg Arg
            20                  25                  30

Pro Ser Pro Ala Arg Glu Leu Leu Pro Gly Pro Gln Pro Asp Arg Val
        35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

```
Lys Arg Gly Gly Val Thr Ala Met Glu Ala Val His Ala Ser Arg Asn
290                 295                 300
Ala Leu Thr Gly Ala Pro Leu Asn Leu Thr Pro Ala Gln Val Val Ala
305                 310                 315                 320
Ile Ala Ser Asn Ile Gly Gly Lys Gln Ala Leu Glu Thr Val Gln Arg
            325                 330                 335
Leu Leu Pro Val Leu Cys Gln Asp His Gly Leu Thr Pro Asp Gln Val
            340                 345                 350
Val Ala Ile Ala Asn Asn Asn Gly Gly Lys Gln Ala Leu Glu Thr Val
            355                 360                 365
Gln Arg Leu Leu Pro Val Leu Cys Gln Asp His Gly Leu Thr Pro Asp
370                 375                 380
Gln Val Val Ala Ile Ala Ser Asn Ile Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser His Asp Gly Gly Lys Gln Ala
                420                 425                 430
Leu Glu Thr Val Gln Arg Leu Leu Pro Val Leu Cys Gln Asp His Gly
                435                 440                 445
Leu Thr Pro Asp Gln Val Val Ala Ile Ala Ser Asn Ile Gly Gly Lys
450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Asn Asn Asn Gly
                485                 490                 495
Gly Lys Gln Ala Leu Glu Thr Val Gln Arg Leu Leu Pro Val Leu Cys
            500                 505                 510
Gln Asp His Gly Leu Thr Pro Asp Gln Val Val Ala Ile Ala Asn Asn
            515                 520                 525
Asn Gly Gly Lys Gln Ala Leu Glu Thr Val Gln Arg Leu Leu Pro Val
530                 535                 540
Leu Cys Gln Asp His Gly Leu Thr Pro Asp Gln Val Val Ala Ile Ala
545                 550                 555                 560
Ser Asn Ile Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
                580                 585                 590
Ile Ala Ser Asn Ile Gly Gly Lys Gln Ala Leu Glu Thr Val Gln Arg
                595                 600                 605
Leu Leu Pro Val Leu Cys Gln Asp His Gly Leu Thr Pro Asp Gln Val
610                 615                 620
Val Ala Ile Ala Asn Asn Asn Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Ser Asn Gly Gly Gly Lys Gln Ala Leu Glu
                660                 665                 670
Thr Val Gln Arg Leu Leu Pro Val Leu Cys Gln Asp His Gly Leu Thr
                675                 680                 685
Pro Asp Gln Val Val Ala Ile Ala Asn Asn Asn Gly Gly Lys Gln Ala
690                 695                 700
Leu Glu Thr Val Gln Arg Leu Leu Pro Val Leu Cys Gln Asp His Gly
```

```
                705                 710                 715                 720
Leu Thr Pro Asp Gln Val Val Ala Ile Ala Asn Asn Asn Gly Gly Lys
                    725                 730                 735
Gln Ala Leu Glu Thr Val Gln Arg Leu Leu Pro Val Leu Cys Gln Asp
                    740                 745                 750
His Gly Leu Thr Pro Asp Gln Val Ala Ile Ala Ser Asn Ile Gly
                    755                 760                 765
Gly Lys Gln Ala Leu Glu Thr Val Gln Arg Leu Leu Pro Val Leu Cys
            770                 775                 780
Gln Asp His Gly Leu Thr Pro Asp Gln Val Ala Ile Ala Asn Asn
785                 790                 795                 800
Asn Gly Gly Lys Gln Ala Leu Glu Thr Val Gln Arg Leu Leu Pro Val
                        805                 810                 815
Leu Cys Gln Asp His Gly Leu Thr Pro Asp Gln Val Ala Ile Ala
                    820                 825                 830
Ser His Asp Gly Gly Lys Gln Ala Leu Glu Thr Val Gln Arg Leu Leu
            835                 840                 845
Pro Val Leu Cys Gln Asp His Gly Leu Thr Pro Asp Gln Val Val Ala
        850                 855                 860
Ile Ala Ser Asn Gly Gly Gly Lys Gln Ala Leu Glu Ser Ile Val Ala
865                 870                 875                 880
Gln Leu Ser Arg Arg Asp Pro Ala Leu Ala Ala Leu Thr Asn Asp His
                    885                 890                 895
Leu Val Ala Leu Ala Cys Leu Gly Gly Arg Pro Ala Leu Asp Ala Val
                900                 905                 910
Lys Lys Gly Leu Pro His Ala Pro Glu Phe Ile Arg Arg Val Asn Arg
            915                 920                 925
Arg Ile Ala Glu Arg Thr Ser His Arg Val Ala Asp Tyr Ala His Val
        930                 935                 940
Val Arg Val Leu Glu Phe Phe Gln Cys His Ser His Pro Ala His Ala
945                 950                 955                 960
Phe Asp Glu Ala Met Thr Gln Phe Gly Met Ser Arg His Gly Leu Val
                    965                 970                 975
Gln Leu Phe Arg Arg Val Gly Val Thr Glu Phe Glu Ala Arg Tyr Gly
                980                 985                 990
Thr Leu Pro Pro Ala Ser Gln Arg Trp Asp Arg Ile Leu Gln Ala Ser
            995                 1000                1005
Gly Met Lys Arg Ala Lys Pro Ser Pro Thr Ser Ala Gln Thr Pro Asp
        1010                1015                1020
Gln Thr Ser Leu His Ala Phe Ala Asp Ser Leu Glu Arg Asp Leu Asp
1025                1030                1035                1040
Ala Pro Ser Pro Met His Glu Gly Asp Gln Thr Arg Ala Ser Ser Arg
                    1045                1050                1055
Lys Arg Ser Arg Ser Asp Arg Ala Val Thr Gly Pro Ser Ala Gln Gln
                1060                1065                1070
Ala Val Glu Val Arg Val Pro Glu Gln Arg Asp Ala Leu His Leu Pro
        1075                1080                1085
Leu Ser Trp Arg Val Lys Arg Pro Arg Thr Arg Ile Trp Gly Gly Leu
        1090                1095                1100
Pro Asp Pro Ile Ser Arg Ser Gln Leu Val Lys Ser Glu Leu Glu Glu
1105                1110                1115                1120
Lys Lys Ser Glu Leu Arg His Lys Leu Lys Tyr Val Pro His Glu Tyr
                    1125                1130                1135
```

```
Ile Glu Leu Ile Glu Ile Ala Arg Asn Ser Thr Gln Asp Arg Ile Leu
            1140                1145                1150

Glu Met Lys Val Met Glu Phe Phe Met Lys Val Tyr Gly Tyr Arg Gly
            1155                1160                1165

Lys His Leu Gly Gly Ser Arg Lys Pro Asp Gly Ala Ile Tyr Thr Val
    1170                1175                1180

Gly Ser Pro Ile Asp Tyr Gly Val Ile Val Asp Thr Lys Ala Tyr Ser
1185                1190                1195                1200

Gly Gly Tyr Asn Leu Pro Ile Gly Gln Ala Asp Glu Met Gln Arg Tyr
                1205                1210                1215

Val Glu Glu Asn Gln Thr Arg Asn Lys His Ile Asn Pro Asn Glu Trp
            1220                1225                1230

Trp Lys Val Tyr Pro Ser Ser Val Thr Glu Phe Lys Phe Leu Phe Val
            1235                1240                1245

Ser Gly His Phe Lys Gly Asn Tyr Lys Ala Gln Leu Thr Arg Leu Asn
    1250                1255                1260

His Ile Thr Asn Cys Asn Gly Ala Val Leu Ser Val Glu Glu Leu Leu
1265                1270                1275                1280

Ile Gly Gly Glu Met Ile Lys Ala Gly Thr Leu Thr Leu Glu Glu Val
                1285                1290                1295

Arg Arg Lys Phe Asn Asn Gly Glu Ile Asn Phe
            1300                1305

<210> SEQ ID NO 53
<211> LENGTH: 1341
<212> TYPE: PRT
<213> ORGANISM: Artificial Sequence
<220> FEATURE:
<223> OTHER INFORMATION: synthetic peptide

<400> SEQUENCE: 53

Met Ala Ser Ser Pro Pro Lys Lys Lys Arg Lys Val Ser Trp Lys Asp
  1               5                  10                  15

Ala Ser Gly Trp Ser Arg Met His Ala Asp Pro Ile Arg Pro Arg Arg
             20                  25                  30

Pro Ser Pro Ala Arg Glu Leu Leu Pro Gly Pro Gln Pro Asp Arg Val
         35                  40                  45

Gln Pro Thr Ala Asp Arg Gly Val Ser Ala Pro Ala Gly Ser Pro Leu
     50                  55                  60

Asp Gly Leu Pro Ala Arg Arg Thr Val Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190
```

-continued

```
Lys Pro Lys Val Arg Ser Thr Val Ala Gln His His Glu Ala Leu Val
        195                 200                 205
Gly His Gly Phe Thr His Ala His Ile Val Ala Leu Ser Gln His Pro
    210                 215                 220
Ala Ala Leu Gly Thr Val Ala Val Thr Tyr Gln His Ile Ile Thr Ala
225                 230                 235                 240
Leu Pro Glu Ala Thr His Glu Asp Ile Val Gly Val Gly Lys Gln Trp
                245                 250                 255
Ser Gly Ala Arg Ala Leu Glu Ala Leu Leu Thr Asp Ala Gly Glu Leu
            260                 265                 270
Arg Gly Pro Pro Leu Gln Leu Asp Thr Gly Gln Leu Val Lys Ile Ala
        275                 280                 285
Lys Arg Gly Gly Val Thr Ala Met Glu Ala Val His Ala Ser Arg Asn
    290                 295                 300
Ala Leu Thr Gly Ala Pro Leu Asn Leu Thr Pro Ala Gln Val Val Ala
305                 310                 315                 320
Ile Ala Ser Asn Ile Gly Gly Lys Gln Ala Leu Glu Thr Val Gln Arg
                325                 330                 335
Leu Leu Pro Val Leu Cys Gln Asp His Gly Leu Thr Pro Asp Gln Val
            340                 345                 350
Val Ala Ile Ala Ser Asn Gly Gly Lys Gln Ala Leu Glu Thr Val
        355                 360                 365
Gln Arg Leu Leu Pro Val Leu Cys Gln Asp His Gly Leu Thr Pro Asp
    370                 375                 380
Gln Val Val Ala Ile Ala Ser His Asp Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser Asn Ile Gly Gly Lys Gln Ala
            420                 425                 430
Leu Glu Thr Val Gln Arg Leu Leu Pro Val Leu Cys Gln Asp His Gly
        435                 440                 445
Leu Thr Pro Asp Gln Val Val Ala Ile Ala Ser Asn Ile Gly Gly Lys
    450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Asn Asn Asn Gly
                485                 490                 495
Gly Lys Gln Ala Leu Glu Thr Val Gln Arg Leu Leu Pro Val Leu Cys
            500                 505                 510
Gln Asp His Gly Leu Thr Pro Asp Gln Val Val Ala Ile Ala Ser Asn
        515                 520                 525
Ile Gly Gly Lys Gln Ala Leu Glu Thr Val Gln Arg Leu Leu Pro Val
    530                 535                 540
Leu Cys Gln Asp His Gly Leu Thr Pro Asp Gln Val Val Ala Ile Ala
545                 550                 555                 560
Ser Asn Gly Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
            580                 585                 590
Ile Ala Ser Asn Gly Gly Gly Lys Gln Ala Leu Glu Thr Val Gln Arg
        595                 600                 605
```

| | | | | | | | | | | | | | | |
|---|---|---|---|---|---|---|---|---|---|---|---|---|---|---|
|Leu|Leu|Pro|Val|Leu|Cys|Gln|Asp|His|Gly|Leu|Thr|Pro|Asp|Gln|Val|
| |610| | | | |615| | | | |620| | | |

Val Ala Ile Ala Ser His Asp Gly Gly Lys Gln Ala Leu Glu Thr Val
625                630                635                640

Gln Arg Leu Leu Pro Val Leu Cys Gln Asp His Gly Leu Thr Pro Asp
        645                650                655

Gln Val Val Ala Ile Ala Ser Asn Gly Gly Lys Gln Ala Leu Glu
        660                665                670

Thr Val Gln Arg Leu Leu Pro Val Leu Cys Gln Asp His Gly Leu Thr
        675                680                685

Pro Asp Gln Val Val Ala Ile Ala Ser His Asp Gly Gly Lys Gln Ala
690                695                700

Leu Glu Thr Val Gln Arg Leu Leu Pro Val Leu Cys Gln Asp His Gly
705                710                715                720

Leu Thr Pro Asp Gln Val Val Ala Ile Ala Ser Asn Gly Gly Lys
                725                730                735

Gln Ala Leu Glu Thr Val Gln Arg Leu Leu Pro Val Leu Cys Gln Asp
        740                745                750

His Gly Leu Thr Pro Asp Gln Val Val Ala Ile Ala Ser Asn Gly Gly
                755                760                765

Gly Lys Gln Ala Leu Glu Thr Val Gln Arg Leu Leu Pro Val Leu Cys
770                775                780

Gln Asp His Gly Leu Thr Pro Asp Gln Val Val Ala Ile Ala Ser His
785                790                795                800

Asp Gly Gly Lys Gln Ala Leu Glu Thr Val Gln Arg Leu Leu Pro Val
        805                810                815

Leu Cys Gln Asp His Gly Leu Thr Pro Asp Gln Val Val Ala Ile Ala
        820                825                830

Ser Asn Ile Gly Gly Lys Gln Ala Leu Glu Thr Val Gln Arg Leu Leu
        835                840                845

Pro Val Leu Cys Gln Asp His Gly Leu Thr Pro Asp Gln Val Val Ala
850                855                860

Ile Ala Ser His Asp Gly Gly Lys Gln Ala Leu Glu Thr Val Gln Arg
865                870                875                880

Leu Leu Pro Val Leu Cys Gln Asp His Gly Leu Thr Pro Asp Gln Val
        885                890                895

Val Ala Ile Ala Ser Asn Gly Gly Gly Lys Gln Ala Leu Glu Ser Ile
        900                905                910

Val Ala Gln Leu Ser Arg Arg Asp Pro Ala Leu Ala Ala Leu Thr Asn
        915                920                925

Asp His Leu Val Ala Leu Ala Cys Leu Gly Gly Arg Pro Ala Leu Asp
930                935                940

Ala Val Lys Lys Gly Leu Pro His Ala Pro Glu Phe Ile Arg Arg Val
945                950                955                960

Asn Arg Arg Ile Ala Glu Arg Thr Ser His Arg Val Ala Asp Tyr Ala
        965                970                975

His Val Val Arg Val Leu Glu Phe Phe Gln Cys His Ser His Pro Ala
        980                985                990

His Ala Phe Asp Glu Ala Met Thr Gln Phe Gly Met Ser Arg His Gly
        995                1000                1005

Leu Val Gln Leu Phe Arg Arg Val Gly Val Thr Glu Phe Glu Ala Arg
        1010                1015                1020

Tyr Gly Thr Leu Pro Pro Ala Ser Gln Arg Trp Asp Arg Ile Leu Gln

```
                    1025                1030                1035                1040
        Ala Ser Gly Met Lys Arg Ala Lys Pro Ser Pro Thr Ser Ala Gln Thr
                            1045                1050                1055

Pro Asp Gln Thr Ser Leu His Ala Phe Ala Asp Ser Leu Glu Arg Asp
                        1060                1065                1070

Leu Asp Ala Pro Ser Pro Met His Glu Gly Asp Gln Thr Arg Ala Ser
                    1075                1080                1085

Ser Arg Lys Arg Ser Arg Ser Asp Arg Ala Val Thr Gly Pro Ser Ala
                1090                1095                1100

Gln Gln Ala Val Glu Val Arg Val Pro Glu Gln Arg Asp Ala Leu His
        1105                1110                1115                1120

Leu Pro Leu Ser Trp Arg Val Lys Arg Pro Arg Thr Arg Ile Trp Gly
                        1125                1130                1135

Gly Leu Pro Asp Pro Ile Ser Arg Ser Gln Leu Val Lys Ser Glu Leu
                    1140                1145                1150

Glu Glu Lys Lys Ser Glu Leu Arg His Lys Leu Lys Tyr Val Pro His
                1155                1160                1165

Glu Tyr Ile Glu Leu Ile Glu Ile Ala Arg Asn Ser Thr Gln Asp Arg
            1170                1175                1180

Ile Leu Glu Met Lys Val Met Glu Phe Phe Met Lys Val Tyr Gly Tyr
        1185                1190                1195                1200

Arg Gly Lys His Leu Gly Gly Ser Arg Lys Pro Asp Gly Ala Ile Tyr
                        1205                1210                1215

Thr Val Gly Ser Pro Ile Asp Tyr Gly Val Ile Val Asp Thr Lys Ala
                    1220                1225                1230

Tyr Ser Gly Gly Tyr Asn Leu Pro Ile Gly Gln Ala Asp Glu Met Gln
                1235                1240                1245

Arg Tyr Val Glu Glu Asn Gln Thr Arg Asn Lys His Ile Asn Pro Asn
            1250                1255                1260

Glu Trp Trp Lys Val Tyr Pro Ser Ser Val Thr Glu Phe Lys Phe Leu
        1265                1270                1275                1280

Phe Val Ser Gly His Phe Lys Gly Asn Tyr Lys Ala Gln Leu Thr Arg
                        1285                1290                1295

Leu Asn His Ile Thr Asn Cys Asn Gly Ala Val Leu Ser Val Glu Glu
                    1300                1305                1310

Leu Leu Ile Gly Gly Glu Met Ile Lys Ala Gly Thr Leu Thr Leu Glu
                1315                1320                1325

Glu Val Arg Arg Lys Phe Asn Asn Gly Glu Ile Asn Phe
            1330                1335                1340

<210> SEQ ID NO 54
<211> LENGTH: 1341
<212> TYPE: PRT
<213> ORGANISM: Artificial Sequence
<220> FEATURE:
<223> OTHER INFORMATION: synthetic peptide

<400> SEQUENCE: 54

Met Ala Ser Ser Pro Lys Lys Lys Arg Lys Val Ser Trp Lys Asp
  1               5                  10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Gln Pro Asp Arg Val
            35                  40                  45

Gln Pro Thr Ala Asp Arg Gly Val Ser Ala Pro Ala Gly Ser Pro Leu
```

-continued

```
               50                  55                  60
Asp Gly Leu Pro Ala Arg Arg Thr Val Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Pro Phe Asp Pro Ser Leu Leu Asp Thr Ser Leu Leu Asp Ser
                100                 105                 110

Met Pro Ala Val Gly Thr Pro His Thr Ala Ala Pro Ala Glu Trp
                115                 120                 125

Asp Glu Ala Gln Ser Ala Leu Arg Ala Ala Asp Asp Pro Pro Thr
130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Glu Lys Ile
                180                 185                 190

Lys Pro Lys Val Arg Ser Thr Val Ala Gln His His Glu Ala Leu Val
                195                 200                 205

Gly His Gly Phe Thr His Ala His Ile Val Ala Leu Ser Gln His Pro
210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
                260                 265                 270

Arg Gly Pro Pro Leu Gln Leu Asp Thr Gly Gln Leu Val Lys Ile Ala
                275                 280                 285

Lys Arg Gly Gly Val Thr Ala Met Glu Ala Val His Ala Ser Arg Asn
                290                 295                 300

Ala Leu Thr Gly Ala Pro Leu Asn Leu Thr Pro Ala Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Asp His Gly Leu Thr Pro Asp Gln Val
                340                 345                 350

Val Ala Ile Ala Ser His Asp Gly Gly Lys Gln Ala Leu Glu Thr Val
                355                 360                 365

Gln Arg Leu Leu Pro Val Leu Cys Gln Asp His Gly Leu Thr Pro Asp
                370                 375                 380

Gln Val Val Ala Ile Ala Ser Asn Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser His Asp Gly Gly Lys Gln Ala
                420                 425                 430

Leu Glu Thr Val Gln Arg Leu Leu Pro Val Leu Cys Gln Asp His Gly
                435                 440                 445

Leu Thr Pro Asp Gln Val Val Ala Ile Ala Ser His Asp Gly Gly Lys
                450                 455                 460

Gln Ala Leu Glu Thr Val Gln Arg Leu Leu Pro Val Leu Cys Gln Asp
465                 470                 475                 480
```

His Gly Leu Thr Pro Asp Gln Val Val Ala Ile Ala Ser Asn Asn Gly
                485                 490                 495

Gly Lys Gln Ala Leu Glu Thr Val Gln Arg Leu Leu Pro Val Leu Cys
                500                 505                 510

Gln Asp His Gly Leu Thr Pro Asp Gln Val Val Ala Ile Ala Ser His
                515                 520                 525

Asp Gly Gly Lys Gln Ala Leu Glu Thr Val Gln Arg Leu Leu Pro Val
        530                 535                 540

Leu Cys Gln Asp His Gly Leu Thr Pro Asp Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
                580                 585                 590

Ile Ala Ser Asn Gly Gly Lys Gln Ala Leu Glu Thr Val Gln Arg
                595                 600                 605

Leu Leu Pro Val Leu Cys Gln Asp His Gly Leu Thr Pro Asp Gln Val
        610                 615                 620

Val Ala Ile Ala Ser Asn Asn Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Ile Gly Gly Lys Gln Ala Leu Glu
                660                 665                 670

Thr Val Gln Arg Leu Leu Pro Val Leu Cys Gln Asp His Gly Leu Thr
                675                 680                 685

Pro Asp Gln Val Val Ala Ile Ala Ser Asn Ile Gly Gly Lys Gln Ala
        690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Asn Gly Gly Lys
                725                 730                 735

Gln Ala Leu Glu Thr Val Gln Arg Leu Leu Pro Val Leu Cys Gln Asp
                740                 745                 750

His Gly Leu Thr Pro Asp Gln Val Val Ala Ile Ala Ser His Asp Gly
                755                 760                 765

Gly Lys Gln Ala Leu Glu Thr Val Gln Arg Leu Leu Pro Val Leu Cys
        770                 775                 780

Gln Asp His Gly Leu Thr Pro Asp Gln Val Val Ala Ile Ala Ser Asn
785                 790                 795                 800

Ile Gly Gly Lys Gln Ala Leu Glu Thr Val Gln Arg Leu Leu Pro Val
                805                 810                 815

Leu Cys Gln Asp His Gly Leu Thr Pro Asp Gln Val Val Ala Ile Ala
                820                 825                 830

Ser His Asp Gly Gly Lys Gln Ala Leu Glu Thr Val Gln Arg Leu Leu
                835                 840                 845

Pro Val Leu Cys Gln Asp His Gly Leu Thr Pro Asp Gln Val Val Ala
        850                 855                 860

Ile Ala Ser Asn Ile Gly Gly Lys Gln Ala Leu Glu Thr Val Gln Arg
865                 870                 875                 880

Leu Leu Pro Val Leu Cys Gln Asp His Gly Leu Thr Pro Asp Gln Val
                885                 890                 895

-continued

Val Ala Ile Ala Ser Asn Gly Gly Lys Gln Ala Leu Glu Ser Ile
            900                 905                 910

Val Ala Gln Leu Ser Arg Pro Asp Pro Ala Leu Ala Ala Leu Thr Asn
        915                 920                 925

Asp His Leu Val Ala Leu Ala Cys Leu Gly Gly Arg Pro Ala Met Asp
    930                 935                 940

Ala Val Lys Lys Gly Leu Pro His Ala Pro Glu Leu Ile Arg Arg Val
945                 950                 955                 960

Asn Arg Arg Ile Gly Glu Arg Thr Ser His Arg Val Ala Asp Tyr Ala
                965                 970                 975

Gln Val Val Arg Val Leu Glu Phe Phe Gln Cys His Ser His Pro Ala
            980                 985                 990

Tyr Ala Phe Asp Glu Ala Met Thr Gln Phe Gly Met Ser Arg Asn Gly
        995                 1000                1005

Leu Val Gln Leu Phe Arg Arg Val Gly Val Thr Glu Leu Glu Ala Arg
    1010                1015                1020

Gly Gly Thr Leu Pro Pro Ala Ser Gln Arg Trp Asp Arg Ile Leu Gln
1025                1030                1035                1040

Ala Ser Gly Met Lys Arg Ala Lys Pro Ser Pro Thr Ser Ala Gln Thr
            1045                1050                1055

Pro Asp Gln Ala Ser Leu His Ala Phe Ala Asp Ser Leu Glu Arg Asp
        1060                1065                1070

Leu Asp Ala Pro Ser Pro Met His Glu Gly Asp Gln Thr Arg Ala Ser
    1075                1080                1085

Ser Arg Lys Arg Ser Arg Ser Asp Arg Ala Val Thr Gly Pro Ser Ala
1090                1095                1100

Gln Gln Ala Val Glu Val Arg Val Pro Glu Gln Arg Asp Ala Leu His
1105                1110                1115                1120

Leu Pro Leu Ser Trp Arg Val Lys Arg Pro Arg Thr Arg Ile Trp Gly
            1125                1130                1135

Gly Leu Pro Asp Pro Ile Ser Arg Ser Gln Leu Val Lys Ser Glu Leu
        1140                1145                1150

Glu Glu Lys Lys Ser Glu Leu Arg His Lys Leu Lys Tyr Val Pro His
    1155                1160                1165

Glu Tyr Ile Glu Leu Ile Glu Ile Ala Arg Asn Ser Thr Gln Asp Arg
    1170                1175                1180

Ile Leu Glu Met Lys Val Met Glu Phe Phe Met Lys Val Tyr Gly Tyr
1185                1190                1195                1200

Arg Gly Lys His Leu Gly Gly Ser Arg Lys Pro Asp Gly Ala Ile Tyr
            1205                1210                1215

Thr Val Gly Ser Pro Ile Asp Tyr Gly Val Ile Val Asp Thr Lys Ala
        1220                1225                1230

Tyr Ser Gly Gly Tyr Asn Leu Pro Ile Gly Gln Ala Asp Glu Met Gln
    1235                1240                1245

Arg Tyr Val Glu Glu Asn Gln Thr Arg Asn Lys His Ile Asn Pro Asn
    1250                1255                1260

Glu Trp Trp Lys Val Tyr Pro Ser Ser Val Thr Glu Phe Lys Phe Leu
1265                1270                1275                1280

Phe Val Ser Gly His Phe Lys Gly Asn Tyr Lys Ala Gln Leu Thr Arg
            1285                1290                1295

Leu Asn His Ile Thr Asn Cys Asn Gly Ala Val Leu Ser Val Glu Glu
        1300                1305                1310

Leu Leu Ile Gly Gly Glu Met Ile Lys Ala Gly Thr Leu Thr Leu Glu 1315                1320                1325

Glu Val Arg Arg Lys Phe Asn Asn Gly Glu Ile Asn Phe
            1330                1335                1340

<210> SEQ ID NO 55
<211> LENGTH: 1341
<212> TYPE: PRT
<213> ORGANISM: Artificial Sequence
<220> FEATURE:
<223> OTHER INFORMATION: synthetic peptide

<400> SEQUENCE: 55

Met Ala Ser Ser Pro Lys Lys Arg Lys Val Ser Trp Lys Asp
 1               5                   10                  15

Ala Ser Gly Trp Ser Arg Met His Ala Asp Pro Ile Arg Pro Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
 50                  55                  60

Asp Gly Leu Pro Ala Arg Arg Thr Val Ser Arg Thr Arg Leu Pro Ser
 65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
                100                 105                 110

Met Pro Ala Val Gly Thr Pro His Thr Ala Ala Pro Ala Glu Trp
                115                 120                 125

Asp Glu Ala Gln Ser Ala Leu Arg Ala Ala Asp Asp Pro Pro Pro Thr
            130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
                180                 185                 190

Lys Pro Lys Val Arg Ser Thr Val Ala Gln His His Glu Ala Leu Val
                195                 200                 205

Gly His Gly Phe Thr His Ala His Ile Val Ala Leu Ser Gln His Pro
            210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
                260                 265                 270

Arg Gly Pro Pro Leu Gln Leu Asp Thr Gly Gln Leu Val Lys Ile Ala
            275                 280                 285

Lys Arg Gly Gly Val Thr Ala Met Glu Ala Val His Ala Ser Arg Asn
                290                 295                 300

Ala Leu Thr Gly Ala Pro Leu Asn Leu Thr Pro Ala Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Asp His Gly Leu Thr Pro Asp Gln Val

```
                340             345             350
Val Ala Ile Ala Ser Asn Asn Gly Gly Lys Gln Ala Leu Glu Thr Val
            355                 360                 365
Gln Arg Leu Leu Pro Val Leu Cys Gln Asp His Gly Leu Thr Pro Asp
        370                 375                 380
Gln Val Val Ala Ile Ala Ser His Asp Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser Asn Gly Gly Gly Lys Gln Ala
            420                 425                 430
Leu Glu Thr Val Gln Arg Leu Leu Pro Val Leu Cys Gln Asp His Gly
        435                 440                 445
Leu Thr Pro Asp Gln Val Val Ala Ile Ala Ser His Asp Gly Gly Lys
    450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser Asn Ile Gly
                485                 490                 495
Gly Lys Gln Ala Leu Glu Thr Val Gln Arg Leu Leu Pro Val Leu Cys
            500                 505                 510
Gln Asp His Gly Leu Thr Pro Asp Gln Val Val Ala Ile Ala Ser His
        515                 520                 525
Asp Gly Gly Lys Gln Ala Leu Glu Thr Val Gln Arg Leu Leu Pro Val
    530                 535                 540
Leu Cys Gln Asp His Gly Leu Thr Pro Asp Gln Val Val Ala Ile Ala
545                 550                 555                 560
Ser His Asp Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
            580                 585                 590
Ile Ala Ser Asn Gly Gly Gly Lys Gln Ala Leu Glu Thr Val Gln Arg
        595                 600                 605
Leu Leu Pro Val Leu Cys Gln Asp His Gly Leu Thr Pro Asp Gln Val
    610                 615                 620
Val Ala Ile Ala Ser Asn Ile Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Ser His Asp Gly Gly Lys Gln Ala Leu Glu
            660                 665                 670
Thr Val Gln Arg Leu Leu Pro Val Leu Cys Gln Asp His Gly Leu Thr
        675                 680                 685
Pro Asp Gln Val Val Ala Ile Ala Ser Asn Ile Gly Gly Lys Gln Ala
    690                 695                 700
Leu Glu Thr Val Gln Arg Leu Leu Pro Val Leu Cys Gln Asp His Gly
705                 710                 715                 720
Leu Thr Pro Asp Gln Val Val Ala Ile Ala Ser Asn Ile Gly Gly Lys
                725                 730                 735
Gln Ala Leu Glu Thr Val Gln Arg Leu Leu Pro Val Leu Cys Gln Asp
            740                 745                 750
His Gly Leu Thr Pro Asp Gln Val Val Ala Ile Ala Ser His Asp Gly
        755                 760                 765
```

```
Gly Lys Gln Ala Leu Glu Thr Val Gln Arg Leu Leu Pro Val Leu Cys
    770                 775                 780

Gln Asp His Gly Leu Thr Pro Asp Gln Val Val Ala Ile Ala Ser Asn
785                 790                 795                 800

Asn Gly Gly Lys Gln Ala Leu Glu Thr Val Gln Arg Leu Leu Pro Val
                805                 810                 815

Leu Cys Gln Asp His Gly Leu Thr Pro Asp Gln Val Val Ala Ile Ala
            820                 825                 830

Ser Asn Ile Gly Gly Lys Gln Ala Leu Glu Thr Val Gln Arg Leu Leu
        835                 840                 845

Pro Val Leu Cys Gln Asp His Gly Leu Thr Pro Asp Gln Val Val Ala
    850                 855                 860

Ile Ala Ser His Asp Gly Gly Lys Gln Ala Leu Glu Thr Val Gln Arg
865                 870                 875                 880

Leu Leu Pro Val Leu Cys Gln Asp His Gly Leu Thr Pro Asp Gln Val
                885                 890                 895

Val Ala Ile Ala Ser Asn Ile Gly Gly Lys Gln Ala Leu Glu Ser Ile
            900                 905                 910

Val Ala Gln Leu Ser Arg Pro Asp Pro Ala Leu Ala Ala Leu Thr Asn
        915                 920                 925

Asp His Leu Val Ala Leu Ala Cys Leu Gly Gly Arg Pro Ala Met Asp
    930                 935                 940

Ala Val Lys Lys Gly Leu Pro His Ala Pro Glu Leu Ile Arg Arg Val
945                 950                 955                 960

Asn Arg Arg Ile Gly Glu Arg Thr Ser His Arg Val Ala Asp Tyr Ala
                965                 970                 975

Gln Val Val Arg Val Leu Glu Phe Phe Gln Cys His Ser His Pro Ala
            980                 985                 990

Tyr Ala Phe Asp Glu Ala Met Thr Gln Phe Gly Met Ser Arg Asn Gly
        995                 1000                1005

Leu Val Gln Leu Phe Arg Arg Val Gly Val Thr Glu Leu Glu Ala Arg
    1010                1015                1020

Gly Gly Thr Leu Pro Pro Ala Ser Gln Arg Trp Asp Arg Ile Leu Gln
1025                1030                1035                1040

Ala Ser Gly Met Lys Arg Ala Lys Pro Ser Pro Thr Ser Ala Gln Thr
                1045                1050                1055

Pro Asp Gln Ala Ser Leu His Ala Phe Ala Asp Ser Leu Glu Arg Asp
            1060                1065                1070

Leu Asp Ala Pro Ser Pro Met His Glu Gly Asp Gln Thr Arg Ala Ser
        1075                1080                1085

Ser Arg Lys Arg Ser Arg Ser Asp Arg Ala Val Thr Gly Pro Ser Ala
    1090                1095                1100

Gln Gln Ala Val Glu Val Arg Val Pro Glu Gln Arg Asp Ala Leu His
1105                1110                1115                1120

Leu Pro Leu Ser Trp Arg Val Lys Arg Pro Arg Thr Arg Ile Trp Gly
                1125                1130                1135

Gly Leu Pro Asp Pro Ile Ser Arg Ser Gln Leu Val Lys Ser Glu Leu
            1140                1145                1150

Glu Glu Lys Lys Ser Glu Leu Arg His Lys Leu Lys Tyr Val Pro His
        1155                1160                1165

Glu Tyr Ile Glu Leu Ile Glu Ile Ala Arg Asn Ser Thr Gln Asp Arg
    1170                1175                1180
```

```
Ile Leu Glu Met Lys Val Met Glu Phe Phe Met Lys Val Tyr Gly Tyr
1185                1190                1195                1200

Arg Gly Lys His Leu Gly Gly Ser Arg Lys Pro Asp Gly Ala Ile Tyr
            1205                1210                1215

Thr Val Gly Ser Pro Ile Asp Tyr Gly Val Ile Val Asp Thr Lys Ala
        1220                1225                1230

Tyr Ser Gly Gly Tyr Asn Leu Pro Ile Gly Gln Ala Asp Glu Met Gln
    1235                1240                1245

Arg Tyr Val Glu Glu Asn Gln Thr Arg Asn Lys His Ile Asn Pro Asn
1250                1255                1260

Glu Trp Trp Lys Val Tyr Pro Ser Ser Val Thr Glu Phe Lys Phe Leu
1265                1270                1275                1280

Phe Val Ser Gly His Phe Lys Gly Asn Tyr Lys Ala Gln Leu Thr Arg
            1285                1290                1295

Leu Asn His Ile Thr Asn Cys Asn Gly Ala Val Leu Ser Val Glu Glu
        1300                1305                1310

Leu Leu Ile Gly Gly Glu Met Ile Lys Ala Gly Thr Leu Thr Leu Glu
    1315                1320                1325

Glu Val Arg Arg Lys Phe Asn Asn Gly Glu Ile Asn Phe
1330                1335                1340

<210> SEQ ID NO 56
<211> LENGTH: 51
<212> TYPE: DNA
<213> ORGANISM: Arabidopsis sp.

<400> SEQUENCE: 56
tatcaagatt ctcttcactt ctctctgtca caccgatgtt tacttctggg a          51

<210> SEQ ID NO 57
<211> LENGTH: 50
<212> TYPE: DNA
<213> ORGANISM: Arabidopsis sp.

<400> SEQUENCE: 57
tccggatgct cctcttgaca aggtctgtat tgtcagttgt ggtttgtcta            50

<210> SEQ ID NO 58
<211> LENGTH: 48
<212> TYPE: DNA
<213> ORGANISM: Arabidopsis sp.

<400> SEQUENCE: 58
ccggatgctc ctcttgacaa ggtctgtatt gtcagttgtg gtttgtct              48

<210> SEQ ID NO 59
<211> LENGTH: 40
<212> TYPE: DNA
<213> ORGANISM: Artificial Sequence
<220> FEATURE:
<223> OTHER INFORMATION: modified Arabidopsis

<400> SEQUENCE: 59
ccggatgctc ctcttgacaa ttgtcagttg tggtttgtct                       40

<210> SEQ ID NO 60
<211> LENGTH: 43
<212> TYPE: DNA
<213> ORGANISM: Artificial Sequence
<220> FEATURE:
<223> OTHER INFORMATION: modified Arabidopsis
```

-continued

<210> SEQ ID NO 61
<211> LENGTH: 33
<212> TYPE: DNA
<213> ORGANISM: Artificial Sequence
<220> FEATURE:
<223> OTHER INFORMATION: modified Arabidopsis

<400> SEQUENCE: 61
ccggatgctc ctcttgacaa ttgtggtttg tct                      33

<210> SEQ ID NO 62
<211> LENGTH: 43
<212> TYPE: DNA
<213> ORGANISM: Artificial Sequence
<220> FEATURE:
<223> OTHER INFORMATION: modified Arabidopsis

<400> SEQUENCE: 62
ccggatgctc ctcttgacaa ggattgtcag ttgtggtttg tct           43

<210> SEQ ID NO 63
<211> LENGTH: 41
<212> TYPE: DNA
<213> ORGANISM: Artificial Sequence
<220> FEATURE:
<223> OTHER INFORMATION: modified Arabidopsis

<400> SEQUENCE: 63
ccggatgctc ctcttgacaa attgtcagtt gtggtttgtc t             41

<210> SEQ ID NO 64
<211> LENGTH: 44
<212> TYPE: DNA
<213> ORGANISM: Artificial Sequence
<220> FEATURE:
<223> OTHER INFORMATION: modified Arabidopsis

<400> SEQUENCE: 64
ccggatgctc ctcttgacaa ggtattgtca gttgtggttt gtct          44

<210> SEQ ID NO 65
<211> LENGTH: 34
<212> TYPE: PRT
<213> ORGANISM: Xanthomonas gardneri

<400> SEQUENCE: 65

Leu Asp Thr Gly Gln Leu Phe Lys Ile Ala Lys Arg Gly Gly Val Thr
1               5                   10                  15

Ala Val Glu Ala Val His Ala Trp Arg Asn Ala Leu Thr Gly Ala Pro
            20                  25                  30

Leu Asn

<210> SEQ ID NO 66
<211> LENGTH: 34
<212> TYPE: PRT
<213> ORGANISM: Xanthomonas campestris

<400> SEQUENCE: 66

Leu Asp Thr Gly Gln Leu Leu Lys Ile Ala Lys Arg Gly Gly Val Thr
1               5                   10                  15

```
Ala Val Glu Ala Val His Ala Trp Arg Asn Ala Leu Thr Gly Ala Pro
            20                  25                  30

Leu Asn

<210> SEQ ID NO 67
<211> LENGTH: 34
<212> TYPE: PRT
<213> ORGANISM: Xanthomonas oryzae

<400> SEQUENCE: 67

Leu Asp Thr Gly Gln Leu Val Lys Ile Ala Lys Arg Gly Gly Val Thr
  1               5                  10                  15

Ala Val Glu Ala Val His Ala Ser Arg Asn Ala Leu Thr Gly Ala Pro
            20                  25                  30

Leu Asn

<210> SEQ

```
                1               5              10              15
Gln Ala Leu Glu Thr Val Gln Arg Leu Leu Pro Val Leu Cys Gln Ala
               20                      25                  30
His Gly

<210> SEQ ID NO 72
<211> LENGTH: 1307
<212> TYPE: PRT
<213> ORGANISM: Artificial Sequence
<220> FEATURE:
<223> OTHER INFORMATION: synthetic peptide

<400> SEQUENCE: 72

Met Ala Ser Ser Pro Lys Lys Arg Lys Val Ser Trp Lys Asp
 1               5                  10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Ala Gln Ser Ala Leu Arg Ala Ala Asp Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
    290                 295                 300

Ala Leu Thr Gly Ala Pro Leu Asn Leu Thr Pro Ala Gln Val Val Ala
305                 310                 315                 320

Ile Ala Ser Asn Asn Gly Gly Lys Gln Ala Leu Glu Thr Val Gln Arg
                325                 330                 335
```

```
Leu Leu Pro Val Leu Cys Gln Asp His Gly Leu Thr Pro Asp Gln Val
            340                 345                 350

Val Ala Ile Ala Ser His Asp Gly Gly Lys Gln Ala Leu Glu Thr Val
            355                 360                 365

Gln Arg Leu Leu Pro Val Leu Cys Gln Asp His Gly Leu Thr Pro Asp
            370                 375                 380

Gln Val Ala Ile Ala Ser Asn Ile Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Gly Gly Lys Gln Ala
            420                 425                 430

Leu Glu Thr Val Gln Arg Leu Leu Pro Val Leu Cys Gln Asp His Gly
            435                 440                 445

Leu Thr Pro Asp Gln Val Val Ala Ile Ala Ser Asn Ile Gly Gly Lys
            450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser His
            515                 520                 525

Asp Gly Gly Lys Gln Ala Leu Glu Thr Val Gln Arg Leu Leu Pro Val
            530                 535                 540

Leu Cys Gln Asp His Gly Leu Thr Pro Asp Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser Asn Ile Gly Gly Lys Gln Ala Leu Glu Thr Val Gln Arg
            595                 600                 605

Leu Leu Pro Val Leu Cys Gln Asp His Gly Leu Thr Pro Asp Gln Val
            610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Gly Gly Gly Lys Gln Ala Leu Glu
            660                 665                 670

Thr Val Gln Arg Leu Leu Pro Val Leu Cys Gln Asp His Gly Leu Thr
            675                 680                 685

Pro Asp Gln Val Val Ala Ile Ala Ser His Asp Gly Gly Lys Gln Ala
            690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Ile Gly Gly Lys
                725                 730                 735

Gln Ala Leu Glu Thr Val Gln Arg Leu Leu Pro Val Leu Cys Gln Asp
            740                 745                 750
```

```
His Gly Leu Thr Pro Asp Gln Val Ala Ile Ala Ser Asn Gly Gly
            755                 760                 765

Gly Lys Gln Ala Leu Glu Thr Val Gln Arg Leu Leu Pro Val Cys
    770                 775                 780

Gln Asp His Gly Leu Thr Pro Asp Gln Val Val Ala Ile Ala Ser Asn
785                 790                 795                 800

Gly Gly Gly Lys Gln Ala Leu Glu Thr Val Gln Arg Leu Leu Pro Val
                805                 810                 815

Leu Cys Gln Asp His Gly Leu Thr Pro Asp Gln Val Val Ala Ile Ala
                820                 825                 830

Ser Asn Ile Gly Gly Lys Gln Ala Leu Glu Thr Val Gln Arg Leu Leu
            835                 840                 845

Pro Val Leu Cys Gln Asp His Gly Leu Thr Pro Asp Gln Val Val Ala
            850                 855                 860

Ile Ala Ser Asn Gly Gly Gly Lys Gln Ala Leu Glu Ser Ile Val Ala
865                 870                 875                 880

Gln Leu Ser Arg Pro Asp Pro Ala Leu Ala Ala Leu Thr Asn Asp His
                885                 890                 895

Leu Val Ala Leu Ala Cys Leu Gly Gly Arg Pro Ala Met Asp Ala Val
                900                 905                 910

Lys Lys Gly Leu Pro His Ala Pro Glu Leu Ile Arg Arg Val Asn Arg
    915                 920                 925

Arg Ile Gly Glu Arg Thr Ser His Arg Val Ala Asp Tyr Ala Gln Val
    930                 935                 940

Val Arg Val Leu Glu Phe Phe Gln Cys His Ser His Pro Ala Tyr Ala
945                 950                 955                 960

Phe Asp Glu Ala Met Thr Gln Phe Gly Met Ser Arg Asn Gly Leu Val
                965                 970                 975

Gln Leu Phe Arg Arg Val Gly Val Thr Glu Leu Glu Ala Arg Gly Gly
                980                 985                 990

Thr Leu Pro Pro Ala Ser Gln Arg Trp Asp Arg Ile Leu Gln Ala Ser
            995                 1000                1005

Gly Met Lys Arg Ala Lys Pro Ser Pro Thr Ser Ala Gln Thr Pro Asp
    1010                1015                1020

Gln Ala Ser Leu His Ala Phe Ala Asp Ser Leu Glu Arg Asp Leu Asp
1025                1030                1035                1040

Ala Pro Ser Pro Met His Glu Gly Asp Gln Thr Arg Ala Ser Ser Arg
                1045                1050                1055

Lys Arg Ser Arg Ser Asp Arg Ala Val Thr Gly Pro Ser Ala Gln Gln
                1060                1065                1070

Ala Val Glu Val Arg Val Pro Glu Gln Arg Asp Ala Leu His Leu Pro
    1075                1080                1085

Leu Ser Trp Arg Val Lys Arg Pro Arg Thr Arg Ile Trp Gly Gly Leu
    1090                1095                1100

Pro Asp Pro Ile Ser Arg Ser Gln Leu Val Lys Ser Glu Leu Glu Glu
1105                1110                1115                1120

Lys Lys Ser Glu Leu Arg His Lys Leu Lys Tyr Val Pro His Glu Tyr
                1125                1130                1135

Ile Glu Leu Ile Glu Ile Ala Arg Asn Ser Thr Gln Asp Arg Ile Leu
                1140                1145                1150

Glu Met Lys Val Met Glu Phe Phe Met Lys Val Tyr Gly Tyr Arg Gly
                1155                1160                1165

Lys His Leu Gly Gly Ser Arg Lys Pro Asp Gly Ala Ile Tyr Thr Val
```

```
                 1170                1175                1180
Gly Ser Pro Ile Asp Tyr Gly Val Ile Val Asp Thr Lys Ala Tyr Ser
1185                1190                1195                1200

Gly Gly Tyr Asn Leu Pro Ile Gly Gln Ala Asp Glu Met Gln Arg Tyr
                 1205                1210                1215

Val Glu Glu Asn Gln Thr Arg Asn Lys His Ile Asn Pro Asn Glu Trp
                 1220                1225                1230

Trp Lys Val Tyr Pro Ser Ser Val Thr Glu Phe Lys Phe Leu Phe Val
                 1235                1240                1245

Ser Gly His Phe Lys Gly Asn Tyr Lys Ala Gln Leu Thr Arg Leu Asn
                 1250                1255                1260

His Ile Thr Asn Cys Asn Gly Ala Val Leu Ser Val Glu Glu Leu Leu
1265                1270                1275                1280

Ile Gly Gly Glu Met Ile Lys Ala Gly Thr Leu Thr Leu Glu Glu Val
                 1285                1290                1295

Arg Arg Lys Phe Asn Asn Gly Glu Ile Asn Phe
                 1300                1305

<210> SEQ ID NO 73
<211> LENGTH: 1409
<212> TYPE: PRT
<213> ORGANISM: Artificial Sequence
<220> FEATURE:
<223> OTHER INFORMATION: synthetic peptide

<400> SEQUENCE: 73

Met Ala Ser Ser Pro Lys Lys Arg Lys Val Ser Trp Lys Asp
 1               5                  10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
                35                  40                  45

Gln Pro Thr Ala Asp Arg Gly Val Ser Ala Pro Ala Gly Ser Pro Leu
        50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
                100                 105                 110

Met Pro Ala Val Gly Thr Pro His Thr Ala Ala Ala Pro Ala Glu Trp
                115                 120                 125

Asp Glu Ala Gln Ser Ala Leu Arg Ala Ala Asp Asp Pro Pro Pro Thr
        130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
                180                 185                 190

Lys Pro Lys Val Arg Ser Thr Val Ala Gln His His Glu Ala Leu Val
                195                 200                 205

Gly His Gly Phe Thr His Ala His Ile Val Ala Leu Ser Gln His Pro
        210                 215                 220

Ala Ala Leu Gly Thr Val Ala Val Thr Tyr Gln His Ile Ile Thr Ala
```

```
            225                 230                 235                 240
Leu Pro Glu Ala Thr His Glu Asp Ile Val Gly Val Gly Lys Gln Trp
                245                 250                 255
Ser Gly Ala Arg Ala Leu Glu Ala Leu Leu Thr Asp Ala Gly Glu Leu
                260                 265                 270
Arg Gly Pro Pro Leu Gln Leu Asp Thr Gly Gln Leu Val Lys Ile Ala
                275                 280                 285
Lys Arg Gly Gly Val Thr Ala Met Glu Ala Val His Ala Ser Arg Asn
            290                 295                 300
Ala Leu Thr Gly Ala Pro Leu Asn Leu Thr Pro Ala Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Asp His Gly Leu Thr Pro Asp Gln Val
                340                 345                 350
Val Ala Ile Ala Ser His Asp Gly Gly Lys Gln Ala Leu Glu Thr Val
                355                 360                 365
Gln Arg Leu Leu Pro Val Leu Cys Gln Asp His Gly Leu Thr Pro Asp
            370                 375                 380
Gln Val Val Ala Ile Ala Ser Asn Ile Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser Asn Gly Gly Lys Gln Ala
                420                 425                 430
Leu Glu Thr Val Gln Arg Leu Leu Pro Val Leu Cys Gln Asp His Gly
            435                 440                 445
Leu Thr Pro Asp Gln Val Val Ala Ile Ala Ser Asn Asn Gly Gly Lys
            450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser Asn Ile Gly
                485                 490                 495
Gly Lys Gln Ala Leu Glu Thr Val Gln Arg Leu Leu Pro Val Leu Cys
                500                 505                 510
Gln Asp His Gly Leu Thr Pro Asp Gln Val Val Ala Ile Ala Ser Asn
            515                 520                 525
Asn Gly Gly Lys Gln Ala Leu Glu Thr Val Gln Arg Leu Leu Pro Val
            530                 535                 540
Leu Cys Gln Asp His Gly Leu Thr Pro Asp Gln Val Val Ala Ile Ala
545                 550                 555                 560
Ser Asn Asn Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
                580                 585                 590
Ile Ala Ser Asn Ile Gly Gly Lys Gln Ala Leu Glu Thr Val Gln Arg
                595                 600                 605
Leu Leu Pro Val Leu Cys Gln Asp His Gly Leu Thr Pro Asp Gln Val
            610                 615                 620
Val Ala Ile Ala Ser Asn Ile Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
```

-continued

```
Gln Val Val Ala Ile Ala Ser Asn Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Ser Asn Ile Gly Gly Lys Gln Ala
690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Ile Gly Gly Lys
            725                 730                 735

Gln Ala Leu Glu Thr Val Gln Arg Leu Leu Pro Val Leu Cys Gln Asp
        740                 745                 750

His Gly Leu Thr Pro Asp Gln Val Val Ala Ile Ala Ser Asn Ile Gly
    755                 760                 765

Gly Lys Gln Ala Leu Glu Thr Val Gln Arg Leu Leu Pro Val Leu Cys
770                 775                 780

Gln Asp His Gly Leu Thr Pro Asp Gln Val Val Ala Ile Ala Ser His
785                 790                 795                 800

Asp Gly Gly Lys Gln Ala Leu Glu Thr Val Gln Arg Leu Leu Pro Val
            805                 810                 815

Leu Cys Gln Asp His Gly Leu Thr Pro Asp Gln Val Val Ala Ile Ala
        820                 825                 830

Ser Asn Ile Gly Gly Lys Gln Ala Leu Glu Thr Val Gln Arg Leu Leu
    835                 840                 845

Pro Val Leu Cys Gln Asp His Gly Leu Thr Pro Asp Gln Val Val Ala
850                 855                 860

Ile Ala Ser His Asp Gly Gly Lys Gln Ala Leu Glu Thr Val Gln Arg
865                 870                 875                 880

Leu Leu Pro Val Leu Cys Gln Asp His Gly Leu Thr Pro Asp Gln Val
            885                 890                 895

Val Ala Ile Ala Ser His Asp Gly Gly Lys Gln Ala Leu Glu Thr Val
        900                 905                 910

Gln Arg Leu Leu Pro Val Leu Cys Gln Asp His Gly Leu Thr Pro Asp
    915                 920                 925

Gln Val Val Ala Ile Ala Ser His Asp Gly Gly Lys Gln Ala Leu Glu
930                 935                 940

Thr Val Gln Arg Leu Leu Pro Val Leu Cys Gln Asp His Gly Leu Thr
945                 950                 955                 960

Pro Asp Gln Val Val Ala Ile Ala Ser Asn Gly Gly Lys Gln Ala
            965                 970                 975

Leu Glu Ser Ile Val Ala Gln Leu Ser Arg Pro Asp Pro Ala Leu Ala
        980                 985                 990

Ala Leu Thr Asn Asp His Leu Val Ala Leu Ala Cys Leu Gly Gly Arg
    995                 1000                1005

Pro Ala Met Asp Ala Val Lys Lys Gly Leu Pro His Ala Pro Glu Leu
1010                1015                1020

Ile Arg Arg Val Asn Arg Arg Ile Gly Glu Arg Thr Ser His Arg Val
1025                1030                1035                1040

Ala Asp Tyr Ala Gln Val Val Arg Val Leu Glu Phe Phe Gln Cys His
            1045                1050                1055

Ser His Pro Ala Tyr Ala Phe Asp Glu Ala Met Thr Gln Phe Gly Met
        1060                1065                1070
```

```
Ser Arg Asn Gly Leu Val Gln Leu Phe Arg Arg Val Gly Val Thr Glu
        1075                1080                1085

Leu Glu Ala Arg Gly Gly Thr Leu Pro Pro Ala Ser Gln Arg Trp Asp
        1090                1095                1100

Arg Ile Leu Gln Ala Ser Gly Met Lys Arg Ala Lys Pro Ser Pro Thr
1105                1110                1115                1120

Ser Ala Gln Thr Pro Asp Gln Ala Ser Leu His Ala Phe Ala Asp Ser
            1125                1130                1135

Leu Glu Arg Asp Leu Asp Ala Pro Ser Pro Met His Glu Gly Asp Gln
        1140                1145                1150

Thr Arg Ala Ser Ser Arg Lys Arg Ser Arg Ser Asp Arg Ala Val Thr
        1155                1160                1165

Gly Pro Ser Ala Gln Gln Ala Val Glu Val Arg Val Pro Glu Gln Arg
        1170                1175                1180

Asp Ala Leu His Leu Pro Leu Ser Trp Arg Val Lys Arg Pro Arg Thr
1185                1190                1195                1200

Arg Ile Trp Gly Gly Leu Pro Asp Pro Ile Ser Arg Ser Gln Leu Val
            1205                1210                1215

Lys Ser Glu Leu Glu Glu Lys Lys Ser Glu Leu Arg His Lys Leu Lys
        1220                1225                1230

Tyr Val Pro His Glu Tyr Ile Glu Leu Ile Glu Ile Ala Arg Asn Ser
        1235                1240                1245

Thr Gln Asp Arg Ile Leu Glu Met Lys Val Met Glu Phe Phe Met Lys
        1250                1255                1260

Val Tyr Gly Tyr Arg Gly Lys His Leu Gly Gly Ser Arg Lys Pro Asp
1265                1270                1275                1280

Gly Ala Ile Tyr Thr Val Gly Ser Pro Ile Asp Tyr Gly Val Ile Val
            1285                1290                1295

Asp Thr Lys Ala Tyr Ser Gly Gly Tyr Asn Leu Pro Ile Gly Gln Ala
            1300                1305                1310

Asp Glu Met Gln Arg Tyr Val Glu Glu Asn Gln Thr Arg Asn Lys His
            1315                1320                1325

Ile Asn Pro Asn Glu Trp Trp Lys Val Tyr Pro Ser Ser Val Thr Glu
        1330                1335                1340

Phe Lys Phe Leu Phe Val Ser Gly His Phe Lys Gly Asn Tyr Lys Ala
1345                1350                1355                1360

Gln Leu Thr Arg Leu Asn His Ile Thr Asn Cys Asn Gly Ala Val Leu
            1365                1370                1375

Ser Val Glu Glu Leu Leu Ile Gly Gly Glu Met Ile Lys Ala Gly Thr
        1380                1385                1390

Leu Thr Leu Glu Glu Val Arg Arg Lys Phe Asn Asn Gly Glu Ile Asn
        1395                1400                1405

Phe

<210> SEQ ID NO 74
<211> LENGTH: 8
<212> TYPE: PRT
<213> ORGANISM: Artificial Sequence
<220> FEATURE:
<223> OTHER INFORMATION: synthetic peptide

<400> SEQUENCE: 74

Lys Ile Ala Lys Arg Gly Gly Val
1               5
```

```
<210> SEQ ID NO 75
<211> LENGTH: 8
<212> TYPE: PRT
<213> ORGANISM: Artificial Sequence
<220> FEATURE:
<223> OTHER INFORMATION: synthetic peptide

<400> SEQUENCE: 75

Lys Ile Ala Asn Gly Gly Gly Val
 1               5

<210> SEQ ID NO 76
<211> LENGTH: 8
<212> TYPE: PRT
<213> ORGANISM: Artificial Sequence
<220> FEATURE:
<223> OTHER INFORMATION: synthetic peptide

<400> SEQUENCE: 76

Lys Ile Ala Asn Ile Gly Gly Val
 1               5

<210> SEQ ID NO 77
<211> LENGTH: 8
<212> TYPE: PRT
<213> ORGANISM: Artificial Sequence
<220> FEATURE:
<223> OTHER INFORMATION: synthetic peptide

<400> SEQUENCE: 77

Lys Ile Ala His Asp Gly Gly Val
 1               5

<210> SEQ ID NO 78
<211> LENGTH: 8
<212> TYPE: PRT
<213> ORGANISM: Artificial Sequence
<220> FEATURE:
<223> OTHER INFORMATION: synthetic peptide

<400> SEQUENCE: 78

Lys Ile Ala Asn Asn Gly Gly Val
 1               5

<210> SEQ ID NO 79
<211> LENGTH: 8
<212> TYPE: PRT
<213> ORGANISM: Artificial Sequence
<220> FEATURE:
<223> OTHER INFORMATION: synthetic peptide

<400> SEQUENCE: 79

Lys Ile Ala Lys Arg Gly Gly Val
 1               5

<210> SEQ ID NO 80
<211> LENGTH: 9
<212> TYPE: PRT
<213> ORGANISM: Artificial Sequence
<220> FEATURE:
<223> OTHER INFORMATION: synthetic peptide

<400> SEQUENCE: 80

Lys Ile Ala Ser Asn Gly Gly Gly Val
 1               5

<210> SEQ ID NO 81
```

```
<211> LENGTH: 9
<212> TYPE: PRT
<213> ORGANISM: Artificial Sequence
<220> FEATURE:
<223> OTHER INFORMATION: synthetic peptide

<400> SEQUENCE: 81

Lys Ile Ala Ser Asn Ile Gly Gly Val
1               5

<210> SEQ ID NO 82
<211> LENGTH: 9
<212> TYPE: PRT
<213> ORGANISM: Artificial Sequence
<220> FEATURE:
<223> OTHER INFORMATION: synthetic peptide

<400> SEQUENCE: 82

Lys Ile Ala Ser His Asp Gly Gly Val
1               5

<210> SEQ ID NO 83
<211> LENGTH: 9
<212> TYPE: PRT
<213> ORGANISM: Artificial Sequence
<220> FEATURE:
<223> OTHER INFORMATION: synthetic peptide

<400> SEQUENCE: 83

Lys Ile Ala Ser Asn Asn Gly Gly Val
1               5

<210> SEQ ID NO 84
<211> LENGTH: 8
<212> TYPE: PRT
<213> ORGANISM: Artificial Sequence
<220> FEATURE:
<223> OTHER INFORMATION: synthetic peptide

<400> SEQUENCE: 84

Lys Ile Ala Lys Arg Gly Gly Val
1               5

<210> SEQ ID NO 85
<211> LENGTH: 9
<212> TYPE: PRT
<213> ORGANISM: Artificial Sequence
<220> FEATURE:
<223> OTHER INFORMATION: synthetic peptide

<400> SEQUENCE: 85

Lys Ile Ala Lys Asn Gly Gly Gly Val
1               5

<210> SEQ ID NO 86
<211> LENGTH: 9
<212> TYPE: PRT
<213> ORGANISM: Artificial Sequence
<220> FEATURE:
<223> OTHER INFORMATION: synthetic peptide

<400> SEQUENCE: 86

Lys Ile Ala Lys Asn Ile Gly Gly Val
1               5

<210> SEQ ID NO 87
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 87

Lys Ile Ala Lys His Asp Gly Gly Val
1               5

<210> SEQ ID NO 88
<211> LENGTH: 9
<212> TYPE: PRT
<213> ORGANISM: Artificial Sequence
<220> FEATURE:
<223> OTHER INFORMATION: synthetic peptide

<400> SEQUENCE: 88

Lys Ile Ala Lys Asn Asn Gly Gly Val
1               5

<210> SEQ ID NO 89
<211> LENGTH: 8
<212> TYPE: PRT
<213> ORGANISM: Artificial Sequence
<220> FEATURE:
<223> OTHER INFORMATION: synthetic peptide

<400> SEQUENCE: 89

Lys Ile Ala Lys Arg Gly Gly Val
1               5

<210> SEQ ID NO 90
<211> LENGTH: 9
<212> TYPE: PRT
<213> ORGANISM: Artificial Sequence
<220> FEATURE:
<223> OTHER INFORMATION: synthetic peptide

<400> SEQUENCE: 90

Lys Ile Ala Ser Asn Gly Gly Gly Lys
1               5

<210> SEQ ID NO 91
<211> LENGTH: 9
<212> TYPE: PRT
<213> ORGANISM: Artificial Sequence
<220> FEATURE:
<223> OTHER INFORMATION: synthetic peptide

<400> SEQUENCE: 91

Lys Ile Ala Ser Asn Ile Gly Gly Lys
1               5

<210> SEQ ID NO 92
<211> LENGTH: 9
<212> TYPE: PRT
<213> ORGANISM: Artificial Sequence
<220> FEATURE:
<223> OTHER INFORMATION: synthetic peptide

<400> SEQUENCE: 92

Lys Ile Ala Ser His Asp Gly Gly Lys
1               5

<210> SEQ ID NO 93
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 93

Lys Ile Ala Ser Asn Asn Gly Gly Lys
 1               5

<210> SEQ ID NO 94
<211> LENGTH: 102
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 39
<223> OTHER INFORMATION: n = A, T, C, or G

<400> SEQUENCE: 94
ctgaccccgg cacaggtggt ggccatcgcc agcmayggng gcggcaagca ggcgctggag      60
acggtgcagc ggctgttgcc ggtgctgtgc caggaccatg gc                        102

<210> SEQ ID NO 95
<211> LENGTH: 102
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 39
<223> OTHER INFORMATION: n = A, T, C, or G

<400> SEQUENCE: 95
ctgaccccgg cacaggtggt ggccatcgcc agcmaytcng gcggcaagca ggcgctggag      60
acggtgcagc ggctgttgcc ggtgctgtgc caggaccatg gc                        102

<210> SEQ ID NO 96
<211> LENGTH: 102
<212> TYPE: DNA
<213> ORGANISM: Artificial Sequence
<220> FEATURE:
<223> OTHER INFORMATION: synthetic oligonucleotide

<400> SEQUENCE: 96
ctgaccccgg cacaggtggt ggccatcgcc agcmayagyg gcggcaagca ggcgctggag      60
acggtgcagc ggctgttgcc ggtgctgtgc caggaccatg gc                        102

<210> SEQ ID NO 97
<211> LENGTH: 102
<212> TYPE: DNA
<213> ORGANISM: Artificial Sequence
<220> FEATURE:
<223> OTHER INFORMATION: synthetic oligonucleotide

<400> SEQUENCE: 97
ctgaccccgg cacaggtggt ggccatcgcc agcmayathg gcggcaagca ggcgctggag      60
acggtgcagc ggctgttgcc ggtgctgtgc caggaccatg gc                        102

<210> SEQ ID NO 98
<211> LENGTH: 34
<212> TYPE: PRT
<213> ORGANISM: Artificial Sequence
<220> FEATURE:
```

<223> OTHER INFORMATION: synthetic peptide

<400> SEQUENCE: 98

Leu Thr Pro Ala Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 99
<211> LENGTH: 34
<212> TYPE: PRT
<213> ORGANISM: Artificial Sequence
<220> FEATURE:
<223> OTHER INFORMATION: synthetic peptide

<400> SEQUENCE: 99

Leu Thr Pro Ala Gln Val Val Ala Ile Ala Ser Asn Ser Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 100
<211> LENGTH: 34
<212> TYPE: PRT
<213> ORGANISM: Artificial Sequence
<220> FEATURE:
<223> OTHER INFORMATION: synthetic peptide

<400> SEQUENCE: 100

Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 101
<211> LENGTH: 63
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 39
<223> OTHER INFORMATION: n = A, T, C, or G

<400> SEQUENCE: 101
ctgaccccgg cacaggtggt ggccatcgcc agcmayggng cggcaagca ggcgctcgag    60 agc                                                                63

<210> SEQ ID NO 102
<211> LENGTH: 63
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 39
<223> OTHER INFORMATION: n = A, T, C, or G

<400> SEQUENCE: 102

```
ctgaccccgg cacaggtggt ggccatcgcc agcmaytcng gcggcaagca ggcgctcgag    60
agc                                                                  63

<210> SEQ ID NO 103
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 103
ctgaccccgg cacaggtggt ggccatcgcc agcmayagyg gcggcaagca ggcgctcgag    60
agc                                                                  63

<210> SEQ ID NO 104
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 104
ctgaccccgg cacaggtggt ggccatcgcc agcmayathg gcggcaagca ggcgctcgag    60
agc                                                                  63

<210> SEQ ID NO 105
<211> LENGTH: 21
<212> TYPE: PRT
<213> ORGANISM: Artificial Sequence
<220> FEATURE:
<223> OTHER INFORMATION: synthetic peptide

<400> SEQUENCE: 105

Leu Thr Pro Ala Gln Val Val Ala Ile Ala Ser Asn Gly Gly Gly Lys
 1               5                  10                  15

Gln Ala Leu Glu Ser
            20

<210> SEQ ID NO 106
<211> LENGTH: 21
<212> TYPE: PRT
<213> ORGANISM: Artificial Sequence
<220> FEATURE:
<223> OTHER INFORMATION: synthetic peptide

<400> SEQUENCE: 106

Leu Thr Pro Ala Gln Val Val Ala Ile Ala Ser Asn Ser Gly Gly Lys
 1               5                  10                  15

Gln Ala Leu Glu Ser
            20

<210> SEQ ID NO 107
<211> LENGTH: 21
<212> TYPE: PRT
<213> ORGANISM: Artificial Sequence
<220> FEATURE:
<223> OTHER INFORMATION: synthetic peptide
```

```
<400> SEQUENCE: 107

Leu Thr Pro Ala Gln Val Val Ala Ile Ala Ser Asn Ile Gly Gly Lys
 1               5                  10                  15

Gln Ala Leu Glu Ser
            20
```